US010435747B2

(12) United States Patent
LaBaer et al.

(10) Patent No.: US 10,435,747 B2
(45) Date of Patent: Oct. 8, 2019

(54) RADIATION BIODOSIMETRY SYSTEMS

(71) Applicants: Joshua LaBaer, Chandler, AZ (US); Kristin Gillis, Mesa, AZ (US); Garrick Wallstrom, Mesa, AZ (US); Jin Park, Phoenix, AZ (US); Vel Murugan, Chandler, AZ (US); Mitch Magee, Chandler, AZ (US)

(72) Inventors: Joshua LaBaer, Chandler, AZ (US); Kristin Gillis, Mesa, AZ (US); Garrick Wallstrom, Mesa, AZ (US); Jin Park, Phoenix, AZ (US); Vel Murugan, Chandler, AZ (US); Mitch Magee, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 152 days.

(21) Appl. No.: 14/823,433

(22) Filed: Aug. 11, 2015

(65) Prior Publication Data
US 2016/0083793 A1 Mar. 24, 2016

Related U.S. Application Data

(60) Provisional application No. 62/038,969, filed on Aug. 19, 2014.

(51) Int. Cl.
*C12Q 1/6883* (2018.01)
*C12Q 1/6827* (2018.01)
(52) U.S. Cl.
CPC ......... *C12Q 1/6883* (2013.01); *C12Q 1/6827* (2013.01); *C12Q 2600/156* (2013.01)
(58) Field of Classification Search
None
See application file for complete search history.

(56) References Cited

U.S. PATENT DOCUMENTS

| | | | | |
|---|---|---|---|---|
| 6,228,575 B1* | 5/2001 | Gingeras | .............. | C12Q 1/6837 435/5 |
| 2003/0175761 A1* | 9/2003 | Sabath | ................. | C12Q 1/6886 435/6.12 |
| 2006/0286558 A1* | 12/2006 | Novoradovskaya | ........................ C12Q 1/6851 435/6.13 | |
| 2007/0122815 A1* | 5/2007 | Horvais | ............... | C12Q 1/6834 435/6.14 |
| 2008/0076122 A1* | 3/2008 | Wyrobek | ............. | C12Q 1/6883 435/6.13 |
| 2009/0023149 A1* | 1/2009 | Knudsen | ............... | C12Q 1/6886 435/6.14 |
| 2010/0196880 A1* | 8/2010 | Satyaraj | ............... | C12Q 1/6883 435/6.1 |
| 2010/0255004 A1* | 10/2010 | DePinho | ................ | A61K 45/06 424/172.1 |
| 2010/0304995 A1* | 12/2010 | Shen | .................... | C12Q 1/6809 506/9 |
| 2011/0152115 A1* | 6/2011 | Staudt | ................. | C12Q 1/6886 506/9 |
| 2013/0136722 A1* | 5/2013 | Mahmud | ............... | A61K 35/28 424/93.7 |
| 2014/0128277 A1* | 5/2014 | Moller | ................. | C12Q 1/6883 506/9 |

FOREIGN PATENT DOCUMENTS

WO     WO 2012/120026 A1 *   9/2012  ............... C12Q 1/68

OTHER PUBLICATIONS

Ahmed et al, Free Radical Biology & Medicine, vol. 44, pp. 1-13 (2008).*
Dieffenbach et al, Genome Research, vol. 3, pp. 30-37 (1993).*
Roux, Genome Research, vol. 4, pp. 185-194 (1994).*
Amundson, S.A., et al., Differential responses of stress genes to low dose-rate gamma irradiation. Mol Cancer Res, 2003. 1(6): p. 445-52.
Amundson, S.A., et al., Identification of potential mRNA biomarkers in peripheral blood lymphocytes for human exposure to ionizing radiation. Radiat Res, 2000. 154(3): p. 342-6.
Anno GH, Young RW, Bloom RM, Mercier JR. Dose response relationships for acute ionizing-radiation lethality. Health Phys. 2003;84:565-575.
Boldrick, J.C., A.A. Alizadeh, M. Diehn, S. Dudoit, C.L. Liu, C.E. Belcher, D. Botstein, L.M. Staudt, P.O. Brown, and D. A. Relman, Stereotyped and specific gene expression programs in humane innate immune responses to bacteria. Proc Natl Acad Sci U S A, 2002. 99(2):p. 972-7.
Braga-Neto, U.M. and E.R. Dougherty, Is cross-validation valid for small-sample microarray classification? Bioinformatics, 2004. 20(3): p. 374-80.
Brengues, M., et al., Biodosimetry on small blood volume using gene expression assay. Health Physics, 2010. 98(2): p. 179-85.
Brun, M., Q. Xu, and E.R. Dougherty, Which is better: holdout or full-sample classifier design? Eurasip J Bioinform Syst Biol, 2008: p. 297945.
Coleman N.C., et al, Medical response to a radiologic/nuclear event: integrated plan from the office of the Asisstant Secretary for preparedness and response, DHHS, Annals of Emergency Medicine, vol. 53(2), Feb. 2009: p. 223-225.
Copeland S, Warren HS, Iowry SF, Calvano SE, Remick D. Acute inflammatory response to endotoxin in mice and humans. Clin Diagn Lab Immunol. 2005;12:60-67.
Feldschuh J. and Enson Y. Prediction of the normal blood volume. Relation of blood volume to body habitus. Circulation. 1977. 56(4 Pt 1):605-12.
Fornace, A.J., Jr., et al., Stress-gene induction by low-dose gamma irradiation. Mil Med, 2002. 167(2 Suppl): p. 13-5.

(Continued)

*Primary Examiner* — Robert T. Crow
(74) *Attorney, Agent, or Firm* — Jessica L. Lewis; Quarles & Brady LLP

(57) ABSTRACT

Disclosed herein are compositions and methods for accurately estimating the absorbed dose of radiation indicated by a subject based on the expression pattern of a panel of radiation-modulated (RM) genes at various time points following exposure of the subject to ionizing radiation.

22 Claims, 15 Drawing Sheets

Specification includes a Sequence Listing.

(56) References Cited

OTHER PUBLICATIONS

Fornace, A.J., Jr., et al., The complexity of radiation stress responses: analysis by informatics and functional genomics approaches. Gene Expr, 1999. 7(4-6): p. 387-400.

Ganguly, D., K. Paul, J. Bagchi, S. Rakshit, L. Mandal, G. Bandyopadhyay, and S. Bandyopadhyay, Granulocyte-macrophage colony-stimulating factor drives monocytes to CD14low CD83+ DCSIGNinterleukin-10-producing myeloid cells with differential effects on T-cell subsets. Immunology, 2007.121(4):p. 499-507.

Golde WT, Gollobin P, Rodriguez LL. A rapid, simple, and humane method for submandibular bleeding of mice using a lancet. Lab Anim (NY). 2005;34:39-43.

Hanczar, B. and E.R. Dougherty, Classification with reject option in gene expression data. Bioinformatics, 2008. 24(17): p. 1889-95.

Hanczar, B., J. Hua, and E.R. Dougherty, Decorrelation of the true and estimated classifier errors in high-dimensional settings. EURASIP J Bioinform Syst Biol, 2007: p. 38473.

Hua, J., et al., Optimal number of features as a function of sample size for various classification rules. Bioinformatics, 2005. 21(8): p. 1509-15.

Kallman RF. The effect of dose rate on mode of acute radiation death of C57BL and BALB/c mice. Radiat Res. 1962;16:796-810.

Kim, S., et al., Strong feature sets from small samples. J Comput Biol, 2002. 9(1): p. 127-46.

Kuo, W.P., et al., A sequence-oriented comparison of gene expression measurements across different hybridization-based technologies. Nat Biotechnol, 2006. 24(7): p. 832-40.

Lee ML, Whitmore GA. Power and sample size for DNA microarray studies. Stat Med. 2002;21:3543-3570.

Lowry SF. Human endotoxemia: a model for mechanistic insight and therapeutic targeting. Shock. 2005; 24 Suppl 1:94-100.

Morgan, T.M., et al., Nonvalidation of reported genetic risk factors for acute coronary syndrome in a large-scale replication study. JAMA, 2007. 297(14): p. 1551-61.

Nifontova IN, Svinareva DA, Chertkov IL, Drize NI, Savchenko VG. Delayed effects of long-term administration of granulocyte colony-stimulating factor to mice. Bull Exp Biol Med. 2008;145:629-633.

Paul, S. and S.A. Amundson, Development of gene expression signatures for practical radiation biodosimetry. Int J Radiat Oncol Biol Phys, 2008. 71(4): p. 1236-1244.

Planning Guidance for Response to a Nuclear Detonation, First Edition, Jan. 16, 2009, developed by Homeland Sceurity Council Interagency Policy Coordination Subcommittee for Preparedness & Response to Radiological and Nuclear Threats.

Schwab G, Hecht T. Recombinant methionyl granulocyte colony-stimulating factor (filgrastim): a new dimension in immunotherapy. Ann Hematol. 1994;69:1-9.

Sima, C. and E.R. Dougherty, What should be expected from feature selection in small-sample settings. Bioinformatics, 2006. 22(19): p. 2430-6.

Sima, C., U. Braga-Neto, and E.R. Dougherty, Superior feature-set ranking for small samples using bolstered error estimation. Bioinformatics, 2005. 21(7): p. 1046-54.

Simon R, Lam A, Li M-C, Ngan M, Menenzes S, Zhao Y. Analysis of gene expression data using BRBArray Tools. Cancer Informatics. 2007;2:11-17.

Warren HS. Editorial: Mouse models to study sepsis syndrome in humans. J Leukoc Biol. 2009;86:199-201.

Waselenko JK, MacVittie TJ, Blakely WF et al. Medical management of acute radiation syndrome: recommendations of the Strategic National Stockpile Radiation Working Group. Ann Intern Med. 2004;140:1037-1051.

Xiao, Y., J. Hua, and E.R. Dougherty, Quantification of the impact of feature selection on the variance of cross-validation error estimation. EURASIP J Bioinform Syst Biol, 2007: p. 16354.

Xu, Q., et al., Confidence intervals for the true classification error conditioned on the estimated error. Technol Cancer Res Treat, 2006. 5(6): p. 579-89.

Zhu H, Melder RJ., Baxter LT. and Jain RK. Physiologically based kinetic model of effector cell biodistribution in mammals: implication for adoptive immunotherapy. Cancer Res. 1996. 56(16):3771-81.

* cited by examiner

| Gene | Regulated | Function | Day 1 | Day 2 | Day 3 | Day 5 | Day 7 |
|---|---|---|---|---|---|---|---|
| HBA2 | Down | Hemoglobin | | ■ | ■ | ■ | |
| PPM1F | Up | Cell Signaling | | ■ | | | |
| PPP2R1A | Down | Cell Signaling | | ■ | | | Up Al |
| CFLAR | Up | DNA Damage/Apoptosis | | | ■ | | |
| DHRS13 | Up | Metabolism | | | ■ | | |
| ACAA1 | Up | Metabolism | | | | ■ | |
| INPP5J | Up | Cell Signaling | | | | ■ | |
| OAZ1 | Down | Metabolism | | | | ■ | ■ |
| PNOC | Down | Cell Signaling | | | | ■ | ■ |
| PDE4B | Up | Metabolism | | | | | ■ |
| SCARB1 | Down | Immune Response | | | | | ■ |
| TMEM9B | Down | Membrane Signaling | | | | | ■ |
| PPP6R3 | Reference | Immune Tolerance | | | | | |
| Number of Biomarkers Used Post-Event Start Day # | | | | 29 | 24 | 22 | |

FIG. 4

| Days Post Exposure | 0 Gy | 2 Gy | 4 Gy | 6 Gy | 7 Gy | 10 Gy | Ave |
|---|---|---|---|---|---|---|---|
| 1 | 80 | 20 | 10 | 40 | 90 | 60 | 50 |
| 2 | 80 | 50 | 40 | 70 | 60 | 60 | 60 |
| 3 | 90 | 40 | 30 | 40 | 70 | 60 | 55 |
| 5 | 90 | 90 | 20 | 30 | 80 | 70 | 63 |
| 7 | 90 | 60 | 50 | 70 | 70 | 70 | 68 |
| Ave | 86 | 52 | 30 | 50 | 74 | 64 | 59 |

Training Performance Data: 29 Biomarkers
% NHP Samples that Tested within 0.5 Gy Cobalt-60 Source Variance ± 2.9% (~0.18 Gy)

FIG. 6

| Test Model Sample Set | Sample Set Number | Performance Rate | |
|---|---|---|---|
| | | Sensitivity True Positive (+) | Specificity True Negative (-) |
| NHP Fractionated (2 Gy Fractions) | 6 Control | - | 100% |
| | 42 Irradiated | 100% | - |
| Human TBI Model (2 Gy Fractions) | 5 Control | - | 100% |
| | 26 Irradiated | 100% | - |
| Normal Human (not Irradiated) | 23 Control | - | 100% |

*No False (-) or False (+) observations for Human TBI and Normal samples.*

SEQUENCE LISTING

<160> NUMBER OF SEQ ID NOS: 31

<210> SEQ ID NO 1
<211> LENGTH: 4184

<212> TYPE: DNA
<213> ORGANISM: Homo sapiens

<400> SEQUENCE: 1

| | | | | | |
|---|---|---|---|---|---|
| atttaagggc | ccgcctctcc | tggctcacag | ctgcttgctg | ctccagcctt | gccctcccag | 60 |
| agctgccgga | cgctcgcggg | tctcggaacg | catcccgccg | cggggggcttc | ggccgtggca | 120 |
| tgggcgccgc | gggcctgctc | gggttttct | tggctctcgt | cgcaccgggg | gtcctcggga | 180 |
| tttcttgtgg | ctctcctccg | cctatcctaa | atggccggat | tagttattat | tctaccccca | 240 |
| ttgctgttgg | taccgtgata | aggtacagtt | gttcaggtac | cttccgcctc | attggagaaa | 300 |
| aaagtctatt | atgcataact | aaagacaaag | tggatggaac | ctgggataaa | cctgctccta | 360 |
| aatgtgaata | tttcaataaa | tattcttctt | gccctgagcc | catagtacca | ggaggataca | 420 |
| aaattagagg | ctctacaccc | tacagacatg | gtgattctgt | gacatttgcc | tgtaaaacca | 480 |
| acttctccat | gaacggaaac | aagtctgttt | ggtgtcaagc | aaataatatg | tgggggccga | 540 |
| cacgactacc | aacctgtgta | agtgttttcc | ctctcgagtg | tccagcactt | cctatgatcc | 600 |
| acaatggaca | tcacacaagt | gagaatgttg | gctccattgc | tccaggattg | tctgtgactt | 660 |
| acagctgtga | atctggttac | ttgcttgttg | gagaaaagat | cattaactgt | ttgtcttcgg | 720 |
| gaaaatggag | tgctgtcccc | cccacatgtg | aagaggcacg | ctgtaaatct | ctaggacgat | 780 |
| tccccaatgg | gaaggtaaag | gagcctccaa | ttctccgggt | tggtgtaact | gcaaactttt | 840 |
| tctgtgatga | agggtatcga | ctgcaaggcc | caccttctag | tcggtgtgta | attgctggac | 900 |
| agggagttgc | ttggaccaaa | atgccagtat | gtgaagaaat | ttttttgccca | tcacctcccc | 960 |
| ctattctcaa | tggaagacat | ataggcaact | cactagcaaa | tgtctcatat | ggaagcatag | 1020 |
| tcacttacac | ttgtgacccg | gacccagagg | aaggagtgaa | cttcatcctt | attggagaga | 1080 |
| gcactctccg | ttgtacagtt | gatagtcaga | agactgggac | ctggagtggc | cctgcccac | 1140 |
| gctgtgaact | ttctacttct | gcggttcagt | gtccacatcc | ccagatccta | agaggccgaa | 1200 |
| tggtatctgg | gcagaaagat | cgatatacct | ataacgacac | tgtgatattt | gcttgcatgt | 1260 |
| ttggcttcac | cttgaagggc | agcaagcaaa | tccgatgcaa | tgcccaaggc | acatgggagc | 1320 |
| catctgcacc | agtctgtgaa | aaggaatgcc | aggcccctcc | taacatcctc | aatgggcaaa | 1380 |
| aggaagatag | acacatggtc | cgctttgacc | ctggaacatc | tataaaatat | agctgtaacc | 1440 |
| ctggctatgt | gctggtggga | gaagaatcca | tacagtgtac | ctctgagggg | gtgtggacac | 1500 |
| cccctgtacc | ccaatgcaaa | gtggcagcgt | gtgaagctac | aggaaggcaa | ctcttgacaa | 1560 |
| aaccccagca | ccaatttgtt | agaccagatg | tcaactcttc | ttgtggtgaa | gggtacaagt | 1620 |
| taagtgggag | tgtttatcag | gagtgtcaag | gcacaattcc | ttggtttatg | gagattcgtc | 1680 |
| tttgtaaaga | aatcacctgc | ccaccacccc | ctgttatcta | caatgggca | cacaccggga | 1740 |
| gttccttaga | agattttcca | tatggaacca | cggtcactta | cacatgtaac | cctgggccag | 1800 |
| aaagaggagt | ggaattcagc | ctcattggag | agagcaccat | ccgttgtaca | agcaatgatc | 1860 |
| aagaaagagg | cacctggagt | ggccctgctc | ccctgtgtaa | actttccctc | cttgctgtcc | 1920 |
| agtgctcaca | tgtccatatt | gcaaatggat | acaagatatc | tggcaaggaa | gccccatatt | 1980 |
| tctacaatga | cactgtgaca | ttcaagtgtt | atagtggatt | tactttgaag | ggcagtagtc | 2040 |
| agattcgttg | caaagctgat | aacacctggg | atcctgaaat | accagtttgt | gaaaaaggct | 2100 |
| gccagtcacc | tcctgggctc | caccatggtc | gtcatacagg | tggaaatacg | gtcttctttg | 2160 |
| tctctgggat | gactgtagac | tacacttgtg | accctggcta | tttgcttgtg | ggaaacaaat | 2220 |

| | |
|---|---|
| ccattcactg tatgccttca ggaaattgga gtccttctgc cccacggtgt gaagaaacat | 2280 |
| gccagcatgt gagacagagt cttcaagaac ttccagctgg ttcacgtgtg gagctagtta | 2340 |
| atacgtcctg ccaagatggg taccagttga ctggacatgc ttatcagatg tgtcaagatg | 2400 |
| ctgaaaatgg aatttggttc aaaaagattc cactttgtaa agttattcac tgtcaccctc | 2460 |
| caccagtgat tgtcaatggg aagcacacag gcatgatggc agaaaacttt ctatatggaa | 2520 |
| atgaagtctc ttatgaatgt gaccaaggat tctatctcct gggagagaaa aaattgcagt | 2580 |
| gcagaagtga ttctaaagga catggatctt ggagcgggcc ttccccacag tgcttacgat | 2640 |
| ctcctcctgt gactcgctgc cctaatccag aagtcaaaca tgggtacaag ctcaataaaa | 2700 |
| cacattctgc atattcccac aatgacatag tgtatgttga ctgcaatcct ggcttcatca | 2760 |
| tgaatggtag tcgcgtgatt aggtgtcata ctgataacac atgggtgcca ggtgtgccaa | 2820 |
| cttgtatcaa aaaagccttc ataggtgtc cacctccgcc taagaccct aacgggaacc | 2880 |
| atactggtgg aaacatagct cgattttctc ctggaatgtc aatcctgtac agctgtgacc | 2940 |
| aaggctacct gctggtggga gaggcactcc ttctttgcac acatgaggga acctggagcc | 3000 |
| aacctgcccc tcattgtaaa gaggtaaact gtagctcacc agcagatatg gatggaatcc | 3060 |
| agaaagggct ggaaccaagg aaaatgtatc agtatgagc tgttgtaact ctggagtgtg | 3120 |
| aagatgggta tatgctggaa ggcagtcccc agagccagtg ccaatcggat caccaatgga | 3180 |
| accctccccct ggcggtttgc agatcccgtt cacttgctcc tgtcctttgt ggtattgctg | 3240 |
| caggtttgat acttcttacc ttcttgattg tcattacctt atacgtgata tcaaaacaca | 3300 |
| gagcacgcaa ttattataca gatacaagcc agaaagaagc ttttcattta gaagcacgag | 3360 |
| aagtatattc tgttgatcca tacaacccag ccagctgatc agaagacaaa ctggtgtgtg | 3420 |
| cctcattgct tggaattcag cggaatattg attagaaaga aactgctcta atatcagcaa | 3480 |
| gtctctttat atggcctcaa gatcaatgaa atgatgtcat aagcgatcac ttcctatatg | 3540 |
| cacttattct caagaagaac atctttatgg taaagatggg agcccagttt cactgccata | 3600 |
| tactcttcaa ggactttctg aagcctcact tatgagatgc ctgaagccag gccatggcta | 3660 |
| taaacaatta catggctcta aaagttttg cccttttaa ggaaggcact aaaaagagct | 3720 |
| gtcctggtat ctagacccat cttctttttg aaatcagcat actcaatgtt actatctgct | 3780 |
| tttggttata atgtgtttt aattatctaa agtatgaagc attttctggg gttatgatgg | 3840 |
| ctttaccttt attaggaagt atggtttat tttgatagta gcttcctcct ctggtggtgt | 3900 |
| taatcatttc attttacccc ttacttggtt tgagtttctc tcacattact gtatatactt | 3960 |
| tgcctttcca taatcactca gtgattgcaa tttgcacaag ttttttttaaa ttatgggaat | 4020 |
| caagatttaa tcctagagat ttggtgtaca attcaggctt tggatgtttc tttagcagtt | 4080 |
| ttgtgataag ttctagttgc ttgtaaaatt tcacttaata atgtgtacat tagtcattca | 4140 |
| ataaattgta attgtaaaga aaacatacaa aaaaaaaaaa aaaa | 4184 |

<210> SEQ ID NO 2
<211> LENGTH: 1442
<212> TYPE: DNA
<213> ORGANISM: Homo sapiens

<400> SEQUENCE: 2

| | |
|---|---|
| agtcgggcag ctctccgggc cggcgtggga gcccgcgctc caaagcccgg tggggggagg | 60 |
| ggcgctcacg caaccgccac tgtctggagc gggctcgcct ctgcggcggc actcaccgcc | 120 |
| cgggctttac tgaagcggag tctagcatgt gcggctgctc cacagcggtg tgggtggcgg | 180 |

```
cggctcctct gcagcagcct cggcagtagg ggtcacggtg gccaagccca ccgtggagct    240
catctgagag ttgtaaggta cgggactgcc tcggtctttg gacgcccncg tctggtagca    300
tcccagatcc agcacgttcc ttccggccct gcaccccggc ccgtgcctc acacccgct     360 accccatgca tccagactct aaggcagccc ctgcatctca gtcctgacat cgctgtccct    420
ggagcatcct ccgctggagc tggagcttga caggatcggc ttcgccgtcg cccagcgtct    480
ggcccaagac ggggcccacg tggtagtcag ccgccggaag cagcagaatg tggaccaggc    540
agtggccacg ctgcaggggg aggggctgag catgacgggc actgtgtgcc atgtggggaa    600
gatgaaggac tgggagcggc tggtggccac agtgagctgc agggaaatgg gcacagagcc    660
aggaggtgga aagggagcc agcctgagcc tccttccctg ctttcctgga cagcattggg     720
cttcagtcct tacaatgtca gtaaaacagc cttgctgggc ctcaacaaga ccttggccat    780
agagctggcc ccaaggaaca ttagggtgaa ctgcctagca cctggactta tcaagactag    840
cttcagcagg atgctctgga tggacaagga aaaagaggaa agcatgaaag aaaccctgcg    900
gataagaagg ttaggcgagc cagaggattc tcttggcatc gtgtctttcc tgtgctctga    960
agatgccagc tacctcactg ggaaacagt gatggtgggt ggaggaaccc cgtcccgcct    1020
ctgaggaccc ggagacagcc cacaggccag agttgggctc tagctcctgg tgctgttcct    1080
gcattcaccc actggccttt cccacctctg ctcaccttac tgttcacctc atcaaatcag    1140
ttctgccctg tgaaaagatc cagccttccc tgccgtcaag gtggtgtctt actcgggatt    1200
cctgctgttg ttgtggcctt gggtaaaggc ctcccctgag aacacaggac aggcctgctg    1260
acaaggctga gtctaccttg gcaaagacca agatatttt tgcccaggcc actggggaat    1320
ttgaggggag atgagagaga aggaagctgg agtggaagga gcagagttgc aaattaacaa    1380
cttgcaaatg aggtgcaaat aaaatgcaga tgattgcgcg gctttgaatc gaaaaaaaaa    1440
aa    1442
```

<210> SEQ ID NO 3
<211> LENGTH: 2168
<212> TYPE: DNA
<213> ORGANISM: Homo sapiens

<400> SEQUENCE: 3

```
ggagttagcc tcgctcaggg cgcggctaag gcgcccagat ggcctgcggg cgccaccacg    60
tccctggtcc cagctcggga gcacatcaga ggcttagagg cgagtgggaa gggactcaga    120
cagtgcagga cgagaaacgc ccgcggcacc aaagcccctc agagcgtcgc ccccgcctct    180
agttctagaa agtcagtttc ccggcactgg caccccggaa cctcaggggc tgccgagctg    240
ggggggcgct caagctgcga ggatccgggc tgccgcgag acgaggagcg ggcgccagg     300 atggggtgca tgaagtccaa gttcctccag gtcggaggca atacattctc aaaaactgaa    360
accagcgcca gccacactg tcctgtgtac gtgccggatc ccacatccac catcaagccg    420
gggcctaata gccacaacag caacacacca ggaatcaggg aggcaggctc tgaggacatc    480
atcgtggttg ccctgtatga ttacgaggcc attcaccacg aagacctcag cttccagaag    540
ggggaccaga tggtggtcct agaggaatcc ggggagtggt ggaaggctcg atccctggcc    600
acccggaagg agggctacat cccaagcaac tatgtcgccc gcgttgactc tctggagaca    660
gaggagtggt tttcaaggg catcagccgg aaggacgcag agcgccaact gctggctccc    720
ggcaacatgc tgggctcctt catgatccgg gatagcgaga ccactaaagg aagctactct    780
```

| | |
|---|---|
| ttgtccgtgc gagactacga ccctcggcag ggagataccg tgaaacatta caagatccgg | 840 |
| accctggaca acgggggctt ctacatatcc ccccgaagca ccttcagcac tctgcaggag | 900 |
| ctggtggacc actacaagaa ggggaacgac gggctctgcc agaaactgtc ggtgccctgc | 960 |
| atgtcttcca agcccagaa gccttgggag aaagatgcct gggagatccc tcgggaatcc | 1020 |
| ctcaagctgg agaagaaact tggagctggg cagtttgggg aagtctggat ggccacctac | 1080 |
| aacaagcaca ccaaggtggc agtgaagacg atgaagccag ggagcatgtc ggtggaggcc | 1140 |
| ttcctggcag aggccaacgt gatgaaaact ctgcagcatg acaagctggt caaacttcat | 1200 |
| gcggtggtca ccaaggagcc catctacatc atcacggagt tcatggccaa aggaagcttg | 1260 |
| ctggactttc tgaaaagtga tgagggcagc aagcagccat tgccaaaact cattgacttc | 1320 |
| tcagcccaga ttgcagaagg catggccttc atcgagcaga gaactacat ccaccgagac | 1380 |
| ctccgagctg ccaacatctt ggtctctgca tccctggtgt gtaagattgc tgactttggc | 1440 |
| ctggcccggg tcattgagga caacgagtac acggctcggg aaggggccaa gttccccatc | 1500 |
| aagtggacag ctcctgaagc catcaacttt ggctccttca ccatcaagtc agacgtctgg | 1560 |
| tcctttggta tcctgctgat ggagatcgtc acctacggcc ggatcccta cccagggatg | 1620 |
| tcaaaccctg aagtgatccg agctctggag cgtggatacc ggatgcctcg cccagagaac | 1680 |
| tgcccagagg agctctacaa catcatgatg cgctgctgga aaaccgtcc ggaggagcgg | 1740 |
| ccgaccttcg aatacatcca gagtgtgctg atgacttct acacggccac agagagccag | 1800 |
| taccaacagc agccatgata gggaggacca gggcagggcc aggggtgcc caggtggtgg | 1860 |
| ctgcaaggtg gctccagcac catccgccag ggcccacacc cccttcctac tcccagacac | 1920 |
| ccaccctcgc ttcagccaca gtttcctcat ctgtccagtg ggtaggttgg actggaaaat | 1980 |
| ctcttttga ctcttgcaat ccacaatctg acattctcag gaagccccca agttgatatt | 2040 |
| tctatttcct ggaatggttg gattttagtt acagctgtga tttggaaggg aaactttcaa | 2100 |
| aatagtgaaa tgaatattta ataaaagat ataaatgcca aagtctttac caaaaaaaaa | 2160 |
| aaaaaaaa | 2168 |

```
<210> SEQ ID NO 4
<211> LENGTH: 4801
<212> TYPE: DNA
<213> ORGANISM: Homo sapiens

<400> SEQUENCE: 4
```

| | |
|---|---|
| aaaggggaa agaaagtgc ggcggaaagt aagaggctca ctggggaaga ctgccgggat | 60 |
| ccaggtctcc ggggtccgct ttggccagag gcgcggaagg aagcagtgcc cggcgacact | 120 |
| gcacccatcc cggctgcttt tgctgcgccc tctcagcttc ccaagaaagg catcgtcatg | 180 |
| tgatcatcac ctaagaacta aacatcagc aggccctaga agcctcactc ttgcccctcc | 240 |
| ctttaatatc tcaaggatg acacttctgt ggtgtgtagt gagtctctac ttttatggaa | 300 |
| tcctgcaaag tgatgcctca gaacgctgcg atgactgggg actagacacc atgaggcaaa | 360 |
| tccaagtgtt tgaagatgag ccagctcgca tcaagtgccc actctttgaa cacttcttga | 420 |
| aattcaacta cagcacagcc cattcagctg gccttactct gatctggtat tggactaggc | 480 |
| aggaccggga ccttgaggag ccaattaact tccgcctccc cgagaaccgc attagtaagg | 540 |
| agaaagatgt gctgtggttc cggcccactc tcctcaatga cactggcaac tatacctgca | 600 |
| tgttaaggaa cactacatat tgcagcaaag ttgcatttcc cttggaagtt gttcaaaaag | 660 |
| acagctgttt caattccccc atgaaactcc cagtgcataa actgtatata gaatatggca | 720 |

```
ttcagaggat cacttgtcca aatgtagatg gatattttcc ttccagtgtc aaaccgacta      780
tcacttggta tatgggctgt tataaaatac agaattttaa taatgtaata cccgaaggta      840
tgaacttgag tttcctcatt gccttaattt caaataatgg aaattacaca tgtgttgtta      900
catatccaga aaatggacgt acgtttcatc tcaccaggac tctgactgta aaggtagtag      960
gctctccaaa aaatgcagtg cccctgtga tccattcacc taatgatcat gtggtctatg     1020
agaaagaacc aggagaggag ctactcattc cctgtacggt ctattttagt tttctgatgg     1080
attctcgcaa tgaggtttgg tggaccattg atggaaaaaa acctgatgac atcactattg     1140
atgtcaccat taacgaaagt ataagtcata gtagaacaga gatgaaaaca gaactcaga      1200 ttttgagcat caagaaagtt acctctgagg atctcaagcg cagctatgtc tgtcatgcta     1260
gaagtgccaa aggcgaagtt gccaaagcag ccaaggtgaa gcagaaagtg ccagctccaa     1320
gatacacagt ggaactggct tgtggttttg gagccacagt cctgctagtg gtgattctca     1380
ttgttgttta ccatgtttac tggctagaga tggtcctatt ttaccgggct cattttggaa     1440
cagatgaaac cattttagat ggaaaagagt atgatattta tgtatcctat gcaaggaatg     1500
cggaagaaga agaatttgta ttactgaccc tccgtggagt tttggagaat gaatttggat     1560
acaagctgtg catctttgac cgagacagtc tgcctggggg aattgtcaca gatgagactt     1620
tgagcttcat tcagaaaagc agacgcctcc tggttgttct aagccccaac tacgtgctcc     1680
agggaaccca agccctcctg gagctcaagg ctggcctaga aaatatggcc tctcggggca     1740
acatcaacgt cattttagta cagtacaaag ctgtgaagga aacgaaggtg aaagagctga     1800 agaggctaa gacggtgctc acggtcatta aatggaaagg ggaaaaatcc aagtatccac     1860
agggcaggtt ctggaagcag ctgcaggtgg ccatgccagt gaagaaaagt cccaggcggt     1920
ctagcagtga tgagcagggc ctctcgtatt catctttgaa aaatgtatga aaggaataat     1980
gaaaagggta aaaagaacaa ggggtgctcc aggaagaaag agtccccca gtcttcattc     2040 gcagtttatg gtttcatagg caaaaataat ggtctaagcc tcccaatagg gataaattta     2100
gggtgactgt gtggctgact attctgcttc ctcaggcaac actaaagttt agaaagatat     2160
catcaacgtt ctgtcaccag tctctgatgc cactatgttc tttgcaggca aagacttgtt     2220
caatgcgaat tccccttct acattgtcta tccctgtttt tatatgtctc cattcttttt      2280
aaaatcttaa catatggagc agcctttcct atgaatttaa atatgccttt aaaataagtc     2340
actgttgaca gggtcatgag tttccgagta tagttttctt tttatcttat ttttactcgt     2400
ccgttgaaaa gataatcaag gcctacattt tagctgagga taatgaactt ttttcctcat     2460
tcggctgtat aatacataac cacagcaaga ctgacatcca cttaggatga tacaaagcag     2520
tgtaactgaa aatgtttctt ttaattgatt taaaggactt gtcttctata ccacccttgt     2580
cctcatctca ggtaatttat gaaatctatg taaacttgaa aaatatttct taattttgt      2640 ttttgctcca gtcaattcct gattatccac aggtcaaccc acattttttc attccttctc     2700
cctatctgct tatatcgcat tgctcattta gagtttgcag gaggctccat actaggttca     2760
gtctgaaaga aatctcctaa tggtgctata gagagggagg taacagaaag actcttttag     2820 ggcattttc tgactcatga aaagagcaca gaaaaggatg tttggcaatt tgtcttttaa      2880
gtcttaacct tgctaatgtg aatactggga aagtgatttt ttctcactcg ttttttgttgc    2940 tccattgtaa agggcggagg tcagtcttag tggccttgag agttgctttt ggcattaata     3000
ttctaagaga attaactgta tttcctgtca cctattcact agtgcaggaa atatacttgc     3060
```

```
tccaaataag tcagtatgag aagtcactgt caatgaaagt tgttttgttt gttttcagta    3120
atattttgct gttttaaga cttggaaaac taagtgcaga gtttacagag tggtaaatat      3180
ctatgttaca tgtagattat acatatatat acacacgtgt atatgagata tatatcttat     3240
atctccacaa acacaaatta tatatataca tatccacaca catacattac atatatctgt     3300
gtatataaat ccacatgcac atgaaatata tatatatata taatttgtgt gtgtgtatgt    3360
gtatgtatat gactttaaat agctatgggt acaatattaa aaaccactgg aactcttgtc    3420 cagttttaa attatgtttt tactggaatg ttttttgtgtc agtgttttct gtacatatta    3480
tttgttaatt cacagctcac agagtgatag ttgtcatagt tcttgccttc cctaagttta    3540
tataaataac ttaagtattg ctacagttta tctaggttgc agtggcatct gctgtgcaca    3600
gagcttccat ggtcactgct aagcagtagc cagccatcgg gcattaattg atttcctact    3660
atattcccag cagacacatt tagaaactaa gctatgttaa cctcagtgct caactatttg    3720
aactgttgag tgataaagga acaaatata actgtaaatg aatcttggta tcctgtgaaa     3780
cagaataatt cgtaatttaa gaaagcccctt atcccggtaa catgaatgtt gatgaacaaa   3840
tgtaaaatta tatcctatat ttaagtaccc ataataaatc atttccctct ataagtgtta    3900
ttgattattt taaattgaaa aaagtttcac ttggatgaaa aagtagaaa agtaggtcat     3960 tcttggatct acttttttt agccttatta atattttcc ctattagaaa ccacaattac     4020
tccctctatt aacccttcac ttactagacc agaaaagaac ttattccaga taagctttga   4080
atatcaattc ttacataaac tttaggcaaa cagggaatag tctagtcacc aaaggaccat   4140
tctcttgcca atgctgcatt ccttttgcac ttttggattc catatttatc ccaaatgctg    4200
ttgggcaccc ctagaaatac cttgatgttt tttctatttta tatgcctgcc tttggtactt   4260
aattttacaa atgctgtaat ataaagcata tcaagtttat gtgatacgta tcattgcaag    4320
agaatttgtt tcaagatttt tttttaatgt tccagaagat ggccaataga gaacattcaa    4380
gggaaatggg gaaacataat ttagagaaca agaacaaacc atgtctcaaa tttttttaaa   4440
aaaaattaat ggtttaaat atatgctata gggacgttcc atgcccaggt taacaaagaa     4500
ctgtgatata tagagtgtct aattacaaaa tcatatacga tttattttaat tctcttctgt  4560 attgtaactt agatgattcc caaggactct aataaaaaat cacttcattg tatttggaaa    4620
caaaaacatc attcattaat tacttattt ctttccatag gttttaatat tttgagagtg     4680 tctttttat tcattcatg aactttgta ttttcattt tcatttgat ttgtaaattt        4740 acttatgtta aaataaaacc atttattttc agctttgaat tttaaaaaaa aaaaaaaaa    4800 a                                                                   4801

<210> SEQ ID NO 5
<211> LENGTH: 1514
<212> TYPE: DNA
<213> ORGANISM: Homo sapiens

<400> SEQUENCE: 5
gagccctgcc tgcgcccgcc cccgaagcgg cgcgggacgc ctggcgccgt ccgcgatccg     60
cagggctgcc cgcttaggct taggcccggc ccgctggcaa agccgagccg cagcatttta   120
tttcgttcgt ggtttccgca caggctggag tttcgtgggt tgggtcgtac ttgggacctc    180
ggcgaagagg acccgtttat tttttttct ttccaaaatg gcagcctcca gtcgcgcaca     240
agtgttatct ctgtaccggg cgatgctgag agagagcaag cgtttcagcg cctacaatta   300
cagaacatat gctgtcagga ggataagaga tgccttcaga gaaaataaaa atgtaaagga  360
```

```
tcctgtagaa attcaaaccc tagtgaataa agccaagaga gaccttggag taattcgtcg      420
acaggtccac attggccaac tgtattcaac tgacaagctg atcattgaga atcgagacat      480
gcccaggacc tagcaagccg ggaccagcc accagtggcg gccagggacc accttcagca       540
tccactctct gtttgagatg ggggctccca aaaccagctt acaatagcct tttgcgctgc      600
ctgtcctgtg ggagctgata aaccaagtca catttgcatt ctgttgcagg cttagtgaaa      660
aaggactgct gtctttcctt ggttcaagtg ttagaatgga gagctggagt tcgttcagaa      720
tagtgctgtg tgttaccacg tctcccctgc accccattcc taccttgtag ctcatgacca      780
ttgtgtatag catttctaca cttttgtttct tggtccttgg caataaaaag aatgatctcc     840
ctgagccttt gacccagat aaaccctcc caattaatgc attttcattt cctactgata       900
caaggcctgg agagggctgt tgggggccct caggagggt tcaactctga acgagaact       960 gccttggtga aggcaagttc aagcaccact tgagactggg ggcagcatgg agtagggcag    1020
ggctacgggg atacacggtg caccctgcaa cttatacctg agcccagtac aacaaaggtg    1080
acgggtgtgt aggtacacac ccagagatgg agcactgcag atcagcaacc tcagccccac   1140
ctgggaattt gctggaaatg caggctcaag cccctcccca cacctggtga atgagagagc   1200
cccagcctga cccaagccca gggcgactcc catacctga agcctgggc atgctgggca     1260 gcaccggtgc ccaaatctgg ctggtggaca aagcacctg gagagttgga gagctttta    1320 aaaagacatc tctcagcact tccctctctg cagattctga ctcagtaagt gaggggtgag    1380
gcacagtcat tttctctat tctgaagctc tcccactgtt ttcaatgttt aaccaactgg     1440
ggacccctgc tctttaagta tattacaggt aataagata ttgtttgtat gcttttaaaa    1500
aaaaaaaaaa aaaa                                                      1514

<210> SEQ ID NO 6
<211> LENGTH: 2379
<212> TYPE: DNA
<213> ORGANISM: Homo sapiens

<400> SEQUENCE: 6 gaccccgag ctgtgctgct cgcggccgcc accgccgggc cccggccgtc cctggctccc       60
ctcctgcctc gagaagggca gggcttctca gaggcttggc gggaaaaaga acggagggag     120
ggatcgcgct gagtataaaa gccggttttc ggggctttat ctaactcgct gtagtaattc     180
cagcgagagg cagagggagc gagcgggcgg ccggctaggg tggaagagcc gggcgagcag     240
agctgcgctg cgggcgtcct gggaagggag atcggagcg aatagggggc ttcgcctctg      300
gcccagccct cccgctgatc ccccagccag cggtccgcaa cccttgccgc atccacgaaa     360
ctttgcccat agcagcgggc gggcactttg cactggaact acaacaccc gagcaaggac      420 gcgactctcc cgacgcgggg aggctattct gcccatttgg ggacacttcc ccgccgctgc    480 caggaccgc ttctctgaaa ggctctcctt gcagctgctt agacgctgga ttttttcgg      540 gtagtggaaa accagcagcc tcccgcgacg atgcccctca cgttagcttc accaacagg      600 aactatgacc tcgactacga ctcggtgcag ccgtatttct actgcgacga ggaggagaac     660
ttctaccagc agcagcagca gagcgagctg cagccccgg cgcccagcga ggatatctgg     720
aagaaattcg agctgctgcc cacccccgcc ctgtccccta gccgccgctc gggctctgc     780 tcgccctcct acgttgcggt cacacccctt ccccttcggg gagacaacga cggcggtggc     840
gggagcttct ccacggccga ccagctggag atggtgaccg agctgctggg aggagacatg     900
```

| | |
|---|---|
| gtgaaccaga gtttcatctg cgacccggac gacgagacct tcatcaaaaa catcatcatc | 960 |
| caggactgta tgtggagcgg cttctcggcc gccgccaagc tcgtctcaga gaagctggcc | 1020 |
| tcctaccagg ctgcgcgcaa agacagcggc agcccgaacc ccgccgcgg ccacagcgtc | 1080 |
| tgctccacct ccagcttgta cctgcaggat ctgagcgccg ccgcctcaga gtgcatcgac | 1140 |
| ccctcggtgg tcttcccta ccctctcaac gacagcagct cgcccaagtc ctgcgcctcg | 1200 |
| caagactcca gcgccttctc tccgtcctcg gattctctgc tctcctcgac ggagtcctcc | 1260 |
| ccgcagggca gccccgagcc cctggtgctc catgaggaga caccgccac caccagcagc | 1320 |
| gactctgagg aggaacaaga agatgaggaa gaaatcgatg ttgtttctgt ggaaaagagg | 1380 |
| caggctcctg gcaaaaggtc agagtctgga tcaccttctg ctggaggcca cagcaaaccct | 1440 |
| cctcacagcc cactggtcct caagaggtgc acgtctcca cacatcagca caactacgca | 1500 |
| gcgcctccct ccactcggaa ggactatcct gctgccaaga gggtcaagtt ggacagtgtc | 1560 |
| agagtcctga cacagatcag caacaaccga aaatgcacca gccccaggtc ctcggacacc | 1620 |
| gaggagaatg tcaagaggcg aacacacaac gtcttggagc gccagaggag gaacgagcta | 1680 |
| aaacggagct tttttgccct gcgtgaccag atcccggagt tggaaaacaa tgaaaaggcc | 1740 |
| cccaaggtag ttatccttaa aaaagccaca gcatacatcc tgtccgtcca agcagaggag | 1800 |
| caaaagctca tttctgaaga ggacttgttg cggaaacgac gagaacagtt gaaacacaaa | 1860 |
| cttgaacagc tacggaactc ttgtgcgtaa ggaaaagtaa ggaaaacgat tccttctaac | 1920 |
| agaaatgtcc tgagcaatca cctatgaact tgtttcaaat gcatgatcaa atgcaacctc | 1980 |
| acaaccttgg ctgagtcttg agactgaaag atttagccat aatgtaaact gcctcaaatt | 2040 |
| ggactttggg cataaaagaa cttttttatg cttaccatct tttttttttc tttaacagat | 2100 |
| ttgtatttaa gaattgtttt taaaaaattt taagatttac acaatgtttc tctgtaaata | 2160 |
| ttgccattaa atgtaaataa ctttaataaa acgtttatag cagttacaca gaatttcaat | 2220 |
| cctagtatat agtacctagt attataggta ctataaaccc taattttttt tatttaagta | 2280 |
| cattttgctt tttaaagttg atttttttct attgttttta gaaaaaataa aataactggc | 2340 |
| aaatatatca ttgagccaaa tcttaaaaaa aaaaaaaaa | 2379 |

<210> SEQ ID NO 7
<211> LENGTH: 3215
<212> TYPE: DNA
<213> ORGANISM: Homo sapiens

<400> SEQUENCE: 7

| | |
|---|---|
| aacccggggc tccgagccgg agccgagtct gcgcctgggg gaggaccatg cggcagtagc | 60 |
| agccatgctg ccctttctgc tggccacact gggcaccaca gccctcaaca acagcaaccc | 120 |
| caaggactac tgctacagcg cccgcatccg cagcactgtc ctgcagggcc tgccctttgg | 180 |
| gggcgtcccc accgtgctgg ctctcgactt catgtgcttc cttgcactgc tgttcttatt | 240 |
| ctctatcctc cggaaggtgg cctggactga tgggcggctg gccttggtga cagatgcaga | 300 |
| caggcttcgg cggcaggaga gggaccgagt ggaacaggaa tatgtggctt cagctatgca | 360 |
| cggggacagc catgaccggt atgagcgtct cacctctgtc tccagctccg ttgactttga | 420 |
| ccaaagggac aatggtttct gttcctggct gacagccatc ttcaggataa aggatgatga | 480 |
| gatccgggac aaatgtgggg gcgatgccgt gcactacctg tcctttcagc ggcacatcat | 540 |
| cgggctgctg gtggttgtgg gcgtcctctc cgtaggcatc gtgctgcctg tcaacttctc | 600 |
| aggggacctg ctggagaaca atgcctacag ctttgggaga accaccattg ccaacttgaa | 660 |

```
atcagggaac aacctgctat ggctgcacac ctccttcgcc ttcctgtatc tgctgctcac    720
cgtctacagc atgcgtagac acacctccaa gatgcgctac aaggaggatg atctggtgaa    780
gcggaccctc ttcatcaatg gaatctccaa atatgcagag tcagaaaaga tcaagaagca    840
ttttgaggaa gcctacccca actgcacagt tctcgaagcc cgcccgtgtt acaacgtggc    900
tcgcctaatg ttcctcgatg cagagaggaa gaaggccgag cggggaaagc tgtacttcac    960
aaacctccag agcaaggaga acgtgcctac catgatcaac cccaagccct gtggccacct   1020
ctgctgctgt gtggtgcgag gctgtgagca ggtggaggcc attgagtact acacaaagct   1080
ggagcagaag ctgaaggaag actacaagcg ggagaaggaa aaggtgaatg agaagcctct   1140
tggcatggcc tttgtcacct ccacaatgga ctatcacc gccatcatcc tgaaggactt     1200
caacgtgtgt aaatgccagg gctgcacctg ccgtggggag ccacgcccct catcctgcag   1260
cgagtccctg cacatctcca actggaccgt gtcctatgcc cctgaccctc agaacatcta   1320
ctgggagcac ctctccatcc gaggcttcat ctggtggctg cgctgcctgg tcatcaatgt   1380
cgtcctcttc atcctcctct tcttcctcac cactccagcc atcatcatca ccaccatgga   1440
caagttcaac gtcaccaagc tgtggagta cctcaacaac cccatcatca cccagttctt    1500 ccccacccctg ctgctgtggt gcttctcggc cctccttccc accatcgtct actactcagc  1560
cttctttgaa gcccactgga cacgctctgg ggagaacagg acaaccatgc acaagtgcta   1620
cactttcctc atcttcatgg tgctgctcct accctgctg ggactgagca gcctggacct    1680
cttcttccgc tggctctttg ataagaaatt cttggctgag gcagctattc ggtttgagtg   1740
tgtgttcctg cccgacaacg gcgccttctt cgtgaactac gtcattgcct cagcctttat   1800
cggcaacgcc atggacctgc tgcgcatccc aggcctgctc atgtacatga tccggctctg   1860
cctggcgcgc tcggccgccg agaggcgcaa cgtgaagcgg catcaggcct acgagttcca   1920
gtttggcgca gcctacgcct ggatgatgtg cgtcttcacg gtggtcatga cctacagtat   1980
cacctgcccc atcatcgtgc ccttcgggct catgtacatg ctgctgaagc acctggtaga   2040
caggtacaat ctctactacg cctacctgcc ggccaagctg gacaagaaga tccactcggg   2100
ggctgtgaac caggtggtgg ccgcgcccat cctctgcctc ttctggctgc tcttcttttc   2160
caccatgcgc acggggttcc tagctccac gtctatgttc acatttgtgg tcctggtcat    2220
caccatcgtc atctgtctct gccacgtctg ctttggacac ttcaaatacc tcagtgccca   2280
caactacaag attgagcaca cggagacaga tactgtggac cccagaagca atggacggcc   2340
ccccactgct gctgctgtcc ccaaatctgc gaaatacatc gctcaggtgc tgcaggactc   2400
agaggtggac ggggatgggg atggggctcc tgggagctca ggggatgagc ccccatcatc   2460
ctcatcccaa gatgaggagt tgctgatgcc acccgacgcc ctcacggaca cagacttcca   2520
gtcttgcgag gacagcctca tagagaatga gattcaccag taagggaggg aggggccct    2580 ggaggccaca tcctgcccca ccccaccccc actccacgg acactaaaac gctaataatt    2640
tattagatct aaagccccttt cctccccagc ccctgctttc attaaggtat ttaaacttgg  2700
gggtttcact gctctccccc atgatggagg gagggagccc ccaacctca gtgaggagag   2760 cccccgagccg gccccggggc aaagaggggt gcagaggag ttcccccaga tcagtacccc   2820
ccacccctcc ccagctagta gcatgaccag gagagggtta atgagagcca agaggagtac   2880
ctggtgcacc tggtgccggt ggctggagac ctgggggggca ggtggatctg gggctgttcc  2940 ccccccctccg ttttttccac cccacagttc ctcctgggat ctggccctcc agggaagtgg  3000
```

```
agcctccagc ccctagggga tgcatgaggg gggaggggt gctgagtggg aggaagagtc    3060
aggctcacag ctggggtggc ctgggggtgg gggtgggcaa ggctgacact ggaaaatggg    3120 ttttgcact gttttttttt tggtttttt gttctttttt gtttttttcc tttaaaataa     3180
aaacaaagaa aagctctgaa aaaaaaaaaa aaaaa                               3215
```

<210> SEQ ID NO 8
<211> LENGTH: 2581
<212> TYPE: DNA
<213> ORGANISM: Homo sapiens

<400> SEQUENCE: 8

```
ccggggccag ggaccagtgg tgggaggagg ctgcggcgct agatgcggac acctggaccg     60
ccgcgccgag gctcccggcg ctcgctgctc ccgcggcccg cgccatgccc tcctacacgg    120
tcaccgtggc cactggcagc cagtggttcg ccggcactga cgactacatc tacctcagcc    180
tcgtgggctc ggcgggctgc agcgagaagc acctgctgga caagcccttc tacaacgact    240
tcgagcgtgg cgcggtggat tcatacgacg tgactgtgga cgaggaactg ggcgagatcc    300
agctggtcag aatcgagaag cgcaagtact ggctgaatga cgactggtac ctgaagtaca    360
tcacgctgaa gacgcccac ggggactaca tcgagttccc ctgctaccgc tggatcaccg    420
gcgatgtcga ggttgtcctg agggatggac gcgcaaagtt ggcccgagat gaccaaattc    480
acattctcaa gcaacaccga cgtaaagaac tggaaacacg gcaaaaacaa tatcgatgga    540
tggagtggaa ccctggcttc cccttgagca tcgatgccaa atgccacaag gatttacccc    600
gtgatatcca gtttgatagt gaaaaggag tggactttgt tctgaattac tccaaagcga    660
tggagaacct gttcatcaac cgcttcatgc acatgttcca gtcttcttgg aatgacttcg    720
ccgactttga gaaaatcttt gtcaagatca gcaaacactat ttctgagcgg gtcatgaatc    780
actggcagga agacctgatg tttggctacc agttcctgaa tggctgcaac cctgtgttga    840
tccggcgctg cacagagctg cccgagaagc tcccggtgac cacggagatg gtagagtgca    900
gcctggagcg gcagctcagc ttggagcagg aggtccagca agggaacatt ttcatcgtgg    960
actttgagct gctggatggc atcgatgcca acaaaacaga cccctgcaca ctccagttcc   1020
tggccgctcc catctgcttg ctgtataaga acctggccaa caagattgtc cccattgcca   1080
tccagctcaa ccaaatcccg ggagatgaga acccctatttt cctcccttcg gatgcaaaat   1140
acgactggct tttggccaaa atctgggtgc gttccagtga cttccacgtc caccagacca   1200
tcacccacct tctgcgaaca catctggtgt ctgaggtttt tggcattgca atgtaccgcc   1260
agctgcctgc tgtgcacccc attttcaagc tgctggtggc acacgtgaga ttcaccattg   1320
caatcaacac caaggcccgt gagcagctca tctgcgagtg tggcctcttt gacaaggcca   1380
acgccacagg gggcggtggg cacgtgcaga tggtgcagag ggccatgaag gacctgaccct   1440 atgcctccct gtgctttccc gaggccatca ggcccggggg catggagagc aaagaagaca   1500
tcccctacta cttctaccgg gacgacggc tcctggtgtg ggaagccatc aggacgttca   1560
cggccgaggt ggtagacatc tactacgagg cgaccaggt ggtggaggag gacccggagc   1620
tgcaggactt cgtgaacgat gtctacgtgt acgcatgcg gggccgcaag tcctcaggct   1680
tccccaagtc ggtcaagagc cgggagcagc tgtcggagta cctgaccgtg gtgatcttca   1740
ccgcctccgc ccagcacgcc gcggtcaact tcggccagta cgactggtgc tcctggatcc   1800
ccaatgcgcc cccaaccatg cgagccccgc caccgactgc caagggcgtg gtgaccattg   1860
agcagatcgt ggacacgctg cccgaccgcg gccgctcctg ctggcatctg ggtgcagtgt   1920
```

```
gggcgctgag ccagttccag gaaaacgagc tgttcctggg catgtaccca gaagagcatt    1980
ttatcgagaa gcctgtgaag gaagccatgg cccgattccg caagaacctc gaggccattg    2040
tcagcgtgat tgctgagcgc aacaagaaga agcagctgcc atattactac ttgtccccag    2100
accggattcc gaacagtgtg gccatctgag cacactgcca gtctcactgt gggaaggcca    2160
gctgccccag ccagatggac tccagcctgc ctggcaggct gtctggccag gcctcttggc    2220
agtcacatct cttcctccga ggccagtacc tttccattta ttctttgatc ttcagggaac    2280
tgcatagatt gatcaaagtg taaacaccat agggacccat ctacacaga gcaggactgc     2340 acagcgtcct gtccacaccc agctcagcat ttccacacca agcagcaaca gcaaatcacg    2400
accactgata gatgtctatt cttgttggag acatgggatg attattttct gttctatttg    2460
tgcttagtcc aattccttgc acatagtagg tacccaattc aattactatt gaatgaatta    2520
agaattggtt gccataaaaa taaatcagtt catttaaaat gaaaaaaaaa aaaaaaaaa     2580 a                                                                    2581

<210> SEQ ID NO 9
<211> LENGTH: 2272
<212> TYPE: DNA
<213> ORGANISM: Homo sapiens

<400> SEQUENCE: 9
agtctccctc cagcgggcgg cgactccggg ttcccctcg cgccctctcg cagaggctcg      60
cccccttccc cgcccaccgt ccctgcgagc gcggcggcg gcggtgggcg tgtgcgcgcg     120
tgaaggacgc cgcctctctc tcgctcctgc gttcgcaggc ggcggctggc ggccggcttc    180
tcgctcgggc agcggcggcg gcggcggcgg cggcttccgg agtcccgctg cgaagatgct    240
caaagtcacg gtgccctcct gctccgcctc gtcctgctct tcggtcaccg ccagtgcggc    300
cccggggacc gcgagcctcg tcccggatta ctggatcgac ggctccaaca gggatgcgct    360
gagcgatttc ttcgaggtgg agtcggagct gggacggggt gctacatcca ttgtgtacag    420
atgcaaacag aaggggaccc agaagcctta tgctctcaaa gtgttaaaga aaacagtgga    480
caaaaaaatc gtaagaactg agataggagt tcttcttcgc ctctcacatc caaacattat    540
aaaacttaaa gagatatttg aaaccctac agaaatcagt ctggtcctag aactcgtcac     600
aggaggagaa ctgtttgata ggattgtgga aaagggatat tacagtgagc gagatgctgc    660
agatgccgtt aaacaaatcc tggaggcagt tgcttatcta catgaaaatg ggattgtcca    720
tcgtgatctc aaaccagaga atcttcttta tgcaactcca gccccagatg caccactcaa    780
aatcgctgat tttggactct ctaaaattgt ggaacatcaa gtgctcatga agacagtatg    840 tggaaccccca gggtactgcg cacctgaaat tcttagaggt tgtgcctatg acctgaggt    900 ggacatgtgg tctgtaggaa taatcaccta catcttactt tgtggatttg aaccattcta    960
tgatgaaaga ggcgatcagt tcatgttcag gagaattctg aattgtgaat attactttat   1020 ctcccccctgg tgggatgaag tatctctaaa tgccaaggac ttggtcagaa aattaattgt   1080
tttggatcca aagaaacggc tgactacatt tcaagctctc cagcatccgt gggtcacagg   1140
taaagcagcc aattttgtac acatggatac cgctcaaaag aagctccaag aattcaatgc    1200
ccggcgtaag cttaaggcag cggtgaaggc tgtggtggcc tcttcccgcc tgggaagtgc    1260
cagcagcagc catggcagca tccaggagag ccacaaggct agccgagacc cttctccaat    1320
ccaagatggc aacgaggaca tgaaagctat tccagaagga gagaaaattc aaggcgatgg    1380
```

| | | |
|---|---|---|
| ggcccaagcc gcagttaagg gggcacaggc tgagctgatg aaggtgcaag ccttagagaa | 1440 | |
| agttaaaggt gcagatataa atgctgaaga ggcccccaaa atggtgccca aggcagtgga | 1500 | |
| ggatgggata aaggtggctg acctggaact agaggagggc ctagcagagg agaagctgaa | 1560 | |
| gactgtggag gaggcagcag ctcccagaga agggcaagga agctctgctg tgggttttga | 1620 | |
| agttccacag caagatgtga tcctgccaga gtactaaaca gcttccttca gatctggaag | 1680 | |
| ccaaacaccg gcattttatg tactttgtcc ttcagcaaga aaggtgtgga agcatgatat | 1740 | |
| gtactatagt gattctgttt ttgaggtgca aaaacatac atatatacca gttggtaatt | 1800 | |
| ctaacttcaa tgcatgtgac tgctttatga aaataatagt gtcttctatg gcatgtaatg | 1860 | |
| gatacctaat accgatgagt taaatcttgc aagttaacac aacgtaacac ttaaaagcat | 1920 | |
| acattttcag caaccagtgg cacatatttg aagtgaatag tagcaaattg tttttgcttt | 1980 | |
| gaaaatctag ccatcctaca tcctttggat ttcttcacaa ggcagtaatt cctttgaact | 2040 | |
| actgcttagc taatactagg tagtgctaaa agacatgttc ccataacttt tacaacattt | 2100 | |
| tacttttat cattgatgtg ttcaaactgt ttacaaggaa atgcttatag atgatagttg | 2160 | |
| tacatatgtg caaaaaaaaa tccacttgca atggtaagaa attgaagtat ccttaaaggc | 2220 | |
| catgaagcca tatgtcccta aaaaaaaaaa aaaaaaaaa aaaaaaaaaa aa | 2272 | |

<210> SEQ ID NO 10
<211> LENGTH: 2175
<212> TYPE: DNA
<213> ORGANISM: Homo sapiens

<400> SEQUENCE: 10

| | | |
|---|---|---|
| gttgtatatc agggccgcgc tgagctgcgc cagctgaggt gtgagcagct gccgaagtca | 60 | |
| gttccttgtg gagccggagc tgggcgcgga ttcgccgagg caccgaggca ctcagaggag | 120 | |
| gcgccatgtc agaaccggct ggggatgtcc gtcagaaccc atgcggcagc aaggcctgcc | 180 | |
| gccgcctctt cggcccagtg acagcgagc agctgagccg cgactgtgat gcgctaatgg | 240 | |
| cgggctgcat ccaggaggcc cgtgagcgat ggaacttcga cttgtcacc gagacaccac | 300 | |
| tggagggtga cttcgcctgg gagcgtgtgc ggggccttgg cctgcccaag ctctaccttc | 360 | |
| ccacggggcc ccggcgaggc cgggatgagt tgggaggagg caggcggcct ggcacctcac | 420 | |
| ctgctctgct gcaggggaca gcagaggaag accatgtgga cctgtcactg tcttgtaccc | 480 | |
| ttgtgcctcg ctcaggggag caggctgaag ggtccccagg tggacctgga gactctcagg | 540 | |
| gtcgaaaacg gcggcagacc agcatgacag atttctacca ctccaaacgc cggctgatct | 600 | |
| tctccaagag gaagccctaa tccgcccaca ggaagcctgc agtcctggaa gcgcgagggc | 660 | |
| ctcaaaggcc cgctctacat cttctgcctt agtctcagtt tgtgtgtctt aattattatt | 720 | |
| tgtgttttaa tttaaacacc tcctcatgta catccctgg ccgccccctg cccccagcc | 780 | |
| tctggcatta gaattattta aacaaaaact aggcggttga atgagaggtt cctaagagtg | 840 | |
| ctgggcattt ttatttatg aaatactatt taaagcctcc tcatcccgtg ttctcctttt | 900 | |
| cctctctccc ggaggttggg tgggccggct tcatgccagc tacttcctcc tccccacttg | 960 | |
| tccgctgggt ggtaccctct ggaggggtgt ggctccttcc catcgctgtc acaggcggtt | 1020 | |
| atgaaattca ccccctttcc tggacactca gacctgaatt cttttttcatt tgagaagtaa | 1080 | |
| acagatggca ctttgaaggg gcctcaccga gtgggggcat catcaaaaac tttggagtcc | 1140 | |
| cctcacctcc tctaaggttg gcagggtga ccctgaagtg agcacagcct agggctgagc | 1200 | |
| tggggacctg gtaccctcct ggctcttgat accccctct gtcttgtgaa ggcaggggga | 1260 | |

```
aggtggggtc ctggagcaga ccaccccgcc tgccctcatg gcccctctga cctgcactgg    1320
ggagcccgtc tcagtgttga gccttttccc tctttggctc ccctgtacct tttgaggagc    1380
cccagctacc cttcttctcc agctgggctc tgcaattccc ctctgctgct gtccctcccc    1440
cttgtccttt cccttcagta ccctctcagc tccaggtggc tctgaggtgc ctgtcccacc    1500
cccaccccca gctcaatgga ctggaagggg aagggacaca caagaagaag ggcaccctag    1560
ttctacctca ggcagctcaa gcagcgaccg ccccctcctc tagctgtggg ggtgagggtc    1620
ccatgtggtg gcacaggccc ccttgagtgg ggttatctct gtgttagggg tatatgatgg    1680
gggagtagat ctttctagga gggagacact ggccccctcaa atcgtccagc gaccttcctc    1740
atccacccca tccctcccca gttcattgca ctttgattag cagcggaaca aggagtcaga    1800
cattttaaga tggtggcagt agaggctatg gacagggcat gccacgtggg ctcatatggg    1860
gctgggagta gttgtctttc ctggcactaa cgttgagccc ctggaggcac tgaagtgctt    1920
agtgtacttg gagtattggg gtctgacccc aaacaccttc cagctcctgt aacatactgg    1980
cctggactgt tttctctcgg ctccccatgt gtcctggttc ccgtttctcc acctagactg    2040
taaacctctc gagggcaggg accacaccct gtactgttct gtgtctttca cagctcctcc    2100
cacaatgctg aatatacagc aggtgctcaa taaatgattc ttagtgactt tacttgtaaa    2160
aaaaaaaaaa aaaaa                                                     2175

<210> SEQ ID NO 11
<211> LENGTH: 2403
<212> TYPE: DNA
<213> ORGANISM: Homo sapiens

<400> SEQUENCE: 11
ggggccttgc cttccgcact cgggcgcagc cgggtggatc tcgagcaggt gcggagcccc      60
gggcggcggg cgcgggtgcg agggatccct gacgcctctg tccctgtttc tttgtcgctc     120
ccagcctgtc tgtcgtcgtt ttggcgcccc cgcctccccg cggtgcgggg ttgcacaccg     180
atcctgggct tcgctcgatt tgccgccgag gcgcctccca gacctagagg ggcgctggcc     240
tggagcagcg ggtcgtctgt gtcctctctc ctctgcgccg cgcccgggga tccgaagggt     300
gcggggctct gaggaggtga cgcgcggggc ctcccgcacc ctggccttgc ccgcattctc     360
cctctctccc agtgtgagc agcctatcag tcaccatgtc cgcagcctgg atcccggctc     420
tcggcctcgg tgtgtgtctg ctgctgctgc ggggccccgc gggcagcgag ggagccgctc     480
ccattgctat cacatgtttt accagaggct tggacatcag gaaagagaaa gcagatgtcc     540
tctgcccagg gggctgccct cttgaggaat tctctgtgta tgggaacata gtatatgctt     600
ctgtatcgag catatgtggg gctgctgtcc acagggagt aatcagcaac tcaggggac      660 ctgtacgagt ctatagccta cctggtcgag aaaactattc ctcagtagat gccaatggca     720
tccagtctca aatgctttct agatggtctg cttctttcac agtaactaaa ggcaaaagta     780
gtacacagga ggccacagga caagcagtgt ccacagcaca tccaccaaca ggtaaacgac     840
taaagaaaac acccgagaag aaaactggca ataaagattg taaagcagac attgcatttc     900
tgattgatgg aagcttaat attgggcagc gccgatttaa tttacagaag aattttgttg     960
gaaaagtggc tctaatgttg ggaattggaa cagaaggacc acatgtgggc cttgttcaag    1020
ccagtgaaca tccaaaaata gaattttact tgaaaaactt tacatcagcc aaagatgttt    1080
tgtttgccat aaaggaagta ggtttcagag ggggtaattc caatacagga aaagccttga    1140
```

```
agcatactgc tcagaaattc ttcacggtag atgctggagt aagaaaaggg atccccaaag    1200
tggtggtggt atttattgat ggttggcctt ctgatgacat cgaggaagca ggcattgtgg    1260
ccagagagtt tggtgtcaat gtatttatag tttctgtggc caagcctatc cctgaagaac    1320
tggggatggt tcaggatgtc acatttgttg acaaggctgt ctgtcggaat aatggcttct    1380
tctcttacca catgcccaac tggtttggca ccacaaaata cgtaaagcct ctggtacaga    1440
agctgtgcac tcatgaacaa atgatgtgca gcaagacctg ttataactca gtgaacattg    1500
cctttctaat tgatggctcc agcagtgttg agatagcaa tttccgcctc atgcttgaat    1560
ttgtttccaa catagccaag acttttgaaa tctcggacat tggtgccaag atagctgctg    1620
tacagtttac ttatgatcag cgcacggagt tcagtttcac tgactatagc accaaagaga    1680
atgtcctagc tgtcatcaga aacatccgct atatgagtgg tggaacagct actggtgatg    1740
ccatttcctt cactgttaga aatgtgtttg ccctataag ggagagcccc aacaagaact    1800
tcctagtaat tgtcacagat gggcagtcct atgatgatgt ccaaggccct gcagctgctg    1860
cacatgatgc aggaatcact atcttctctg ttggtgtggc ttgggcacct ctggatgacc    1920
tgaaagatat ggcttctaaa ccgaaggagt ctcacgcttt cttcacaaga gagttcacag    1980
gattagaacc aattgtttct gatgtcatca gaggcatttg tagagatttc ttagaatccc    2040
agcaataatg gtaacatttt gacaactgaa agaaaagta caaggggatc cagtgtgtaa    2100
attgtattct cataatactg aaatgcttta gcatactaga atcagataca aaactattaa    2160
gtatgtcaac agccatttag gcaaataagc actcctttaa agccgctgcc ttctggttac    2220
aatttacagt gtactttgtt aaaaacactg ctgaggcttc ataatcatgg ctcttagaaa    2280
ctcaggaaag aggagataat gtggattaaa accttaagag ttctaaccat gcctactaaa    2340
tgtacagata tgcaaattcc atagctcaat aaaagaatct gatacttaga ccaaaaaaaa    2400
aaa                                                                  2403

<210> SEQ ID NO 12
<211> LENGTH: 1315
<212> TYPE: DNA
<213> ORGANISM: Homo sapiens

<400> SEQUENCE: 12
ctactctgtc accgcccctg ggaagagtgg aacccatact tgctggtctg atccatgcac      60 aaggcgggc tgctaggcct ctgtgcccgg gcttggaatt cggtgcggat ggccagctcc     120
gggatgaccc gccgggaccc gctcgcaaat aaggtggccc tggtaacggc ctccaccgac     180
gggatcggct tcgccatcgc ccggcgtttg gcccaggacg gggcccatgt ggtcgtcagc     240
agccggaagc agcagaatgt ggaccaggcg gtggccacgc tgcaggggga ggggctgagc     300
gtgacgggca ccgtgtgcca tgtggggaag gcggaggacc gggagcggct ggtggccacg     360
gctgtgaagc ttcatggagg tatcgatatc ctagtctcca atgctgctgt caacccttc     420 tttggaagca taatggatgt cactgaggag gtgtgggaca agactctgga cattaatgtg     480
aaggccccag ccctgatgac aaaggcagtg gtgccagaaa tggagaaacg aggaggcggc     540
tcagtggtga tcgtgtcttc catagcagcc ttcagtccat ctcctggctt cagtccttac     600
aatgtcagta aacagccctt gctgggcctg accaagaccc tggccataga gctggcccca     660
aggaacatta gggtgaactg cctagcacct ggacttatca agactagctt cagcaggatg     720
ctctggatgg acaaggaaaa agaggaaagc atgaagaaa ccctgcggat aagaaggtta     780
ggcgagccag aggattgtgc tggcatcgtg tctttcctgt gctctgaaga tgccagctac     840
```

| | |
|---|---|
| atcactgggg aaacagtggt ggtgggtgga ggaaccccgt cccgcctctg aggaccggga | 900 |
| gacagcccac aggccagagt tgggctctag ctcctggtgc tgttcccgca ttcacccact | 960 |
| ggcctttccc acctctgctc accttactgt tcacctcatc aaatcagttc tgccctgtga | 1020 |
| aaagatccag ccttccctgc cgtcaaggtg gcgtcttact cgggatttct gctgttgttg | 1080 |
| tggccttggg taaaggcctc ccctgagaac acaggacagg cctgctgaca aggctgagtc | 1140 |
| taccttggca aagaccaaga tatttttttcc cgggccactg gggaatctga ggggtgatgg | 1200 |
| gagagaagga acctggagtg gaaggagcag agttgcaaat taacaacttg caaatgaggt | 1260 |
| gcaaataaaa tgcagatgat tgcgcggctt tgaatccaaa aaaaaaaaaa aaaaa | 1315 |

<210> SEQ ID NO 13
<211> LENGTH: 3661
<212> TYPE: DNA
<213> ORGANISM: Homo sapiens

<400> SEQUENCE: 13

| | |
|---|---|
| cccaagactg tccccgctgg aggcggtaga gggatccaga agtaatgaga tgctaatgag | 60 |
| tcgcgaataa agcccgggcg cgcccccgcg ccctcgcgg aagcccacac tccgcgcgac | 120 |
| tccaggcgca cgccccgggc cgccccgcat cccagcatcc ccgcccgatc tcggcgtttc | 180 |
| cgccccgcc cccgccccg cctcccacc cgctcagacc tggttgccag cccaacagga | 240 |
| agcggcccct cccggcttcg gagccgccgc cactcatctc tgcccagctg ctgccctccc | 300 |
| caggaggcct ccatggcttc acctacctcc accaacccag cgcatgccca ctttgagagc | 360 |
| ttcctgcagg cccagctgtg ccaggacgtg ctgagcagct tccaggagct gtgtggggcc | 420 |
| ctggggctgg aacccggtgg ggggctgccc cagtaccaca agatcaagga ccagctcaac | 480 |
| tactggagcg ccaagtcact gtggaccaag ctggacaagc gagcaggcca gcctgtctac | 540 |
| cagcagggcc gggcctgcac cagcaccaag tgcctggtgg tgggtgctgg accttgcggg | 600 |
| ctgcgggtcg ctgtggagct ggcgctgctg ggggcccgag tggtgctggt ggaaaagcgc | 660 |
| accaagttct ctcgccacaa cgtgctccac ctctggccct tcaccatcca cgacctgcgg | 720 |
| gcactcggtg ctaagaagtt ctacgggcgc ttctgcaccg gcaccctgga ccacatcagc | 780 |
| atcaggcagc tccagctgct tctgctgaag gtagcattgc tgctgggggt ggaaattcac | 840 |
| tggggtgtca ctttcactgg cctccagccc cctcctagga aggggagtgg ctggcgtgcc | 900 |
| cagctccaac ccaaccccccc tgcccagctg ccaactatg aatttgacgt ccttatctcg | 960 |
| gctgcaggag gtaaattcgt ccctgaaggc ttcaaagttc gagaaatgcg aggcaaactg | 1020 |
| gccattggca tcacagccaa ctttgtgaat ggacgcaccg tggaggagac acaggtgccg | 1080 |
| gagatcagtg gtgtagccag gatctacaac cagagcttct tccagagcct tctcaaagcc | 1140 |
| acaggcattg atctggagaa cattgtgtac tacaaggacg acacccacta ctttgtgatg | 1200 |
| acagccaaga agcagtgcct gctgcggctg ggggtgctgc ccaggactg gccagacacc | 1260 |
| aatcggctgc tgggcagtgc caatgtggtg cccgaggctc tgcagcgctt tacccgggca | 1320 |
| gctgctgact tgccacccca tggcaagctc gggaaactag agtttgccca ggatgcccat | 1380 |
| gggcagcctg atgtctctgc ctttgacttc acgagcatga tgcgggcaga gagttctgct | 1440 |
| cgtgtgcaag agaagcatgg cgcccgcctg ctgctgggac tggtggggga ctgcctggtg | 1500 |
| gagcccttct ggccctggg cactggagtg gcacggggct tcctggcagc ctttgatgca | 1560 |
| gcctggatgg tgaagcggtg ggcagagggc gctgagtccc tagaggtgtt ggctgagcgt | 1620 |

```
gagagcctgt accagcttct gtcacagaca tccccagaaa acatgcatcg caatgtggcc     1680
cagtatgggc tggacccagc caccgctac cccaacctga acctccgggc agtgaccccc      1740
aatcaggtac gagacctgta tgatgtgcta gccaaggagc ctgtgcagag gaacaacgac     1800
aagacagata cagggatgcc agccaccggg tcggcaggca cccaggagga gctgctacgc     1860
tggtgccagg agcagacagc tgggtacccg ggagtccacg tctccgattt gtcttcctcc     1920
tgggctgatg ggctagctct gtgtgccctg gtgtaccggc tgcagcctgg cctgctggaa     1980
ccctcagagc tgcaggggct gggagctctg gaagcaactg cttgggcact aaaggtggca     2040
gagaatgagc tgggcatcac accggtggtg tctgcacagg ccgtggtagc agggagtgac     2100
ccactgggcc tcattgccta cctcagccac ttccacagtg ccttcaagag catggcccac     2160
agcccaggcc ctgtcagcca ggcctcccca gggacctcca gtgctgtatt attccttagt     2220
aaacttcaga ggaccctgca gcgatcccgg gccaaggaaa atgcagagga tgctggtggc     2280
aagaagctgc gcttggagat ggaggccgag ccccaagta ctgaggtgcc acctgaccca      2340
gagcctggtg taccctgac accccatcc caacaccagg aggccggtgc tggggacctg      2400
tgtgcacttt gtggggaaca cctctatgtc ctggaacgcc tctgtgtcaa cggccatttc     2460
ttccaccgga gctgcttccg ctgccatacc tgtgaggcca cactgtggcc aggtggctac     2520
gagcagcacc aggagatggg acatttctac tgcctccagc acctgcccca gacagaccac     2580
aaagcggaag gcagcgatag aggccctgag agtccggagc tccccacacc aagtgagaat     2640
agcatgccac caggcctctc aactcccaca gcctcgcagg agggggccgg tcctgttcca     2700
gatcccagcc agcccacccg tcggcagatc cgcctctcca gcccggagcg ccagcggttg     2760
tcctccctta accttacccc tgacccggaa atggagcctc cacccaagcc tcccgcagc      2820 tgctccgcct tggcccgcca cgccctggag agcagctttg tgggctgggg cctgccagtc     2880
cagagccctc aagctcttgt ggccatggag aaggaggaaa agagagtcc cttctccagt      2940 gaagaggaag aagaagatgt gcctttggac tcagatgtgg aacaggccct gcagacctt      3000 gccaagacct caggcaccat gaataactac ccaacatggc gtcggactct gctgcgccgt     3060
gcgaaggagg aggagatgaa gaggttctgc aaggcccaga ccatccaacg gcgactaaat     3120
gagattgagg ctgccttgag ggagctagag gccgagggcg tgaagctgga gctggccttg     3180
aggcgccaga gcagttcccc agaacagcaa aagaaactat gggtaggaca gctgctacag     3240
ctcgttgaca agaaaaacag cctggtggct gaggaggccg agctcatgat cacggtgcag     3300
gaattgaatc tggaggagaa acagtggcag ctggaccagg agctacgagg ctacatgaac     3360
cgggaagaaa acctaaagac agctgctgat cggcaggctg aggaccaggt cctgaggaag     3420
ctggtggatt tggtcaacca gagagatgcc ctcatccgct tccaggagga gcgcaggctc     3480
agcgagctgg ccttggggac aggggcccag ggctagacga gggtgggccg tctgctttcg     3540
ttccacaaaa gaaagcacct caccccagca cagtgccacc cctgttcatc tgggctgcct     3600
ggcagagagc cttgctgttt acaattaaaa tgtttctgcc acaaaaaaaa aaaaaaaaa      3660 a                                                                    3661
```

<210> SEQ ID NO 14
<211> LENGTH: 651
<212> TYPE: DNA
<213> ORGANISM: Homo sapiens

<400> SEQUENCE: 14

```
atgtccatag ccctgaagca ggtattcaac aaggacaaga ccttccgacc caagaggaaa     60
```

| | |
|---|---|
| tttgaacctg gcacacagag gtttgagctg cacaaacggg ctcaggcatc cctcaactcg | 120 |
| ggtgtggacc tgaaggcggc tgtgcagttg cccagtgggg aggaccagaa tgactgggtg | 180 |
| gcagtacatg tggtggactt cttcaatcgg atcaacctca tctatggcac catctgtgag | 240 |
| ttctgcaccg agcggacctg tcctgtgatg tcagggggcc ccaaatatga gtatcggtgg | 300 |
| caggatgatc tcaagtataa gaagccaaca gcgctgccag ctccccagta catgaacctt | 360 |
| cttatggatt ggattgaggt tcagatcaac aacgaggaaa tatttccaac atgcgtgggt | 420 |
| gttcccttcc caaagaactt ccttcagatc tgcaagaaga tcctgtgccg ccttttccgg | 480 |
| gtctttgtcc acgtctatat ccaccacttc gaccgggtca ttgtgatggg tgcagaggcc | 540 |
| catgtcaaca cctgctacaa acacttctat tactttgtca cagagatgaa cctcatagac | 600 |
| cgcaaggagc tagagccttt gaaagaaatg acgagcagga tgtgtcacta a | 651 |

<210> SEQ ID NO 15
<211> LENGTH: 2471
<212> TYPE: DNA
<213> ORGANISM: Homo sapiens

<400> SEQUENCE: 15

| | |
|---|---|
| gcgttacagg ccctttggcg cctgcgtatt cgtgaagtgt gaaaaaagcg cgcctctgtt | 60 |
| gggacgggaa atcagccttt ctattggtca gggttagaaa ccccgccttt gaggcatttt | 120 |
| caaccaatgg aagcgcggca ttcttcattt aaactgtcta taaatttctg cctagtcaaa | 180 |
| gttaagagtg gcgccaggga tttgaaccgc gctgacgaag tttggtgatc catcttccga | 240 |
| gtatcgccgg gatttcgaat cgcgatgatc atccctctc tagaggagct ggactccctc | 300 |
| aagtacagtg acctgcagaa cttagccaag agtctgggtc tccgggccaa cctgagggca | 360 |
| accaagttgt taaaagcctt gaaaggctac attaaacatg aggcaagaaa aggaaatgag | 420 |
| aatcaggatg aaagtcaaac ttctgcatcc tcttgtgatg agactgagat acagatcagc | 480 |
| aaccaggaag aagctgagag acagccactt ggccatgtca ccaaaacaag gagaaggtgc | 540 |
| aagactgtcc gtgtggaccc tgactcacag cagaatcatt cagagataaa ataagtaat | 600 |
| cccactgaat tccagaatca tgaaaagcag gaaagccagg atctcagagc tactgcaaaa | 660 |
| gttccttctc caccagacga gcaccaagaa gctgagaatg ctgtttcctc aggtaacaga | 720 |
| gattcaaagg taccttcaga aggaaagaaa tctctctaca cagatgagtc atccaaacct | 780 |
| ggaaaaaata aagaactgc aatcactact ccaaacttta agaagcttca tgaagctcat | 840 |
| tttaaggaaa tggagtccat tgatcaatat attgagagaa aaaagaaaca ttttgaagaa | 900 |
| cacaattcca tgaatgaact gaagcagcag cccatcaata agggaggggt caggactcca | 960 |
| gtacctccaa gaggaagact ctctgtggct ctactcccca tcagccaacg acgctcgcaa | 1020 |
| ggccggtctt gtggccctgc aagtcagagt accttgggtc tgaaggggtc actcaagcgc | 1080 |
| tctgctatct ctgcagctaa aacggggtgtc aggttttcag ctgctactaa agataatgag | 1140 |
| cataagcgtt cactgaccaa gactccagcc agaaagtctg cacatgtgac cgtgtctggg | 1200 |
| ggcaccccaa aaggcgaggc tgtgcttggg acacacaaat taaagaccat cacggggaat | 1260 |
| tctgctgctg ttattacccc attcaagttg acaactgagg caacgcagac tccagtctcc | 1320 |
| aataagaaac cagtgtttga tcttaaagca gtttgtctc gtcccctcaa ctatgaacca | 1380 |
| cacaaaggaa agctaaaacc atgggggcaa tctaagaaaa ataattatct aaatcaacat | 1440 |
| gtcaacagaa ttaacttcta caagaaaact tacaaacaac cccatctcca gacaaaggaa | 1500 |

```
gagcaacgga agaaacgcga gcaagaacga aggagaaga aagcaaaggt tttgggaatg      1560
cgaaggggcc tcattttggc tgaagattaa taatttttta acatcttgta aatattcctg      1620
tattctcaac ttttttcctt ttgtaaattt tttttttttg ctgtcatccc cactttagtc      1680
acgagatctt tttctgctaa ctgttcatag tctgtgtagt gtccatgggt tcttcatgtg      1740
ctatgatctc tgaaaagacg ttatcacctt aaagctcaaa ttctttggga tggttttttac     1800 ttaagtccat taacaattca ggtttctaac gagacccatc ctaaaattct gtttctagat      1860
ttttaatgtc aagttcccaa gttccccctg ctggttctaa tattaacaga actgcagtct      1920
tctgctagcc aatagcattt acctgatggc agctagttat gcaagcttca ggagaatttg      1980
aacaataaca agaatagggt aagctgggat agaaaggcca cctcttcact ctctatagaa      2040
tatagtaacc tttatgaaac ggggccatat agtttggtta tgacatcaat attttaccta      2100
ggtgaaattg tttaggctta tgtaccttcg ttcaaatatc ctcatgtaat tgccatctgt      2160
cactcactat attcacaaaa ataaaactct acaactcatt ctaacattgc ttacttaaaa      2220
gctacatagc cctatcgaaa tgcgaggatt aatgctttaa tgcttttaga gacagggtct      2280
cactgtgttg cccaggctgg tctcaaactc caccaaatgt acttcttatt cattttatgg      2340
aaaagactag gctttgctta gtatcatgtc catgtttcct tcacctcagt ggagcttctg      2400
agttttatac tgctcaagat cgtcataaat aaaatttttt ctcattgtca tagaaaaaaa      2460
aaaaaaaaaa a                                                           2471

<210> SEQ ID NO 16
<211> LENGTH: 2685
<212> TYPE: DNA
<213> ORGANISM: Homo sapiens

<400> SEQUENCE: 16
gcggaggcgg cctgccgggg tggttcggct tcccgttgcc gcctcgggcg ctgtacccag        60
agctcgaaga ggagcagcgc ggccgcgcgg acccggcaag gctgggccgg actcggggct       120
cccgagggac gccatgcggg gaggcagggg cgccccttc tggctgtggc cgctgcccaa       180
gctggcgctc ctgcctctgt tgtgggtgct tttccagcgg acgcgtcccc agggcagcgc      240
cgggccactg cagtgctacg gagttggacc cttgggcgac ttgaactgct cgtgggagcc      300
tcttggggac ctgggagccc cctccgagtt acacctccag agccaaaagt accgttccaa      360 caaacccag actgtggcag tggcagccgg acggagctgg gtggccattc ctcgggaaca       420
gctcaccatg tctgacaaac tccttgtctg gggcactaag gcaggccagc ctctctggcc      480
ccccgtcttc gtgaacctag aaacccaaat gaagccaaac gcccccggc tgggccctga      540 cgtggacttt tccgaggatg accccctgga ggccactgtc cattgggccc acctacatg      600 gccatctcat aaagttctga tctgccagtt ccactaccga agatgtcagg aggcggcctg      660
gaccctgctg gaaccggagc tgaagaccat accctgacc cctgttgaga tccaagattt     720
ggagctagcc actggctaca aagtgtatgg ccgctgccgg atggagaaag aagaggattt      780
gtggggcgag tggagcccca ttttgtcctt ccagacaccg ccttctgctc caaaagatgt      840
gtgggtatca gggaacctct gtgggacgcc tggaggagag gaacctttgc ttctatggaa      900
ggccccaggg ccctgtgtgc aggtgagcta caaagtctgg ttctggttg aggtcgtga      960 gctgagtcca gaaggaatta cctgctgctg ctccctaatt cccagtgggg cggagtgggc     1020
cagggtgtcc gctgtcaacg ccacaagctg ggagcctctc accaacctct ctttggtctg     1080
cttggattca gcctctgccc ccgtagcgt ggcagtcagc agcatcgctg ggagcacgga      1140
```

```
gctactggtg acctggcaac cggggcctgg ggaaccactg gagcatgtag tggactgggc    1200
tcgagatggg gaccccctgg agaaactcaa ctgggtccgg cttccccctg ggaacctcag    1260
tgctctgtta ccagggaatt tcactgtcgg ggtccoctat cgaatcactg tgaccgcagt    1320
ctctgcttca ggcttggcct ctgcatcctc cgtctggggg ttcagggagg aattagcacc    1380
cctagtgggg ccaacgcttt ggcgactcca agatgcccct ccagggaccc cgccatagc    1440 gtggggagag gtcccaaggc accagcttcg aggccacctc acccactaca ccttgtgtgc    1500
acagagtgga accagcccct ccgtctgcat gaatgtgagt ggcaacacac agagtgtcac    1560
cctgcctgac cttccttggg gtccctgtga gctgtgggtg acagcatcta ccatcgctgg    1620
acagggccct cctggtccca tcctccggct tcatctacca gataacaccc tgaggtggaa    1680
agttctgccg ggcatcctat tcttgtgggg cttgttcctg ttggggtgtg gcctgagcct    1740
ggccacctct ggaaggtgct accacctaag gcacaaagtg ctgccccgct gggtctggga    1800
gaaagttcct gatcctgcca acagcagttc aggccagccc cacatggagc aagtacctga    1860
ggcccagccc cttggggact tgcccatcct ggaagtggag gagatggagc cccgccggt    1920 tatggagtcc tcccagcccg cccaggccac cgccccgctt gactctgggt atgagaagca    1980
cttcctgccc acacctgagg agctgggcct tctggggccc cccaggccac aggttctggc    2040
ctgaaccaca cgtctggctg ggggctgcca gccaggctag agggatgctc atgcaggttg    2100
caccccagtc ctggattagc cctcttgatg gatgaagaca ctgaggactc agagaggctg    2160
agtcacttac ctgaggacac ccagccaggc agagctggga ttgaaggacc cctatagaga    2220
agggcttggc ccccatgggg aagacacgga tggaaggtgg agcaaaggaa aatacatgaa    2280
attgagagtg gcagctgcct gccaaaatct gttccgctgt aacagaactg aatttggacc    2340
ccagcacagt ggctcacgcc tgtaatccca gcactttggc aggccaaggt ggaaggatca    2400
cttagagcta ggagtttgag accagcctgg gcaatatagc aagacccctc actacaaaaa    2460
taaaacatca aaaacaaaaa caattagctg ggcatgatgg cacacacctg tagtccgagc    2520
cacttgggag gctgaggtgg gaggatcggt tgagcccagg agttcgaagc tgcagggacc    2580
tctgattgca ccactgcact ccaggctggg taacagaatg agaccttatc tcaaaaataa    2640
acaaactaat aaaagcaaa aaaaaaaaaa aaaaaaaaaa aaaaa                     2685
```

<210> SEQ ID NO 17
<211> LENGTH: 622
<212> TYPE: DNA
<213> ORGANISM: Homo sapiens

<400> SEQUENCE: 17

```
cataaaccct ggcgcgctcg cgggccggca ctcttctggt ccccacagac tcagagagaa      60
cccaccatgg tgctgtctcc tgccgacaag accaacgtca aggccgcctg ggtaaggtc      120 ggcgcgcacg ctggcgagta tggtgcggag gccctggaga gatgttcct gtccttcccc      180 accaccaaga cctacttccc gcacttcgac ctgagccacg gctctgccca ggttaagggc     240
cacggcaaga aggtggccga cgcgctgacc aacgccgtgg cgcacgtgga cgacatgccc     300
aacgcgctgt ccgccctgag cgacctgcac gcgcacaagc ttcgggtgga cccggtcaac    360
ttcaagctcc taagccactg cctgctggtg accctggccg ccacctcccc gccgagttc    420 accccctgcgg tgcacgcctc cctggacaag ttcctggctt ctgtgagcac cgtgctgacc    480
tccaaatacc gttaagctgg agcctcggta gccgttcctc ctgcccgctg ggcctcccaa    540
```

| | |
|---|---|
| cgggccctcc tcccctcctt gcaccggccc ttcctggtct ttgaataaag tctgagtggg | 600 |
| cagcaaaaaa aaaaaaaaaa aa | 622 |

<210> SEQ ID NO 18
<211> LENGTH: 5199
<212> TYPE: DNA
<213> ORGANISM: Homo sapiens

<400> SEQUENCE: 18

| | |
|---|---|
| agggacggga agtgggcggg gccggccggc agcagcttgc gggacacgga gccgcgagga | 60 |
| gacagctgag gcccgcggag accagggggt gaagcctgga gaccctcttg ccctggccta | 120 |
| gctgcaggcc cccgggatgc tttgggcatg tcctctggag ccccacagaa gagcagccca | 180 |
| atggccagtg gagctgagga gaccccaggc ttcctggaca cgctcctgca agacttccca | 240 |
| gccctgctga acccagagga ccctctgcca tggaaggccc agggacggt gctcagccag | 300 |
| gaggaggtgg agggcgagct ggctgagctg gccatgggct ttctgggcag caggaaggcc | 360 |
| ccgccaccac ttgctgctgc tctggcccac gaagcagttt cacagctgct acagacagac | 420 |
| ctttccgaat tcaggaagtt gcccaggag gaagaagaag aggaggagga cgatgacgag | 480 |
| gaggaaaagg cccctgtgac cttgctggat gcccaaagcc tggcacagag tttctttaac | 540 |
| cgcctttggg aagtcgccgg ccagtggcag aagcaggtgc cattggctgc ccgggcctca | 600 |
| cagcggcagt ggctggtctc catccacgcc atccggaaca ctcgccgcaa gatggaggac | 660 |
| cggcacgtgt ccctcccttc cttcaaccag ctcttcggct tgtctgaccc tgtgaaccgc | 720 |
| gcctactttg ctgtgtttga tggtcacgga ggcgtggatg ctgcgaggta cgccgctgtc | 780 |
| cacgtgcaca ccaacgctgc ccgccagcca gagctgccca cagaccctga gggagccctc | 840 |
| agagaagcct tccgcgcac cgaccagatg tttctcagga agccaagcg agagcggctg | 900 |
| cagagcggca ccacaggtgt gtgtgcgctc attgcaggag cgaccctgca cgtcgcctgg | 960 |
| ctcgggatt cccaggtcat tttggtacag caggacagg tggtgaagct gatgagcca | 1020 |
| cacagaccag aacggcagga tgagaaggcg cgcattgaag cattgggtgg ctttgtgtct | 1080 |
| cacatggact gctggagagt caacgggacc ctggccgtct ccagagccat cggggatgtc | 1140 |
| ttccagaagc cctacgtgtc tggggaggcc gatgcagctt cccgggcgct gacgggctcc | 1200 |
| gaggactacc tgctgcttgc ctgtgatggc ttctttgacg tcgtacccca ccaggaagtt | 1260 |
| gttggcctgg tccagagcca cctgaccagg cagcagggca gcgggctccg tgtcgccgag | 1320 |
| gagctggtgg ctgcggcccg ggagcgggc tcccacgaca acatcacggt catggtggtc | 1380 |
| ttcctcaggg accccaaga gctgctggag ggcgggaacc agggagaagg ggaccccag | 1440 |
| gcagaaggga ggaggcagga cttgccctcc agccttccag aacctgagac ccaggctcca | 1500 |
| ccaagaagct aggtggtttc caggcccctg ccctcccctt cctcccatcc ttgtccttct | 1560 |
| ctccctcaga agcctcagga cccaacaggt ggcaggcagt ggacagggtg cccgccccac | 1620 |
| agtgctttcc ccagcacccc agagccagtc gggacacccc ccgcagcccg tcctggtggc | 1680 |
| tgtggaactg cactgggtgg cgggcagatg gtggaaggca gcttaggaga cctcaccaaa | 1740 |
| gagaagatgg accggctctt gctcccagct cctattaggc ccggggtggg accagaggtc | 1800 |
| ataggtgccc aacggcagcc aaaccaaaga cactggtgtg catgggcag catggttgtg | 1860 |
| cacgtgggac cctggggcgg acccaggagc caaactcttg aagcaccccc tgggtcaggc | 1920 |
| ccagcagcgc agtggccagc cccagtttcc cattgctcct ctctgcggcc agggccaggt | 1980 |
| gggttcatat ttacagatat gcccagccag tcctggtcgg ccacaccagt gtcccaaaga | 2040 |

```
ggagagcgca gcagagccag gggtctgttc tgtagcagcc accccctgc ccccactcca    2100 gggcagccat gatgtgcttg gcccaccag ggccttccgg gctgctctct tccctgagcc    2160
cggaaccggc gacgcacatg tgtcttttgt tggtgtgttt gttttttttcc agggaggtct  2220 aattccgaag cagtattcca ggttttctct ttgttttatc agtgccaaga tgacctgttg   2280
tgtcatataa tttaagcaga gcttagcatt tattttattc tttagaaaac ttaagtattt   2340 actttttttaa agctattttt caaggaacct tttttttgcag tattattgaa tttattttct  2400
aaatcaggat tgaaacagga acttttccag gtggtgttaa taagccattc aagtgcctta   2460
cacagctttg aagaaactag gactgcagtg ggctcggata ggcccattga ggttttttaga 2520 aaagcaggat ttgttttgtt agggaggcat gattttggtg agatctttct ggaagagttt   2580
tccgcctctt tgtgatgctg aacacccca aggttctccc ctcccccgc tgcccaggtg    2640 actggcagga gctgcgactg ccacgtagtg gtgcctgggc ccgacagcgg ggctctgggc  2700
atcccgggtg accttggccc atctgcctgc attcccaccc ccttgggcct ggctggatcc   2760
caggcagagg gaccttgctg ctgtgtgatt ggaacattcc caaatatctt gtgaatttgt   2820
aatcaaattg gtctcattgg gaaagactct taattaagag gctcaggcaa gcacagaggc   2880
agcccgtggg tctctgtctc agtctggagg cagcagggat gctgctggga gtccatggca   2940
caggccacag cccctcacct tgccgcggtg gctggcagca cgcctgcctt gctctgcccc   3000
atgccctgaa caggcatgag agctccacgt ccccctagtgc accctgagag ggggctcaca  3060
agtgaccgat cctgggtgcc tcagggagct cactgagggc gtgcaaagtt gaaagtggca   3120
aggctggggg agggtgtcgg gtagagggaa gagggcaggg ggctagggga ggactcagag   3180
gccatctgca gggccaagcc acaggaaggg ctgagctgga ggtgggcagg gctgctccag   3240
gcaggtcaga gcagtgcagg gggaggagag gagaaaggga ggaagctggg ctgtgtggtc   3300
cccatgaagg cattcagagt ccacctgcag acagcgagag ccccaggaag gtttgcacag   3360
ctgtgcccca agcaccttgg cctcctctca gctcgccgag gaggcacgct agagccgcct   3420
tcccggtggg agccctctgt cccacaggga gcgggagcc agctttgctg gggccctacc    3480
tgcatgccca gccttacccc tcattctcac agcacagatg aggttgagac catgcagtca   3540
atgcattgct taaggtctct tatttacaaa aaaaaaccttt aaacatagtc gctgtcattc  3600
agacattcag agaatggttg ccacaaaca atgaccaagt attgcttggc ttaacttgaa    3660
ggcctgctgt ctccttctgg gggtcaggga cgcagctcca ccctcaccac tagcccaccc   3720
tgcccgtggg cataaccttg acgaagagag agaatgattg gcatctgctt ttctcttttc   3780
tttgctaata attctgttcc tggctgccga gagtgaagtt tcaccatgtg gaggtttggc   3840
tcctatcacc tggtggtctg attcatacc tagcctgagg ctccactgga agatctcgca    3900
gcctcagtgt atgggaaacc ctttcccag gcttgtccca gcactgccgc tccccacccc    3960
tgagccagga ccccagagga tggccatgcc ccgtgcctgg cagaggtctg gtgccagcac   4020
tgggagctgc tccgcccttg ccttggggcc gagggagccc tcgtccaccc ctgcacagca   4080
gctgggcaca gaggagcgct cttccatctt gaccaggact gcaccaagaa gcaccaggtg   4140
tcttcagcct ccaacctccg gggcgacctt ctcttccagc cacagtccca tgagggcccc   4200
tagccaggga cactggtctg taaattgtaa tcctttctcc agcccagctc tccacttgtt   4260
ccttgtgtga gctgagcagg cagtgcacct ctgagtgtcc ctttttgtaag gcccaggggt  4320 tgcactgagt ctgcagaggc cgcgacctcc tagaacgctg tgggtgcagg tgagccggcg   4380
```

| | |
|---|---|
| tgtcctgggg agatgctgcc agcacacagg ggccctcctg ctgccagcag gttggggtgg | 4440 |
| ttaagtctta ttagtgtcta ttcttaaaat taagtgggct ggagaagaat ggagctccac | 4500 |
| atgccagcac cgtatatgga atacaaaagc tggggaagca gggcctgcct tacaggtgtg | 4560 |
| gctgactctg agcccaggcc tgcaggggtg gagggcagtc cctcagaatc ccagaggcag | 4620 |
| tcccagcctc agaacccagg ataggaaatg ggtgtgttta gtggggaaag ggacggggtg | 4680 |
| cagacggcag ggccagtatg gggcccctc cctctcctct cctctcctat ggtgagccca | 4740 |
| gcgtgggcac cgggccgtct cagccgtgtt cccagggctg ggaggacagc tctggccctt | 4800 |
| cttaggccta gcctcgtccc aagctaaatg taagccagtt gggctgtgtt aaaggaagca | 4860 |
| gtgttttgg ttcgattctg cctctgtagc tcaaggggg cagccccag agtcctgtgc | 4920 |
| attctgccaa ggctccatag ctttgccaaa tgcacggagc tctgccattc cggtgcagtg | 4980 |
| caggccttgc gaagggttta tctgcgttcg tctcggtggg cttctcctgc atgggagttg | 5040 |
| tgttcctgtg caaggggag ctttgctcca ggacaggatg actgtcttcc ctattcttag | 5100 |
| ggacaagtcc caagatgcca gaaaggcagt ctcccaagga cccaccatgc agaagtgtca | 5160 |
| ataaaccaca agttctgaac tctgtaaaaa aaaaaaaaa | 5199 |

<210> SEQ ID NO 19
<211> LENGTH: 1767
<212> TYPE: DNA
<213> ORGANISM: Homo sapiens

<400> SEQUENCE: 19

| | |
|---|---|
| atggcggcgg ccgacggcga cgactcgctg taccccatcg cggtgctcat agacgaactc | 60 |
| cgcaatgagg acgttcagct tcgcctcaac agcatcaaga agctgtccac catcgccttg | 120 |
| gcccttgggg ttgaaaggac ccgaagtgag cttctgcctt tccttacaga taccatctat | 180 |
| gatgaagatg aggtcctcct ggccctggca gaacagctgg gaaccttcac taccctggtg | 240 |
| ggaggcccag agtacgtgca ctgcctgctg ccaccgctgg agtcgctggc cacagtggag | 300 |
| gagacagtgg tgcgggacaa ggcagtggag tccttacggg ccatctcaca cgagcactcg | 360 |
| ccctctgacc tggaggcgca cttttgtgccg ctagtgaagc ggctggcggg cggcgactgg | 420 |
| ttcacctccc gcacctcggc ctgcggcctc ttctccgtct gctacccccg agtgtccagt | 480 |
| gctgtgaagg cggaacttcg acagtacttc cggaacctgt gctcagatga caccccccatg | 540 |
| gtgcggcggg ccgcagcctc caagctgggg gagtttgcca aggtgctgga gctggacaac | 600 |
| gtcaagagtg agatcatccc catgttctcc aacctggcct ctgacgagca ggactcggtg | 660 |
| cggctgctgg cggtggaggc gtgcgtgaac atcgcccagc ttctgcccca ggaggatctg | 720 |
| gaggccctgg tgatgcccac tctgcgccag gccgctgaag caagtcctg gcgcgtccgc | 780 |
| tacatggtgg ctgacaagtt cacagagctc cagaaagcag tggggcctga gatcaccaag | 840 |
| acagacctgg tccctgcctt ccagaacctg atgaaagact gtgaggccga ggtgagggcc | 900 |
| gcagcctccc acaaggtcaa agagttctgt gaaaacctct cagctgactg tcgggagaat | 960 |
| gtgatcatgt cccagatctt gcctgcatc aaggagctgg tgtccgatgc caaccaacat | 1020 |
| gtcaagtctg ccctggcctc agtcatcatg ggtctctctc ccatcttggg caaagacaac | 1080 |
| accatcgagc acctcttgcc cctcttcctg gctcagctga aggatgagtg ccctgaggta | 1140 |
| cggctgaaca tcatctctaa cctggactgt gtgaacgagg tgattggcat ccggcagctg | 1200 |
| tcccagtccc tgctccctgc cattgtggag ctggctgagg acgccaagtg gcgggtgcgg | 1260 |
| ctggccatca ttgagtacat gccctcctg gctggacagc tgggagtgga gttctttgat | 1320 |

```
gagaaactta actccttgtg catggcctgg cttgtggatc atgtatatgc catccgcgag    1380
gcagccacca gcaacctgaa gaagctagtg gaaaagtttg ggaaggagtg ggcccatgcc    1440
acaatcatcc ccaaggtctt ggccatgtcc ggagacccca actacctgca ccgcatgact    1500
acgctcttct gcatcaatgt gctgtctgag gtctgtgggc aggacatcac caccaagcac    1560
atgctaccca cggttctgcg catggctggg gacccggttg ccaatgtccg cttcaatgtg    1620
gccaagtctc tgcagaagat agggcccatc ccggacaaca gcaccttgca gagtgaagtc    1680
aagcccatcc tagagaagct gacccaggac caggatgtgg acgtcaaata ctttgcccag    1740
gaggctctga ctgttctgtc tctcgcc                                        1767
```

<210> SEQ ID NO 20
<211> LENGTH: 10640
<212> TYPE: DNA
<213> ORGANISM: Homo sapiens

<400> SEQUENCE: 20

```
atactcagtc acacaagcca tagcaggaaa cagcgagctt gcagcctcac cgacgagtct      60
caactaaaag ggactcccgg agctaggggt ggggactcgg cctcacacag tgagtgccgg     120
ctattggact tttgtccagt gacagctgag acaacaagga ccacgggagg aggtgtagga     180
gagaagcgcc gcgaacagcg atcgcccagc accaagtccg cttccaggct ttcggtttct     240
ttgcctccat cttgggtgcg ccttcccggc gtctagggga gcgaaggctg aggtggcagc     300
ggcaggagag tccggccgcg acaggacgaa ctcccccact ggaaaggatt ctgaaagaaa     360
tgaagtcagc cctcagaaat gaagttgact gcctgctggc tttctgttga ctggcccgga     420
gctgtactgc aagacccttg tgagcttccc tagtctaaga gtaggatgtc tgctgaagtc     480
atccatcagg ttgaagaagc acttgataca gatgagaagg agatgctgct cttttttgtgc    540 cgggatgttg ctatagatgt ggttccacct aatgtcaggg accttctgga tattttacgg     600
gaaagaggta agctgtctgt cggggacttg gctgaactgc tctacagagt gaggcgattt     660
gacctgctca aacgtatctt gaagatggac agaaaagctg tggagaccca cctgctcagg     720
aaccctcacc ttgtttcgga ctatagagtg ctgatggcag agattggtga ggatttggat     780
aaatctgatg tgtcctcatt aattttcctc atgaaggatt acatgggccg aggcaagata     840
agcaaggaga gagtttcttt ggaccttgtg gttgagttgg agaaactaaa tctggttgcc     900
ccagatcaac tggatttatt agaaaaatgc ctaaagaaca tccacagaat agacctgaag     960
acaaaaatcc agaagtacaa gcagtctgtt caaggagcag ggacaagtta caggaatgtt    1020
ctccaagcag caatccaaaa gagtctcaag gatccttcaa ataacttcag gctccataat    1080
gggagaagta agaacaaag acttaaggaa cagcttggcg ctcaacaaga accagtgaag    1140
aaatccattc aggaatcaga agctttttg cctcagagca tacctgaaga gagatacaag    1200
atgaagagca agcccctagg aatctgcctg ataatcgatt gcattggcaa tgagacagag    1260
cttcttcgag acaccttcac ttccctgggc tatgaagtcc agaaattctt gcatctcagt    1320
atgcatggta tatcccagat tcttggccaa tttgcctgta tgcccgagca ccgagactac    1380
gacagctttg tgtgtgtcct ggtgagccga ggaggctccc agagtgtgta tggtgtggat    1440
cagactcact cagggctccc cctgcatcac atcaggagga tgttcatggg agattcatgc    1500
ccttatctag cagggaagcc aaagatgttt tttattcaga actatgtggt gtcagagggc    1560
cagctggagg acagcagcct cttggaggtg gatgggccag cgatgaagaa tgtggaattc    1620
```

```
aaggctcaga agcgagggct gtgcacagtt caccgagaag ctgacttctt ctggagcctg    1680
tgtactgcgg acatgtccct gctggagcag tctcacagct caccatccct gtacctgcag    1740
tgcctctccc agaaactgag acaagaaaga aaacgcccac tcctggatct tcacattgaa    1800
ctcaatggct acatgtatga ttggaacagc agagtttctg ccaaggagaa atattatgtc    1860
tggctgcagc acactctgag aaagaaactt atcctctcct acacataaga aaccaaaagg    1920
ctgggcgtag tggctcacac ctgtaatccc agcactttgg gaggccaagg agggcagatc    1980
acttcaggtc aggagttcga gaccagcctg gccaacatgg taaacgctgt ccctagtaaa    2040
aatacaaaaa ttagctgggt gtgggtgtgg gtacctgtat tcccagttac ttgggaggct    2100
gaggtgggag gatcttttga acccaggagt tcagggtcat agcatgctgt gattgtgcct    2160
acgaatagcc actgcatacc aacctgggca atatagcaag atcccatctc tttaaaaaaa    2220
aaaaaaaagg acaggaacta tcttactcaa tgtattagtc atgtttctct agagggacag    2280
aactaatagg atacatgtat ataaaaaggg gagtttatta aggagtattg actcacatga    2340
tcacagggtt aggtcccaca ataggtcatc tgcaagcaag gaagccaatt caagtcccaa    2400
agctgaagaa cttggagtcc aatgtttgag ggcaggaagc attcagcatg agagaaagat    2460
ggaggccaga agactacacc agtctagtct ttccatgttt tgcctgcttt tattctggca    2520
gtgctggcag ctgattagat ggtgcccacc cagattgagg atggtctgcc tttcccagtc    2580
cactgactca aatgttaaat ctcctttggc agcaccctca cagatgtacc cgggaacact    2640
ttgcatcctt ctattcaatc aagttgatac tcagtattaa ccatcacagt ccatttgggc    2700
aactatacca aattaccata gaccaggtga cttaaacagc agttatttct cacagttccg    2760
gaggctggga aatccaacat ctaagtggta gcatatctgg tgtctggtaa ggcatgcttc    2820
cagatcttac cagatgtcag tcttttgatg ttctcacatg gcagaaaaag aggatgcaaa    2880
ctctcaagta tatctttaag ggcacaaatt ccattcatga gggctctacc ctcatcacct    2940
aattacctcc caaaggcccc accttctgat actgtcactt tggggatact gtctcccctt    3000
tgaattctgg ggggaataca aacattcagt ttgtaacaat agccttatga tttagaggtt    3060
acttgttcat tcacctagac ctcaaattgc attttacagc tagtcaagta tatctttctc    3120
tgatttgata gtgtgaccta aaaggggacc attgtttgaa atatcattag agttgcttat    3180
tattattatt attattatta ttattattat tattattatt attgagacag agtttcattc    3240
tgctgcccag gctggagtgc agtggcatca tcttggctca ttgcaacctc tgccttctgg    3300
gttcaagcga ttctcctgcc tcagcctccc gagtagctgg gattacaggc tcctgccacc    3360
acacccggct aattttttgta ttttttagtgg agacagggtt tccaccatgt tggccagcgt    3420
ggtcttgaac tcctgacctc aggtgattca ccagcctcgg cctcccaaag tgctgggatt    3480
acaggtgtga gccactgcac ctggcctatt attatttta aatttttttt ttttaattga    3540
tcattcttgg gtgtttctca cagagggtga tttggcaggg tcacaggaca atagtggagg    3600
gaaggtcagc agataaacaa gtgaacaaag gtctctggtt ttcctaggca gaggaccctg    3660
cggccttccg cagtgtttgt gtccctgggt acttgagatt agggagtggt gatgactctt    3720
aaggagcatg ctgccttcaa gcatctgttt aacaaagcac atcttgcact gcccttaatc    3780
catttaaccc tgagtggaca cagcacatgt ttcagagagc acagggttgg gggtaaggtc    3840
atagatcaac agcatcctaa ggcagaagaa ttttcttag tacagaacaa aatgaagtct    3900
cccatgtcta cttcttcta cacagacaca gcaacaatct gatttctcta tcttttcccc    3960
acctttcccc cttttctatt ccacaaaacc gccatcgtca tcatggcctg ttctcaatga    4020
```

```
gctgttgggt acacctccca gacgggtgg cggctgggca gagggctcc tcacttccca    4080
gatgggcgg ccaggcggac gcgccccca cctccctccc ggacgggata gctggccggg    4140
cggggctga cccccacct ccctcccga cggggcggct ggccgggcgg gggctgaccc    4200
ccacgcctcc ctcccggacg gggcggctgc caggcggagg ggctcctcac ttctcagacg    4260
gggtggctgc tgggcggaga cgctcctcac ttcccagaca gggtggctgt cgggcggagg    4320
ggctcctcac ttctcagacg gggcagctgc gggcggaggg gctcctcact tctcagacgg    4380
ggtggccggg cagagaagct cctcacatcc cagacggggg ggcggggcag aggcgctccc    4440
cacatctcag acgatgggcg gccgggcaga gacgctcctc acttcatccc agacggggtg    4500
gcggccgggc agaagctgta atctcggcac cctgggggc caaggcaggc ggctgggagg    4560
cggaggccgt agccagctga gatcacacca ctgcactcca gcctgggcaa cattgagcac    4620
tgagtggacg agactctgcc cgcaatcccg gcacctcggg aggccgaggc tggcagatca    4680
ctcgcagtca ggagctggag accagccgg ccaacacagt gaaaccctgt ctccaccaaa    4740
aaaatacgaa aaccagtcag gcgtggcggc gcccgcaatg gcaggcacgc ggcaggccga    4800
ggcgggagaa tcaggcaggg aggctgcagt gagccgagat ggcagcagta cagtccagct    4860
tcggctcggc atcagaggga gaccgtgggg agagggagaa gagagggagg gggagagggc    4920
tattttaaa atttttaaa attgctgaac agggtaccct ctgggcagtg tgtcagaata    4980
ccacttttta aatatttat gatttattta ttttctatt tcttgaggtt ttaactgatg    5040
tgtatctgta tgtctatttg tgtatatttt gtcatgatca tgtaacagag tctgaaaagt    5100
gtcgaagaga cagttttcag gaacaacaag caattattcc tactttccaa gttattttga    5160
tgccatggtg gctcatacct ataatctgag tactttggga ggctgaggtg gactgatcac    5220
ttgagcccag gagtttgaga ccagcctggg caacatagca agactccatc tctacaaaaa    5280
aagacaaaat ttagctgagc gtggtggcgt gttcctgtag tcccagctac ttgggaggct    5340
gaagtgagtg gatcccctga gcccagagag gtcaaggttg tgatgagctg tgatcacacc    5400
actgcacttc agcatgggag acagagtgag accctgtttc agaaaaaata aataaataaa    5460
accaccagca ccacaaacaa caacaaaaag ttattttgta cttgttttga gcacaggact    5520
cctgagggta tctttgcatt taatattaca taggggtgcc agtgggaagt aatgtgtatg    5580
cttggcctca tgagctaaaa ccctgtgtta attatgacag aaggaaagtg tgtgagagag    5640
atcttaacta cctagcagct ctagctgcca tcttgaacca tgaagatacg ggccacacgt    5700
agggtagct gggtagtgag cagcaagaag ccttgttgga tgagggcacg aaggagcaga    5760
atcactggaa tcactgtgtc agccctaatt acctacctct ggactttat gtgaggggaa    5820
aaaaaattga cagtttatat ttatctcaac ctagttaacc caagtgatgc attgttatga    5880
gattaaaatg tttggaggcc gggtgcggtg gctcacgcct ataatcccag cctttggga    5940
ggccaaggcg gcggatcac gaggtcagga gatcaagacc atcctggcta acatgtaaaa    6000
ccccgtctct actaaaaata caaaaatta gccaggcgtt gtggcggtcg cctgtagtcc    6060
ctgctatttg ggaggccgag gcaagagaac ggcatgaacc tgggaggtgg agcttgcagc    6120
gagctgagat cttgccactg cactccagcc tgggcgacag tgcgagactc tgtctcaaaa    6180
ataaataaat aaataaataa taaataaaat gtttggaatg ttggcttcat ccctgggatg    6240
caaggctggt tcaacatacg caaatcaaga aacataattc atcacataaa cagaactaaa    6300
gacaaaaacc acatgattat ctcaatagat acagaaaagg ccttcaataa aattcaacgt    6360
```

```
tgcttcatgt taaaaactct caataaacta ggtattgatg gaaaatatct caaaataata    6420
accatttatg acaaacccac agccattatc atactgaatg ggcaaaagct ggaagcattc    6480
cccttgaaaa ctggcacaag acagggatgc cgtctcacca ctcctattta acatagtatt    6540
ggaagttctg gccaagaaaa tcaggcaaga gaaacaaata aggggtattc aaataggaaa    6600
agaggaagta aaactgtgtt tgcagatgac atgatactat atctagaaaa cccccattatc   6660
tccacccaaa agttccttaa gctgataagc aacttcagca aagtctcagg atacaaaatc    6720
aatgtgcaga atcacaagc attctataca ccaacaatac acaagcagag agccaaatca    6780
tgaatgaact cccattcaca gttgctagaa agagaataaa atacctagga atacagctaa    6840
taagatgtga aggatctctt caaggagaac tacaaaccac tgctcaagga aataagagag    6900
gacacaaatg aaaaaacatt ccattctcgt ggataggaag aatcaatatc atgaaaatgg    6960
ccatactacc caaagtaatt tataggttca ttgctattcc cattaaacta ctattgacat    7020
tcttcacaga attagaaaaa aactactttta aaattcaaat ggaaccaaaa aagagcccgt    7080
ataaccaaga caacaataag caaaaagaac aaagctggaa gcatcacact acccaacttc    7140
aaagtatact gcaaggctac agtagccaaa atggcatggt actggtacaa aaacagacac    7200
atagaccaat ggaacagaat agagaccaga gaaagaagcc cacacatcta cagccatctg    7260
atcatcgaca aacctgacaa aaacaagcaa tggggaaaag attccctatt taataaatgg    7320
tgctgggaaa actggctagc catatgcaga aaattgaaac tgaccccttc cttcacacctt    7380
atacaaaaat taactcaaga ttaaagactt aatgtaaaac ctaaaactat aaaaacccta    7440
gaagaaaatc tatttaatac cattcaagac ataggcacaa gcaaaggttt catgacaaaa    7500
acatcaaaag caattgcaac aaaagcaaaa attacaaatg ggatctaatt aaactaaaga    7560
gctcctgcac agcaaaagaa actatcatta gagtgaacag gcaacctaca gaatgggaga    7620
acattttgc aatctatcca tctgacaaag gtctaatatc cagaacctac aaggaactta    7680
aaacaaattt acaaggaaaa aaacaacccc atcaaaaagt ggacaaagga catgaacaga    7740
cacttctcaa agaagacat ttatgtggcc aacaaacata aaaaaaaag ctcaaccttta    7800
ctgatcatta gagaaatgca aaggagaacc acaatgagat accatctcat gccggtcaga    7860
atggtgatta ttaaaaagtc aaaaaacaac agatgctggc gaggctgtgg agaagtagga    7920
acacttttac attgttggtg ggaatgtaaa ttagttcaac cgttgtggaa gtgtgtgtgg    7980
ctattcctca aagatctaga actagaaata ctatttgtcc cagcaatccc attactgggt    8040
atatacccaa aggaatataa accatttat tataaagata catgcacatt tttgttcatt    8100
gcagcactct tcacaatagc aaagacacaa tagcaaatgc ccatcaaaga tagactggat    8160
aaagaaaatg tggtacatat acaccatgga atactgtgca gtgcagccat tacagctttt    8220
ggtgatacag tgaatcagat ttttcattaa ttctttttaat tggttattac tgaacgtgaa    8280
aaagtaatgt ttgtattgaa atcttgagtc tggccatgtt tctattttaa attcataaag    8340
aattctaaca agaggaattc caagaatgtc ataaatggat gtttctccat ggatgaagga    8400
actgttttat tcacttgctg ataattcagc ctaatccagt ttgacatcat atagataagt    8460
agttgaatta tggatttaaa atacatatca ttttctaact ccaaaggtaa tacttattta    8520
aatggttttg aaaatataga aaggcacaat ttcttttaa atctgttatt ctccaccacc    8580
actcaatctg tctatcatct atctctccat tcattcttcc atttgtttat atctgttaat    8640
ctttgtatgt gttcatgtat agcttttaca tgattggaat cataatgcat attccatttt    8700
gaagtctgct ttttttaca caaaaatatg ttgtgaatat tttcctatat tatgaaatat    8760
```

```
cattagctga gcttttagaa ttgactgcat gttttggtac catttagata tagtttaaga    8820
tacttagaag ttatgtggct ttgccactat ggatgaatct tatttactca atattaatta    8880
cttacaaata acctcaccta aacactactc agccataaaa aggaatgaat taatgacatt    8940
cacagcaacc tggagactat tactctaaag gaagtaactg aggaatggaa aaccaaacat    9000
tgtatgttct cactcataag tgggagataa gctatgagga tgcaaaggca taagaaggat    9060
acaatggact ttggggactt aggggaaagg gtggagaggg ggtgaaggat aaagaatac     9120 aaattgggtt cagtgtatac tgctcaggtg atgggtgcac cagaatctca caagtaacca    9180
cttaattact tacgcatgta accagatacc acctgttccc caaacaccta tggaaataat    9240
tttgtttttt ttttaaaaa aggaatgaga tcatgtcctt tgcagggaca tggatgaagc     9300
tggaagccat tatcctcagc aaactaacag aggagcagga aaccaaacac cacatgttct    9360
cacttgtaag cggaagctga acaatgagaa cacacggaca cagggatgag atcaacacac    9420 actgggggcct gatgcagggg ccgtagcggg gagagcatca ggataactag ctaatgcatg   9480
tggggcttaa tacctaggtg ataggttgat aggtgcagca aaccaccatg ggacacgttt    9540
acctatgtaa caaacccgca catcctgcac ttgtatccag aacttaaaat attttaaaaa    9600
tctttagaga atacaaaaaa aaaaaaaaag attcttcaat gcatacacaa taaaattgca    9660
gttcagtcaa acattggaag tcttttctctg actgtctagt tggtatcttc atttttcagct  9720 tcttcaagat cccactccaa acactgttag ctcagccaaa ttgaacagct catatctcct    9780
acctctggat ctttggttct ggtgattgta tatttctgga ccatctggaa ccccagcata    9840
tcaccctacc ccacatctcc acatccccaa aatataacca tacttcaagg gcagttcaaa    9900
taccatctcc ttctatcctc catgaagtca gttatctctt ccattggaat tatcgccccc    9960
tctcctgaac agtactattt cgtgtgaatc tcctccaagc cttctttca ttttatatct     10020 catgctgtaa ttcttggaaa gtatgctgta gctcaagtgc agaattctca tcagtttat     10080 ctttatatct ctcctaaaca cttacctga tgaagagcct ggcatacaca taaatatata     10140
ttgaatgaat cagtgatgga ttgaaaagag aaatgatgga tctcctaaat tttaacttt    10200 ataaaatatt ttgatacatt catgacctta ctttagcaag caatgaacgt gatgtaaact    10260
attgttgata tagttttat attggaagtg taagtagttt gtggcatggg attgtgacat     10320
atcctaggtt tcctcatctt cttttttattg aaatgtaatt cacaagccat aaaatttgcc   10380
cctttaaagt aaatgatgca gtggatttta gtatattaac agagttgtgc aatcatcacc    10440
actatctaat tccagaacat ttccatctac ctagaaactc cataccagtg agctgccact    10500
ctaatcctcc tcttccccca gcctctagaa acaataatcc attttctgtc tctatgattt    10560
gcctgttcta gatattttat aaaaataaac atgtggcctt tcgtgtctga cttccttcac    10620
ttaaaaaaaa aaaaaaaaaa                                                10640

<210> SEQ ID NO 21
<211> LENGTH: 1939
<212> TYPE: DNA
<213> ORGANISM: Homo sapiens

<400> SEQUENCE: 21
cgcctccgcc ttcggaggct gacgcgcccg ggcgccgttc caggcctgtg cagggcggat      60
cggcagccgc ctggcggcga tccagggcgg tgcgggggcct gggcgggagc cgggaggcgc   120
ggccggcatg gagcgcgctgc tgctgggcgc ggggttgctg ctgggcgctt acgtgcttgt   180
```

```
ctactacaac ctggtgaagg ccccgccgtg cggcggcatg ggcaacctgc ggggccgcac        240
ggccgtggtc acgggcgcca acagcggcat cggaaagatg acggcgctgg agctggcgcg        300
ccggggagcg cgcgtggtgc tggcctgccg cagccaggag cgcggggagg cggctgcctt        360
cgacctccgc caggagagtg ggaacaatga ggtcatcttc atggccttgg acttggccag        420
tctggcctcg gtgcgggcct tgccactgc ctttctgagc tctgagccac ggttggacat         480
cctcatccac aatgccggta tcagttcctg tggccggacc cgtgaggcgt ttaacctgct        540
gcttcgggtg aaccatatcg gtcccttct gctgacacat ctgctgctgc cttgcctgaa         600
ggcatgtgcc cctagccgcg tggtggtggt agcctcagct gcccactgtc ggggacgtct        660
tgacttcaaa cgcctggacc gcccagtggt gggctggcgg caggagctgc gggcatatgc       720
tgacactaag ctggctaatg tactgtttgc ccgggagctc gccaaccagc ttgaggccac       780
tggcgtcacc tgctatgcag cccacccagg gcctgtgaac tcggagctgt cctgcgcca        840 tgttcctgga tggctgcgcc cacttttgcg cccattggct tggctggtgc tccgggcacc      900 aagaggggt gcccagacac ccctgtattg tgctctacaa gagggcatcg agcccctcag       960
tgggagatat tttgccaact gccatgtgga agaggtgcct ccagctgccc gagacgaccg      1020
ggcagcccat cggctatggg aggccagcaa gaggctggca gggcttgggc ctggggagga     1080
tgctgaaccc gatgaagacc cccagtctga ggactcagag gccccatctt ctctaagcac    1140
ccccacccct gaggagccca cagtttctca accttacccc agccctcaga gctcaccaga    1200
tttgtctaag atgacgcacc gaattcaggc taaagttgag cctgagatcc agctctccta     1260
accctcaggc caggatgctt gccatggcac ttcatggtcc ttgaaaacct cggatgtgtg    1320
cgaggccatg ccctggacac tgacgggttt gtgatcttga cctccgtggt tactttctgg    1380
ggccccaagc tgtgccctgg acatctcttt tcctggttga aggaataatg ggtgattatt   1440
tcttcctgag agtgacagta accccagatg agagatagg ggtatgctag acactgtgct    1500
tctcggaaat ttggatgtag tattttcagg ccccacccct tattgattctg atcagctctg   1560 gagcagaggc agggagtttg caatgtgatg cactgccaac attgagaatt agtgaactga   1620 tcccctttgca accgtctagc taggtagtta aattaccccc atgttaatga agcggaatta   1680
ggctcccgag ctaagggact cgcctagggt ctcacagtga gtaggaggag ggcctgggat    1740
ctgaacccaa gggtctgagg ccagggccga ctgccgtaag atgggtgctg agaagtgagt   1800
cagggcaggg cagctggtat cgaggtgccc catgggagta aggggacgcc ttccgggcgg    1860
atgcagggct ggggtcatct gtatctgaag cccctcggaa taaagcgcgt tgaccgccga   1920
aaaaaaaaaa aaaaaaaa                                                    1939
```

```
<210> SEQ ID NO 22
<211> LENGTH: 1840
<212> TYPE: DNA
<213> ORGANISM: Homo sapiens

<400> SEQUENCE: 22
```

```
gggttcccag gccgactctc cttgtggttg gctgaggctg gaggtggacg ggacttttgg        60
agggtcgctc gcgtctgttc gcagagctgt gggcggagtt gaggccttgg aggctgagat       120
gtggttctgc gcgtgtgcgg acggctgtct gttaactccg cggtcagttc ccggactggt       180
ggctggtctg cagggttgac ctgcgcaatg cagaggctgc aggtagtgct gggccacctg      240
aggggtccgg ccgattccgg ctggatgccg caggccgcgc cttgcctgag cggtgccccg      300
caggcctcgg ccgcggacgt ggtggtggtg cacgggcggc gcacggccat ctgccgggcg      360
```

| | | |
|---|---|---|
| ggccgcggcg gcttcaagga caccaccccc gacgagcttc tctcggcagt catgaccgcg | 420 | |
| gttctcaagg acgtgaatct gaggccggaa cagctggggg acatctgtgt cggaaatgtg | 480 | |
| ctgcagcctg gggccggggc aatcatggcc cgaatcgccc agtttctgag tgacatcccg | 540 | |
| gagactgtgc ctttgtccac tgtcaataga cagtgttcgt cggggctaca ggcagtggcc | 600 | |
| agcatagcag gtggcatcag aaatgggtct tatgacattg gcatggcctg tggggtggag | 660 | |
| tccatgtccc tggctgacag agggaaccct ggaaatatta cttcgcgctt gatggagaag | 720 | |
| gagaaggcca gagattgcct gattcctatg ggataaacct ctgagaatgt ggctgagcgg | 780 | |
| tttggcattt cacgggagaa gcaggatacc tttgccctgg cttcccagca gaaggcagca | 840 | |
| agagcccaga gcaagggctg tttccaagct gagattgtgc ctgtgaccac cacggtccat | 900 | |
| gatgacaagg gcaccaagag gagcatcact gtgacccagg atgagggtat ccgcccccagc | 960 | |
| accaccatgg agggcctggc caaactgaag cctgccttca gaaagatgg ttctaccaca | 1020 | |
| gctgaaaact ctagccaggt gagtgatggg gcagctgcca tcctgctggc ccggaggtcc | 1080 | |
| aaggcagaag agttgggcct tcccatcctt ggggtcctga ggtcttatgc agtggttggg | 1140 | |
| gtcccacctg acatcatggg cattggacct gcctatgcca tcccagtagc tttgcaaaaa | 1200 | |
| gcagggctga cagtgagtga cgtggacatc ttcgagatca atgaggcctt tgcaagccag | 1260 | |
| gctgcctact gtgtggagaa gctacgactc ccccctgaga aggtgaaccc cctgggggt | 1320 | |
| gcagtggcct tagggcaccc actgggctgc actggggcac acaggtcat cacgctgctc | 1380 | |
| aatgagctga agcgccgtgg gaagagggca tacggagtgg tgtccatgtg catcgggact | 1440 | |
| ggaatgggag ccgctgccgt ctttgaatac cctgggaact gagtgaggtc ccaggctgga | 1500 | |
| ggcgctacgc agacagtcct gctgctctag cagcaaggca gtaacaccac aaaagcaaaa | 1560 | |
| ccacatggga aaactcagca ctggtggtgg tggcagtgga cagatcaagg cacttcaact | 1620 | |
| catttggaaa atgtgaacac tgatgacatg gtataggagt gggtgggtg ttgagccacc | 1680 | |
| catcagaccc tctttagctg tgcaagataa aagcagcctg ggtcacccag ccacaaggc | 1740 | |
| catggttaat tcttaaggca aggcaaatcc atggatgaga agtgcaatgg gcatagtaaa | 1800 | |
| agtgcatgaa tttatcttaa aaaaaaaaaa aaaaaaaaaa | 1840 | |

<210> SEQ ID NO 23
<211> LENGTH: 3407
<212> TYPE: DNA
<213> ORGANISM: Homo sapiens

<400> SEQUENCE: 23

| | | |
|---|---|---|
| caggttgaaa tggctgatga catcactggt tcccgggagc ggtagagctg gagccggagc | 60 | |
| caagggagtc caggctgccg ggggctgcag acatggaggg ccagagcagc aggggcagca | 120 | |
| ggaggccagg gacccgggct ggcctgggtt ccctgcccat gccccagggt gttgcccaaa | 180 | |
| ctggggcacc ctccaaggtg gactcaagtt ttcagctccc agcaaagaag aacgcagccc | 240 | |
| taggaccctc ggaaccaagg ttggctctgg cacctgtagg gccacgggca gctatgtcag | 300 | |
| cttcctcgga aggaccgagg ctggctctgg catctccccg accaatcctg gctccactgt | 360 | |
| gtacccctga agggcagaaa acagctactg cccaccgcag ctccagcctg gccccaacat | 420 | |
| ctgtgggcca gctggtgatg tctgcctcag ctggaccaaa gcctccccca gcgaccacag | 480 | |
| gctcagttct ggctccgacg tccctggggc tggtgatgcc tgcctcagca gggccaagat | 540 | |
| ctcccccagt caccctgggg cccaatctgg ccccaacctc cagagaccag aagcaggagc | 600 | |

```
cacctgcctc cgtgggaccc aagccaacac tggcagcctc tggcctgagc ctggccctgg    660
cttctgagga gcagccccca gaactcccct ccaccccttc cccggtgccc agtccagttc    720
tgtctccaac tcaggaacag gccctggctc agcatccac ggcatcaggc gcagcctctg    780
tgggacagac atcagctaga aagagggatg ccccagcccc tagacctctc cctgcttctg    840
aggggcatct ccagcctcca gctcagacat ctggtcctac aggctcccca ccctgcatcc    900
aaacctcccc agaccctcgg ctctcccct ccttccgagc ccggcctgag ccctccaca    960
gcagccctga ggatcctgtt tgccacggc caccccagac cttgcccttg gatgtgggcc   1020
agggtccttc agagcctggc actcactccc ctggacttct gtcccccacc ttccggcctg   1080
gggccccctc aggccagact gtgccccac ctctgcccaa gccaccccga tcacccagcc   1140
gttccccaag ccactcccg aatcgctctc cctgtgttcc cccagcccct gacatggccc   1200
tcccaaggct tggcacacag agtacagggc ctggcaggtg cctgagcccc aaccttcagg   1260
cccaagaagc cccagcccca gtcaccacct cctcttctac atccaccctg tcatcctccc   1320
cttggtcagc tcagcctacc tggaagagcg accccggctt ccggatcact gtggtcacat   1380
ggaacgtggg cactgccatg cccccagacg atgtcacatc cctcctccac ctgggcggtg   1440
gtgacgacag cgacggcgca gacatgatcg ccatagggtt gcaggaagtg aactccatgc   1500
tcaacaagcg actcaaggac gccctcttca cggaccagtg gagtgagctg ttcatggatg   1560
cgctagggcc cttcaacttc gtgctggtga gttcggtgag gatgcagggt gtcatcctgc   1620
tgctgttcgc caagtactac cacctgccct tcctgcgaga cgtgcagacc gactgcacgc   1680
gcactggcct gggcggctac tggggtaaca agggtggcgt gagcgtgcgc ctggcggcct   1740
tcgggcacat gctctgcttc ctgaactgcc acttgcctgc gcatatggac aaggcggagc   1800
agcgcaaaga caacttccag accatcctca gcctccagca gttccaaggg ccgggcgcac   1860
agggcatcct ggatcatgac ctcgtgttct ggttcgggga cctgaacttc cgcattgaga   1920
gctatgacct gcactttgtc aagtttgcca tcgacagtga ccagctccat cagctctggg   1980
agaaggacca gctcaacatg gccaagaaca cctggcccat tctgaagggc tttcaggagg   2040
ggccctcaa cttcgctccc accttcaagt ttgatgtggg taccaacaaa tacgatacca   2100
gtgccaagaa acggaagcca gcttggacag accgtatcct atggaaggtc aaggctccag   2160
gtggggtcc cagcccctca ggacggaaga gccaccgact ccaggtgacg cagcacagct   2220
accgcagcca catggaatac acagtcagcg accacaagcc tgtggctgcc cagttcctcc   2280
tgcagtttgc cttcagggac gacatgccac tggtgcggct ggaggtggca gatgagtggg   2340
tgcggcccga gcaggcggtg gtgaggtacc gcatggaaac agtgttcgcc cgcagctcct   2400
gggactggat cggcttatac cgggtgggtt tccgccattg caaggactat gtggcttatg   2460
tctgggccaa acatgaagat gtggatggga ataccaccac ggtaacattc agtgaggaat   2520
cactgcccaa gggccatgga gacttcatcc tgggctacta tagtcacaac acagcatcc   2580
tcatcggcat cactgaaccc ttccagatct cgctgccttc ctcggagttg gccagcagca   2640
gcacagacag ctcaggcacc agctcagagg gagaggatga cagcacactg gagctccttg   2700
cacccaagtc ccgcagcccc agtcctgca agtccaagcg acaccgcagc cgcagcccgg   2760
gactggccag gttccctggg cttgccctac ggccctcatc ccgtgaacgc cgtggtgcca   2820
gccgtagccc ctcaccccag agccgccgcc tgtcccgagt ggctcctgac aggagcagta   2880
atggcagcag ccggggcagt agtgaagagg ggccctctgg gttgcctggc ccctgggcct   2940
tcccaccagc tgtgcctcga agcctgggcc tgttgccgc cttgcgccta gagactgtag   3000
```

```
accctggtgg tggtggctcc tggggacctg atcgggaggc cctggcgccc aacagcctgt   3060
ctcctagtcc ccagggccat cggggggctgg aggaagggggg cctggggccc tgagggtggg   3120
```

```
accctggtgg tggtggctcc tggggacctg atcgggaggc cctggcgccc aacagcctgt   3060
ctcctagtcc ccagggccat cggggggctgg aggaaggggg cctggggccc tgagggtggg   3120
gtaggcagat gggccaaggt gaccaccatt ctgcctcaat cttttgcaag cccacctgcc   3180
tctctcctgc tgctcctcca gctgtatctg cacctgcctc tctgtcctgg ccaggggtgg   3240
acaactgggg tcccccaaaa ctcagtcctg gcacctcaac tgtgacaatc agcaaagccc   3300
cacccaggcc cccatctggg atgatgggag agctctggca gatgtcccaa tcctggaggt   3360
catccattag gaattaaatt ctccagcctc aaaaaaaaaa aaaaaaa              3407
```

<210> SEQ ID NO 24
<211> LENGTH: 1146
<212> TYPE: DNA
<213> ORGANISM: Homo sapiens

<400> SEQUENCE: 24

```
ttttgcgaac ggcgagcagc ggcggcggcg cggagagacg cagcggaggt tttcctggtt    60
tcggaccccca gcggccggat ggtgaaatcc tccctgcagc ggatcctcaa tagccactgc   120
ttcgccagag agaaggaagg ggataaaccc agcgccacca tccacgccag ccgcaccatg   180
ccgctcctaa gcctgcacag ccgcggcggc agcagcagtg agagttccag ggtctccctc   240
cactgctgta gtaacccggg tccgggggcct cggtggtgct cctgatgccc ctcacccacc   300
cctgaagatc ccaggtgggc gagggaatag tcagagggat cacaatcttt cagctaactt   360
attctactcc gatgatcggc tgaatgtaac agaggaacta acgtccaacg acaagacgag   420
gattctcaac gtccagtcca ggctcacaga cgccaaacgc attaactggc gaacagtgct   480
gagtggcggc agcctctaca tcgagatccc gggcggcgcg ctgcccgagg ggagcaagga   540
cagctttgca gttctcctgg agttcgctga ggagcagctg cgagccgacc atgtcttcat   600
ttgcttccac aagaaccgcg aggacagagc cgccttgctc cgaaccttca gcttttgggg  660
cttttgagatt gtgagaccgg ggcatccctt tgtccccaag agacccgacg cttgcttcat   720
ggcctacacg ttcgagagag agtcttcggg agaggaggag gagtagggcc gcctcggggc   780
tgggcatccg gccccctgggg ccaccccttg tcagccgggt gggtaggaac cgtagactcg   840
ctcatctcgc ctgggtttgt ccgcatgttg taatcgtgca aataaacgct cactccgaat   900
tagcggtgta tttcttgaag tttaatattg tgtttgtgat actgaagtat ttgctttaat   960
tctaaataaa aatttatatt ttactttttt attgctggtt taagatgatt cagattatcc  1020
ttgtactttg aggagaagtt tcttatttgg agtcttttgg aaacagtctt agtcttttaa  1080
cttggaaaga tgaggtatta atcccctcca ttgctctcca aaagccaata aagtgattac  1140
acccga                                                            1146
```

<210> SEQ ID NO 25
<211> LENGTH: 1215
<212> TYPE: DNA
<213> ORGANISM: Homo sapiens

<400> SEQUENCE: 25

```
gccaggaagg cttgcaggtt ctgctgtttg gttgctgaag ggggtcagtg tgtgtatgtg    60
tcatggaggt gggcagggaa ggggagggct gtgcgtgggg gagaggatat atatgctggt   120
gtggctgaga aagcggaacc gagcctcgca tccatcggag ggagccgggg actgacagct   180
ctcagcacct gcttcctgct cctgcaccat gaaagtcctg ctttgtgacc tgctgctgct   240
```

```
cagtctcttc tccagtgtgt tcagcagttg tcagagggac tgtctcacat gccaggagaa      300
gctccaccca gccctggaca gcttcgacct ggaggtgtgc atcctcgagt gtgaagagaa      360
ggtcttcccc agcccctct  ggactccatg caccaaggtc atggccagga gctcttggca     420
gctcagccct gccgcccag  agcatgtggc ggctgctctc taccagccga gagcttcgga     480
gatgcagcat ctgcggcgaa tgccccgagt ccggagcttg ttccaggagc aggaagagcc     540
cgagcctggc atggaggagg ctggtgagat ggagcagaag cagctgcaga agagatttgg     600
gggcttcacc ggggcccgga agtcggccag gaagttggcc aatcagaagc ggttcagtga     660
gtttatgagg caatacttgg tcctgagcat gcagtccagc cagcgccggc gcaccctgca     720
ccagaatggt aatgtgtagc cggaagggc  gctcctccca gctgtaccgg ccactgcaac     780
ccatgagcgt ccaggtgatc ccccaaacag catgtgctca gccccagacc tgccgcctgg     840
gaatcaggat tccttcttcc ccaaggcact gagcgcctgc agatcccgca ggcttcgttt      900
gcctccagaa ccttcccgtc tgattgttcc tccccagccc cctggcatgt ttcaccacaa     960
ccctgttgct acatcagagt gtattttttgt aattcctcta gctaccattt caatagcccc    1020
atctctcctg ctcacccgcc tcttgcccct tctaggggca ggtgaaagga ataggaaatt     1080
gaacctgggg ttttgacttg ccactgccat aacttgttg  taaaagagct gttctttttg    1140
actgattgtt ttaaacaacg atttctccat taaacttcta ctgagcaaat ggttaataaa     1200
aaaaaaaaaa aaaaa                                                      1215

<210> SEQ ID NO 26
<211> LENGTH: 4264
<212> TYPE: DNA
<213> ORGANISM: Homo sapiens

<400> SEQUENCE: 26
agagcgctgc ggccgcggcg gtgcagcaga ggcgcctcgg gcaggaggag ggcggcttct       60
gcgagggcag cctgaggtat taaaaagtgt cagcaaactg cattgaataa cagacatcct      120 aagagggat  attttccacc tctataatga agaaagcag  gagtgtgatg acggtgatgg     180
ctgatgataa tgttaaagat tattttgaat gtagcttgag taaatcctac agttcttcca     240
gtaacacact tgggatcgac ctctggagag ggagaaggtg ttgctcagga aacttacagt     300
taccaccact gtctcaaaga cagagtgaaa gggcaaggac tcctgaggga gatggtatt     360 ccaggccgac cacactgcct ttgacaacgc ttccaagcat tgctattaca actgtaagcc     420
aggagtgctt tgatgtggaa aatggcccct ccccaggtcg gagtccactg gatccccagg     480
ccagctcttc cgctgggctg gtacttcacg ccacctttcc tgggcacagc cagcgcagag     540
agtcatttct ctacagatca gacagcgact atgacttgtc accaaggcg  atgtcgagaa     600 actcttctct tccaagcgag caacacggcg atgacttgat tgtaactcct tttgcccagg     660
tccttgccag cttgcgaagt gtgagaaaca acttcactat actgacaaac cttcatggta    720
catctaacaa gaggtcccca gctgctagtc agcctcctgt ctccagagtc aacccacaag      780
aagaatctta tcaaaaatta gcaatggaaa cgctggagga attagactgg tgtttagacc     840
agctagagac catacagacc taccggtctg tcagtgagat ggcttctaac aagttcaaaa     900
gaatgctgaa ccgggagctg acacacctct cagagatgag ccgatcaggg aaccaggtgt     960
ctgaatacat ttcaaatact ttcttagaca gcagaatga  tgtggagatc ccatctccta    1020
cccagaaaga cagggagaaa aagaaaaagc agcagctcat gacccagata agtggagtga     1080
agaaattaat gcatagttca agcctaaaca atacaagcat ctcacgcttt ggagtcaaca    1140
```

```
ctgaaaatga agatcacctg gccaaggagc tggaagacct gaacaaatgg ggtcttaaca    1200
tctttaatgt ggctggatat tctcacaata gaccccTaac atgcatcatg tatgctatat    1260
tccaggaaag agacctccta aagacattca gaatctcatc tgacacattt ataacctaca    1320
tgatgacttt agaagaccat taccattctg acgtggcata tcacaacagc ctgcacgctg    1380
ctgatgtagc ccagtcgacc catgttctcc tttctacacc agcattagac gctgtcttca    1440
cagatttgga gatcctggct gccattttg cagctgccat ccatgacgtt gatcatcctg     1500
gagtctccaa tcagtttctc atcaacacaa attcagaact tgctttgatg tataatgatg    1560
aatctgtgtt ggaaaatcat caccttgctg tgggtttcaa actgctgcaa gaagaacact    1620
gtgacatctt catgaatctc accaagaagc agcgtcagac actcaggaag atggttattg    1680
acatggtgtt agcaactgat atgtctaaac atatgagcct gctggcagac ctgaagacaa    1740
tggtagaaac gaagaaagtt acaagttcag gcgttcttct cctagacaac tataccgatc    1800
gcattcaggt ccttcgcaac atggtacact gtgcagacct gagcaacccc ccaagtcct    1860 tggaattgta tcggcaatgg acagaccgca tcatggagga ttttttccag cagggagaca    1920
aagagcggga gaggggaatg gaaattagcc caatgtgtga taaacacaca gcttctgtgg    1980
aaaaatccca ggttggtttc atcgactaca ttgtccatcc attgtgggag acatgggcag    2040
atttggtaca gcctgatgct caggacattc tcgataccTt agaagataac aggaactggt    2100
atcagagcat gatacctcaa agtccctcac caccactgga cgagcagaac agggactgcc    2160
agggtctgat ggagaagttt cagtttgaac tgactctcga tgaggaagat tctgaaggac    2220
ctgagaagga gggagaggga cacagctatt tcagcagcac aaagacgctt tgtgtgattg    2280
atccagaaaa cagagattcc ctgggagaga ctgacataga cattgcaaca gaagacaagt    2340
cccccgtgga tacataatcc ccctctccct gtggagatga acattctatc cttgatgagc    2400
atgccagcta tgtggtaggg ccagcccacc atggggcca agacctgcac aggacaaggg     2460
ccacctggcc tttcagttac ttgagtttgg agtcagaaag caagaccagg aagcaaatag    2520
cagctcagga aatcccacgg ttgacttgcc ttgatggcaa gcttggtgga gagggctgaa    2580
gctgttgctg ggggccgatt ctgatcaaga cacatggctt gaaaatgaa gacacaaaac     2640 tgagagatca ttctgcacta agtttcggga acttatcccc gacagtgact gaactcactg    2700
actaataact tcatttatga atcttctcac ttgtcccttt gtctgccaac ctgtgtgcct    2760
tttttgtaaa acatttcat gtctttaaaa tgcctgttga atacctggag tttagtatca    2820
acttctacac agataagctt tcaaagttga caaacttttt tgactctttc tggaaaaggg    2880
aaagaaaata gtcttccttc tttcttgggc aatatcccttc actttactac agttacttt    2940 gcaaacagac agaaaggata cacttctaac cacatttTac ttccttcccc tgttgtccag    3000
tccaactcca cagtcactct taaaacttct ctctgtttgc ctgcctccaa cagtactttt    3060 aacttttgc tgtaaacaga ataaaattga acaaattagg gggtagaaag gagcagtggt     3120
gtcgttcacc gtgagagtct gcatagaact cagcagtgtg ccctgctgtg tcttggaccc    3180
tgccccccac aggagttgta cagtccctgg ccctgttccc tacctcctct cttcacccCg    3240
ttaggctgtt ttcaatgtaa tgctgccgtc cttctcttgc actgccttct gcgctaacac    3300
ctccattcct gttTataacc gtgtatttat tacttaatgt atataatgta atgttttgta    3360
agttattaat ttatatatct aacattgcct gccaatggtg gtgttaaatt tgtgtagaaa    3420
actctgccta agagttacga cttttTcttg taatgttttg tattgtgtat tatataaccc    3480
```

| | |
|---|---:|
| aaacgtcact tagtagagac atatggcccc cttggcagag aggacagggg tgggcttttg | 3540 |
| ttcaaagggt ctgcccttc cctgcctgag ttgctacttc tgcacaaccc ctttatgaac | 3600 |
| cagttttgga aacaatattc tcacattaga tactaaatgg tttatactga gcttttactt | 3660 |
| ttgtatagct tgatagggc aggggcaat gggatgtagt ttttacccag gttctatcca | 3720 |
| aatctatgtg ggcatgagtt gggttataac tggatcctac tatcattgtg gctttggttc | 3780 |
| aaaaggaaac actacatttg ctcacagatg attcttctga atgctcccga actactgact | 3840 |
| ttgaagaggt agcctcctgc ctgccattaa gcaggaatgt catgttccag ttcattacaa | 3900 |
| aagaaaacaa taaacaatg tgaattttta taataaaatg tgaactgatg tagcaaatta | 3960 |
| cgcaaatgtg aagcctcttc tgataacact tgttaggcct cttactgatg tcagtttcag | 4020 |
| tttgtaaaat atgtttcatg ctttcagttc agcattgtga ctcagtaatt acagaaaatg | 4080 |
| gcacaaatgt gcatgaccaa tgtatgtcta tgaacactgc attgtttcag gtggacattt | 4140 |
| tatcattttc aaatgtttct cacaatgtat gttatagtat tattattata tattgtgttc | 4200 |
| aaatgcattc taaagagact tttatatgag gtgaataaag aaaagcatga ttagattaaa | 4260 |
| aaaa | 4264 |

<210> SEQ ID NO 27
<211> LENGTH: 2759
<212> TYPE: DNA
<213> ORGANISM: Homo sapiens

<400> SEQUENCE: 27

| | |
|---|---:|
| gctcaggccc cgcccctgcc gccggaatcc tgaagcccaa ggctgcccgg gggcggtccg | 60 |
| gcggcgccgg cgatggggca taaaaccact ggccacctgc cgggctgctc ctgcgtgcgc | 120 |
| tgccgtcccg gatccaccgt gcctctgcgg cctgcgtgcc cggagtcccc gcctgtgtcg | 180 |
| tctctgtcgc cgtccccgtc tcctgccagg cgcggagccc tgcgagccgc gggtgggccc | 240 |
| caggcgcgca gacatgggct gctccgccaa agcgcgctgg gctgccgggg cgctgggcgt | 300 |
| cgcggggcta ctgtgcgctg tgctgggcgc tgtcatgatc gtgatggtgc cgtcgctcat | 360 |
| caagcagcag gtccttaaga acgtgcgcat cgacccagt agcctgtcct tcaacatgtg | 420 |
| gaaggagatc cctatcccct tctatctctc cgtctacttc tttgacgtca tgaaccccag | 480 |
| cgagatcctg aagggcgaga agccgcaggt gcggagcgc gggcccctacg tgtacaggga | 540 |
| gttcaggcac aaaagcaaca tcaccttcaa caacaacgac accgtgtcct tcctcgagta | 600 |
| ccgcaccttc cagttccagc cctccaagtc ccacggctcg gagagcgact acatcgtcat | 660 |
| gcccaacatc ctggtcttgg gtgcggcggt gatgatggag aataagccca tgaccctgaa | 720 |
| gctcatcatg accttggcat tcaccaccct cggcgaacgt gccttcatga accgcactgt | 780 |
| gggtgagatc atgtggggct acaaggaccc ccttgtgaat ctcatcaaca gtactttcc | 840 |
| aggcatgttc cccttcaagg acaagttcgg attatttgct gagctcaaca actccgactc | 900 |
| tgggctcttc acggtgttca cggggggtcca gaacatcagc aggatccacc tcgtggacaa | 960 |
| gtggaacggg ctgagcaagg ttgacttctg gcattccgat cagtgcaaca tgatcaatgg | 1020 |
| aacttctggg caaatgtggc cgcccttcat gactcctgag tcctcgctgg agttctacag | 1080 |
| cccggaggcc tgccgatcca tgaagctaat gtacaaggag tcagggtgt ttgaaggcat | 1140 |
| ccccacctat cgcttcgtgg ctcccaaaac cctgtttgcc aacgggtcca tctacccacc | 1200 |
| caacgaaggc ttctgcccgt gcctggagtc tggaattcag aacgtcagca cctgcaggtt | 1260 |
| cagtgccccc ttgtttctct cccatcctca cttcctcaac gctgacccgg ttctggcaga | 1320 |

| | |
|---|---|
| agcggtgact ggcctgcacc ctaaccagga ggcacactcc ttgttcctgg acatccaccc | 1380 |
| ggtcacggga atccccatga actgctctgt gaaactgcag ctgagcctct acatgaaatc | 1440 |
| tgtcgcaggc attggacaaa ctgggaagat tgagcctgtg gtcctgccgc tgctctggtt | 1500 |
| tgcagagagc ggggccatgg aggggagac tcttcacaca ttctacactc agctggtgtt | 1560 |
| gatgcccaag gtgatgcact atgcccagta cgtcctcctg gcgctgggct gcgtcctgct | 1620 |
| gctggtccct gtcatctgcc aaatccggag ccaagagaaa tgctatttat tttggagtag | 1680 |
| tagtaaaaag ggctcaaagg ataaggaggc cattcaggcc tattctgaat ccctgatgac | 1740 |
| atcagctccc aagggctctg tgctgcagga agcaaaactg tagggtcctg aggacaccgt | 1800 |
| gagccagcca ggcctggccg ctgggcctga ccggcccccc agcccctaca cccgcttct | 1860 |
| cccggactct cccagcggac agccccccag ccccacagcc tgagcctccc agctgccatg | 1920 |
| tgcctgttgc acacctgcac acacgccctg gcacacatac acacatgcgt gcaggcttgt | 1980 |
| gcagacactc agggatggag ctgctgctga agggacttgt agggagaggc tcgtcaacaa | 2040 |
| gcactgttct ggaaccttct ctccacgtgg cccacaggcc tgaccacagg ggctgtgggt | 2100 |
| cctgcgtccc cttcctcggg tgagcctggc ctgtcccgtt cagccgttgg gcccaggctt | 2160 |
| cctcccctcc aaggtgaaac actgcagtcc cggtgtggtg gctccccatg caggacgggc | 2220 |
| caggctggga gtgccgcctt cctgtgccaa attcagtggg gactcagtgc ccaggccctg | 2280 |
| gccacgagct ttggccttgg tctacctgcc aggccaggca aagcgccttt acacaggcct | 2340 |
| cggaaaacaa tggagtgagc acaagatgcc ctgtgcagct gcccgagggt ctccgcccac | 2400 |
| cccggccgga ctttgatccc cccgaagtct tcacaggcac tgcatcgggt tgtctggcgc | 2460 |
| ccttttcctc cagcctaaac tgacatcatc ctatggactg agccggccac tctctggccg | 2520 |
| aagtggccgc aggctgtgcc cccgagctgc ccccaccccc tcacagggtc cctcagatta | 2580 |
| taggtgccca ggctgaggtg aagaggcctg ggggccctgc cttccgggcg ctcctggacc | 2640 |
| ctggggcaaa cctgtgaccc ttttctactg gaatagaaat gagttttatc atctttgaaa | 2700 |
| aataattcac tcttgaagta ataaacgttt aaaaaaatgg gaaaaaaaaa aaaaaaaa | 2759 |

<210> SEQ ID NO 28
<211> LENGTH: 2184
<212> TYPE: DNA
<213> ORGANISM: Homo sapiens

<400> SEQUENCE: 28

| | |
|---|---|
| gtgcgcgaac ggctccggcc cgcacgggtc gccagaggcg actgtgtgac actcggagtt | 60 |
| tgctggggtc tccgtgggcg ggaggacttt ccagcgcaat ggcgactccc taagccccgc | 120 |
| agcttctgcg cccgggaaag atatccaaga gatgcaaagc tctactgggc ccaggctgcc | 180 |
| accccagagg cccccttccg tcccggggcc ggggctaggc caaggcgggc accaggactg | 240 |
| cccagcctcc cggcccttcg cactggtaac cggttccggg gcggatgctt tttgcatctg | 300 |
| acccggcgcg cccggtgacg ccttcgcgtc cagacggaag tgcgggcgga ggatccccag | 360 |
| ccgggtccca agcctgtgcc tgagcctgag cctgagcctg agcccgagcc gggagccggt | 420 |
| cgcgggggct ccgggctgtg ggaccgctgg gcccccagca tggcgaccc tgtggggagg | 480 |
| ccttcttcgg cttggctcct tgctcagcct gtcgtgcctg gcgctttccg tgctgctgct | 540 |
| ggcgcagctg tcagacgccg ccaagaattt cgaggatgtc agatgtaaat gtatctgccc | 600 |
| tccctataaa gaaaattctg ggcatatttta taataagaac atatctcaga agattgtga | 660 |

```
ttgccttcat gttgtggagc ccatgcctgt gcggggcct gatgtagaag catactgtct    720
acgctgtgaa tgcaaatatg aagaaagaag ctctgtcaca atcaaggtta ccattataat    780
ttatctctcc attttgggcc ttctacttct gtacatggta tatcttactc tggttgagcc    840
catactgaag aggcgcctct ttggacatgc acagttgata cagagtgatg atgatattgg    900
ggatcaccag cctttttgcaa atgcacacga tgtgctagcc cgctcccgca gtcgagccaa    960
cgtgctgaac aaggtagaat atgcacagca gcgctggaag cttcaagtcc aagagcagcg   1020
aaagtctgtc tttgaccggc atgttgtcct cagctaattg ggaattgaat tcaaggtgac   1080
tagaaagaaa caggcagaca actgaaagaa actgactggg ttttgctggg tttcatttta   1140
ataccttgtt gatttcacca actgttgctg aagattcaa aactggaagc aaaaacttgc   1200
ttgatttttt tttcttgtta acgtaataat agagacattt ttaaaagcac acagctcaaa   1260
gtcagccaat aagtcttttc ctatttgtga cttttactaa taaaaataaa tctgcctgta   1320
aattatcttg aagtccttta cctggaacaa gcactctctt tttcaccaca tagttttaac   1380
ttgactttca agataatttt cagggttttt gttgttgttg tttttttttt gtttgttttg   1440
gtgggagagg ggagggatgc ctgggaagtg gttaacaact tttttcaagt cactttacta   1500
aacaaacttt tgtaaataga ccttaccttc tattttcgag tttcatttat attttgcagt   1560
gtagccagcc tcatcaaaga gctgacttac tcatttgact tttgcactga ctgtattatc   1620
tgggtatctg ctgtgtctgc acttcatggt aaacgggatc taaatgcct ggtggctttt   1680
cacaaaaagc agattttctt catgtactgt gatgtctgat gcaatgcatc ctagaacaaa   1740
ctggccattt gctagtttac tctaaagact aaacatagtc ttggtgtgtg tggtcttact   1800
catcttctag taccttttaag gacaaatcct aaggacttgg acacttgcaa taaagaaatt   1860
ttattttaaa cccaagcctc cctggattga taatatatac acatttgtca gcatttccgg   1920
tcgtggtgag aggcagctgt ttgagctcca atgtgtgcag ctttgaacta gggctggggt   1980
tgtgggtgcc tcttctgaaa ggtctaacca ttattggata actggctttt ttcttcctat   2040
gtcctctttg gaatgtaaca ataaaaataa ttttgaaac atccatcagt gtatctatct   2100
atgtctccta gttttttcct cctccctctt tgctgtata atgagattga agatataaag   2160
acattttgta ccctgtaaaa aaaa                                            2184
```

<210> SEQ ID NO 29
<211> LENGTH: 5135
<212> TYPE: DNA
<213> ORGANISM: Homo sapiens

<400> SEQUENCE: 29

```
aactcaaggc ctgcttgata cgtccgccat tttgggcgct tcgctgatgg tgtcggtgag     60
cgcgtttccc gcctgagcgc aactagcggc gggtcgtggg cacctccagg agagcttgtt   120
tcatatccat atcccactgt attcctgcta atctgctaat gcagtaaatt ggaggaaaac   180
tgttaccagg ataacctgta atgggcaagg agccacaaag aagaaaacat ttctttaat    240
ttttaaactt ggtttgaaag accagcatgt tttggaaatt tgatcttcac tcatcatccc   300
acatagacac acttctagaa agagaagatg taacactgaa ggagttaatg gatgaggaag   360
atgttttaca ggaatgtaaa gctcagaacc gcaaacttat agagtttctg ttaaaagcag   420
aatgtctcga gatttagtc tcattcatta tagaagaacc acctcaagac atggatgaaa   480
agatcagata caagtatcca atatatcctt gtgagttgct cacttctgat gtctcccaga   540
tgaatgatag actgggagaa gatgaatcct tgctaatgaa attatatagc ttcctcctaa   600
```

```
acgattcccc tttgaatcca ctacttgcca gtttcttcag caaggtgcta agtattctta     660
tcagcagaaa accagaacag attgtggatt tcttaaagaa gaagcatgat tttgtagacc     720
ttattataaa gcacatagga acttctgcta tcatggattt gttgctcagg ctcctgacgt     780
gtatcgaacc tccacagccc aggcaagatg tgctgaattg gttaaatgag gagaaaatta    840
tccagaggct tgtggaaata gttcatccat cgcaagaaga agatcgacat tcaaatgcat    900
cacaatcact ttgtgaaatt gttcgcctga gcagagacca gatgttacaa attcagaaca    960
gtacagagcc cgaccccctg cttgccactc tagaaaagca agaaattata gagcagcttc    1020
tatcaaatat tttccacaag gagaaaaatg agtcagccat agtcagtgca atccagatat    1080
tgctgacttt acttgagaca cgacgaccaa catttgaagg ccatatagag atctgcccac    1140
caggcatgag ccattcagct tgttcagtaa acaagagtgt tctagaagcc atcagaggaa    1200
gacttggatc ttttcatgaa ctcctgctgg agccacccaa gaaaagtgtg atgaagacca    1260
catggggtgt gctggatcct cctgtgggga atacccggtt gaatgtcatt aggttgatat    1320
ccagcctgct tcaaaccaat accagcagta taaatgggga ccttatggag ctgaatagca    1380
ttggagtcat attgaacatg ttcttcaagt atacatggaa taacttttg catacacaag     1440 tggaaatttg tattgcactg attcttgcaa gtccttttga aaacacagaa aatgccacaa    1500
ttaccgatca agactccact ggtgataatt tgttattaaa acatcttttc caaaaatgtc    1560
aattaataga acgaatactt gaagcctggg aaatgaatga gaagaaacag gctgagggag    1620
gaagacggca tggttacatg ggacacctaa cgaggatagc taactgtatc gtgcacagca    1680
ctgacaaggg ccccaacagt gcattagtgc agcagcttat caagatcttc ccgacgaag    1740 tcagggaacg atgggagacg ttctgcacaa gctccttagg agaaactaac aagaggaaca    1800
cggtagatct agttacaacc tgccatattc attcatccag tgatgatgaa attgacttta    1860
aagaaacggg tttctcacag gattcttctt tgcagcaagc cttttctgat tatcagatgc    1920
aacaaatgac gtccaatttt attgaccagt ttggcttcaa cgatgagaag tttgcagatc    1980
aagatgacat tggcaatgtt tcttttgatc gagtatcaga catcaacttt actctcaata    2040
caaatgaaag tggaaatatt gccttgtttg aagcatgttg taaggaaaga atacaacagt    2100
ttgatgatgg tggctctgat gaggaagata tatgggagga aaagcacatc gcattcacac    2160
cagaatccca aagacgatcc agctcgggga gtacagacag tgaggaaagt acagactctg    2220
aagaagaaga tggagcaaag caagacttgt ttgaacccag cagtgccaac acggaggata    2280
aaatggaggt ggacctgagt gaaccaccca actggtcagc taactttgat gtcccaatgg    2340
aaacaaccca cggtgctcca ttggattctg tgggatctga tgtctggagc acagaggagc    2400
cgatgccaac taaagagacg ggctgggctt cttttcaga gttcacgtct tccctgagca    2460
caaaagattc tttaaggagt aattctccag tggaaatgga aaccagcact gaacccatgg    2520
accctctgac tccagtgcg gctgccctgg cagtgcagcc agaagcggca ggcagtgtgg     2580
ccatggaagc cagctctgac ggagaggagg atgcagaaag tacagacaag gtaactgaga    2640
cagtgatgaa tggcggcatg aaggaaacgc tcagcctcac tgtagatgcc aagacagaga    2700
ctgcggtctt caaaagtgag gaagggaaac tgtctacctc tcaagatgct gcttgtaaag    2760
acgcagagga gtgtccgag actgcagagg cgaagtgcgc ggcgcccagg cctcccagca    2820
gcagtcccga gcagagtgcc tccgatgcct gtcgttgct ccttaggact ggccaaccaa     2880
gcgcaccagg tgacacttca gtgaatggcc ctgtatgacg ggtgacgtct gctgctgctg    2940
```

```
actgaggact gcagaccgcc accactcagg ggctctggag gggtcagctg gagcccacca    3000
agctgtcact gctgcactca ctctgcaagg gatcaggacc agcaaccttt atattctaga    3060
ttctaagaca ttgtacagag aaattcagaa gtgtaaaaat attgcacatt gacaaatacc    3120
aagaatttt  gcgtatgttt atattgtatt gttctaaata atgggtagcc tgtgaaataa    3180
gatcttgcca cccatgtaat aatagtagta atactatagt taaaatggct gtaagaatag    3240
ttttataaaa gtgaatacac agatctattg tatttgaaac ataactttga caattattag    3300
tgtgaccaaa gtattaggcg gttttcatac attttttcacc ttgtacaaaa ttatgaattc    3360
attttttcctc caggccgaca aggagttgta gaatgaaaat gccctctaag tgttattttg    3420
gttgttctaa cttacaaaag tgattttgaa taagaaatat ttggtgttct ttttataacc    3480
agttttgat  tggtaattgt tttctgtatt gtttaaaacg gatcaaaaat gtaagtctat    3540
tggtagagat taagtaaagt atttattgct acatcatagt tgataaattg atgttatcgt    3600
aaagccatat gttctgttca agtcttgttt gcttgaaatg attattccta caagtgaaac    3660
actagactat ttggagtgta tatggcttgt gttttgggat tttttttttt tttttttggc    3720
ttttgttttt gtttgttttt ttgtttcatt tggtagttca tctgccttt  aacccattca    3780
ccaaaattta ccttgttaac aagcatcacc aatgaacatt tcagagcaat ctgcatattt    3840
aacagaccta aaataaatcc tattaggcaa gtcagttgaa aatgctcgtg ctgctaatgg    3900
aattagagtg cgttcatttt acaggctagt attttaaaag tagaaatcaa aatctggcac    3960
cgaagcatgc taattgttta ctgtaccttg tgaggttttc actcataaat ttaaaccagt    4020
gtatttttt  agaactggtt tgtgtatata tatagtgatt atggatacta attcaatgta    4080
atttataatt ttctatgtca atacaaaaat acatcacagc cttctcaaac agctcaagca    4140
atatattgta tattgccata tcgtctggtg aaagggttaa attacttcac ctcttgcact    4200
tttagatgca aatcagtttt tcatttctgt aatagaaaat tattcacgta tttttacatc    4260
atttgttttt cctgaccagt atttaaaacc aaaaggatat tctgaaaaat ggccaacaat    4320
tttttagaa gtagcatccc aagcagcgtg cctaaacatt acattgcata tggaaataaa    4380
agaatcaaac gtctaatgcc ttattatttc tgatttcctt tttcatttta agtggtgtgg    4440
agattccagc actcccagga cagtggagtc agcagtaagc cctgggacag gtggcaaggg    4500
tgggtccctt gacctttgca cgcctcctca ggaaccccct ttcccgggtg agccctctc     4560
tgaagagact gtccttgggc ctcctctgga agcagcaccc ccagaggaca gggctcctcc    4620
tgcttgcctc agggctgcct gacttgaatg gcgttgacc  tcggggatta ctggtagata    4680
atatgctctg gtctcgcctg gtggtgagtt ttgccagcca tggccagggt ttggctccac    4740
tggtggcaca cgtggcctcc gtggtatgga cctggtggct tctccatccc actgtggcct    4800
ctgtggtatg gacctggtgg cttctccatc ctacccaagg taacagtgtc ttgcttcatc    4860
ccactgactg ctgggagaga gcctctggga cttttctttg gggcatcatt ttgttttgtc    4920
tttcgtagca gggaaaggat atgacaatgg ggaggacagt tctttggag gttggagggg    4980
ccaagccaag gacaggagca agtgtgccct cattttgttt ctacttttaa tttctgtgtg    5040
ttggccatac tgaattatga gactaacaga tgtctacaat acaatacctg tattcaaaat    5100
aacaaaaata aagcctgatt ctttgtttct agaaa                               5135
```

<210> SEQ ID NO 30
<211> LENGTH: 76
<212> TYPE: DNA
<213> ORGANISM: Homo sapiens

```
<400> SEQUENCE: 30
tgagggagga agacggcatg gttacatggg acacctaacg aggatagcta actgtatcgt      60
gcacagcact gacaag                                                      76

<210> SEQ ID NO 31
<211> LENGTH: 66
<212> TYPE: DNA
<213> ORGANISM: Homo sapiens

<400> SEQUENCE: 31
gacagatttc taccactcca aacgccggct gatcttctcc aagaggaagc cctaatccgc      60
ccacag                                                                 66
```

RADIATION BIODOSIMETRY SYSTEMS

CROSS-REFERENCE TO RELATED APPLICATIONS

This application claims the benefit of U.S. Provisional Application No. 62/038,969, filed Aug. 19, 2014, which is hereby incorporated by reference in its entirety for all purposes.

STATEMENT REGARDING FEDERALLY SPONSORED RESEARCH OR DEVELOPMENT

This invention was made with the government support under HHS0100201000008-C awarded by the Biomedical Advanced Research and Development Authority. The government has certain rights in the invention.

BACKGROUND

Radiation exposure is one of the most serious hazards of the modern era. The health consequences to individuals and populations exposed to radiological incidents, accidental or otherwise, can range from negligible to fatal depending on the amount of radiation that is absorbed by an individual. Yet, it is often difficult or impossible to quickly determine the absorbed dose of radiation for an individual or population after a radiological event and thereby determine an appropriate course of treatment. This is particularly critical when large numbers of individuals are potentially affected by radiation exposure and must be quickly "triaged" to prioritize treatment strategies. Thus, there is a great need for systems that quickly estimate, post-hoc, the absorbed dose of radiation by an individual resulting from an ionizing radiation exposure incident.

BRIEF SUMMARY OF THE INVENTION

Disclosed herein are compositions and methods for accurately estimating the absorbed dose of radiation suffered by a subject based on the expression pattern in RNA obtained from peripheral blood of a panel of radiation-modulated (RM) genes at various time points following exposure of the subject to ionizing radiation.

Accordingly in one aspect provided herein is a radiation biodosimetry assay system, comprising a plurality of nucleic acid amplification reactions comprising (i) mRNA or cDNA from a human subject suspected of (but not necessarily) suffering from radiation exposure; (ii) primer pairs capable of hybridizing under stringent conditions to mRNAs or cDNAs comprising the nucleotide sequences referred to in Table 4 or the complementary sequences thereof, wherein each primer pair hybridizes to a different one of the mRNAs or cDNAs; and (iii) a thermostable enzyme suitable for amplification of target amplicon sequences from the mRNAs or cDNAs. A mathematical algorithm that converts gene expression results to estimated absorbed dose of radiation.

In some embodiments the one or more nucleic acid amplification reactions further comprise detectably labeled TaqMan® probes capable of hybridizing under stringent conditions to the mRNAs or cDNAs. In some embodiments the thermostable enzyme is a thermostable polymerase.

In some embodiments the mRNA is from a subject that was exposed to radiation about 4-hours to about seven days prior to the time at which a biological sample comprising the mRNA was obtained.

In another aspect provided herein is a radiation biomarker assay kit, comprising a nucleic acid probe set consisting essentially of nucleic acid probes that hybridize specifically with nucleic acid targets comprising at least one of the nucleotide sequences referred to in SEQ ID NOs: 1-29 or the complementary sequences thereof. In some embodiments the probe set comprises no more than 100 probes. In some embodiments the probe set consists of the nucleic acid probes that hybridize specifically with the nucleic acid targets.

In some embodiments the nucleic acid probe set comprises primer pairs and TaqMan probes suitable for qPCR analysis of mRNAs or cDNAs comprising at least one of the nucleotide sequences referred to in SEQ ID NOS: 1-29 or the complementary sequences thereof. In some embodiments the nucleic acid probes are provided in a multi-well plate. In some embodiments, where the nucleic acid probes are provided in a multi-well plate, at least two nucleic acid probes that hybridize to at least two different nucleic acid targets are in the same wells of the multi-well plate.

In some embodiments the kit also includes radiation exposure positive and negative control mRNA samples or cDNAs thereof. In another aspect provided herein is a method for assessing a dose of ionizing radiation absorbed by a subject, comprising (i) determining the mRNA expression levels of mRNAs comprising at least one of the nucleotide sequences referred to in SEQ ID NOs: 1-29 in a biological sample, comprising mRNA from the subject, to obtain an expression profile; and (ii) transforming the gene expression profile and when available, the duration of time from exposure to sample collection, into a measure of absorbed dose of radiation for the subject based on a mathematical algorithm. In one embodiment, the algorithm utilizes multiple random forest regression trees to estimate absorbed dose and confidence limits and then a top-level logic layer to combine outputs into a single estimated absorbed dose with confidence limits.

In some embodiments the method further includes treating the subject based on the estimated absorbed dose of radiation determined in step (ii).

In some embodiments the absorbed dose of ionizing radiation is determined within about seven days of subject exposure to ionizing radiation.

In some embodiments the method also includes a step of obtaining the biological sample from the subject prior to step (i).

In a further aspect provided herein is a method for radiation treatment triage of a subject in need thereof comprising (i) determining the mRNA expression levels of mRNAs comprising the nucleotide sequences referred to in at least one of SEQ ID NOs: 1-29 (or any other sequence identifier included herein, in any combination) in a biological sample comprising leukocyte mRNA from the subject to obtain a gene expression profile; and (ii) providing a suitable treatment for radiation exposure to the subject based on the expression levels of the genes.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

Figure 1A:
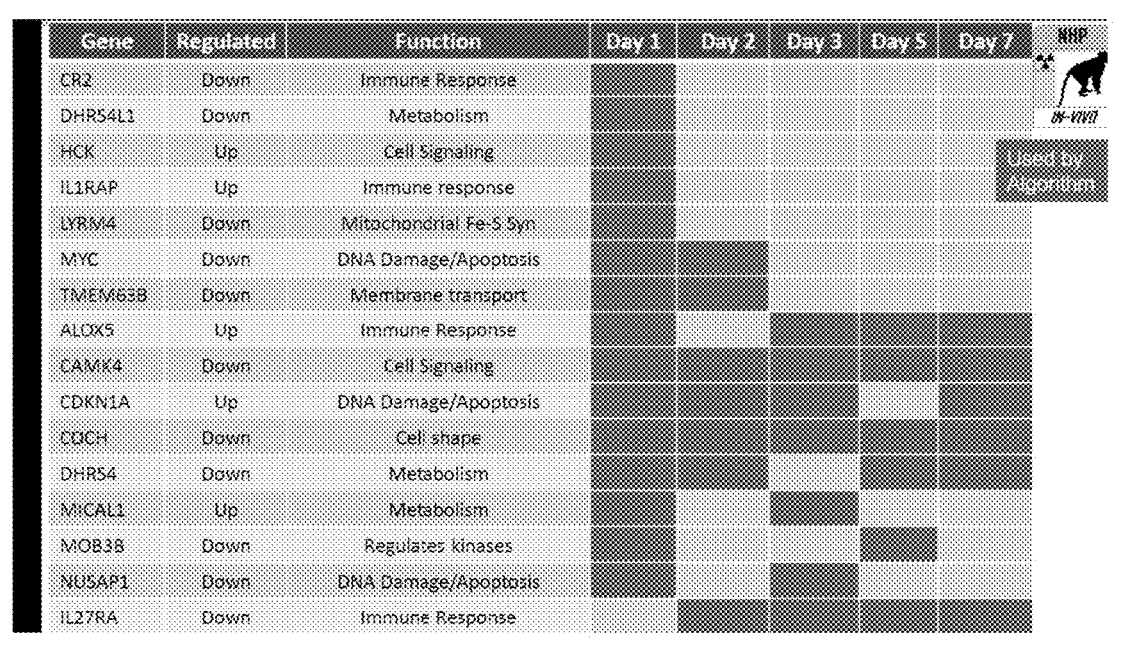

FIG. 1A show tables listing a set of 28 radiation modulated (RM) genes and their expression pattern at various time points following absorption of ionizing radiation.

FIG. 1B show tables listing a set of 28 radiation modulated (RM) genes and their expression pattern at various time points following absorption of ionizing radiation.

FIG. 4 shows a table providing the percentage accuracy (within 0.5 Gy) of the biodosimetry algorithm's absorbed radiation dose estimate based on expression of 29 RM genes in peripheral blood from NHPs at various time points (1-7 days) following exposure to irradiation doses ranging from 0 Gy to 10 Gy.

FIG. 6 shows a table describing the sensitivity and specificity of the biodosimetry algorithm in various NHP and human irradiation models.

DETAILED DESCRIPTION

Figure 2:
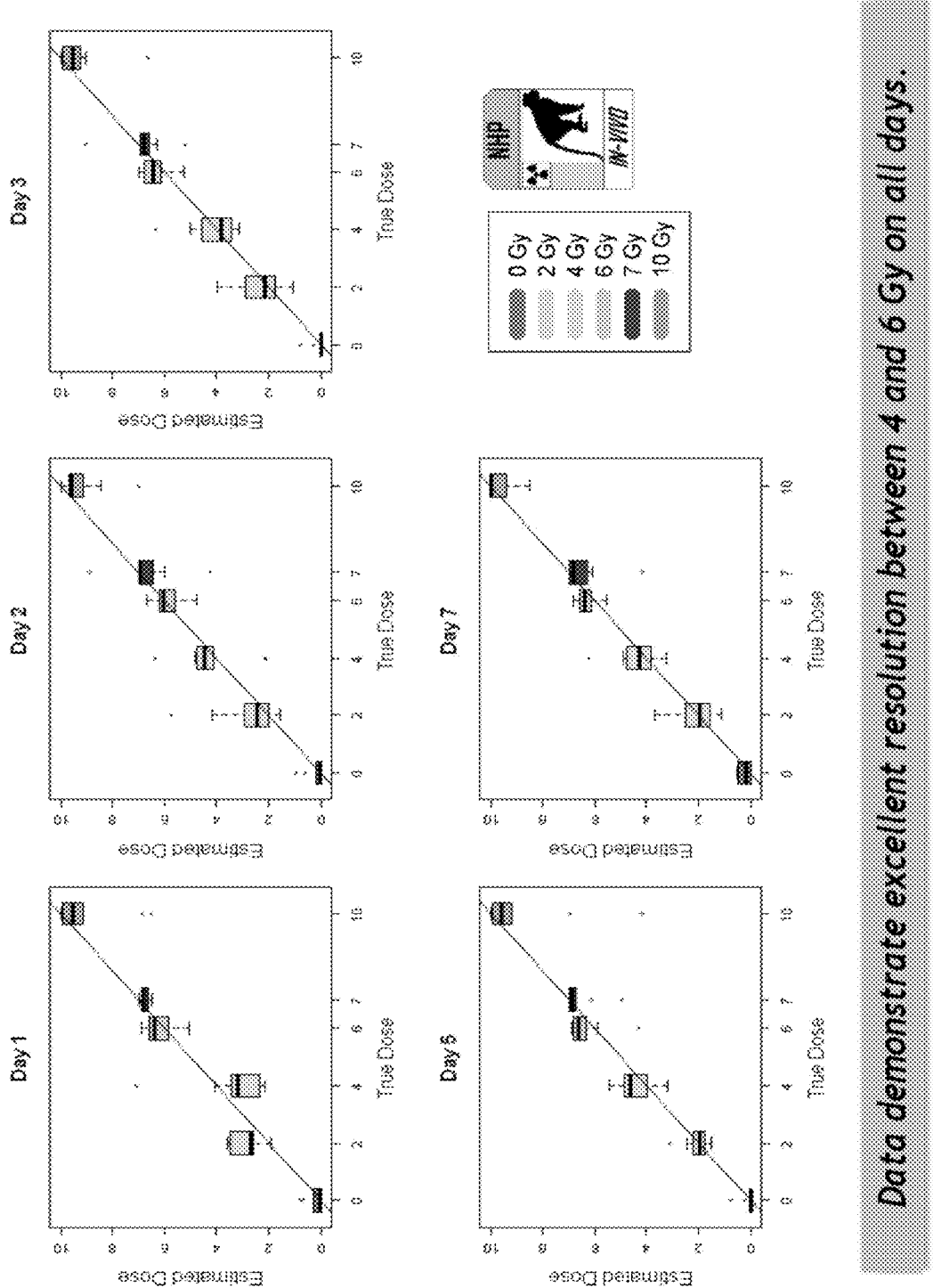
FIG. 2 shows a time series (days 1-7) of plots of actual delivered ionizing radiation dosage values (0 Gy to 10 Gy) versus estimated absorbed dose of radiation based on changes in RM gene expression in peripheral blood
Figure 3:
FIG. 3 shows a table providing the percentage accuracy (within 1 Gy) of the biodosimetry algorithm's absorbed radiation dose estimate based on expression of 29 RM genes in peripheral blood collected from rhesus macaque non-human primate (NHPs) at various time points (1-7 days) following exposure to irradiation doses ranging from 0 Gy to 10 Gy.
Figure 5:
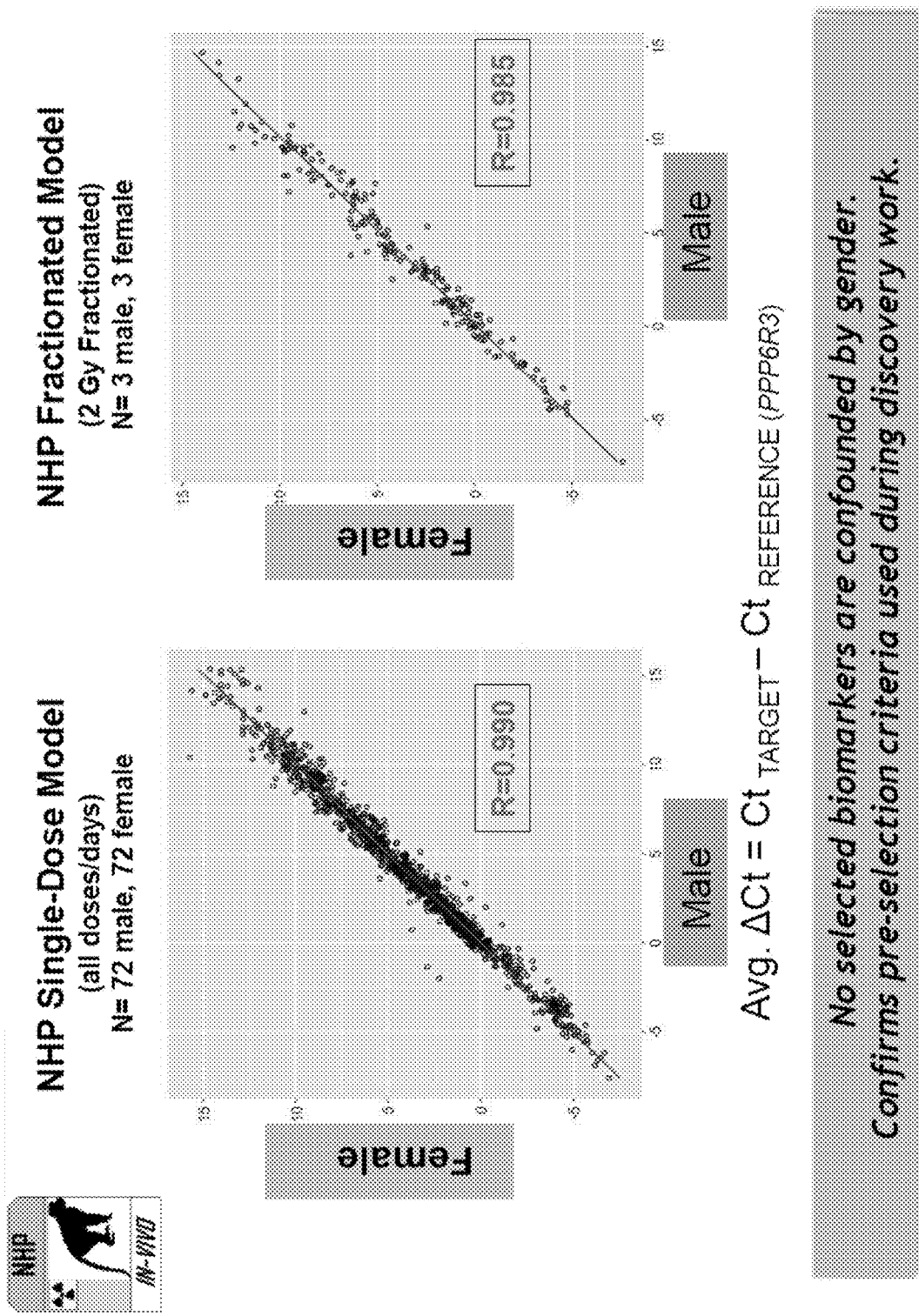
FIG. 5 shows scatter plots of changes in RM gene expression in male vs. female NHPs following radiation exposure of various doses and at different time points following radiation exposure. As shown, male and female RM gene expression responses were very closely correlated for the 29 RM genes.
Figure 7:
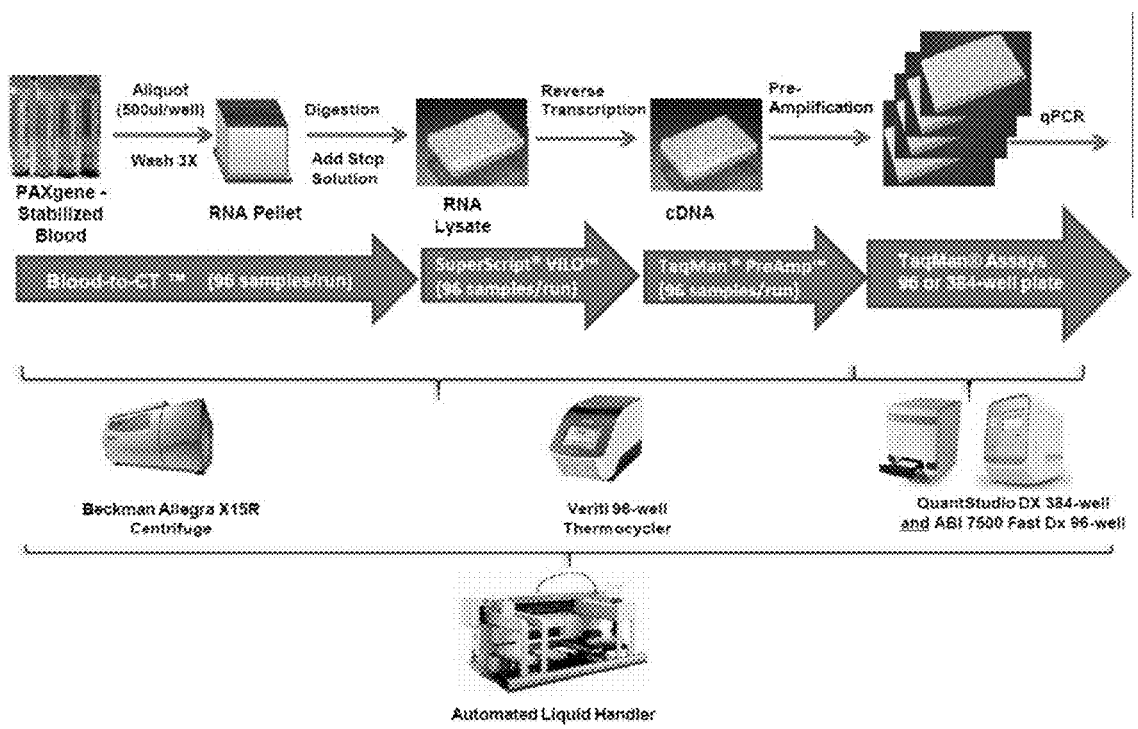
FIG. 7 shows an overview of an exemplary, non-limiting, embodiment of biodosimetry workflow illustrating the steps of: blood sample collection, RNA isolation, reverse transcription to obtain cDNA, pre-amplification of the cDNA, and qPCR assay of a RM biomarker and reference gene panel.

In General.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention.

The present invention provides methods for estimating absorbed dose of ionizing radiation by a subject, which includes the steps of: (i) determining the mRNA expression levels of mRNAs comprising the nucleotide sequences referred to in SEQ ID NOs: 1-29 in a biological sample comprising peripheral blood mRNA collected from the subject to obtain an expression profile; and (ii) transforming the gene expression profile and when available, the duration of time from exposure to sample collection into an estimated absorbed dose of ionizing radiation and confidence limits for a subject based on a mathematical algorithm. For each of several durations for which training data were available, one primary random forest was developed to estimate absorbed dose of radiation. Additional secondary random forests were developed to provide more accurate dosimetry in narrow dosage intervals. The top-level logic layer uses the primary random forest to generate an initial estimate of absorbed dose of radiation, and based on that value, may select additional random forests to construct more refined estimates of absorbed dose, with confidence limits.

In some embodiments the method also includes treating the subject based on the absorbed dose of ionizing radiation determined in step (ii) above. In some embodiments the absorbed dose of ionizing radiation is determined within about seven days of exposure to the ionizing radiation, e.g., within about 30 minutes, 1 hour, 3 hours, 6 hours, 8 hours, 24 hours, 1 day, 2 days, 3 days, 4 days, 5 days, 6 days, or another time period within seven days following ionizing irradiation. In some embodiments, the absorbed dose of ionizing radiation is within the range of about 0.5 Grays (Gy) to about 10 Gy, e.g., about 1 Gy, 2 Gy, 3 Gy, 4 Gy, 6 Gy, 7 Gy, 8 Gy, 9 Gy, or another absorbed dose of ionizing radiation from about 0.5 Gy to about 10 Gy.

In some embodiments, the method also includes obtaining the biological sample from the irradiated subject prior to step (i) above.

In one embodiment, a whole blood sample, or other blood fraction containing lymphocytes, (including a finger stick or POC device) is collected from a subject known to be or suspected of being irradiated into a PAXgene™ Blood RNA tube. The PAXgene™ Blood RNA contains an additive that stabilizes in vitro gene expression and RNA degradation. Subsequently, RNA is extracted from the stabilized blood sample by using a Stabilized Blood-to-CT™ Nucleic Acid Preparation Kit for qPCR (Life Technologies, Inc.). The RNA sample is then subjected to reverse transcription, e.g., using the Invitrogen™ SuperScript® VILO™ (Variable Input, Linear Output) cDNA synthesis kit (Life Technologies, Inc.) or equivalent kit. Afterwards, the resulting cDNA is pre-amplified using a TaqMan® PreAmp Master Mix Kit (Life Technologies, Inc.) and the pre-amplified cDNA is then assayed by TaqMan®-based qPCR in a 96-well or 384-well format using QuantStudio™ Dx or ABI7500 Fast Dx quantitative Real-Time PCR Instruments (Life Technologies, Inc.). Typically, expression levels of RM mRNAs will be expressed as a difference in $C_T$ between a test gene and a reference ("housekeeping") gene $C_T$.

In some embodiments the panel of RM mRNAs to be assayed include at least some combination of mRNAs for one or all of the following (human) genes: CR2 (SEQ ID NO: 1), DHRS4L1 (SEQ ID NO: 2), HCK (SEQ ID NO: 3), IL1RAP (SEQ ID NO: 4), LYRM4 (SEQ ID NO: 5), MYC (SEQ ID NO: 6), TMEM63B (SEQ ID NO: 7), ALOX5 (SEQ ID NO: 8), CAMK4 (SEQ ID NO: 9), CDKN1A (SEQ ID NO: 10), COCH (SEQ ID NO: 11), DHRS4 (SEQ ID NO: 12), MICAL1 (SEQ ID NO: 13), MOB3B (SEQ ID NO: 14), NUSAP1 (SEQ ID NO: 15), IL27RA (SEQ ID NO: 16), HBA2 (SEQ ID NO: 17), PPM1F (SEQ ID NO: 18), PPP2R1A (SEQ ID NO: 19), CFLAR (SEQ ID NO: 20), DHRS13 (SEQ ID NO: 21), ACAA1 (SEQ ID NO: 22), INPP5J (SEQ ID NO: 23), OAZ1 (SEQ ID NO: 24), PNOC (SEQ ID NO: 25), PDE4B (SEQ ID NO: 26), SCARB1 (SEQ ID NO: 27), TMEM9B (SEQ ID NO: 28), PPP6R3 (SEQ ID NO: 29), CXXC5, CD97, TEX10, SPECC1, ALAS2, ALPK1, ESD, GPR183, PPM1K, and SLC6A6 (collectively, SEQ ID NOs: 1-29).

In other embodiments RM mRNAs to be assayed can include at least some combination of one or all of the following genes: ADAM17, AKT1, ANK1, ANXA3, ARHGAP26, ARID4A, ATG2A, ATIC, BCL11A, BCL6, BID, CFLAR, CIT, CPVL, CYTH4, DDB2, DDX58, DTL, EHBPL1, FCGR2A, FGR, HPRT1, HSP90AB1, HTRA2, IDOL, IRF1, JMJD1C, KIAA0101, LARP4B, LRRC6, LYN, MAP3K11, MAPK3, MDM1, MKNK1, MXD1, NAIP, NFE2L2, NRG1, NUSAP, PCNA, PGK1, PMP22, RARA, RNASE6, RPL13A, RPL6, RPS14, SP110, SPOCK2, TAPBP, TBP, TCF3, TNFRSF1A, TNFRSF1B, TNFSF14, USP38, WDR48, XAF1, ZAK, NPM1, CPSF1, COASY, DNAJC10, DYNLRB1, ELK4, GPRIN, NDE1, PGS1, PPM1K, and PTAFR. In some embodiments, the reference gene to be assayed is PPP6R3. In other embodiments the reference gene to be assayed may be USP38, WDR48 or LARP4B or some combination thereof.

In some embodiments, qPCR reactions are multiplexed such that multiple mRNAs (including a reference mRNA) are assayed in a single qPCR reaction.

Also disclosed herein is a method for radiation treatment triage of a subject in need thereof, which includes the steps of: (i) determining the mRNA expression levels of mRNAs comprising the nucleotide sequences referred to in any of SEQ ID NOS: 1-29 (or any combination of any other SEQ ID NO provided herein) in a biological sample comprising mRNA from the subject to obtain an expression profile; and (ii) providing a suitable treatment for radiation exposure to the subject based on the expression levels of the genes. Exemplary treatments for radiation exposure based on radiation dosage are shown in Table 1 below:

TABLE 1

Exemplary treatments for radiation exposure based on radiation dosage.

| Symptoms and treatment strategy | | Mild (1-2 Gy) | Moderate (2-4 Gy) | Severe (4-6 Gy) | Very severe (6-8 Gy) | Lethal (a) (>8 Gy) |
| --- | --- | --- | --- | --- | --- | --- |
| Vomiting | Onset | After 2 hr. | After 1-2 hrs. | Within 1 hr. | Within 30 min. | Within 10 min. |
| | Incidence | 10-50% | 70-90% | 100% | 100% | 100% |
| Diarrhea | Onset | None | None | Mild 3-8 hrs. | Heavy 1-3 hrs. | Heavy |
| | Incidence | | | <10% | >10% | Within min.-1 hr. almost 100% |
| Headache | Onset | Slight | Mild | Moderate 4-24 hrs. | Severe 3-4 hrs. | Severe 1-2 hrs. |
| | Incidence | | | 50% | 80% | 80-90% |

TABLE 1-continued

Exemplary treatments for radiation exposure based on radiation dosage.

| Symptoms and treatment strategy | | Mild (1-2 Gy) | Moderate (2-4 Gy) | Severe (4-6 Gy) | Very severe (6-8 Gy) | Lethal (a) (>8 Gy) |
|---|---|---|---|---|---|---|
| Consciousness | Onset Incidence | Alert | Alert | Alert | Possibility of impairment | Unconsciousness by order of seconds or minutes Seconds-minutes 100% (>50 Gy) |
| Body Temperature | Onset Incidence | Normal | Increased 1-3 hrs. 10-80% | Fever 1-2 hrs. 80-100% | High fever <1 hrs. 100% | High fever <1 hrs. 100% |
| Treatment Strategy | | Outpatient observation | Observation at general hospital, treatment at specialized hospital if required | Treatment at specialized Hospital | Treatment at specialized hospital | Palliative treatment (a) (advanced medical care including stem cell transplantation) |

Also described herein is a radiation biodosimetry assay system that includes multiple nucleic acid amplification reactions containing the following: (i) mRNA or cDNA from a human subject suspected of suffering from radiation exposure; (ii) primer pairs capable of hybridizing under stringent conditions to mRNAs or cDNAs comprising the nucleotide sequences referred to in SEQ ID NOS: 1-29 (or any other SEQ ID NO provided herein), or the complementary sequences thereof, wherein each primer pair hybridizes to a different one of the mRNAs or cDNAs; and (iii) A mathematical algorithm the converts gene expression results to estimated absorbed dose of radiation.

In one embodiment, the mathematical algorithm of the present invention The Radiation Biodosimetry Absorbed Dose Estimation algorithm described herein takes as input sample qPCR data, sample barcode, and available information about the date and time of the exposure event and sample collection. The primary output of the algorithm is an absorbed dose report that contains an estimated absorbed dose and a dose interval that provides a range of dose values for the patient based on prediction intervals. The algorithm contains 6 basic steps, which are summarized in Table 2.

In Step 1, patient qPCR data are combined with the available information about the date and time of the event and sample collection using the patient barcode.

In Step 2, several quality control metrics are calculated for the qPCR data. Depending on the values of these metrics, the algorithm may determine that a sample requires re-testing. If the sample does not require re-testing, the quality control metrics will be utilized in the estimation of absorbed radiation dose, and in particular may affect the estimation interval.

In step 3, the qPCR data are checked against expected ranges for each biomarker.

In step 4, quality control metrics and the results of the biomarker range checks are used to determine whether specific biomarker values are invalid and whether sufficient biomarker values are valid for dose estimation.

Figure 8:
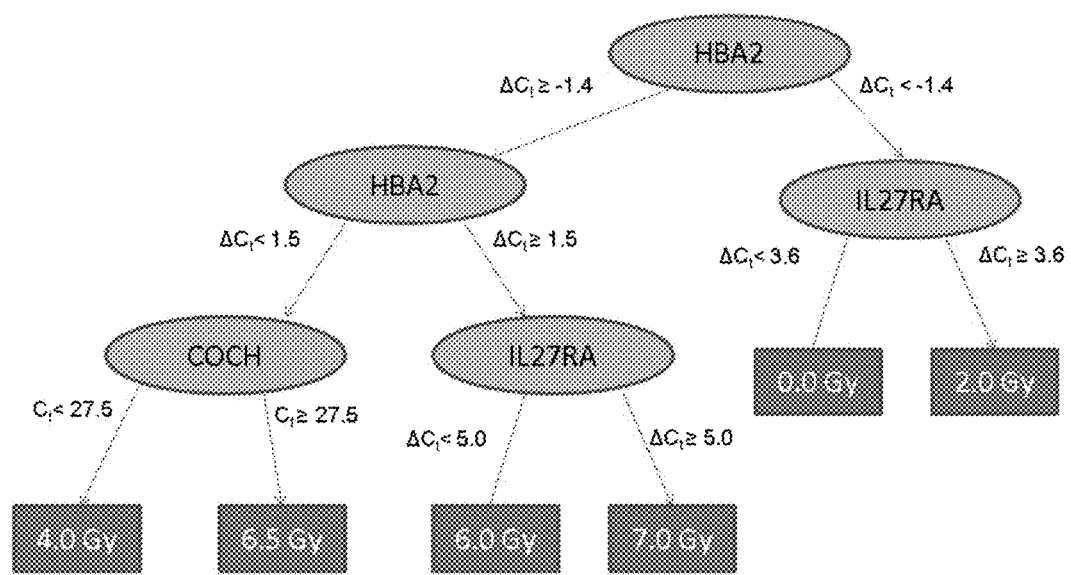
FIG. 8 shows a single regression tree in a random forest example. This tree generates an estimated absorbed dose using the relative expression levels of gene biomarkers, HBA2 and IL27RA, and the absolute expression level of gene biomarker, COCH.

In step 5, the qPCR data and the available temporal information for the event and sample collection are processed through a random forest-based mathematical algorithm that yields an estimated dose and a dose interval. The mathematical algorithm in Step 5 utilizes Random Forests™ method, introduced by Breiman (2001). Random forests is a popular machine-learning tool for prediction that combines large numbers of classification or regression trees to yield accurate and robust predictions. A random forest is a collection of classification or regression trees that we denote by $R=\{T_1, \ldots, T_n\}$. The input to the forest is a vector X of relative and/or absolute expression levels of a set of genes. In a regression random forest, each tree $T_i$ takes X as input and outputs an estimate of absorbed dose, $T_i(X)$. For example, FIG. 8 depicts a single tree in a random forest that utilizes the relative expression levels for two gene biomarkers (HBA2 and IL27RA) and the absolute expression level for one gene biomarker (COCH). The estimate of absorbed dose from a regression random forest R is then the average of estimated absorbed doses from the trees within the forest. We write this estimate as:

$$AD = R(X) = \frac{1}{n} \times \sum_{i=1}^{n} T_i(X)$$

In a classification random forest, samples are partitioned into several non-intersecting groups. For example, samples may be partitioned based upon dose and each group then represents an interval for the absorbed dose. Each tree $T_i$ takes as input X and outputs the identity of a single group, $T_i(X)$. The output from the classification random forest is a probability distribution on the set of groups, where the probability assigned to each group is the proportion of trees that yield the group.

The inputs to the mathematical algorithm in Step 5 are a set of absolute and relative expression levels, X for a set of genes, and a probability distribution $\pi$ that reflects the uncertainty in D, the duration of time from irradiation to sample collection. If the duration of time is known precisely, $\pi$ will be a point mass distribution on that known duration of time. If the duration is only known to fall within an interval, then $\pi$ may be any probability distribution on that interval such as a uniform distribution or a symmetric triangular distribution. If the duration is entirely unknown or not provided, then $\pi$ may be calculated using a classification random forest that takes as input X and yields as output a probability distribution over a fixed set of duration values.

The outputs are an estimated absorbed dose, AD and a 95% prediction interval for the absorbed dose, ($AD_{low}$, $AD_{high}$). For NHP samples that were irradiated with a single acute dose (NHP SD), these outputs are computed in two steps. First, we compute an initial estimate of absorbed dose, AD$^I$. Secondly, we correct for bias in the estimate to yield the final estimate of absorbed dose, AD and generate the 95% prediction interval.

A novel aspect of our algorithm is the use of multiple random forests for each of several fixed durations, $D_1, \ldots, D_k$. For duration $D_i$, we use $n_i$ random forests, denoted by $RF_{i,1}, \ldots, RF_{i,n_i}$, to construct initial estimates of absorbed dose. A decision tree $T_i$ combines the outputs from $RF_{i,1}, \ldots, RF_{i,n_i}$ into a single initial estimate of absorbed dose. One additional random forest, denoted by $RF_i^E$, is a quantile regression random forest for error that uses the expression values X' and the output from $T_i$ for bias correction and construction of prediction intervals. These $n_i+1$ random forests utilize different, but possibly overlapping sets of genes, may be trained on different sets of samples and may include both regression forests and classification forests. Hence, if the duration is known to equal $D_i$, the initial estimate of absorbed dose, denoted by AD$^I$($D_i$), is computed as:

$$AD^I(D_i)=T_i(RF_{i,1}(X'), \ldots ,RF_{i,n_i}(X'))$$

This estimate and the transformed expression levels X' are then passed to the random forest $RF_i^E$. The output from $RF_i^E$ is the conditional probability distribution for the error in the estimate AD$^I$($D_i$). We denote the cumulative distribution function for this conditional distribution by F ($\bullet|D=D_i$). The bias corrected estimate of absorbed dose is then AD($D_i$)=AD$^I$($D_i$)−F$^{-1}$(0.5). If the duration is known to equal D* where $D_i$<D*<$D_{i+1}$, the estimated absorbed dose is computed as:

$$AD(D^*) = \frac{D_{i+1} - D^*}{D_{i+1} - D_i} \times AD(D_i) + \frac{D^* - D_i}{D_{i+1} - D_i} \times AD(D_{i+1})$$

The final estimate of absorbed dose is computed by averaging over the probability distribution $\pi$, that is, AD=∫AD(D)×$\pi$(D)dD.

Similarly, we define F($\bullet|D=D^*$) by:

$$F(\cdot \mid D = D^*) = \frac{D_{i+1} - D^*}{D_{i+1} - D_i} \times F(\cdot \mid D = D_i) + \frac{D^* - D_i}{D_{i+1} - D_i} \times F(\cdot \mid D = D_{i+1})$$

The 95% prediction interval for the absorbed dose is then found by solving the equations:

$$\int F(e_1|D)\times\pi(D)dD=0.025, \text{ and}$$

$$\int F(e_2|D)\times\pi(D)dD=0.975$$

for $e_1$ and $e_2$, respectively, and setting AD$_{low}$=AD−$e_2$ and AD$_{high}$=AD−$e_1$.

In step 6, an absorbed dose estimation report is constructed utilizing the estimated dose and dose interval.

Figure 9:
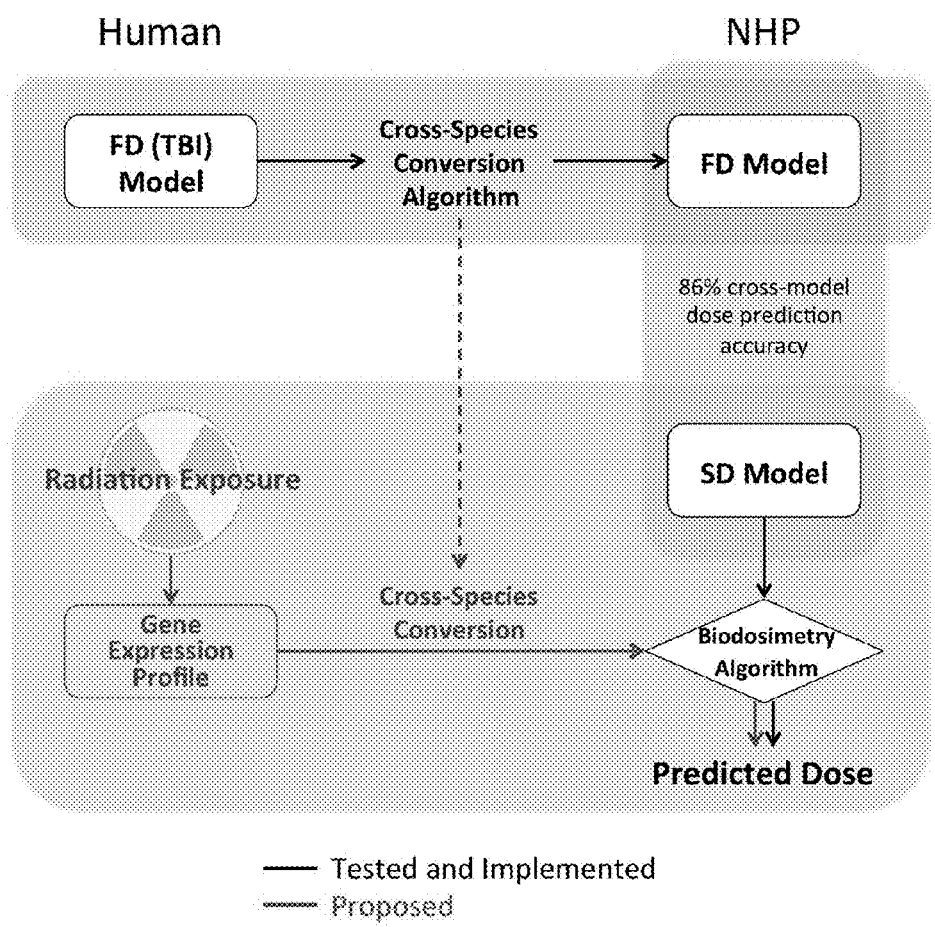
FIG. 9 shows a schematic overview on human and NHP data sets, cross-species conversion approaches to utilize the NHP single-dose (SD) biodosimetry algorithm to predict absorbed dose in human in case of acute radiation exposure. Cross-species conversion algorithms were developed with human and NHP fractionated-dose (FD) models that showed a good cross-model compatibility with NHP SD models.

In actual events of acute radiation exposure, to predict absorbed dose of human samples with the NHP-based biodosimetry algorithm, conceptually, gene expression measurements of each biomarker in a human sample need to be transformed by cross-species (i.e. human to NHP) algorithms. Ideal cross-conversion models could be built on two directly comparable single-dose (SD) data sets in human and NHP. However, due to practical difficulties in obtaining human blood samples with single acute irradiation, as an alternative, we obtain samples from human subjects who undergo total body irradiation (TBI). Unlike the acute single-dose (SD) irradiation that we used for development of a biodosimetry algorithm, these subjects under a fractionated dose (FD) schedule were irradiated three times (1.2 Gy each) a day for 6 days. Therefore, we obtained gene expression data from NHP-equivalents of human TBI subjects that underwent the identical fractionated irradiation, and developed novel gene-specific cross-species conversion algorithms. These algorithms will be used to transform human values prior to dose prediction (FIG. 9).

Figure 10A:
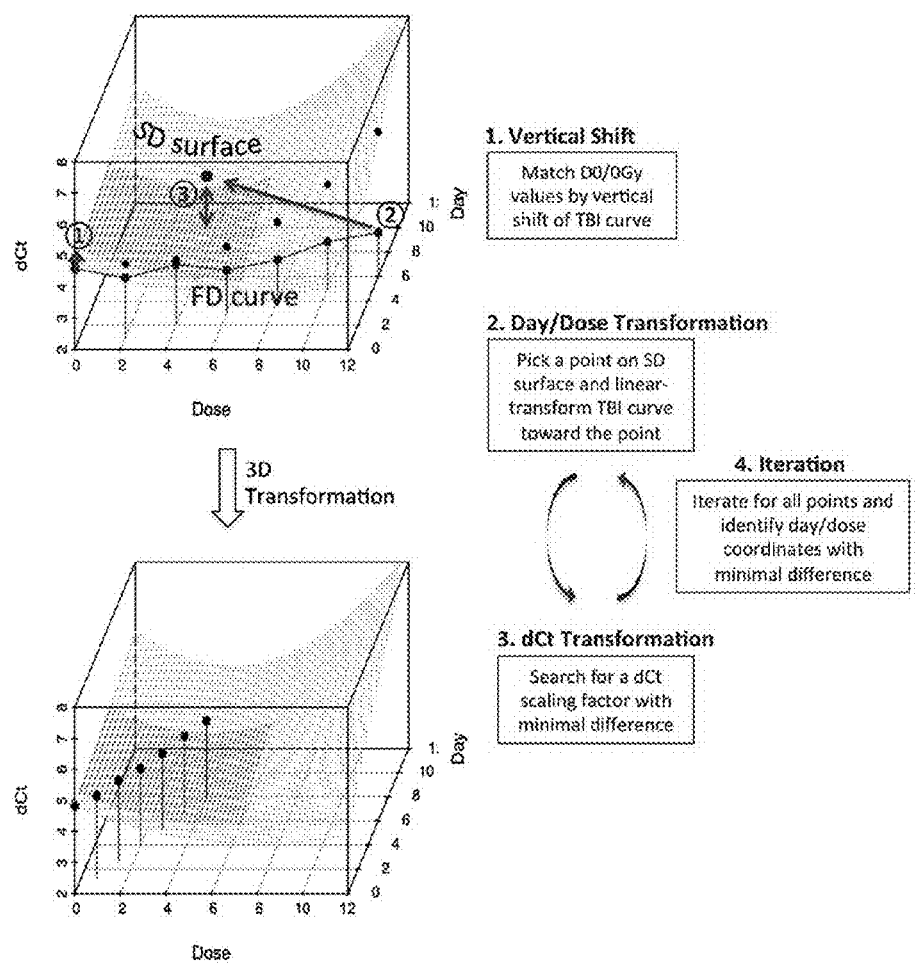
FIG. 10A shows a schematic overview on the approach to convert NHP fractionated dose (FD) data to the corresponding values in NHP single-dose (SD) data by 3-dimensional linear scaling of day, dose, and expression values.

Unlike SD models that measure gene expression levels over the time after a single acute irradiation, data from a FD model has a linear relationship between cumulative dose and day. Therefore, prior to development of cross-species conversion algorithms based on human and NHP FD data sets, we first examined whether expression profiles of biomarker genes in NHP FD model were comparable to those in NHP SD model and thus could predict absorbed dose via the NHP SD model-based biodosimetry algorithm. For meta analyses of FD and SD data sets, we developed a three-dimensional (3D) curve fitting strategy to match the FD data to the SD data. Specifically, for each biomarker b we generate an FD curve of the mean expression level of NHP FD samples (2 Gy per day for 6 days) as a function of cumulative dose and day, FD$_b$(dose, day), and a SD response surface of the mean expression level of NHP SD samples (0 to 6 days, 0 to 7 Gy) as a function of dose and day, SD$_b$(dose, day) (FIG. 10A). First, the entire FD curve for each biomarker is shifted to match the mean basal level (i.e. 0 Gy/Day 0) of SD values, which produces a scaling factor $\alpha_b$ for expression values for each biomarker. The shifted FD curve is denoted FD$_b$'(dose, day)=FD$_b$(dose, day)+$\alpha_b$, where $\alpha_b$=SD$_b$(0, 0)−FD$_b$(0, 0). Second, for each biomarker, optimal biomarker-specific dose and day scaling factors, $\beta_{b,dose}$ and $\beta_{b,day}$, are found that minimize the sum of absolute differences between the SD and scaled FD data.

Specifically, $\beta_{b,dose}$ and $\beta_{b,day}$ minimize the following expression, $$\sum_{d1,d2} \left| \frac{FD_b'(d1, d2)}{FD_b'(12, 6)} \times SD_b(\beta_{b,dose} \times d1, \beta_{b,day} \times d2) - SD_b(\beta_{b,dose} \times d1, \beta_{b,day} \times d2) \right|$$

Figure 10B:
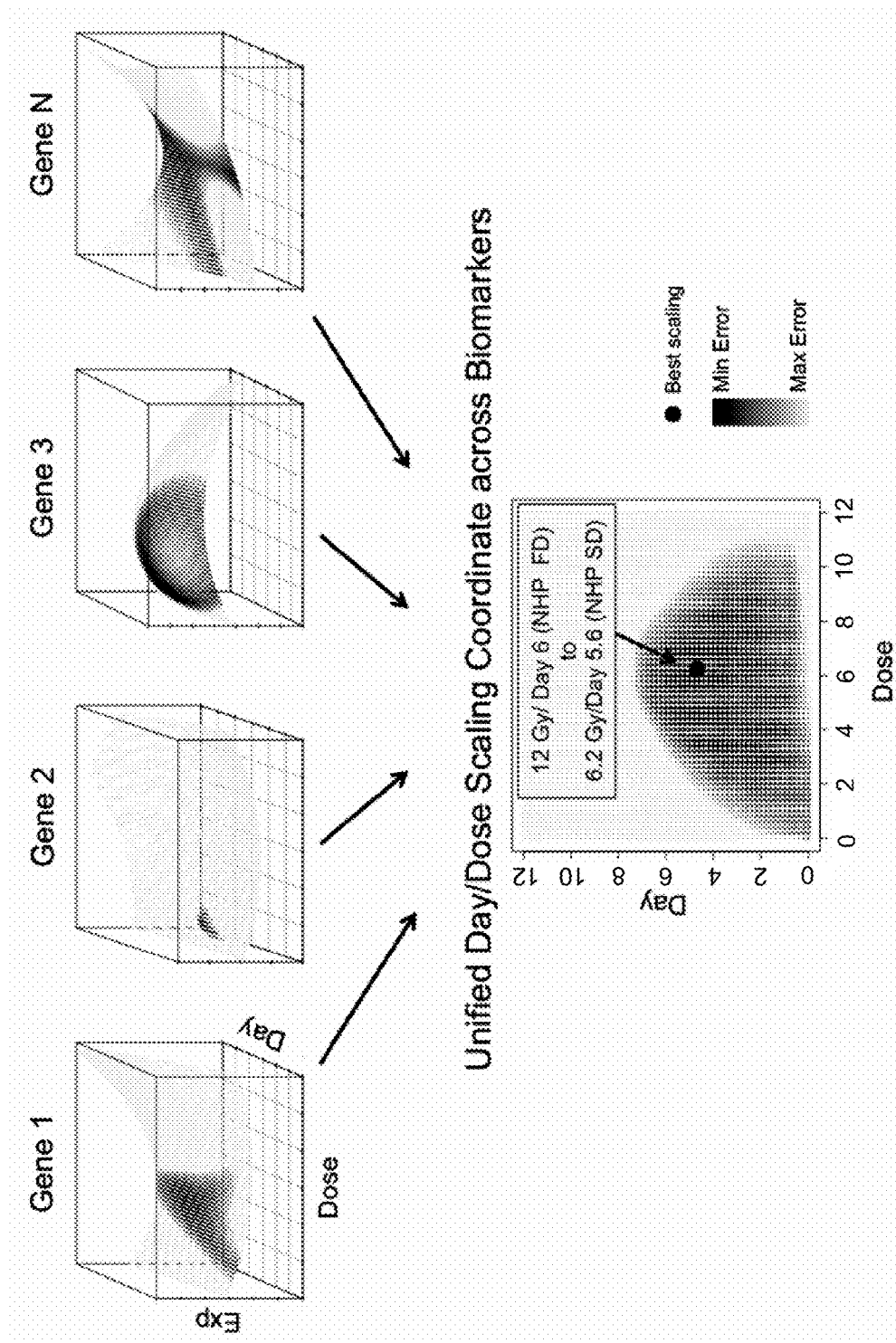
FIG. 10B shows the optimal range (in blue) of dose/day scaling factors for 12 Gy/day-6 data points of individual biomarkers (top panels) and a unified scaling factor (bottom panel) for 29 tested biomarkers.

By repeating this for all biomarkers and searching for common dose and day scaling factors that minimize the sum of absolute differences across biomarkers, doses and days, unified FD to SD scaling factors of $\beta_{dose}$=0.517 for dose (i.e. 12 Gy to 6.2 Gy) and $\beta_{day}$=0.933 for day (i.e. day 6 to day 5.6) (FIG. 10B) are obtained.

Mathematically, $\beta_{dose}$ and $\beta_{day}$ are defined to minimize $$\sum_b \sum_{d1,d2} \left| \frac{FD_b'(d1, d2)}{FD_b'(12, 6)} \times SD_b(\beta_{dose} \times d1, \beta_{day} \times d2) - SD_b(\beta_{dose} \times d1, \beta_{day} \times d2) \right|.$$

Third, linear transformation of FD curves by the scaling factors yields the converted expression values, $$FD_b''(d1, d2) = \frac{FD_b'(d1, d2)}{FD_b'(12, 6)} \times SD_b(\beta_{dose} \times d1, \beta_{day} \times d2). \quad \text{(FIG. 10A)}$$

Figure 11A:
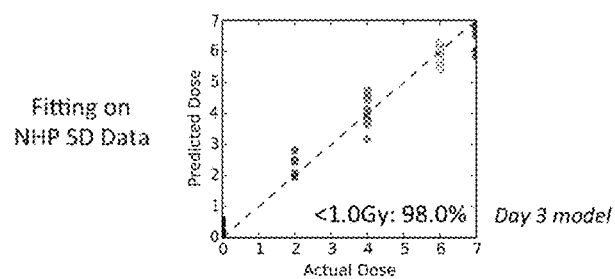
FIG. 11A shows dose prediction performances of a random forests model based on 7 correlated biomarker genes on NHP SD data (for day 3, as an example).
Figure 11B:
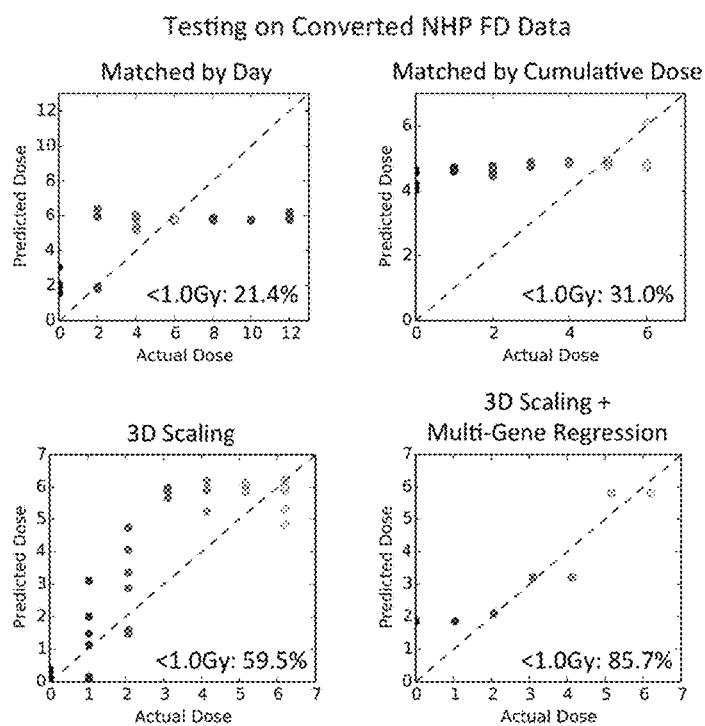
FIG. 11B shows dose prediction performances of a random forests model based on 7 correlated biomarker genes on converted NHP FD values across all days by matching day/cumulative dose, 3D scaling, and 3D scaling followed by multi-gene regression. Prediction accuracies within 1.0 Gy are shown.

To test the conversion strategy from NHP FD to NHP SD data, based on seven biomarkers (COCH, DHRS4L1, IL27RA, INPP5J, PNOC, SCARB1, and TEX10 in this example) with correlated dose responses between the data sets, random forests dose prediction models were generated on NHP SD data, which showed 84% to 98% dose prediction accuracy across days for the model fitting on NHP SD data (FIG. 11A). When expression values of NHP FD data were converted by matching days or doses and then applied to the NHP SD random forests model, dose prediction accuracies within 1.0 Gy were only 21% and 31%, respectively. After the FD values were transformed by the 3D scaling factors (i.e. for expression value, dose, and day), the accuracy was increased to 60% (FIG. 11B).

To increase performance of conversion algorithm, we explored a multi-gene regression approach that utilizes linear combinations of gene expression values rather than the expression values of individual biomarkers. This concept has been applied to predict missing values in large gene expression data sets. Since the biomarkers are functionally related within the key biological pathways related to radiation response, we hypothesized that expression profiles of other biomarkers could be informative in predicting expression values of a given gene. We employed Ridge regressions that provide robustness by constraining the size of coefficients by minimizing the summed squares of residuals and coefficients. By using converted NHP FD values by 3D scaling, a multi-gene regression model for each biomarker was generated with all seven genes that were used to build NHP SD biodosimetry algorithm. When the predicted values by the multi-gene regression models were applied to NHP SD algorithm, dose prediction accuracy was increased substantially to 86% (FIG. 11B).

Figure 12A:
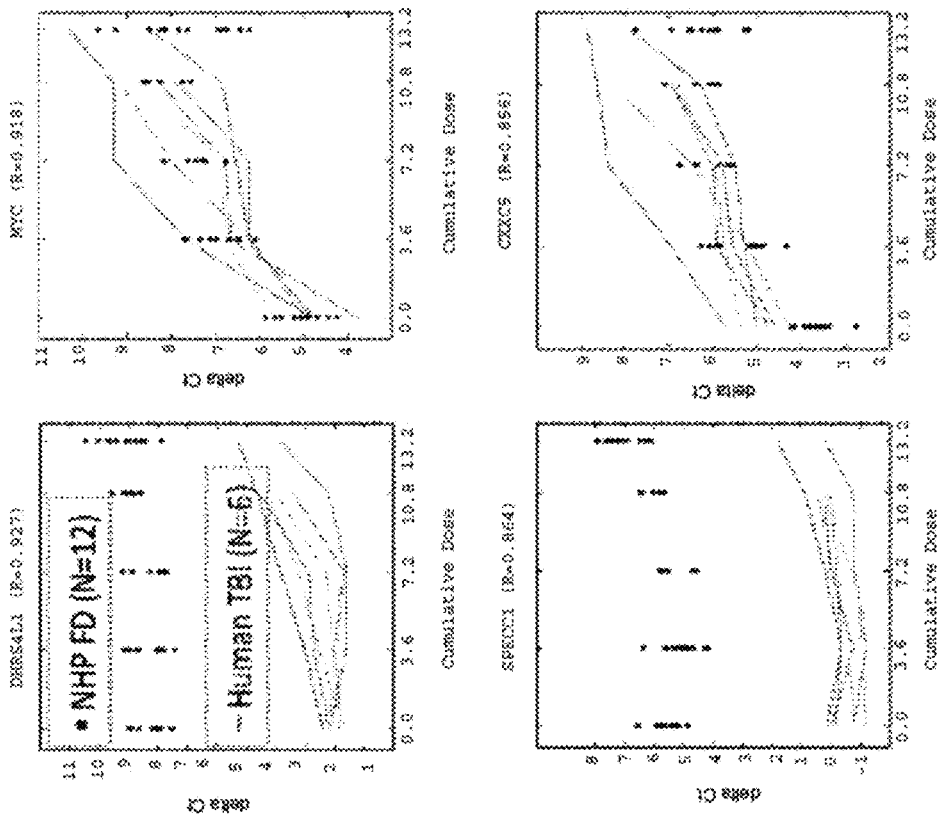
FIG. 12A shows correlation of individual biomarker expression values between NHP fractionated dose (FD) and human TBI, magnitude of expressional changes across dose, and mean absolute difference (MAD) between NHP FD and human TBI data points.
Figure 12B:
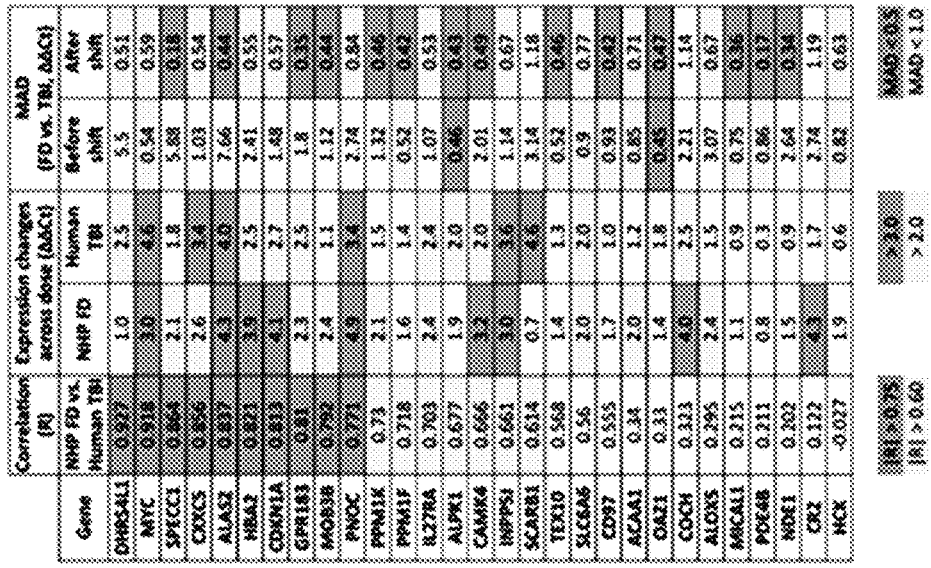
FIG. 12B shows dose response curves of the top 4 inter-species correlated genes in NHP FD and human TBI data.

Absolute gene expression values of biomarker genes are highly variable between NHP and human, and, thus, using an NHP biodosimetry algorithm to predict absorbed dose in human requires another step of cross-species expression value transformation from human to NHP. To explore the conversion strategies, we compared two data sets, for human and NHP, that were obtained from subjects treated with an identical irradiation schedule (3 times of irradiation at 1.2 Gy per day for 4 days), which is being used for total body irradiation (TBI) in clinical therapeutic setting. Among 29 biomarkers tested, although 17 genes had inter-species correlation coefficient above 0.6 between these two data sets (FIG. 12A), many genes showed substantial differences in absolute expression levels across doses (FIG. 12B). Therefore, we calculated the mean difference of expression for each biomarker and then applied the value to shift the entire expression values the gene across doses. This process decreased the mean absolute differences to less than 1.0 ΔCt for the majority of 29 biomarkers (FIG. 12A, last two columns).

Figure 13A:
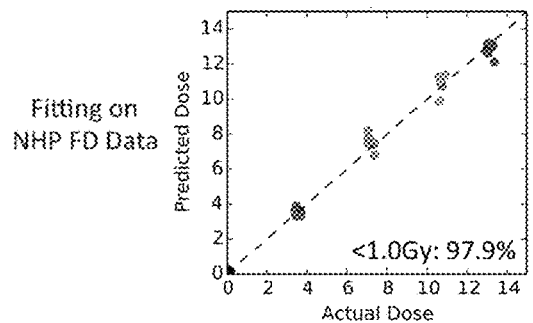
FIG. 13A shows dose prediction performances of a random forests model based on 10 inter-species biomarker genes on NHP FD data.
Figure 13B:
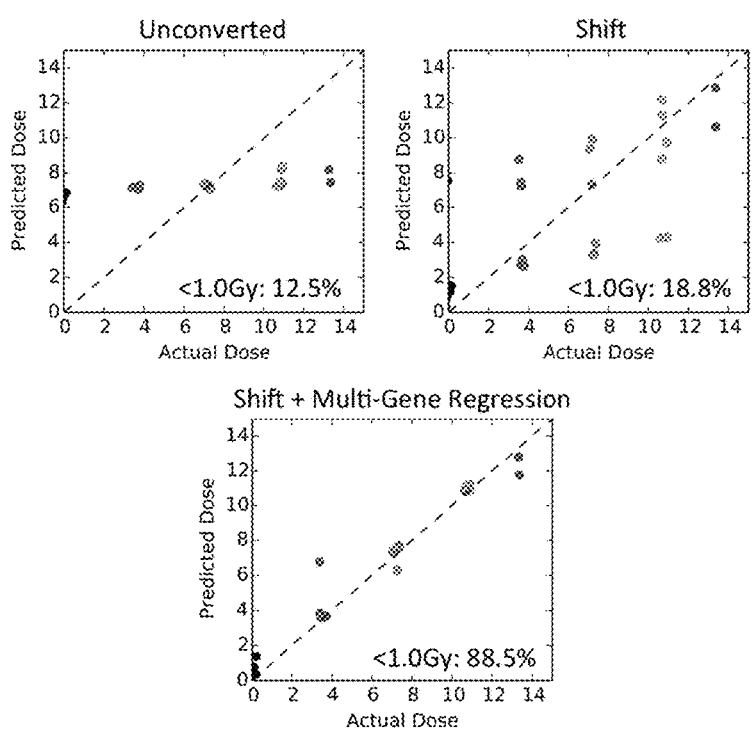
FIG. 13B shows dose prediction performances of a random forests model based on 10 inter-species biomarker genes on unconverted and converted human TBI values by value shift, and value shift followed by multi-gene regression. Prediction accuracies within 1.0 Gy are shown.

To test the conversion strategy from human TBI to NHP FD data, based on 10 biomarkers (DHRS4L1, MYC, SPECC1, CXXC5, ALAS2, HBA2, CDKN1A, GPR183, MOB3B, and PNOC in this example) with inter-species correlation above 0.75 (FIG. 12A), random forests dose prediction models were generated on NHP FD data, which showed a 98% dose prediction accuracy during the model fitting on NHP FD data (FIG. 13A). Applying the converted human TBI values to NHP FD random forests model, prediction accuracy within 1.0 Gy was 13%. When expression values of human TBI data were vertically shifted by the predetermined shift factors and then applied to the NHP FD random forests model, dose prediction accuracies within 1.0 Gy was increase marginally to 19%.

We then tested whether the multi-gene regression approaches could improve the cross-species conversion process. As previously done for NHP FD to NHP SD conversion, we also employed Ridge regressions. By using converted human TBI values by vertical shifting factors, a multi-gene regression model for each biomarker was generated with all 10 genes that were used to build the NHP FD biodosimetry algorithm in this example. When the predicted values by the multi-gene regression models were applied to NHP FD algorithm, dose prediction accuracy was increased substantially to 89%.

TABLE 2

| | | | | | | |
|---|---|---|---|---|---|---|
| | | | Algorithm Function. | | | |
| Step 1 | Combine Patient Barcode with Date/Time Event | Traceability | Barcode | Unique barcode | Adds all needed information to qPCR data | Flags data for operator intervention |
| Step 2 | Quality Control Check | Negative Control | 96-Well Prep Plate No Template Control (NTC) or Reagent Blank | Ct (Ref)(2) > 37 | Cross-Contamination in Sample Prep | Retest Samples |
| | | Positive Controls | qPCR Standard Curve: 10, 0.1, 0.01, 0.001 ng/μL (Based on standard pooled RNA). | 1. Ct (Ref) ± 1 each conc. 2. Amplification Efficiency | 1. LLOD Verified 2. Reproducibility Verified 3. Amplification verifies expected qPCR function across linear range. | Flags data- may affect Doses Estimate and Dose interval Or Require sample retest and Alerts Operator (No operator override) |
| | | | Exogenous Control: Sample RNA Spike-in | Ct (Xeno ™) ± 1 | Inhibitors Sample Integrity | |
| | | | Endogenous Control: Reference Gene(1) | Ct (Ref) ± 1 | 1. Adequate Sample RNA Input. 2.Control for variable RNA input | |
| Step 3 | Biomarker Range Check | Process QC | Biomarker integrity | QC flag | Usability of each Biomarker Value | |
| Step 4 | Apply QC and | Process QC | Analytical integrity | QC flag | Usability of each | |

TABLE 2-continued

Algorithm Function.

| | | | | | Biomarker Range Flags | Biomarker Value | |
|---|---|---|---|---|---|---|---|
| Step 5 | Calculate Estimated Dose | Quantitative | Endogenous Control | Absorbed dose (Gy) | Estimated absorbed Dose | Checks for intended use dose range | |
| | Calculate Dose Interval | Measurement Confidence | Confidence Interval | Dose Range | Dose Interval | Checks for acceptable confidence interval | |
| Step 6 | Combine Estimated Dose and Dose Interval | Report | Report | Gy | Dose Estimation Report | Clinic Review/Approval | |

In one embodiment, the target mRNAs or cDNAs to which the primers hybridize are those from the following (human) RM genes: CR2, DHRS4L1, HCK, IL1RAP, LYRM4, MYC, TMEM63B, ALOX5, CAMK4, CDKN1A, COCH, DHRS4, MICAL1, MOB3B, NUSAP1, IL27RA, HBA2, PPM1F, PPP2R1A, CFLAR, DHRS13, ACAA1, INPP5J, OAZ1, PNOC, PDE4B, SCARB1, and TMEM9B.

In other embodiments, mRNAs or cDNAs to which primers hybridize may include the following genes: ADAM17, AKT1, ANK1, ANXA3, ARHGAP26, ARID4A, ATG2A, ATIC, BCL11A, BCL6, BID, CFLAR, CIT, CPVL, CYTH4, DDB2, DDX58, DTL, EHBPL1, FCGR2A, FGR, HPRT1, HSP90AB1, HTRA2, IDOL, IL27RA, IRF1, JMJD1C, KIAA0101, LARP4B, LRRC6, LYN, MAP3K11, MAPK3, MDM1, MKNK1, MXD1, NAIP, NFE2L2, NRG1, NUSAP, PCNA, PGK1, PMP22, PPP2RA1, RARA, RNASE6, RPL13A, RPL6, RPS14, SCARB1, SP110, SPOCK2, TAPBP, TBP, TCF3, TNFRSF1A, TNFRSF1B, TNFSF14, USP38, WDR48, XAF1, ZAK, NPM1, ALAS2, ALPK1, CD97, CPSF1, COASY, CXXC5, DNAJC10, DYNLRB1, ELK4, ESD, GPR183, GPRIN, NDE1, PGS1, PPM1K, PTAFR, SLC6A6, SPECC1, and TEX10.

In some embodiments, primers are also included that hybridize to PPP6R3 mRNA or cDNA, where PPP6R3 and its mRNA levels serve as a reference gene for relative quantification of RM gene expression levels in an amplification reaction. In other embodiments primers may be included that hybridize to USP38, WDR48 or LARP4B mRNA or cDNA to serve as the reference gene or some combination thereof.

In some embodiments, the nucleic acid amplification reactions are qPCR reactions. In some embodiments the qPCR reactions are TaqMan® qPCR reactions that include, in addition to the target primer pairs, TaqMan® probes that hybridize under stringent conditions to the RM gene or reference gene mRNAs or cDNAs. TaqMan® probe-based qPCR assays are well known in the art as described in, e.g., U.S. Pat. Nos. 5,677,152, 5,773,258 and 5,804,375.

Exemplary RM and reference gene primer and TaqMan probe sequences are listed below in Table 3.

TABLE 3

RM and reference gene primer and TaqMan probe sequences.

| Gene | Assay ID | Amplicon Sequence | Length (bp) | Tm |
|---|---|---|---|---|
| PPP6R3 | Hs002177 59_m1 | TGAGGGAGGAAGACGGCATGGTTAC ATGGACACCTAACGAGGATAGCTA ACTGTATCGTGCACAGCACTGACAAG (SEQ ID NO: 30) | 76 | 55-65° C. |

TABLE 3-continued

RM and reference gene primer and TaqMan probe sequences.

| Gene | Assay ID | Amplicon Sequence | Length (bp) | Tm |
|---|---|---|---|---|
| CDKN1A | Hs002177 59_m1 | GACAGATTTCTACCACTCCAAACGCC GGCTGATCTTCTCCAAGAGGAAGCCC TAATCCGCCCACAG (SEQ ID NO: 31) | 66 | 55-65° C. |

Typically, stringent hybridization reaction conditions are defined by use of TaqPath™ qPCR Mastermix chemistry and cycling conditions listed below in Table 4.

TABLE 4

Thermal Cycling Conditions for Target/Primer/Probe Hybridization.

| | Incubation | Activation | PCR Cycle (40 cycles) | |
|---|---|---|---|---|
| Step | Hold | Hold | Denature | Anneal/Extend |
| Temperature | 50° C. | 95° C. | 95° C. | 60° C. |
| Time | 2 min. | 20 sec. | 1 sec. | 20 sec. |
| Volume | | | 10 µL | |

In some embodiments the plurality of nucleic acid amplification reactions are multiplexed such that multiple mRNAs (including a reference mRNA) are assayed in a single qPCR reaction, i.e., nine qPCR reactions would be needed to assay the entire panel of RM gene mRNAs from one sample, where each of the reactions are "tetraplexed," 14 reactions would be needed per sample where each reaction is "triplexed", and 28 reactions would be needed per sample when each qPCR reactions includes primers to a single RM gene mRNA and a reference gene mRNA. In some embodiments, the plurality of qPCR reactions can include different multiplexing, i.e., some reactions may contain primer pairs directed to three RM gene mRNAs and others a primer pair to only two or a single RM gene mRNA. The plurality of reactions can be provided in a number of formats, e.g., 96-, 384-, or even 1536-well formats.

In various embodiments, the mRNA or cDNA in the biodosimetry assay system is from a biological sample from a subject subjected to radiation exposure from about 30 minutes to about seven days prior to the time point at which the biological sample was obtained from the subject, e.g., one hour, three hours, 4 hours, six hours, twelve hours, 1 day, 2 days, 3 days, 4 days, 5 days, 7 days or another time period before biological sample collection from the subject ranging from about 30 minutes to about seven days.

Also contemplated herein is a radiation biomarker assay kit that includes a nucleic acid probe set consisting essentially of nucleic acid probes that hybridize specifically with nucleic acid targets comprising at least one of SEQ ID NOS: 1-29 or the complementary sequences thereof.

In some embodiments the probe set includes no more than about 200 probes, e.g., PCR primers. In other embodiments the probe set includes no more than about 100 probes.

In some embodiments the nucleic acid probe set includes primer pairs and TaqMan probes suitable for qPCR analysis of mRNAs or cDNAs comprising at least one of SEQ ID NOS: 1-29.

In some embodiments the kit also includes a thermostable polymerase suitable for qPCR, e.g., Taq polymerase and variants thereof known in the art.

In some embodiments a qPCR probe set in the kit is provided in a multi-well plate format. In some a multi-well plate is provided in which at least two nucleic acid probes that hybridize to at least two different nucleic acid targets are in the same wells, i.e., the probes can be multiplexed, as described above such that up to four different targets can be assayed by qPCR in the same reaction.

In some embodiments the kit also includes radiation exposure positive and negative control mRNA samples, which ensure that a qPCR biodosimetry assay is working properly, i.e., modulation of RM gene expression is detected in the positive control sample and no modulation of RM gene expression is detected in the negative control sample.

EXAMPLES

The invention will be more fully understood upon consideration of the following non-limiting Examples. The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

Example 1

Description of Test Experiments Used to Develop Biomarkers

Rhesus macaque non-human primate (NHP) in vivo testing was conducted to produce single-dose biodosimetry samples and age/gender confounded samples to calibrate the biodosimeter.

NHP In Vivo Dose Response to Radiation:

The animal test laboratory completed NHP Cobalt-60 irradiations at 0, 2, 4, and 6 (LD30/60), 7 Gy (LD70/60), and 10 Gy with cohorts of 16 (8 male and 8 female), at dose rate of approximately 0.6 Gy/min. Samples of 2.5 ml peripheral blood (PAXgene tube) were obtained from each rhesus macaque −2 week and −24 hr. prior to irradiation and 4 hr., 24 hr., 36 hr. post radiation, and on days 2, 3, 5, and 7 for a total of 9 blood draws per animal. Samples (0.5 ml) were also obtained in EDTA tubes to determine WBC differentials. Tests were staged to provide 4 NHP at each condition to determine target genes using discovery techniques (Phase 1), 10 NHP at each condition to determine biomarkers and 2 NHP at each condition to test the biodosimeter (algorithm) accuracy (Phase 2).

NHP Confounder Analysis; Old Age and Juvenile.

The animal test laboratory completed testing of 4 rhesus macaques (2 male and 2 female) exposed to 6 Gy (LD30/60) at a dose rate of approximately 0.6 Gy/min for both geriatric (>15 years) and juvenile (10-14 months) cohorts. Samples of 2.5 ml peripheral blood (PAXgene tube) were collected from each NHP −2 week and −24 hr. prior to irradiation and 4 hr., 24 hr., 36 hr. post radiation, and on days 2, 3, 5, and 7 for a total of 9 blood draws per animal. Samples (0.5 ml) were also obtained in EDTA tubes to determine WBC differentials.

NHP Fractionated Dose Testing:

Two NHP models were developed to compare NHP gene response to human gene response for fractionated dose radiotherapy models.

NHP Fractionated Dose Models:

Blood (2.5 ml) was collected from 6 female and 6 male rhesus NHP into PAXgene tubes. The NHP were irradiated in vivo to parallel the 4 human in vivo test protocols as described below. For Study 1: Twelve (12) NHPs were exposed to 1.5 Gy twice per day (dose rate 0.6-0.8 Gy/min.) for 4 days at the same time each day. The blood samples were collected within 24 hr. prior to irradiation and 24 hrs. after each daily exposure (6 draws). For Study 2: Twelve (12) NHPs were exposed to 1.2 Gy (dose rate 0.6-0.8 Gy/min.) 3 times per day at the same time each day for 4-days. Blood samples were collected prior to irradiation and 24 hr. following each exposure (prior to the next exposure) for a total of 6 draws. The NHPs were irradiated by LINAC. At the time of sample collection, a complete differential white cell count was conducted.

Human Fractionated Dose Models:

Four human in vivo models were co-developed with Mayo Clinic, City of Hope and Stanford to provide blood samples from humans undergoing whole body and fractional radiation.

Model 1—Bone Marrow Transplant Patients (BMT): Radiation dose is 1.65 to 2 Gy twice daily for 3 to 4 days. Samples are taken prior to and 24 hr. after daily irradiations. The last draw is on Day-7; 7 days after the first dose. (4-6 samples/Series).

Model 2—Bone Marrow Transplant Patients (BMT): Radiation dose is 1.2 Gy three times daily for 4 days. Samples are taken prior to and 24 hr. after irradiation daily irradiations. The last draw is on Day-3 or 4; 3 or 4 days after the first dose. (5-7 samples/Series).

Model 3—Bone Marrow Transplant Patients (BMT): Radiation dose is a single fraction related to models 1 and 2. Samples are taken prior to and every 24 hr. after irradiation. The last draw is on Day-6; 6 days after the first dose. (6-7 samples/Series).

Model 4—X-Ray Therapy (XRT) Patients (>7% bone marrow exposure): Radiation dose is 2-8 Gy each day for multiple days. Samples are taken prior to and 24 hr. after irradiation. The last draw is taken 7 days after the last exposure.

TABLE 5

Nucleotide Sequences of Biodosimetry Biomarker Genes

CR2 (SEQ ID NO: 1; GenBank NM_001006658.2).

ATTTAAGGGCCCGCCTCTCCTGGCTCACAGCTGCTTGCTGCTCCAGCCTTGCCCTCCC
AGAGCTGCCGGACGCTCGCGGGTCTCGGAACGCATCCCGCCGCGGGGGCTTCGGCC
GTGGCATGGGCGCCGCGGGCCTGCTCGGGGTTTTCTTGGCTCTCGTCGCACCGGGGG
TCCTCGGGATTTCTTGTGGCTCTCCTCCGCCTATCCTAAATGGCCGGATTAGTTATTA
TTCTACCCCCATTGCTGTTGGTACCGTGATAAGGTACAGTTGTTCAGGTACCTTCCGC
CTCATTGGAGAAAAAAGTCTATTATGCATAACTAAAGACAAAGTGGATGGAACCTG
GGATAAACCTGCTCCTAAATGTGAATATTTCAATAAATATTCTTCTTGCCCTGAGCCC
ATAGTACCAGGAGGATACAAAATTAGAGGCTCTACACCCTACAGACATGGTGATTC
TGTGACATTTGCCTGTAAAACCAACTTCTCCATGAACGGAAACAAGTCTGTTTGGTG
TCAAGCAAATAATATGTGGGGCCGACACGACTACCAACCTGTGTAAGTGTTTTCCC
TCTCGAGTGTCCAGCACTTCCTATGATCCACAATGGACATCACACAAGTGAGAATGT
TGGCTCCATTGCTCCAGGATTGTCTGTGACTTACAGCTGTGAATCTGGTTACTTGCTT
GTTGGAGAAAAGATCATTAACTGTTTGTCTTCGGGAAAATGGAGTGCTGTCCCCCCC
ACATGTGAAGAGGCACGCTGTAAATCTCTAGGACGATTTCCCAATGGGAAGGTAAA
GGAGCCTCCAATTCTCCGGGTTGGTGTAACTGCAAACTTTTTCTGTGATGAAGGGTA
TCGACTGCAAGGCCCACCTTCAGTCGGTGTGTAATTGCTGGACAGGGAGTTGCTTG
GACCAAAATGCCAGTATGTGAAGAAATTTTTTGCCCATCACCTCCCCCTATTCTCAA
TGGAAGACATATAGGCAACTCACTAGCAAATGTCTCATATGGAAGCATAGTCACTTA
CACTTGTGACCCGGACCCAGAGGAAGGAGTGAACTTCATCCTTATTGGAGAGAGCA
CTCTCCGTTGTACAGTTGATAGTCAGAAGACTGGGACCTGGAGTGGCCCTGCCCCAC
GCTGTGAACTTTCTACTTCTGCGGTTCAGTGTCCACATCCCCAGATCCTAAGGAGGCC
GAATGGTATCTGGGCAGAAAGATCGATATACCTATAACGACACTGTGATATTTGCTT
GCATGTTTGGCTTCACCTTGAAGGGCAGCAAGCAAATCCGATGCAATGCCCAAGGC
ACATGGGAGCCATCTGCACCAGTCTGTGAAAAGGAATGCCAGGCCCCTCCTAACAT
CCTCAATGGGCAAAAGGAAGATAGAACACATGGTCCGCTTTGACCCTGGAACATCTA
TAAAATATAGCTGTAACCCTGGCTATGTGCTGGTGGGAGAAGAATCCATACAGTGTA
CCTCTGAGGGGTGTGGACACCCCCTGTACCCCAATGCAAAGTGGCAGCGTGTGAA
GCTACAGGAAGGCAACTCTTGACAAAACCCCAGCACCAATTTGTTAGACCAGATGT
CAACTCTTCTTGTGGTGAAGGGTACAAGTTAAGTGGGAGTGTTTATCAGGAGTGTCA
AGGCACAATTCCTTGGTTTATGGAGATTCGTCTTTGTAAAGAAATCACCTGCCCACC
ACCCCCTGTTATCTACAATGGGGCACACACCGGGAGTTCCTTAGAAGATTTTCCATA
TGGAACCACGGTCACTTACACATGTAACCCTGGGCCAGAAAGAGGAGTGGAATTCA
GCCTCATTGGAGAGAGCACCATCCGTTGTACAAGCAATGATCAAGAAAGAGGCACC
TGGAGTGGCCCTGCTCCCCTGTGTAAACTTTCCCTCCTTGCTGTCCAGTGCTCACATG
TCCATATTGCAAATGGATACAAGATATCTGGCAAGGAAGCCCCATATTTCTACAATG
ACACTGTGACATTCAAGTGTTATAGTGGATTTACTTTGAAGGGCAGTAGTCAGATTC
GTTGCAAAGCTGATAACACCTGGGATCCTGAAATACCAGTTTGTGAAAAAGGCTGC
CAGTCACCTCCTGGGCTCCACCATGGTCGTCATACAGGTGGAAATACGGTCTTCTTT
GTCTCTGGGATGACTGTAGACTACACTTGTGACCCTGGCTATTTGCTTGTGGGAAAC
AAATCCATTCACTGTATGCCTTCAGGAAATTGGAGTCCTTCTGCCCCACGGTGTGAA
GAAACATGCCAGCATGTGAGACAGAGTCTTCAAGAACTTCCAGCTGGTTCACGTGTG
GAGCTAGTTAATACGTCCTGCCAAGATGGGTACCAGTTGACTGGACATGCTTATCAG
ATGTGTCAAGATGCTGAAAATGGAATTTGGTTCAAAAAGATTCCACTTTGTAAAGTT
ATTCACTGTCACCCCTCCACCAGTGATTGTCAATGGGAAGCACACAGGCATGATGGCA
GAAAACTTTCTATATGGAAATGAAGTCTCTTATGAATGTGACCAAGGATTCTATCTC
CTGGGAGAGAAAAATTGCAGTGCAGAAGTGATTCTAAAGGACATGGATCTTGGAG
CGGGCCTTCCCCACAGTGCTTACGATCTCCTCCTGTGACTCGCTGCCCTAATCCAGA
AGTCAAACATGGGTACAAGCTCAATAAAAACACATTCTGCATATTCCCACAATGACAT
AGTGTATGTTGACTGCAATCCTGGCTTCATCATGAATGGTAGTCGCGTGATTAGGTG
TCATACTGATAACACATGGGTGCCAGGTGTGCCAACTTGTATCAAAAAAGCCTTCAT
AGGGTGTCCACCTCCGCCTAAGACCCCTAACGGGAACCATACTGGTGGAAACATAG
CTCGATTTTCTCCTGGAATGTCAATCCTGTACAGCTGTGACCAAGGCTACCTGCTGGT
GGGAGAGGCACTCCTTCTTTGCACACATGAGGGAACCTGGAGCCAACCTGCCCCTC
ATTGTAAAGAGGTAAACTGTAGCTCACCAGCAGATATGGATGGAATCCAGAAAGGG
CTGGAACCAAGGAAATGTATCAGTATGGAGCTGTTGTAACTCTGGAGTGTGAAGA
TGGGTATATGCTGGAAGGCAGTCCCCAGAGCCAGTGCCAATCGGATCACCAATGGA
ACCCTCCCCTGGCGGTTTGCAGATCCCGTTCACTTGCTCCTGTCCTTTGTGGTATTGC
TGCAGGTTTGATACTTCTTACCTTCTTGATTGTCATTACCTTATACGTGATATCAAAA
CACAGAGCACGCAATTATTATACAGATACAAGCCAGAAAGAAGCTTTTCATTTAGA
AGCACGAGAAGTATATTCTGTTGATCCATACAACCCAGCCAGCTGATCAGAAGACA
AACTGGTGTGTGCCTCATTGCTTGGAATTCAGCGGAATATTGATTAGAAAGAAACTG
CTCTAATATCAGCAAGTCTCTTTATATGGCCTCAAGATCAATGAAATGATGTCATAA
GCGATCACTTCCTATATGCACTTATTCTCAAGAAGAACATCTTTATGGTAAAGATGG
GAGCCCAGTTTCACTGCCATATACTCTTCAAGGACTTTCTGAAGCCTCACTTATGAG
ATGCCTGAAGCAGGCCATGGCTATAAACAATTACATGGCTCTAAAAAGTTTTGCCC
TTTTTAAGGAAGGCACTAAAAGAGCTGTCCTGGTATCTAGACCCCATCTTCTTTTTG
AAATCAGCATACTCAATGTTACTATCTGCTTTTGGTTATAATGTGTTTTTAATTATCT
AAAGTATGAAGCATTTTCTGGGGTTATGATGGCTTTACCTTTATTAGGAAGTATGGT
TTTATTTTGATAGTAGCTTCCTCCTCTGGTGGTGTTAATCATTTCATTTTTTACCCTTAC
TTGGTTTGAGTTTCTCTCACATTACTGTATATACTTTGCCTTTCCATAATCACTCAGTG
ATTGCAATTTGCACAAGTTTTTTAAATTATGGGAATCAAGATTTAATCCTAGAGATT
TGGTGTACAATTCAGGCTTTGGATGTTTCTTTAGCAGTTTTGTGATAAGTTCTAGTTG
CTTGTAAAATTTCACTTAATAAATGTGTACATTAGTCATTCAATAAATTGTAATTGTAA
AGAAAACATACAAAAAAAAAAAAAAAA

TABLE 5-continued

Nucleotide Sequences of Biodosimetry Biomarker Genes

DHRS4L1 (SEQ ID NO: 2; GenBank NM_001277864.1).

AGTCGGGCAGCTCTCCGGGCCGGCGTGGGAGCCCGCGCTCCAAAGCCCGGTGGGGG
GAGGGGCGCTCACGCAACCGCCACTGTCTGGAGCGGGCTCGCCTCTGCGGCGGCAC
TCACCGCCCGGGCTTTACTGAAGCGGAGTCTAGCATGTGCGGCTGCTCCACAGCGGT
GTGGGTGGCGGCGGCTCCTCTGCAGCAGCCTCGGCAGTAGGGGTCACGGTGGCCAA
GCCCACCGTGGAGCTCATCTGAGAGTTGTAAGGTACGGGACTGCCTCGGTCTTTGGG
ACGCCCCGTCTGGTAGCATCCCAGATCCAGCACGTTCCTTCCGGCCCTGCACCCCGG
CCCGGTGCCTCACACCCCGCTACCCCATGCATCCAGACTCTAAGGCAGCCCCTGCAT
CTCAGTCCTGACATCGCTGTCCCTGGAGCATCCTCCGCTGGAGCTGGAGCTTGACAG
GATCGGCTTCGCCGTCGCCCAGCGTCTGGCCCAAGACGGGGCCCACGTGGTAGTCA
GCCGCCGGAAGCAGCAGAATGTGGACCAGGCAGTGGCCACGCTGCAGGGGGAGGG
GCTGAGCATGACGGGCACTGTGTGCCATGTGGGGAAGATGAAGGACTGGGAGCGGC
TGGTGGCCACAGTGAGCTGCAGGGAAATGGGCACAGAGCCAGGAGGTGGAAAAGG
GAGCCAGCCTGAGCCTCCTTCCCTGCTTTCCTGGACAGCATTGGGCTTCAGTCCTTAC
AATGTCAGTAAAACAGCCTTGCTGGGCCTCAACAAGACCTTGGCCATAGAGCTGGC
CCCAAGGAACATTAGGGTGAACTGCCTAGCACCTGGACTTATCAAGACTAGCTTCAG
CAGGATGCTCTGGATGGACAAGGAAAAAGAGGAAAGCATGAAAGAAACCCTGCGG
ATAAGAAGGTTAGGCGAGCCAGAGGATTCTCTTGGCATCGTGTCTTTCCTGTGCTCT
GAAGATGCCAGCTACCTCACTGGGGAAACAGTGATGGTGGGTGGAGGAACCCCGTC
CCGCCTCTGAGGACCCGGAGACAGCCCACAGGCCAGAGTTGGGCTCTAGCTCCTGG
TGCTGTTCCTGCATTCACCCACTGGCCTTTCCCACCTCTGCTCACCTTACTGTTCACC
TCATCAAATCAGTTCTGCCCTGTGAAAAGATCCAGCCTTCCCTGCCGTCAAGGTGGT
GTCTTACTCGGGATTCCTGCTGTTGTTGTGGCCTTGGGTAAAGGCCTCCCCTGAGAA
CACAGGACAGGCCTGCTGACAAGGCTGAGTCTACCTTGGCAAAGACCAAGATATTT
TTTGCCCAGGCCACTGGGGAATTTGAGGGGAGATGAGAGAGAAGGAAGCTGGAGTG
GAAGGAGCAGAGTTGCAAATTAACAACTTGCAAATGAGGTGCAAATAAAATGCAGA
TGATTGCGCGGCTTTGAATCGAAAAAAAAAAA

HCK (SEQ ID NO: 3; GenBank NM_001172129.1).

GGAGTTAGCCTCGCTCAGGGCGCGGCTAAGGCGCCCAGATGGCCTGCGGCGCCAC
CACGTCCCTGGTCCCAGCTCGGGAGCACATCAGAGGCTTAGAGGCGAGTGGGAAGG
GACTCAGACAGTGCAGGACGAGAAACGCCCGCGGCACCAAAGCCCCTCAGAGCGTC
GCCCCCGCCTCTAGTTCTAGAAAGTCAGTTTCCCGGCACTGGCACCCCGGAACCTCA
GGGGCTGCCGAGCTGGGGGGGCGCTCAAGCTGCGAGGATCCGGGCTGCCCGCGAGA
CGAGGAGCGGGCGCCCAGGATGGGGTGCATGAAGTCCAAGTTCCTCCAGGTCGGAG
GCAATACATTCTCAAAAACTGAAACCAGCGCCAGCCCACACTGTCCTGTGTACGTGC
CGGATCCCACATCCACCATCAAGCCGGGGCCTAATAGCCACAACAGCAACACACCA
GGAATCAGGGAGGCAGGCTCTGAGGACATCATCGTGGTTGCCCTGTATGATTACGA
GGCCATTCACCACGAAGACCTCAGCTTCCAGAAGGGGGACCAGATGGTGGTCCTAG
AGGAATCCGGGGAGTGGTGGAAGGCTCGATCCCTGGCCACCCGGAAGGAGGGCTAC
ATCCCAAGCAACTATGTCGCCCGCGTTGACTCTCTGGAGACAGAAGGAGTGGTTTTC
AAGGGGCATCAGCCGGAAGGACGCAGAGCGCCAACTGCTGGCTCCCGGCAACATGCT
GGGCTCCTTCATGATCCGGGATAGCGAGACCACTAAAGGAAGCTACTCTTTGTCCGT
GCGAGACTACGACCCTCGGCAGGGAGATACCGTGAAACATTACAAGATCCGGACCC
TGGACAACGGGGGCTTCTACATATCCCCCGAAGCACCTTCAGCACTCTGCAGGAGC
TGGTGGACCACTACAAGAAGGGGAACGACGGGCTCTGCCAGAAACTGTCGGTGCCC
TGCATGTCTTCCAAGCCCCAGAAGCCTTGGGAGAAAGATGCCTGGGAGATCCCTCG
GGAATCCCTCAAGCTGGAGAAGAAACTTGGAGCTGGGCAGTTTGGGGAAGTCTGGA
TGGCCACCTACAACAAGCACACCAAGGTGGCAGTGAAGACGATGAAGCCAGGGAG
CATGTCGGTGGAGGCCTTCCTGGCAGAGGCCAACGTGATGAAAACTCTGCAGCATG
ACAAGCTGGTCAAACTTCATGCGGTGGTCACCAAGGAGCCCATCTACATCATCACG
GAGTTCATGGCCAAAGGAAGCTTGCTGGACTTTCTGAAAAGTGATGAGGGCAGCAA
GCAGCCATTGCCAAAACTCATTGACTTCTCAGCCCAGATTGCAGAAGGCATGGCCTT
CATCGAGCAGAGGAACTACATCCACCGAGACCTCCGAGCTGCCAACATCTTGGTCTC
TGCATCCCTGGTGTGTAAGATTGCTGACTTTGGCCTGGCCCGGGTCATTGAGGACAA
CGAGTACACGGCTCGGGAAGGGGCCAAGTTCCCCATCAAGTGGACAGCTCCTGAAG
CCATCAACTTTGGCTCCTTCACCATCAAGTCAGACGTCTGGTCCTTTGGTATCCTGCT
GATGGAGATCGTCACCTACGGCCGGATCCCTTACCCAGGGATGTCAAACCCTGAAG
TGATCCGAGCTCTGGAGCGTGGATACCGGATGCCTCGCCCAGAGAACTGCCCAGAG
GAGCTCTACAACATCATGATGCGCTGCTGGAAAAACCGTCCGGAGGAGCGGCCGAC
CTTCGAATACATCCAGAGTGTGCTGGATGACTTCTACACGGCCACAGAGAGCCAGTA
CCAACAGCAGCCATGATAGGGAGGACCAGGGCAGGGCCAGGGGGTGCCCAGGTGG
TGGCTGCAAGGTGGCTCCAGCACCATCCGCCAGGGCCCACACCCCCTTCCTACTCCC
AGACACCCACCCTCGCTTCAGCCACAGTTTCCTCATCTGTCCAGTGGGTAGGTTGGA
CTGGAAAATCTCTTTTTGACTCTTGCAATCCACAATCTGACATTCTCAGGAAGCCCCC
AAGTTGATATTTCTATTTCCTGGAATGGTTGGATTTTAGTTACAGCTGTGATTTGGAA
GGGAAACTTTCAAAATAGTGAAATGAATATTTAAATAAAAGATATAAATGCCAAAG
TCTTTTACCAAAAAAAAAAAAAAAAA

IL1RAP (SEQ ID NO: 4; GenBank NM_002182.3).

AAAGGGGGAAAAGAAAGTGCGGCGGAAAGTAAGAGGCTCACTGGGGAAGACTGCC
GGGATCCAGGTCTCCGGGGTCCGCTTTGGCCAGAGGCGCGGAAGGAAGCAGTGCCC
GGCGACACTGCACCCATCCCGGCTGCTTTTGCTGCGCCCTCTCAGCTTCCCAAGAAA
GGCATCGTCATGTGATCATCACCTAAGAACTAGAACATCAGCAGGCCCTAGAAGCC

TABLE 5-continued

Nucleotide Sequences of Biodosimetry Biomarker Genes

```
TCACTCTTGCCCCTCCCTTTAATATCTCAAAGGATGACACTTCTGTGGTGTGTAGTGA
GTCTCTACTTTTATGGAATCCTGCAAAGTGATGCCTCAGAACGCTGCGATGACTGGG
GACTAGACACCATGAGGCAAATCCAAGTGTTTGAAGATGAGCCAGCTCGCATCAAG
TGCCCACTCTTTGAACACTTCTTGAAATTCAACTACAGCACAGCCCATTCAGCTGGC
CTTACTCTGATCTGGTATTGGACTAGGCAGGACCGGGACCTTGAGGAGCCAATTAAC
TTCCGCCTCCCCGAGAACCGCATTAGTAAGGAGAAAGATGTGCTGTGGTTCCGGCCC
ACTCTCCTCAATGACACTGGCAACTATACCTGCATGTTAAGGAACACTACATATTGC
AGCAAAGTTGCATTTCCCTTGGAAGTTGTTCAAAAAGACAGCTGTTTCAATTCCCCC
ATGAAACTCCCAGTGCATAAACTGTATATAGAATATGGCATTCAGAGGATCACTTGT
CCAAATGTAGATGGATATTTTCCTTCCAGTGTCAAACCGACTATCACTTGGTATATG
GGCTGTTATAAAATACAGAATTTTAATAATGTAATACCCGAAGGTATGAACTTGAGT
TTCCTCATTGCCTTAATTTCAAATAATGGAAATTACACATGTGTTGTTACATATCCAG
AAAATGGACGTACGTTTCATCTCACCAGGACTCTGACTGTAAAGGTAGTAGGCTCTC
CAAAAAATGCAGTGCCCCCTGTGATCCATTCACCTAATGATCATGTGGTCTATGAGA
AAGAACCAGGAGAGGAGCTACTCATTCCCTGTACGGTCTATTTTAGTTTTCTGATGG
ATTCTCGCAATGAGGTTTGGTGGACCATTGATGGAAAAAAACCTGATGACATCACTA
TTGATGTCACCATTAACGAAAGTATAAGTCATAGTAGAACAGAAGATGAAACAAGA
ACTCAGATTTTGAGCATCAAGAAAGTTACCTCTGAGGATCTCAAGCGCAGCTATGTC
TGTCATGCTAGAAGTGCCAAAGGCGAAGTTGCCAAAGCAGCCAAGGTGAAGCAGAA
AGTGCCAGCTCCAAGATACACAGTGGAACTGGCTTGTGGTTTTGGAGCCACAGTCCT
GCTAGTGGTGATTCTCATTGTTGTTTACCATGTTTACTGGCTAGAGATGGTCCTATTT
TACCGGGCTCATTTTGGAACAGATGAAACCATTTTAGATGGAAAAGAGTATGATATT
TATGTATCCTATGCAAGGAATGCGGAAGAAGAAGAATTTGTATTACTGACCCTCCGT
GGAGTTTTGGAGAATGAATTTGGATACAAGCTGTGCATCTTTGACCGAGACAGTCTG
CCTGGGGGAATTGTCACAGATGAGACTTTGAGCTTCATTCAGAAAAGCAGACGCCTC
CTGGTTGTTCTAAGCCCCAACTACGTGCTCCAGGGAACCCAAGCCCTCCTGGAGCTC
AAGGCTGGCCTAGAAAAATATGGCCTCTCGGGGCAACATCAACGTCATTTTAGTACAG
TACAAAGCTGTGAAGGAAACGAAGGTGAAAGAGCTGAAGAGGGCTAAGACGGTGC
TCACGGTCATTAAATGGAAAGGGGAAAAATCCAAGTATCCACAGGGCAGGTTCTGG
AAGCAGCTGCAGGTGGCCATGCCAGTGAAGAAAAGTCCCAGGCGGTCTAGCAGTGA
TGAGCAGGGCCTCTCGTATTCATCTTTGAAAAATGTATGAAAGGAATAATGAAAAG
GGTAAAAAGAACAAGGGGTGCTCCAGGAAGAAAGAGTCCCCCCAGTCTTCATTCGC
AGTTTATGGTTTCATAGGCAAAATAATGGTCTAAGCCTCCCAATAGGGATAAATTT
AGGGTGACTGTGTGGCTGACTATTCTGCTTCCTCAGGCAACACTAAAGTTTAGAAAG
ATATCATCAACGTTCTGTCACCAGTCTCTGATGCCACTATGTTCTTTGCAGGCAAAG
ACTTGTTCAATGCGAATTTCCCCTTCTACATTGTCTATCCCTGTTTTTATATGTCTCCA
TTCTTTTTAAAATCTTAACATATGGAGCAGCCTTTCCTATGAATTTAAATATGCCTTT
AAAATAAGTCACTGTTGACAGGGTCATGAGTTTCCGAGTATAGTTTTCTTTTTATCTT
ATTTTTACTCGTCCGTTGAAAAGATAATCAAGGCCTACATTTTAGCTGAGGATAATG
AACTTTTTTCCTCATTCGGCTGTATAATACATAACCACAGCAAGACTGACATCCACTT
AGGATGATACAAAGCAGTGTAACTGAAAATGTTTCTTTTAATTGATTTAAAGGACTT
GTCTTCTATACCACCCTTGTCCTCATCTCAGGTAATTTATGAAATCTATGTAAACTTG
AAAAATATTTCTTAATTTTTGTTTTTGCTCCAGTCAATTCCTGATTATCCACAGGTCA
ACCCACATTTTTTCATTCCTTCTCCCTATCTGCTTATATCGCATTGCTCATTTAGAGTT
TGCAGGAGGCTCCATACTAGGTTCAGTCTGAAAGAAATCTCCTAATGGTGCTATAGA
GAGGGAGGTAACAGAAAGACTCTTTTAGGGCATTTTTCTGACTCATGAAAAGAGCA
CAGAAAAGGATGTTTGGCAATTTGTCTTTTAAGTCTTAACCTTGCTAATGTGAATACT
GGGAAAGTGATTTTTTCTCACTCGTTTTTGTTGCTCCATTGTAAAGGGCGGAGGTCA
GTCTTAGTGGCCTTGAGAGTTGCTTTTGGCATTAATATTCTAAGAGAATTAACTGTAT
TTCCTGTCACCTATTCACTAGTGCAGGAAATATACTTGCTCCAAATAAGTCAGTATG
AGAAGTCACTGTCAATGAAAGTTGTTTTGTTTGTTTTCAGTAATATTTTGCTGTTTTT
AAGACTTGGAAAACTAAGTGCAGAGTTTACAGAGTGGTAAATATCTATGTTACATGT
AGATTATACATATATATACACACGTGTATATGAGATATATATCTTTATATCTCCACAA
ACACAAATTATATATATACATATCCACACACATACATTACATATATCTGTGTATATA
AATCCACATGCACATGAAATATATATATATATATAATTTGTGTGTGTGTATGTGTAT
GTATATGACTTTAAATAGCTATGGGTACAATATTAAAAACCACTGGAACTCTTGTCC
AGTTTTTAAATTATGTTTTTACTGGAATGTTTTTGTGTCAGTGTTTTCTGTACATATTA
TTTGTTAATTCACAGCTCACAGAGTGATAGTTGTCATAGTTCTTGCCTTCCCTAAGTT
TATATAAATAACTTAAGTATTGCTACAGTTTATCTAGGTTGCAGTGGCATCTGCTGTG
CACAGAGCTTCCATGGTCACTGCTAAGCAGTAGCCAGCCATCGGGCATTAATTGATT
TCCTACTATATTCCCAGCAGACACATTTAGAAACTAAGCTATGTTAACCTCAGTGCT
CAACTATTTGAACTGTTGAGTGATAAAGGAAACAAATATAACTGTAAATGAATCTTG
GTATCCTGTGAAACAGAATAATTCGTAATTTAAGAAAGCCCTTATCCCGGTAACATG
AATGTTGATGAACAAATGTAAAATTATATCCTATATTTAAGTACCCATAATAAATCA
TTTCCCTCTATAAGTGTTATTGATTATTTTAAATTGAAAAAGTTTCACTTGGATGAA
AAAAGTAGAAAAGTAGGTCATTCTTGGATCTACTTTTTTTAGCCTTATTAATATTTT
TCCCTATTAGAAACCACAATTACTCCCTCTATTAACCCTTCACTTACTAGACCAGAA
AAGAACTTATTCCAGATAAGCTTTGAATATCAATTCTTACATAAACTTTAGGCAAAC
AGGGAATAGTCTAGTCACCAAAGGACCATTCTCTTGCCAATGCTGCATTCCTTTTGC
ACTTTTGGATTCCATATTTATCCCAAATGCTGTTGGGCACCCCTAGAAATACCTTGAT
GTTTTTCTATTTATATGCCTGCCTTTGGTACTTAATTTTACAAATGCTGTAATATAA
AGCATATCAAGTTTATGTGATACGTATCATTGCAAGAGAATTTGTTTCAAGATTTTTT
TTTAATGTTCCAGAAGATGGCCAATAGAGAACATTCAAGGGAAATGGGGAACATA
ATTTAGAGAACAAGAACAAACCATGTCTCAAATTTTTTTAAAAAAAATTAATGGTTT
TAAATATATGCTATAGGGACGTTCCATGCCCAGGTTAACAAAGAACTGTGATATATA
GAGTGTCTAATTACAAAATCATATACGATTTATTTAATTCTCTTCTGTATTGTAACTT
AGATGATTCCCAAGGACTCTAATAAAAAATCACTTCATTGTATTTGGAAACAAAAC
ATCATTCATTAATTACTTATTTTCTTTCCATAGGTTTTAATATTTTGAGAGTGTCTTTT
```

TABLE 5-continued

Nucleotide Sequences of Biodosimetry Biomarker Genes

TTATTTCATTCATGAACTTTTGTATTTTTCATTTTTCATTTGATTTGTAAATTTACTTAT
GTTAAAAATAAACCATTTATTTTCAGCTTTGAATTTTAAAAAAAAAAAAAAAAAA

LYRM4 (SEQ ID NO: 5; GenBank NM_020408.5).

GAGCCCTGCCTGCGCCCGCCCCCGAAGCGGCGCGGGACGCCTGGCGCCGTCCGCGA
TCCGCAGGGCTGCCCGCTTAGGCTTAGGCCCGGCCCGCTGGCAAAGCCGAGCCGCA
GCATTTTATTTCGTTCGTGGTTTCCGCACAGGCTGGAGTTTCGTGGGTTGGGTCGTAC
TTGGGACCTCGGCGAAGAGGACCCGTTTATTTTTTTTCTTTCCAAAATGGCAGCCTC
CAGTCGCGCACAAGTGTTATCTCTGTACCGGGCGATGCTGAGAGAGGAGCAAGCGTTT
CAGCGCCTACAATTACAGAACATATGCTGTCAGGAGGATAAGAGATGCCTTCAGAG
AAAATAAAAATGTAAAGGATCCTGTAGAAATTCAAACCCTAGTGAATAAAGCCAAG
AGAGACCTTGGAGTAATTCGTCGACAGGTCCACATTGGCCAACTGTATTCAACTGAC
AAGCTGATCATTGAGAATCGAGACATGCCCAGGACCTAGCAAGCCGGGGACCAGCC
ACCAGTGGCGGCCAGGGACCACCTTCAGCATCCACTCTCTGTTTGAGATGGGGGCTC
CCAAAACCAGCTTACAATAGCCTTTTGCGCTGCCTGTCCTGTGGGAGCTGATAAACC
AAGTCACATTTGCATTCTGTTGCAGGCTTAGTGAAAAAGGACTGCTGTCTTTCCTTG
GTTCAAGTGTTAGAATGGAGAGCTGGAGTTCGTTCAGAATAGTGCTGTGTGTTACCA
CGTCTCCCCTGCACCCCATTCCTACCTTGTAGCTCATGACCATTGTGTATAGCATTTC
TACACTTTGTTTCTTGGTCCTTGGCAATAAAAAGAATGATCTCCCTGAGCCTTTGACC
CCAGATAAACCCCTCCCAATTAATGCATTTTCATTTCCTACTGATACAAGGCCTGGA
GAGGGCTGTTGGGGGCCCTCAGGGAGGGTTCAACTCTGAGACGAGAACTGCCTTGG
TGAAGGCAAGTTCAAGCACCACTTGAGACTGGGGGCAGCATGGAGTGAGGGCAGGGC
TACGGGGATACACGGTGCACCCTGCAACTTATACCTGAGCCCAGTACAACAAAGGT
GACGGGTGTGTAGGTACACACCCAGAGATGGAGCACTGCAGATCAGCAACCTCAGC
CCCACCTGGGAATTTGCTGGAAATGCAGGCTCAAGCCCCTCCCCACACCTGGTGAAT
GAGAGAGCCCCAGCCTGACCCAAGCCCAGGGCGACTCCCATACCCTGAAGCCTGGG
GCATGCTGGGCAGCACCGGTGCCCAAATCTGGCTGGTGGACAGAAGCACCTGGAGA
GTTGGAGAGCTTTTTAAAAAGACATCTCTCAGCACTTCCCTCTCTGCAGATTCTGACT
CAGTAAGTGAGGGGTGAGGCACAGTCATTTTTCTCTATTCTGAAGCTCTCCCACTGT
TTTCAATGTTTAACCAACTGGGGACCCCTGCTCTTTAAGTATATTACAGGTAATAAA
GATATTGTTTGTATGCTTTTAAAAAAAAAAAAAAAAAAA.

MYC (SEQ ID NO: 6; GenBank NM_002467).

GACCCCCGAGCTGTGCTGCTCGCGGCCGCCACCGCCGGGCCCCGGCCGTCCCTGGCT
CCCCTCCTGCCTCGAGAAGGGCAGGGCTTCTCAGAGGCTTGGCGGGAAAAAGAACG
GAGGGAGGGATCGCGCTGAGTATAAAAGCCGGTTTTCGGGGCTTTATCTAACTCGCT
GTAGTAATTCCAGCGAGAGGCAGAGGGAGCGAGCGGGCGGCCGGCTAGGGTGGAA
GAGCCGGGCGAGCAGAGCTGCGCTGCGGGCGTCCTGGGAAGGGAGATCCGGAGCG
AATAGGGGGCTTCGCCTCTGGCCCAGCCCTCCCGCTGATCCCCCAGCCAGCGGTCCG
CAACCCTTGCCGCATCCACGAAACTTTGCCCATAGCAGCGGGCGGGCACTTTGCACT
GGAACTTACAACACCCGAGCAAGGACGCGACTCTCCCGACGCGGGGAGGCTATTCT
GCCCATTTGGGGACACTTCCCCGCCGCTGCCAGGACCCGCTTCTCTGAAAGGCTCTC
CTTGCAGCTGCTTAGACGCTGGATTTTTTTCGGGTAGTGGAAAACCAGCAGCCTCCC
GCGACGATGCCCCTCAACGTTAGCTTCACCAACAGGAACTATGACCTCGACTACGAC
TCGGTGCAGCCGTATTTCTACTGCGACGAGGAGGAGAACTTCTACCAGCAGCAGCA
GCAGAGCGAGCTGCAGCCCCCGGCGCCCAGCGAGGATATCTGGAAGAAATTCGAGC
TGCTGCCCACCCCGCCCCTGTCCCCTAGCCGCCGCTCCGGGCTCTGCTCGCCCTCCTA
CGTTGCGGTCACACCCTTCTCCCTTCGGGGAGACAACGACGGCGGTGGCGGGAGCTT
CTCCACGGCCGACCAGCTGGAGATGGTGACCGAGCTGCTGGGAGGAGACATGGTGA
ACCAGAGTTTCATCTGCGACCCGGACGACGAGACCTTCATCAAAAACATCATCATCC
AGGACTGTATGTGGAGCGGCTTCTCGGCCGCCGCCAAGCTCGTCTCAGAGAAGCTG
GCCTCCTACCAGGCTGCGCGCAAAGACAGCGGCAGCCCGAACCCCGCCCGCGGCCA
CAGCGTCTGCTCCACCTCCAGCTTGTACCTGCAGGATCTGAGCGCCGCCGCCTCAGA
GTGCATCGACCCCTCGGTGGTCTTCCCCTACCCTCTCAACGACAGCAGCTCGCCCAA
GTCCTGCGCCTCGCAAGACTCCAGCGCCTTCTCTCCGTCCTCGGATTCTCTGCTCTCC
TCGACGGAGTCCTCCCCGCAGGGCAGCCCCGAGCCCCTGGTGCTCCATGAGGAGAC
ACCGCCCACCACCAGCAGCGACTCTGAGGAGGAACAAGAAGATGAGGAAGAAATC
GATGTTGTTTCTGTGGAAAAGAGGCAGGCTCCTGGCAAAAGGTCAGAGTCTGGATC
ACCTTCTGCTGGAGGCCACAGCAAACCTCCTCACAGCCCACTGGTCCTCAAGAGGTG
CCACGTCTCCACACATCAGCACAACTACGCAGCGCCTCCCTCCACTCGGAAGGACTA
TCCTGCTGCCAAGAGGGTCAAGTTGGACAGTGTCAGAGTCCTGAGACAGATCAGCA
ACAACCGAAAATGCACCAGCCCCAGGTCCTCGGACACCGAGGAGAATGTCAAGAGG
CGAACACACAACGTCTTGGAGCGCCAGAGGAGGAACGAGCTAAAACGGAGCTTTTT
TGCCCTGCGTGACCAGATCCCGGAGTTGGAAAACAATGAAAAGGCCCCCAAGGTAG
TTATCCTTAAAAAGCCACAGCATACATCCTGTCCGTCCAAGCAGAGGAGCAAAAG
CTCATTTCTGAAGAGGACTTGTTGCGGAAACGACGAGAACAGTTGAAACACAAACT
TGAACAGCTACGGAACTCTTGTGCGTAAGGAAAAGTAAGGAAAACGATTCCTTCTA
ACAGAAATGTCCTGAGCAATCACCTATGAACTTGTTTCAAATGCATGATCAAATGCA
ACCTCACAACCTTGGCTGAGTCTTGAGACTGAAAGATTTAGCCATAATGTAAACTGC
CTCAAATTGGACTTTGGGCATAAAAGAACTTTTTTATGCTTACCATCTTTTTTTTTCT
TTAACAGATTTGTATTTAAGAATTGTTTTTAAAAAATTTTAAGATTTACACAATGTTT
CTCTGTAAATATTGCCATTAAATGTAAATAACTTTAATAAAACGTTTATAGCAGTTA
CACAGAATTTCAATCCTAGTATATAGTACCTAGTATTATAGGTACTATAAACCCTAA
TTTTTTTTATTTAAGTACATTTTGCTTTTTAAAGTTGATTTTTTTCTATTGTTTTTAGAA
AAAATAAAATAACTGGCAAATATATCATTGAGCCAAATCTTAAAAAAAAAAAAAAA

TABLE 5-continued

Nucleotide Sequences of Biodosimetry Biomarker Genes

TMEM63B (SEQ ID NO: 7; GenBank NM_018426.1).

```
AACCCGGGGCTCCGAGCCGGAGCCGAGTCTGCGCCTGGGGGAGGACCATGCGGCAG
TAGCAGCCATGCTGCCCTTTCTGCTGGCCACACTGGGCACCACAGCCCTCAACAACA
GCAACCCCAAGGACTACTGCTACAGCGCCCGCATCCGCAGCACTGTCCTGCAGGGC
CTGCCCTTTGGGGGCGTCCCCACCGTGCTGGCTCTCGACTTCATGTGCTTCCTTGCAC
TGCTGTTCTTATTCTCTATCCTCCGGAAGGTGGCCTGGGACTATGGCGGCTGGCCTT
GGTGACAGATGCAGACAGGCTTCGGCGGCAGGAGAGGGACCGAGTGGAACAGGAA
TATGTGGCTTCAGCTATGCACGGGGACAGCCATGACCGGTATGAGCGTCTCACCTCT
GTCTCCAGCTCCGTTGACTTTGACCAAAGGGACAATGGTTTCTGTTCCTGGCTGACA
GCCATCTTCAGGATAAAGGATGATGAGATCCGGGACAAATGTGGGGGCGATGCCGT
GCACTACCTGTCCTTTCAGCGGCACATCATCGGGCTGCTGGTGGTTGTGGGCGTCCT
CTCCGTAGGCATCGTGCTGCCTGTCAACTTCTCAGGGGACCTGCTGGAGAACAATGC
CTACAGCTTTGGGAGAACCACCATTGCCAACTTGAAATCAGGGAACAACCTGCTATG
GCTGCACACCTCCTTCGCCTTCCTGTATCTGCTGCTCACCGTCTACAGCATGCGTAGA
CACACCTCCAAGATGCGCTACAAGGAGGATGATCTGGTGAAGCGGACCCTCTTCAT
CAATGGAATCTCCAAATATGCAGAGTCAGAAAAGATCAAGAAGCATTTTGAGGAAG
CCTACCCCAACTGCACAGTTCTCGAAGCCCGCCCGTGTTACAACGTGGCTCGCCTAA
TGTTCCTCGATGCAGAGAGGAAGAAGGCCGAGCGGGGAAAGCTGTACTTCACAAAC
CTCCAGAGCAAGGAGAACGTGCCTACCATGATCAACCCCAAGCCCTGTGGCCACCT
CTGCTGCTGTGGTGCGAGGCTGTGAGCAGGTGGAGGCCATTGAGTACTACACAA
AGCTGGAGCAGAAGCTGAAGGAAGACTACAAGCGGGAGAAGGAGAAGGTGAATGA
GAAGCCTCTTGGCATGGCCTTTGTCACCTTCCACAATGAGACTATCACCGCCATCAT
CCTGAAGGACTTCAACGTGTGTAAATGCCAGGGCTGCACCTGCCGTGGGGAGCCAC
GCCCCTCATCCTGCAGCGAGTCCCTGCACATCTCCAACTGGACCGTGTCCTATGCCC
CTGACCCTCAGAACATCTACTGGGAGCACCTCTCCATCCGAGGCTTCATCTGGTGGC
TGCGCTGCCTGGTCATCAATGTCGTCCTCTTCATCCTCCTCTTCTTCCTCACCACTCC
AGCCATCATCATCACCACCATGGACAAGTTCAACGTCACCAAGCCTGTGGAGTACCT
CAACAACCCCATCATCACCCAGTTCTTCCCCACCCTGCTGCTGTGGTGCTTCTCGGCC
CTCCTTCCCACCATCGTCTACTACTCAGCCTTCTTTGAAGCCCACTGGACACGCTCTG
GGGAGAACAGGACAACCATGCACAAGTGCTACACTTTCCTCATCTTCATGGTGCTGC
TCCTACCCTCGCTGGGACTGAGCAGCCTGGACCTCTTCTTCCGCTGGCTCTTTGATAA
GAAATTCTTGGCTGAGGCAGCTATTCGGTTTGAGTGTGTGTTCCTGCCCGACAACGG
CGCCTTCTTCGTGAACTACGTCATTGCCTCAGCCTTTATCGGCAACGCCATGGACCT
GCTGCGCATCCCAGGCCTGCTCATGTACATGATCCGGCTCTGCCTGGCGCGCTCGGC
CGCCGAGAGGCGCAACGTGAAGCGGCATCAGGCCTACGAGTTCCAGTTTGGCGCAG
CCTACGCCTGGATGATGTGCGTCTTCACGGTGGTCATGACCTACAGTATCACCTGCC
CCATCATCGTGCCCTTCGGGCTCATGTACATGCTGCTGAAGCACCTGGTAGACAGGT
ACAATCTCTACTACGCCTACCTGCCGGCCAAGCTGGACAAGAAGATCCACTCGGGG
GCTGTGAACCAGGTGGTGGCCGCGCCCATCCTCTGCCTCTTCTGGCTGCTCTTCTTTT
CCACCATGCGCACGGGGTTCCTAGCTCCCACGTCTATGTTCACATTTGTGGTCCTGGT
CATCACCATCGTCATCGTCTCTGCCACGTCTGCTTTGGACACTTCAAATACCTCAGT
GCCCACAACTACAAGATTGAGCACACGGAGACAGATACTGTGGACCCCAGAAGCAA
TGGACGGCCCCCCACTGCTGCTGCTGTCCCCAAATCTGCGAAATACATCGCTCAGGT
GCTGCAGGACTCAGAGGTGGACGGGGATGGGGATGGGGCTCCTGGGAGCTCAGGGG
ATGAGCCCCATCATCCTCATCCCAAGATGAGGAGTTGCTGATGCCACCCGACGCCC
TCACGGACACAGACTTCCAGTCTTGCGAGGACAGCCTCATAGAGAATGAGATTCAC
CAGTAAGGGAGGGAGGGGCCCTGGAGGCCCACATCCTGCCCCACCCCACCCCCACT
CCCACGGACACTAAAACGCTAATAATTTATTAGATCTAAAGCCCCTTCCTCCCCAGC
CCCTGCTTTCATTAAGGTATTTAAACTTGGGGGTTTCACTGCTCTCCCCATGATGGA
GGGAGGGAGCCCCCCAACCTCAGTGAGGAGAGCCCCGAGCCGGCCCCGGGGCAAA
GAGGGGTGCAGAGGGAGTTCCCCCAGATCAGTACCCCCCACCCCTCCCCAGCTAGT
AGCATGACCAGGAGAGGGTTAATGAGAGCCAAGAGGAGTACCTGGTGCACCTGGTG
CCGGTGGCTGGAGACCTGGGGGGCAGGTGGATCTGGGGCTGTTCCCCCCCCTCCGTT
TTTTCCACCCCACAGTTCCTCCTGGGATCTGGCCCTCCAGGGAAGTGGAGCCTCCAG
CCCCTAGGGGATGCATGAGGGGGGAGGGGGTGCTGAGTGGGAGGAAGAGTCAGGC
TCACAGCTGGGGTGGCCTGGGGGTGGGGGTGGGCAAGGCTGACACTGGAAAATGGG
TTTTTGCACTGTTTTTTTTTGGTTTTTTTGTTCTTTTTTGTTTTTTTCCTTTAAAATAA
AAACAAAGAAAAGCTCTGAAAAAAAAAAAAAAAAAA
```

ALOX5 (SEQ ID NO: 8; GenBank NM_000698.3).

```
CCGGGGCCAGGGACCAGTGGTGGGAGGAGGCTGCGGCGCTAGATGCGGACACCTG
GACCGCCGCGCCGAGGCTCCCGGCGCTCGCTGCTCCCGCGGCCCGCGCCATGCCCTC
CTACACGGTCACCGTGGCCACTGGCAGCCAGTGGTTCGCCGGCACTGACGACTACAT
CTACCTCAGCCTCGTGGGCTCGGCGGCTGCAGCGAGAAGCACCTGCTGGACAAGC
CCTTCTACAACGACTTCGAGCGTGGCGCGGTGGATTCATACGACGTGACTGTGGACG
AGGAACTGGGCGAGATCCAGCTGGTCAGAATCGAGAAGCGCAAGTACTGGCTGAAT
GACGACTGGTACCTGAAGTACATCACGCTGAAGACGCCCCACGGGGACTACATCGA
GTTCCCCTGCTACCGCTGGATCACCGGCGATGTCGAGGTTGTCCTGAGGGATGGACG
CGCAAAGTTGGCCCGAGATGACCAAATTCACATTCTCAAGCAACACCGACGTAAAG
AACTGGAAACACGGCAAAAACAATATCGATGGATGGAGTGGAACCCTGGCTTCCCC
TTGAGCATCGATGCCAAATGCCACAAGGATTTACCCCGTGATATCCAGTTTGATAGT
GAAAAAGGAGTGGACTTTGTTCTGAATTACTCCAAAGCGATGGAGAACCTGTTCATC
AACCGCTTCATGCACATGTTCCAGTCTTCTTGGAATGACTTCGCCGACTTTGAGAAA
ATCTTTGTCAAGATCAGCAACACTATTTCTGAGCGGGTCATGAATCACTGGCAGGAA
GACCTGATGTTTGGCTACCAGTTCCTGAATGGCTGCAACCCTGTGTTGATCGGCGC
TGCACAGAGCTGCCCGAGAAGCTCCCGGTGACCACGGAGATGGTAGAGTGCAGCCT
```

TABLE 5-continued

Nucleotide Sequences of Biodosimetry Biomarker Genes

```
GGAGCGGCAGCTCAGCTTGGAGCAGGAGGTCCAGCAAGGGAACATTTTCATCGTGG
ACTTTGAGCTGCTGGATGGCATCGATGCCAACAAAACAGACCCCTGCACACTCCAGT
TCCTGGCCGCTCCCATCTGCTTGCTGTATAAGAACCTGGCCAACAAGATTGTCCCCA
TTGCCATCCAGCTCAACCAAATCCCGGGAGATGAGAACCCTATTTTCCTCCCTTCGG
ATGCAAAATACGACTGGCTTTTGGCCAAAATCTGGGTGCGTTCCAGTGACTTCCACG
TCCACCAGACCATCACCCACCTTCTGCGAACACATCTGGTGTCTGAGGTTTTTGGCA
TTGCAATGTACCGCCAGCTGCCTGCTGTGCACCCCATTTTCAAGCTGCTGGTGGCAC
ACGTGAGATTCACCATTGCAATCAACACCAAGGCCCGTGAGCAGCTCATCTGCGAG
TGTGGCCTCTTTGACAAGGCCAACGCCACAGGGGGCGGTGGGCACGTGCAGATGGT
GCAGAGGGCCATGAAGGACCTGACCTATGCCTCCCTGTGCTTTCCCGAGGCCATCAA
GGCCCGGGGCATGGAGAGCAAAGAAGACATCCCCTACTACTTCTACCGGGACGACG
GGCTCCTGGTGTGGGAAGCCATCAGGACGTTCACGGCCGAGGTGGTAGACATCTAC
TACGAGGGCGACCAGGTGGTGGAGGAGGACCCGGAGCTGCAGGACTTCGTGAACGA
TGTCTACGTGTACGGCATGCGGGCCGCAAGTCCTCAGGCTTCCCCAAGTCGGTCAA
GAGCCGGGAGCAGCTGTCGGAGTACCTGACCGTGGTGATCTTCACCGCCTCCGCCCA
GCACGCCGCGGTCAACTTCGGCCAGTACGACTGGTGCTCCTGGATCCCCAATGCGCC
CCCAACCATGCGAGCCCCGCCACCGACTGCCAAGGGCGTGGTGACCATTGAGCAGA
TCGTGGACACGCTGCCCGACCGCGGCCGCTCCTGCTGGCATCTGGGTGCAGTGTGGG
CGCTGAGCCAGTTCAGGAAAACGAGCTGTTCCTGGGCATGTACCCAGAAGAGCAT
TTTATCGAGAAGCCTGTGAAGGAAGCCATGGCCCGATTCCGCAAGAACCTCGAGGC
CATTGTCAGCGTGATTGCTGAGCGCAACAAGAAGAAGCAGCTGCCATATTACTACTT
GTCCCCAGACCGGATTCCGAACAGTGTGGCCATCTGAGCACACTGCCAGTCTCACTG
TGGGAAGGCCAGCTGCCCAGCCAGATGGACTCCAGCCTGCCTGGCAGGCTGTCTG
GCCAGGCCTCTTGGCAGTCACATCTCTTCCTCCGAGGCCAGTACCTTTCCATTTATTC
TTTGATCTTCAGGGAACTGCATAGATTGATCAAAGTGTAAACACCATAGGGACCCAT
TCTACACAGAGCAGGACTGCACAGCGTCCTGTCCACACCCAGCTCAGCATTTCCACA
CCAAGCAGCAACAGCAAATCACGACCACTGATAGATGTCTATTCTTGTTGGAGACAT
GGGATGATTATTTTCTGTTCTATTTGTGCTTAGTCCAATTCCTTGCACATAGTAGGTA
CCCAATTCAATTACTATTGAATGAATTAAGAATTGGTTGCCATAAAAATAAATCAGT
TCATTTAAAATGAAAAAAAAAAAAAAAAAAAA
```

CAMK4 (SEQ ID NO: 9; GenBank NM_001744.4).

```
AGTCTCCCTCCAGCGGGCGGCGACTCCGGGTTCCCCCTCGCGCCCTCTCGCAGAGGC
TCGCCCCCTTCCCCGCCCACCGTCCCTGCGAGCGCGGGCGGCGGCGGTGGGCGTGTG
CGCGCGTGAAGGACGCCGCCTCTCTCGCTCCTGCGTTCGCAGGCGGCGGCTGGCG
GCCGGCTTCTCGCTCGGGCAGCGGCGGCGGCGGCGGCGGCTTCCGGAGTCCCG
CTGCGAAGATGCTCAAAGTCACGGTGCCCTCCTGCTCCGCCTCGTCTGCTCTTCGG
TCACCGCCAGTGCGGCCCCGGGGACCGCGAGCCTCGTCCCGGATTACTGGATCGAC
GGCTCCAACAGGGATGCGCTGAGCGATTTCTTCGAGGTGGAGTCGGAGCTGGGACG
GGGTGCTACATCCATTGTGTACAGATGCAAACAGAAGGGGACCCAGAAGCCTTATG
CTCTCAAAGTGTTAAAGAAAACAGTGGACAAAAAATCGTAAGAACTGAGATAGGA
GTTCTTCTTCGCCTCTCACATCCAAACATTATAAAACTTAAAGAGATATTTGAAACC
CCTACAGAAATCAGTCTGGTCCTAGAACTCGTCACAGGAGGAGAACTGTTTGATAG
GATTGTGGAAAAGGGATATTACAGTGAGCGAGATGCTGCAGATGCCGTTAAACAAA
TCCTGGAGGCAGTTGCTTATCTACATGAAAATGGGATTGTCCATCGTGATCTCAAAC
CAGAGAATCTTCTTTATGCAACTCCAGCCCCAGATGCACCACTCAAAATCGCTGATT
TTGGACTCTCTAAAATTGTGGAACATCAAGTGCTCATGAAGACAGTATGTGGAACTCC
CAGGGTACTGCGCACCTGAAATTCTTAGAGGTTGTGCCTATGGACCTGAGGTGGACA
TGTGGTCTGTAGGAATAATCACCTACATCTTACTTTGTGGATTTGAACCATTCTATGA
TGAAAGAGGCGATCAGTTCATGTTCAGGAGAATTCTGAATTGTGAATATTACTTTAT
CTCCCCCTGGTGGGATGAAGTATCTCTAAATGCCAAGGACTTGGTCAGAAAATTAAT
TGTTTTGGATCCAAAGAAACGGCTGACTACATTTCAAGCTCTCCAGCATCCGTGGGT
CACAGGTAAAGCAGCCAATTTTGTACACATGGATACCGCTCAAAAGAAGCTCCAAG
AATTCAATGCCCGGCGTAAGCTTAAGGCAGCGGTGAAGGCTGTGGTGGCCTCTTCCC
GCCTGGGAAGTGCCAGCAGCAGCCATGGCAGCATCCAGGAGAGCCACAAGGCTAGC
CGAGACCCTTCTCCAATCCAAGATGGCAACGAGGACATGAAAGCTATTCCAGAAGG
AGAGAAAATTCAAGGCGATGGGGCCCAAGCCGCAGTTAAGGGGGCACAGGCTGAG
CTGATGAAGGTGCAAGCCTTAGAGAAAGTTAAAGGTGCAGATATAAATGCTGAAGA
GGCCCCCAAAATGGTGCCCAAGGCAGTGGAGGATGGGATAAAGGTGGCTGACCTGG
AACTAGAGGAGGGCCTAGCAGAGGAGAAGCTGAAGACTGTGGAGGAGGCAGCAGC
TCCCAGAGAAGGGCAAGGAAGCTCTGCTGTGGGTTTGAAGTTCCACAGCAAGATG
TGATCCTGCCAGAGTACTAAACAGCTTCCTTCAGATCTGGAAGCCAAACACCGGCAT
TTTATGTACTTTGTCCTTCAGCAAGAAAGGTGTGGAAGCATGATATGTACTATAGTG
ATTCTGTTTTTGAGGTGCAAAAAACATACATATATACCAGTTGGTAATTCTAACTTC
AATGCATGTGACTGCTTTATGAAAATAATAGTGTCTTCTATGGCATGTAATGGATAC
CTAATACCGATGAGTTAAATCTTGCAAGTTAACACAACGTAACACTTAAAAGCATAC
ATTTTCAGCAACCAGTGGCACATATTTGAAGTGAATAGTAGCAAATTGTTTTGCTTT
GAAAATCTAGCCATCCTACATCCTTTGGATTTCTTCACAAGGCAGTAATTCCTTTGAA
CTACTGCTTAGCTAATACTAGGTAGTGCTAAAAGACATGTTCCCATAACTTTTACAA
CATTTTACTTTTTATCATTGATGTGTTCAAACTGTTTACAAGGAGATGCTTATAGATG
ATAGTTGTACATATGTGCAAAAAAAAATCCACTTGCAATGGTAAGAAATTGAAGTA
TCCTTAAAGGCCATGAAGCCATATGTCCCTAAAAAAAAAAAAAAAAAAAAAAAAAA
AAAAAAAA
```

CDKN1A (SEQ ID NO: 10; NM_000389.4).

```
GTTGTATATCAGGGCCGCGCTGAGCTGCGCCAGCTGAGGTGTGAGCAGCTGCCGAA
```

TABLE 5-continued

Nucleotide Sequences of Biodosimetry Biomarker Genes

```
GTCAGTTCCTTGTGGAGCCGGAGCTGGGCGCGGATTCGCCGAGGCACCGAGGCACT
CAGAGGAGGCGCCATGTCAGAACCGGCTGGGGATGTCCGTCAGAACCCATGCGGCA
GCAAGGCCTGCCGCCGCCTCTTCGGCCCAGTGGACAGCGAGCAGCTGAGCCGCGAC
TGTGATGCGCTAATGGCGGGCTGCATCCAGGAGGCCCGTGAGCGATGGAACTTCGA
CTTTGTCACCGAGACACCACTGGAGGGTGACTTCGCCTGGGAGCGTGTGCGGGGCCT
TGGCCTGCCCAAGCTCTACCTTCCCACGGGGCCCCGGCGAGGCCGGGATGAGTTGG
GAGGAGGCAGGCGGCCTGGCACCTCACCTGCTCTGCTGCAGGGGACAGCAGAGGAA
GACCATGTGGACCTGTCACTGTCTTGTACCCTTGTGCCTCGCTCAGGGGAGCAGGCT
GAAGGGTCCCCAGGTGGACCTGGAGACTCTCAGGGTCGAAAACGGCGGCAGACCAG
CATGACAGATTTCTACCACTCCAAACGCCGGCTGATCTTCTCCAAGAGGAAGCCCTA
ATCCGCCCACACAGGAAGCCTGCAGTCCTGGAAGCGCGAGGGCCTCAAAGGCCCGCTC
TACATCTTCTGCCTTAGTCTCAGTTTGTGTGTCTTAATTATTATTTGTGTTTTAATTTA
AACACCTCCTCATGTACATACCCTGGCCGCCCCCTGCCCCCCAGCCTCTGGCATTAG
AATTATTTAAACAAAAACTAGGCGGTTGAATGAGAGGTTCCTAAGAGTGCTGGGCA
TTTTTATTTTATGAAATACTATTTAAAGCCTCCTCATCCCGTGTTCTCCTTTTCCTCTC
TCCCGGAGGTTGGGTGGGCCGGCTTCATGCCAGCTACTTCCTCCTCCCCACTTGTCC
GCTGGGTGGTACCCTCTGGAGGGGTGTGGCTCCTTCCCATCGCTGTCACAGGCGGTT
ATGAAATTCACCCCCTTTCCTGGACACTCAGACCTGAATTCTTTTTCATTTGAGAAGT
AAACAGATGGCACTTTGAAGGGGCCTCACCGAGTGGGGGCATCATCAAAAACTTTG
GAGTCCCCTCACCTCCTCTAAGGTTGGGCAGGGTGACCCTGAAGTGAGCACAGCCTA
GGGCTGAGCTGGGGACCTGGTACCCTCCTGGCTCTTGATACCCCCCTCTGTCTTGTG
AAGGCAGGGGGAAGGTGGGGTCCTGGAGCAGACCACCCCGCCTGCCCTCATGGCCC
CTCTGACCTGCACTGGGGAGCCCGTCTCAGTGTTGAGCCTTTTCCCTCTTTGGCTCCC
CTGTACCTTTTGAGGAGCCCCAGCTACCCTTCTTCTCCAGCTGGGCTCTGCAATTCCC
CTCTGCTGCTGTCCCTCCCCCTTGTCCTTTCCCTTCAGTACCCTCTCAGCTCCAGGTG
GCTCTGAGGTGCCTGTCCCACCCCCACCCCCAGCTCAATGGACTGGAAGGGGAAGG
GACACACAAGAAGAAGGGCACCCTAGTTCTACCTCAGGCAGCTCAAGCAGCGACCG
CCCCCTCCTCTAGCTGTGGGGGTGAGGGTCCCATGTGGTGGCACAGGCCCCCTTGAG
TGGGGTTATCTCTGTGTTAGGGGTATATGATGGGGGAGTAGATCTTTCTAGGAGGGA
GACACTGGCCCCTCAAATCGTCCAGCGACCTTCCTCATCCACCCCATCCCTCCCCAG
TTCATTGCACTTTGATTAGCAGCGGAACAAGGAGTCAGACATTTTAAGATGGTGGCA
GTAGAGGCTATGGACAGGGCATGCCACGTGGGCTCATATGGGGCTGGGAGTAGTTG
TCTTTCCTGGCACTAACGTTGAGCCCCTGGAGGCACTGAAGTGCTTAGTGTACTTGG
AGTATTGGGGTCTGACCCCAAACACCTTCCAGCTCCTGTAACATACTGGCCTGGACT
GTTTTCTCTCGGCTCCCCATGTGTCCTGGTTCCCGTTTCTCCACCTAGACTGTAAACC
TCTCGAGGGCAGGGACCACACCCTGTACTGTTCTGTGTCTTTCACAGCTCCTCCCAC
AATGCTGAATATACAGCAGGTGCTCAATAAATGATTCTTAGTGACTTTACTTGTAAA
AAAAAAAAAAAAAA
```

COCH (SEQ ID NO: 11; AY358900.1).

```
GGGGCCTTGCCTTCCGCACTCGGGCGCAGCCGGGTGGATCTCGAGCAGGTGCGGAG
CCCCGGGCGGCGGGCGCGGGTGCGAGGGATCCCTGACGCCTCTGTCCCTGTTTCTTT
GTCGCTCCCAGCCTGTCTGTCGTCGTTTTGGCGCCCCGCCTCCCCGCGGTGCGGGG
TTGCACACCGATCCTGGGCTTCGCTCGATTTGCCGCCGAGGCGCCTCCCAGACCTAG
AGGGGCGCTGGCCTGGAGCAGCGGGTCGTCTGTGTCCTCTCTCCTCTGCGCCGCGCC
CGGGGATCCGAAGGGTGCGGGGCTCTGAGGAGGTGACGCGCGGGGCCTCCCGCACC
CTGGCCTTGCCCGCATTCTCCCTCTCTCCCAGGTGTGAGCAGCCTATCAGTCACCATG
TCCGCAGCCTGGATCCCGGCTCTCGGCCTCGGTGTGTGTCTGCTGCTGCTGCCGGGG
CCCGCGGGCAGCGAGGGAGCCGCTCCCATTGCTATCACATGTTTTACCAGAGGCTTG
GACATCAGGAAAGAGAAAGCAGATGTCCTCTGCCCAGGGGGCTGCCCTCTTGAGGA
ATTCTCTGTGTATGGGAACATAGTATATGCTTCTGTATCGAGCATATGTGGGGCTGC
TGTCCACAGGGGAGTAATCAGCAACTCAGGGGGACCTGTACGAGTCTATAGCCTAC
CTGGTCGAGAAAACTATTCCTCAGTAGATGCCAATGGCATCCAGTCTCAAATGCTTT
CTAGATGGTCTGCTTCTTTCACAGTAACTAAAGGCAAAGTAGTACACAGGAGGCC
ACAGGACAAGCAGTGTCCACAGCACATCCACCAACAGGTAAAGACTAAAGAAAA
CACCCGAGAAGAAAACTGGCAATAAAGATTGTAAAGCAGACATTGCATTTCTGATT
GATGGAAGCTTTAATATTGGGCAGCGCCGATTTAATTTACAGAAGAATTTTGTTGGA
AAAGTGGCTCTAATGTTGGGAATTGGAACAGAAGGACCACATGTGGGCCTTGTTCA
AGCCAGTGAACATCCCAAAATAGAATTTTACTTGAAAAACTTTACATCAGCCAAAG
ATGTTTTGTTTGCCATAAAGGAAGTAGGTTTCAGAGGGGGTAATTCCAATACAGGAA
AAGCCTTGAAGCATACTGCTCAGAAATTCTTCACGGTAGATGCTGGAGTAAGAAAA
GGGATCCCCAAAGTGGTGGTGGTATTTATTGATGGTTGGCCTTCTGATGACATCGAG
GAAGCAGGCATTGTGGCCAGAGAGTTTGGTGTCAATGTATTTATAGTTTCTGTGGCC
AAGCCTATCCCTGAAGAACTGGGGATGGTTCAGGATGTCACATTTGTTGACAAGGCT
GTCTGTCGGAATAATGGCTTCTTCTCTTACCACATGCCCAACTGGTTTGGCACCACA
AAATACGTAAAGCCTCTGGTACAGAAGCTGTGCACTCATGAACAAATGATGTGCAG
CAAGACCTGTTATAACTCAGTGAACATTGCCTTTCTAATTGATGGCTCCAGCAGTGT
TGGAGATAGCAATTTCCGCCTCATGCTTGAATTTGTTTCCAACATAGCCAAGACTTTT
GAAATCTCGGACATTGGTGCCAAGATAGCTGCTGTACAGTTTACTTATGATCAGCGC
ACGGAGTTCAGTTTCACTGACTATAGCACCAAAGAGAATGTCCTAGCTGTCATCAGA
AACATCCGCTATATGAGTGGTGGAACAGCTACTGGTGATGCCATTTCCTTCACTGTT
AGAAATGTGTTTGGCCCTATAAGGGAGAGCCCCAACAAGAACTTCCTAGTAATTGTC
ACAGATGGGCAGTCCTATGATGATGTCCAAGGCCCTGCAGCTGCTGCACATGATGCA
GGAATCACTATCTTCTCTGTTGGTGTGGCTTGGGCACCTCTGGATGACCTGAAAGAT
ATGGCTTCTAAACCGAAGGAGTCTCACGCTTTCTTCACAAGAGAGTTCACAGGATTA
GAACCAATTGTTTCTGATGTCATCAGAGGCATTTGTAGAGATTTCTTAGAATCCCAG
CAATAATGGTAACATTTTGACAACTGAAAGAAAAAGTACAAGGGGATCCAGTGTGT
```

TABLE 5-continued

Nucleotide Sequences of Biodosimetry Biomarker Genes

AAATTGTATTCTCATAATACTGAAATGCTTTAGCATACTAGAATCAGATACAAAACT
ATTAAGTATGTCAACAGCCATTTAGGCAAATAAGCACTCCTTTAAAGCCGCTGCCTT
CTGGTTACAATTTACAGTGTACTTTGTTAAAAACACTGCTGAGGCTTCATAATCATG
GCTCTTAGAAACTCAGGAAAGAGGAGATAATGTGGATTAAAACCTTAAGAGTTCTA
ACCATGCCTACTAAATGTACAGATATGCAAATTCCATAGCTCAATAAAAGAATCTGA
TACTTAGACCAAAAAAAAAAA

DHRS4 (SEQ ID NO: 12; NM_021004.3).

CTACTCTGTCACCGCCCCTGGGAAGAGTGGAACCCATACTTGCTGGTCTGATCCATG
CACAAGGCGGGGCTGCTAGGCCTCTGTGCCCGGGCTTGGAATTCGGTGCGGATGGC
CAGCTCCGGGATGACCCGCCGGGACCCGCTCGCAAATAAGGTGGCCCTGGTAACGG
CCTCCACCGACGGGATCGGCTTCGCCATCGCCCGGCGTTTGGCCCAGGACGGGGCCC
ATGTGGTCGTCAGCAGCCGGAAGCAGCAGAATGTGGACCAGGCGGTGGCCACGCTG
CAGGGGGAGGGGCTGAGCGTGACGGGCACCGTGTGCCATGTGGGGAAGGCGGAGG
ACCGGGAGCGGCTGGTGGCCACGGCTGTGAAGCTTCATGGAGGTATCGATATCCTA
GTCTCCAATGCTGCTGTCAACCCTTTCTTTGGAAGCATAATGGATGTCACTGAGGAG
GTGTGGGACAAGACTCTGGACATTAATGTGAAGGCCCCAGCCCTGATGACAAAGGC
AGTGGTGCCAGAAATGGAGAAACGAGGAGGCGGCTCAGTGGTGATCGTGTCTTCCA
TAGCAGCCTTCAGTCCATCTCCTGGCTTCAGTCCTTACAATGTCAGTAAAACAGCCTT
GCTGGGCCTGACCAAGACCCTGGCCATAGAGCTGGCCCCAAGGAACATTAGGGTGA
ACTGCCTAGCACCTGGACTTATCAAGACTAGCTTCAGCAGGATGCTCTGGATGGACA
AGGAAAAAGAGGAAAGCATGAAAGAAACCCTGCGGATAAGAAGGTTAGGCGAGCC
AGAGGATTGTGCTGGCATCGTGTCTTTCCTGTGCTCTGAAGATGCCAGCTACATCAC
TGGGGAAACAGTGGTGGTGGGTGGAGGAACCCCGTCCCGCCTCTGAGGACCGGGAG
ACAGCCCACAGGCCAGAGTTGGGCTCTAGCTCCTGGTGCTGTTCCCGCATTCACCCA
CTGGCCTTTCCCACCTCTGCTCACCTTACTGTTCACCTCATCAAATCAGTTCTGCCCT
GTGAAAAGATCCAGCCTTCCCTGCCGTCAAGGTGGCGTCTTACTCGGGATTTCTGCT
GTTGTTGTGGCCTTGGGTAAAGGCCTCCCCTGAGAACACAGGACAGGCCTGCTGACA
AGGCTGAGTCTACCTTGGCAAAGACCAAGATATTTTTTCCCGGGCCACTGGGGAATC
TGAGGGGTGATGGGAGAGAAGGAACCTGGAGTGGAAGGAGCAGAGTTGCAAATTA
ACAACTTGCAAATGAGGTGCAAATAAAATGCAGATGATTGCGCGGCTTTGAATCCA
AAAAAAAAAAAAAAAAA

MICAL1 (SEQ ID NO: 13; NM_022765.3).

CCCAAGACTGTCCCCGCTGGAGGCGGTAGAGGGATCCAGAAGTAATGAGATGCTAA
TGAGTCGCGAATAAAGCCCGGGCGGCGCCCCGCGCCCCTCGCGGAAGCCCACACTC
CGCGCGACTCCAGGCGCACGCCCCGGGCCGCCCCGCATCCCAGCATCCCCGCCCGA
TCTCGGCGTTTCCGCCCCCGCCCCCGCCCCGCCCTCCCACCCGCTCAGACCTGGTTG
CCAGCCCAACAGGAAGCGGCCCCTCCCGGCTTGGAGCCGCCGCCACTCATCTCTGC
CCAGCTGCTGCCCTCCCCAGGAGGCCTCCATGGCTTCACCTACCTCCACCAACCCAG
CGCATGCCCACTTTGAGAGCTTCCTGCAGGCCCAGCTGTGCCAGGACGTGCTGAGCA
GCTTCCAGGAGCTGTGTGGGGCCCTGGGGCTGGAACCCGGTGGGGGGCTGCCCCAG
TACCACAAGATCAAGGACCAGCTCAACTACTGGAGCGCCAAGTCACTGTGGACCAA
GCTGGACAAGCGAGCAGGCCAGCCTGTCTACCAGCAGGGCCGGGCCTGCACCAGCA
CCAAGTGCCTGGTGGTGGGTGCTGGACCTTGCGGGCTGCGGGTCGCTGTGGAGCTGG
CGCTGCTGGGGGCCCGAGTGGTGCTGGTGGAAAAGCGCACCAAGTTCTCTCGCCAC
AACGTGCTCCACCTCTGGCCCTTCACCATCCACGACCTGCGGGCACTCGGTGCTAAG
AAGTTCTACGGGCGCTTCTGCACCGGCACCCTGGACCACATCAGCATCAGGCAGCTC
CAGCTGCTTCTGCTGAAGGTAGCATTGCTGCTGGGGGTGGAAATTCACTGGGGTGTC
ACTTTCACTGGCCTCCAGCCCCTCCTAGGAAGGGGAGTGGCTGGCGTGCCCAGCTC
CAACCCAACCCCCCTGCCCAGCTGGCCAACTATGAATTTGACGTCCTTATCTCGGCT
GCAGGAGGTAAATTCGTCCCTGAAGGCTTCAAAGTTCGAGAAATGCGAGGCAAACT
GGCCATTGGCATCACAGCCAACTTTGTGAATGGACGCACCGTGGAGGAGACACAGG
TGCCGGAGATCAGTGGTGTAGCCAGGATCTACAACCAGAGCTTCTTCCAGAGCCTTC
TCAAAGCCACAGGCATTGATCTGGAGAACATTGTGTACTACAAGGACGACACCCAC
TACTTTGTGATGACAGCCAAGAAGCAGTGCCTGCTGCGGCTGGGGGTGCTGCGCCA
GGACTGGCCAGACACCAATCGGCTGCTGGGCAGTGCCAATGTGGTGCCCGAGGCTC
TGCAGCGCTTTACCCGGGCAGCTGCTGACTTTGCCACCCATGGCAAGCTCGGGAAAC
TAGAGTTTGCCCAGGATGCCCATGGGCAGCCTGATGTCTCTGCCTTTGACTTCACGA
GCATGATGCGGGCAGAGAGTTCTGCTCGTGTGCAAGAGAAGCATGGCGCCCGCCTG
CTGCTGGGACTGGTGGGGGACTGCCTGGTGGAGCCCTTCTGGCCCCTGGGCACTGGA
GTGGCACGGGGCTTCCTGGCAGCCTTTGATGCAGCCTGGATGGTGAAGCGGTGGGC
AGAGGGCGCTGAGTCCCTAGGGTGTTGGCTGAGCGTGAGAGCCTGTACCAGCTTCT
GTCACAGACATCCCCAGAAAACATGCATCGCAATGTGGCCCAGTATGGGCTGGACC
CAGCCACCCGCTACCCCAACCTGAACCTCCGGGCAGTGACCCCCAATCAGGTACGA
GACCTGTATGATGTGCTAGCCAAGGAGCCTGTGCAGAGGAACAACGACAAGACAGA
TACAGGGATGCCAGCCACCGGGTCGGCAGGCACCCAGGAGGAGCTGCTACGCTGGT
GCCAGGAGCAGACAGCTGGGTACCCGGGAGTCCACGTCTCCGATTTGTCTTCCTCCT
GGGCTGATGGGCTAGCTCTGTGTGCCCTGGTGTACCGGCTGCAGCCTGGCCTGCTGG
AACCCTCAGAGCTGCAGGGGCTGGGAGCTCTGGAAGCAACTGCTTGGGCACTAAAG
GTGGCAGAGAATGAGCTGGGCATCACACCGGTGGTCTGCACAGGCCGTGGTAGC
AGGGAGTGACCCACTGGGCCTCATTGCCTACCTCAGCCACTTCCACAGTGCCTTCAA
GAGCATGGCCCACAGCCCAGGCCCTGTCAGCCAGGCCTCCCCAGGGACCTCCAGTG
CTGTATTATTCCTTAGTAAACTTCAGAGGACCCTGCAGCGATCCCGGGCAAGGAAA
ATGCAGAGGATGCTGGTGGCAAGAAGCTGCGCTTGGAGATGGAGGCCGAGACCCCA
AGTACTGAGGTGCCACCTGACCCAGAGCCTGGTGTACCCCTGACACCCCCATCCCAA

TABLE 5-continued

Nucleotide Sequences of Biodosimetry Biomarker Genes

CACCAGGAGGCCGGTGCTGGGGACCTGTGTGCACTTTGTGGGGAACACCTCTATGTC
CTGGAACGCCTCTGTGTCAACGGCCATTTCTTCCACCGGAGCTGCTTCCGCTGCCAT
ACCTGTGAGGCCACACTGTGGCCAGGTGGCTACGAGCAGCACCCAGGAGATGGACA
TTTCTACTGCCTCCAGCACCTGCCCCAGACAGACCACAAAGCGGAAGGCAGCGATA
GAGGCCCTGAGAGTCCGGAGCTCCCCACACCAAGTGAGAATAGCATGCCACCAGGC
CTCTCAACTCCCACAGCCTCGCAGGAGGGGGCCGGTCCTGTTCCAGATCCCAGCCAG
CCCACCCGTCGGCAGATCCGCCTCTCCAGCCCGGAGCGCCAGCGGTTGTCCTCCCTT
AACCTTACCCCTGACCCGGAAATGGAGCCTCCACCCAAGCCTCCCCGCAGCTGCTCC
GCCTTGGCCCGCCACGCCCTGGAGAGCAGCTTTGTGGGCTGGGGCCTGCCAGTCCAG
AGCCCTCAAGCTCTTGTGGCCATGGAGAAGGAGGAAAAAGAGAGTCCCTTCTCCAG
TGAAGAGGAAGAAGAAGATGTGCCTTTGGACTCAGATGTGGAACAGGCCCTGCAGA
CCTTTGCCAAGACCTCAGGCACCATGAATAACTACCCAACATGGCGTCGGACTCTGC
TGCGCCGTGCGAAGGAGGAGGAGATGAAGAGGTTCTGCAAGGCCCAGACCATCCAA
CGGCGACTAAATGAGATTGAGGCTGCCTTGAGGGAGCTAGAGGCCGAGGGCGTGAA
GCTGGAGCTGGCCTTGAGGCGCCAGAGCAGTTCCCCAGAACAGCAAAAGAAACTAT
GGGTAGGACAGCTGCTACAGCTCGTTGACAAGAAAAACAGCCTGGTGGCTGAGGAG
GCCGAGCTCATGATCACGGTGCAGGAATTGAATCTGGAGGAGAAACAGTGGCAGCT
GGACCAGGAGCTACGAGGCTACATGAACCGGGAAGAAAACCTAAAGACAGCTGCT
GATCGGCAGGCTGAGGACCAGGTCCTGAGGAAGCTGGTGGATTTGGTCAACCAGAG
AGATGCCCTCATCCGCTTCCAGGAGGAGCGCAGGCTCAGCGAGCTGGCCTTGGGGA
CAGGGGGCCCAGGGCTAGACGAGGGTGGGCCGTCTGCTTTCGTTCCCACAAAGAAAG
CACCTCACCCCAGCACAGTGCCACCCCTGTTCATCTGGGCTGCCTGGCAGAGAGCCT
TGCTGTTTACAATTAAAATGTTTCTGCCACAAAAAAAAAAAAAAAAAAA

MOB3B (SEQ ID NO: 14; AJ580636.1).

ATGTCCATAGCCCTGAAGCAGGTATTCAACAAGGACAAGACCTTCCGACCCAAGAG
GAAATTTGAACCTGGCACACAGAGGTTTGAGCTGCACAAACGGGCTCAGGCATCCC
TCAACTCGGGTGTGGACCTGAAGGCGGCTGTGCAGTTGCCCAGTGGGGAGGACCAG
AATGACTGGGTGGCAGTACATGTGGTGGACTTCTTCAATCGGATCAACCTCATCTAT
GGCACCATCTGTGAGTTCTGCACCGAGCGGACCTGTCCTGTGATGTCAGGGGGCCCC
AAATATGAGTATCGGTGGCAGGATGATCTCAAGTATAAGAAGCCAACAGCGCTGCC
AGCTCCCCAGTACATGAACCTTCTTATGGATTGGATTGAGGTTCAGATCAACAACGA
GGAAATATTTCCAACATGCGTGGGTGTTCCCTTCCCAAAGAACTTCCTTCAGATCTG
CAAGAAGATCCTGTGCCGCCTTTTCCGGGTCTTTGTCCACGTCTATATCCACCACTTC
GACCGGGTCATTGTGATGGGTGCAGAGGCCCATGTCAACACCTGCTACAAACACTTC
TATTACTTTGTCACAGAGATGAACCTCATAGACCGCAAGGAGCTAGAGCCTTTGAAA
GAAATGACGAGCAGGATGTGTCACTAA

NUSAP1 (SEQ ID NO: 15; NM_016359.4).

GCGTTACAGGCCCTTTGGCGCCTGCGTATTCGTGAAGTGTGAAAAAGCGCGCCTCT
GTTGGGACGGGAAATCAGCCTTTCTATTGGTCAGGGTTAGAAACCCCGCCTTTGAGG
CATTTTCAACCAATGGAAGCGCGGCATTCTTCATTTAAACTGTCTATAAATTTCTGCC
TAGTCAAAGTTAAGAGTGGCGCCAGGGATTTGAACCGCGCTGACGAAGTTTGGTGA
TCCATCTTCCGAGTATCGCCGGGATTTCGAATCGCGATGATCATCCCCTCTCTAGAG
GAGCTGGACTCCCTCAAGTACAGTGACCTGCAGAACTTAGCCAAGAGTCTGGGTCTC
CGGGCCAACCTGAGGGCAACCAAGTTGTTAAAAGCCTTGAAAGGCTACATTAAACA
TGAGGCAAGAAAAGGAAATGAGAATCAGGATGAAAGTCAAACTTCTGCATCCTCTT
GTGATGAGACTGAGATACAGATCAGCAACCAGGAAGAAGCTGAGAGACAGCCACTT
GGCCATGTCACCAAAACAAGGAGAAGGTGCAAGACTGTCCGTGTGGACCCTGACTC
ACAGCAGAATCATTCAGAGATAAAAATAAGTAATCCCACTGAATTCCAGAATCATG
AAAAGCAGGAAAGCCAGGATCTCAGAGCTACTGCAAAAGTTCCTTCTCCACCAGAC
GAGCACCAAGAAGCTGAGAATGCTGTTTCCTCAGGTAACAGAGATTCAAAGGTACC
TTCAGAAGGAAAGAAATCTCTACACAGATGAGTCATCCAAACCTGGAAAAAATA
AAAGAACTGCAATCACTACTCCAAACTTTAAGAAGCTTCATGAAGCTCATTTTAAGG
AAATGGAGTCCATTGATCAATATATTGAGAGAAAAAAGAAACATTTTGAAGAACAC
AATTCCATGAATGAACTGAAGCAGCAGCCCATCAATAAGGGAGGGGTCAGGACTCC
AGTACCTCCAAGAGGAAGACTCTCTGTGGCTTCTACTCCCATCAGCCAACGACGCTC
GCAAGGCCGGTCTTGTGGCCCTGCAAGTCAGAGTACCTTGGGTCTGAAGGGGTCACT
CAAGCGCTCTGCTATCTCTGCAGCTAAAACGGGTGTCAGGTTTTCAGCTGCTACTAA
AGATAATGAGCATAAGCGTTCACTGACCAAGACTCCAGCCAGAAAGTCTGCACATG
TGACCGTGTCTGGGGGCACCCCAAAAGGCGAGGCTGTGCTTGGGACACACAAATTA
AAGACCATCACGGGGAATTCTGCTGCTGTTATTACCCCATTCAAGTTGACAACTGAG
GCAACGCAGACTCCAGTCTCCAATAAGAAACCAGTGTTTGATCTTAAAGCAAGTTTG
TCTCGTCCCCTCAACTATGAACCACACAAAGGAAAGCTAAAACCATGGGGGCAATC
TAAAGAAAATAATTATCTAAATCAACATGTCAACAGAATTAACTTCTACAAGAAAA
CTTACAAACAACCCCATCTCCAGACAAAGGAAGAGCAACGGAAGAAACGCGAGCA
AGAACGAAAGGAGAAGAAAGCAAAGGTTTTGGGAATGCGAAGGGGCCTCATTTTGG
CTGAAGATTAATAATTTTTTAACATCTTGTAAATATTCCTGTATTCTCAACTTTTTTCC
TTTTGTAAATTTTTTTTTTTGCTGTCATCCCCACTTTAGTCACGAGATCTTTTTCTGC
TAACTGTTCATAGTCTGTGTAGTGTCCATGGGTTCTTCATGTGCTATGATCTCTGAAA
AGACGTTATCACCTTAAAGCTCAAATTCTTTGGGATGGTTTTTACTTAAGTCCATTAA
CAATTCAGGTTTCTAACGAGACCCATCCTAAAATTCTGTTTCTAGATTTTTAATGTCA
AGTTCCCAAGTTCCCCTGCTGGTTCTAATATTAACAGAACTGCAGTCTTCTGCTAGC
CAATAGCATTTACCTGATGGCAGCTAGTTATGCAAGCTTCAGGAGAATTTGAACAAT
AACAAGAATAGGGTAAGCTGGGATAGAAAGGCCACCTCTTCACTCTCTATAGAATA
TAGTAACCTTTATGAAACGGGGCCATATAGTTTGGTTATGACATCAATATTTTACCT

TABLE 5-continued

Nucleotide Sequences of Biodosimetry Biomarker Genes

AGGTGAAATTGTTTAGGCTTATGTACCTTCGTTCAAATATCCTCATGTAATTGCCATC
TGTCACTCACTATATTCACAAAAATAAAACTCTACAACTCATTCTAACATTGCTTACT
TAAAAGCTACATAGCCCTATCGAAATGCGAGGATTAATGCTTTAATGCTTTTAGAGA
CAGGGTCTCACTGTGTTGCCCAGGCTGGTCTCAAACTCCACCAAATGTACTTCTTATT
CATTTTATGGAAAAGACTAGGCTTTGCTTAGTATCATGTCCATGTTTCCTTCACCTCA
GTGGAGCTTCTGAGTTTTATACTGCTCAAGATCGTCATAAATAAAATTTTTTCTCATT
GTCATAGAAAAAAAAAAAAAAAAAAA

IL27RA (SEQ ID NO: 16; NM_004843.3).

GCGGAGGCGGCCTGCCGGGGTGGTTCGGCTTCCCGTTGCCGCCTCGGGCGCTGTACC
CAGAGCTCGAAGAGGAGCAGCGCGGCCGCGCGGACCCGGCAAGGCTGGGCCGGAC
TCGGGGCTCCCGAGGGACGCCATGCGGGGAGGCAGGGGCGCCCCTTTCTGGCTGTG
GCCGCTGCCCAAGCTGGCGCTGCTGCCTCTGTTGTGGGTGCTTTTCCAGCGGACGCG
TCCCCAGGGCAGCGCCGGGCCACTGCAGTGCTACGGAGTTGGACCCTTGGGCGACT
TGAACTGCTCGTGGGAGCCTCTTGGGGACCTGGGAGCCCCCTCCGAGTTACACCTCC
AGAGCCAAAAGTACCGTTCCAACAAAACCCAGACTGTGGCAGTGGCAGCCGGACGG
AGCTGGGTGGCCATTCCTCGGGAACAGCTCACCATGTCTGACAAACTCCTTGTCTGG
GGCACTAAGGCAGGCCAGCCTCTCTGGCCCCCCGTCTTCGTGAACCTAGAAACCCAA
ATGAAGCCAAACGCCCCCCGGCTGGGCCCTGACGTGGACTTTTCCGAGGATGACCC
CCTGGAGGCCACTGTCCATTGGGCCCCACCTACATGGCCATCTCATAAAGTTCTGAT
CTGCCAGTTCCACTACCGAAGATGTCAGGAGGCGGCCTGGACCCTGCTGGAACCGG
AGCTGAAGACCATACCCCTGACCCCTGTTGAGATCCAAGATTTGGAGCTAGCCACTG
GCTACAAAGTGTATGGCCGCTGCCGGATGGAGAAAGAAGAGGATTTGTGGGGCGAG
TGGAGCCCCATTTTGTCCTTCCAGACACCGCCTTCTGCTCCAAAAGATGTGTGGGTA
TCAGGGAACCTCTGTGGGACGCCTGGAGGAGAGGAACCTTTGCTTCTATGGAAGGC
CCCAGGGCCCTGTGTGCAGGTGAGCTACAAAGTCTGGTTCTGGGTTGGAGGTCGTGA
GCTGAGTCCAGAAGGAATTACCTGCTGCTGCTCCCTAATTCCCAGTGGGGCGGAGTG
GGCCAGGGTGTCCGCTGTCAACGCCACAAGCTGGGAGCCTCTCACCAACCTCTCTTT
GGTCTGCTTGGATTCAGCCTCTGCCCCCCGTAGCGTGGCAGTCAGCAGCATCGCTGG
GAGCACGGAGCTACTGGTGACCTGGCAACCGGGGCCTGGGGAACCACTGGAGCATG
TAGTGGACTGGGCTCGAGATGGGGACCCCCTGGAGAAACTCAACTGGGTCCGGCTT
CCCCCTGGGAACCTCAGTGCTCTGTTACCAGGGAATTTCACTGTCGGGGTCCCCTAT
CGAATCACTGTGACCGCAGTCTCTGCTTCAGGCTTGGCCTCTGCATCCTCCGTCTGG
GGGTTCAGGGAGGAATTAGCACCCCTAGTGGGGCAACGCTTTGGCGACTCCAAGA
TGCCCCTCCAGGGACCCCCGCCATAGCGTGGGGAGAGGTCCCAAGGCACCAGCTTC
GAGGCCACCTCACCCACTACACCTTGTGTGCACAGAGTGGAACCAGCCCCTCCGTCT
GCATGAATGTGAGTGGCAACACACAGAGTGTCACCCTGCCTGACCTTCCTTGGGGTC
CCTGTGAGCTGTGGGTGACAGCATCTACCATCGCTGGACAGGGCCCTCCTGGTCCCA
TCCTCCGGCTTCATCTACCAGATAACACCCTGAGGTGGAAAGTTCTGCCGGGCATCC
TATTCTTGTGGGGCTTGTTCCTGTTGGGGTGTGGCCTGAGCCTGGCCACCTCTGGAA
GGTGCTACCACCTAAGGCACAAAGTGCTGCCCCGCTGGGTCTGGGAGAAAGTTCCT
GATCCTGCCAACAGCAGTTCAGGCCAGCCCCACATGGAGCAAGTACCTGAGGCCCA
GCCCCTTGGGGACTTGCCCATCCTGGAAGTGGAGGAGATGGAGCCCCCGCCGGTTA
TGGAGTCCTCCCAGCCCGCCCAGGCCACCGCCCCGCTTGACTCTGGGTATGAGAAGC
ACTTCCTGCCCACACCTGAGGAGCTGGGCCTTCTGGGGCCCCCAGGCCACAGGTTC
TGGCCTGAACCACACGTCTGGCTGGGGGCTGCCAGCCAGGCTAGAGGGATGCTCAT
GCAGGTTGCACCCCAGTCCTGGATTAGCCCTCTTGATGGATGAAGACACTGAGGACT
CAGAGAGGCTGAGTCACTTACCTGAGGACACCCAGCCAGGCAGAGCTGGGATTGAA
GGACCCCTATAGAGAAGGGCTTGGCCCCCATGGGGAAGACACGGATGGAAGGTGGA
GCAAAGGAAAATACATGAAATTGAGAGTGGCAGCTGCCTGCCAAAATCTGTTCCGC
TGTAACAGAACTGAATTTGGACCCCAGCACAGTGGCTCACGCCTGTAATCCCAGCAC
TTTGGCAGGCCAAGGTGGAAGGATCACTTAGAGCTAGGAGTTTGAGACCAGCCTGG
GCAATATAGCAAGACCCCTCACTACAAAAATAAAACATCAAAAACAAAAACAATTA
GCTGGGCATGATGGCACACACCTGTAGTCCGAGCCACTTGGGAGGCTGAGGTGGGA
GGATCGGTTGAGCCCAGGAGTTCGAAGCTGCAGGGACCTCTGATTGCACCACTGCA
CTCCAGGCTGGGTAACAGAATGAGACCTTATCTCAAAAATAAACAAACTAATAAAA
AGCAAAAAAAAAAAAAAAAAAAAAAAAAAAA

HBA2 (SEQ ID NO: 17; NM_000517.4).

CATAAACCCTGGCGCGCTCGCGGGCCGGCACTCTTCTGGTCCCCACAGACTCAGAGA
GAACCCACCATGGTGCTGTCTCCTGCCGACAAGACCAACGTCAAGGCCGCCTGGGG
TAAGGTCGGCGCGCACGCTGGCGAGTATGGTGCGGAGGCCCTGGAGAGGATGTTCC
TGTCCTTCCCCACCACCAAGACCTACTTCCCGCACTTCGACCTGAGCCACGGCTCTG
CCCAGGTTAAGGGCCACGGCAAGAAGGTGGCCGACGCGCTGACCAACGCCGTGGCG
CACGTGGACGACATGCCCAACGCGCTGTCCGCCCTGAGCGACCTGCACGCGCACAA
GCTTCGGGTGGACCCGGTCAACTTCAAGCTCCTAAGCCACTGCCTGCTGGTGACCCT
GGCCGCCCACCTCCCCGCCGAGTTCACCCCTGCGGTGCACGCCTCCCTGGACAAGTT
CCTGGCTTCTGTGAGCACCGTGCTGACCTCCAAATACCGTTAAGCTGGAGCCTCGGT
AGCCGTTCCTCCTGCCCGCTGGGCCTCCCAACGGGCCCTCCTCCCCTCCTTGCACCG
GCCCTTCCTGGTCTTTGAATAAAGTCTGAGTGGGCAGCAAAAAAAAAAAAAAAAAA

PPM1F (SEQ ID NO: 18; NM_014634).

AGGGACGGGAAGTGGGCGGGGCCGGCCGGCAGCAGCTTGCGGGACACGGAGCCGC
GAGGAGACAGCTGAGGCCCGCGGAGACCAGGGGGTGAAGCCTGGAGACCCTCTTGC
CCTGGCCTAGCTGCAGGCCCCCGGGATGCTTTGGGCATGTCCTCTGGAGCCCCACAG

TABLE 5-continued

Nucleotide Sequences of Biodosimetry Biomarker Genes

```
AAGAGCAGCCCAATGGCCAGTGGAGCTGAGGAGACCCCAGGCTTCCTGGACACGCT
CCTGCAAGACTTCCCAGCCCTGCTGAACCCAGAGGACCCTCTGCCATGGAAGGCCCC
AGGGACGGTGCTCAGCCAGGAGGAGGTGGAGGGCGAGCTGGCTGAGCTGGCCATG
GGCTTTCTGGGCAGCAGGAAGGCCCCGCCACCACTTGCTGCTGCTCTGGCCCACGAA
GCAGTTTCACAGCTGCTACAGACAGACCTTTCCGAATTCAGGAAGTTGCCCAGGGAG
GAAGAAGAAGAGGAGGAGGACGATGACGAGGAGGAAAAGGCCCCTGTGACCTTGC
TGGATGCCCAAAGCCTGGCACAGAGTTTCTTTAACCGCCTTTGGGAAGTCGCCGGCC
AGTGGCAGAAGCAGGTGCCATTGGCTGCCCGGGCCTCACAGCGGCAGTGGCTGGTC
TCCATCCACGCCATCCGGAACACTCGCCGCAAGATGGAGGACCGGCACGTGTCCCT
CCCCTTCCTTCAACCAGCTCTTCGGCTTGTCTGACCCTGTGAACCGCGCCTACTTTGCT
GTGTTTGATGGTCACGGAGGCGTGGATGCTGCGAGGTACGCCGCTGTCCACGTGCAC
ACCAACGCTGCCCGCCAGCCAGAGCTGCCCACAGACCCTGAGGGAGCCCTCAGAGA
AGCCTTCCGGCGCACCGACCAGATGTTTCTCAGGAAAGCCAAGCGAGAGCGGCTGC
AGAGCGGCACCACAGGTGTGTGTGCGCTCATTGCAGGAGCGACCCTGCACGTCGCC
TGGCTCGGGGATTCCCAGGTCATTTTGGTACAGCAGGGACAGGTGGTGAAGCTGAT
GGAGCCACACAGACCAGAACGGCAGGATGAGAAGGCGCGCATTGAAGCATTGGGT
GGCTTTGTGTCTCACATGGACTGCTGGAGAGTCAACGGGACCCTGGCCGTCTCCAGA
GCCATCGGGGATGTCTTCCAGAAGCCCTACGTGTCTGGGGAGGCCGATGCAGCTTCC
CGGGCGCTGACGGGCTCCGAGGACTACCTGCTGCTTGCCTGTGATGGCTTCTTTGAC
GTCGTACCCCACCAGGAAGTTGTTGGCCTGGTCCAGAGCCACCTGACCAGGCAGCA
GGGCAGCGGGCTCCGTGTCGCCGAGGAGCTGGTGGCTGCGGCCCGGGAGCGGGGCT
CCCACGACAACATCACGGTCATGGTGGTCTTCCTCAGGGACCCCCAAGAGCTGCTGG
AGGGCGGGAACCAGGGAGAAGGGGACCCCCAGGCAGAAGGGAGGAGGCAGGACTT
GCCCTCCAGCCTTCCAGAACCTGAGACCCAGGCTCCACCAAGAAGCTAGGTGGTTTC
CAGGCCCCTGCCCTCCCCTTCCTCCCATCCTTGTCCTTCTCTCCCTCAGAAGCCTCAG
GACCCAACAGGTGGCAGGCAGTGGACAGGGTGCCCGCCCCACAGTGCTTTCCCCAG
CACCCCAGAGCCAGTCGGGACACCCCCCGCAGCCCGTCCTGGTGGCTGTGGAACTG
CACTGGGTGGCGGGCAGATGGTGGAAGGCAGCTTAGGAGACCTCACCAAAGAGAA
GATGGACCGGCTCTTGCTCCCAGCTCCTATTAGGCCCGGGGTGGGACCAGAGGTCAT
AGGTGCCCAACGGCAGCCAAACCAAAGACACTGGTGTGCATGGGGCAGCATGGTTG
TGCACGTGGGACCCTGGGGCGGACCCAGGAGCCAAACTCTTGAAGCACCCCCTGGG
TCAGGCCCAGCAGCGGAGTGGCCAGCCCCAGTTTCCCATTGCTCCTCTCTGCGGCCA
GGGCCAGGTGGGTTCATATTTACAGATATGCCCAGCCAGTCCTGGTCGGCCACACCA
GTGTCCCAAAGAGGAGAGCGCAGCAGAGCCAGGGGTCTGTTCTGTAGCAGCCACCC
CCCTGCCCCCACTCCAGGGCAGCCATGATGTGCTTGGGCCCACCAGGGCCTTCCGGG
CTGCTCTCTTCCCTGAGCCCGGAACCGGCGACGCACATGTGTCTTTTGTTGGTGTGTT
TGTTTTTTTCCAGGGAGGTCTAATTCCGAAGCAGTATTCCAGGTTTTCTCTTTGTTTT
ATCAGTGCCAAGATGACCTGTTGTGTCATATAATTTAAGCAGAGCTTAGCATTTATT
TTATTCTTTAGAAAACTTAAGTATTTACTTTTTTAAAGCTATTTTTCAAGGAACCTTTT
TTTGCAGTATTATTGAATTTATTTTCTAAATCAGGATTGAAACAGGAAGTTTTCCAGG
TGGTGTTAATAAGCCATTCAAGTGCCTTACACAGCTTTGAAGAAACTAGGACTGCAG
TGGGCTCGGATAGGCCCATTGAGGTTTTTAGAAAAGCAGGATTTGTTTTGTTAGGGA
GGCATGATTTTGGTGAGATCTTTCTGGAAGAGTTTTCCGCCTCTTTGTGATGCTGAAC
ACCCCCAAGGTTCTCCCCTCCCCCCGCTGCCCAGGTGACTGGCAGGAGGCTGCGACTG
CCACGTAGTGGTGCCTGGGCCCGACAGCGGGGCTCTGGGCATCCCGGGTGACCTTG
GCCCATCTGCCTGCATTCCCACCCCCTTGGGCCTGGCTGGATCCCAGGCAGAGGGAC
CTTGCTGCTGTGTGATTGGAACATTCCCAAATATCTTGTGAATTTGTAATCAAATTGG
TCTCATTGGGAAAGACTCTTAATTAAGAGGCTCAGGCAAGCACAGAGGCAGCCCGT
GGGTCTCTGTCTCAGTCTGGAGGCAGCAGGGATGCTGCTGGGAGTCCATGGCACAG
GCCACAGCCCCTCACCTTGCCGCGGTGGCTGGCAGCACGCCTGCCTTGCTCTGCCCC
ATGCCCTGAACAGGCATGAGAGCTCCACGTCCCCTAGTGCACCCTGAGAGGGGCT
CACAAGTGACCGATCCTGGGTGCCTCAGGGAGCTCACTGAGGGCGTGCAAAGTTGA
AAGTGGCAAGGCTGGGGAGGGTGTCGGGTAGAGGGAAGAGGGCAGGGGGCTAGG
GGAGGACTCAGAGGCCATCTGCAGGGCCAAGCCACAGGAAGGGCTGAGCTGGAGG
TGGGCAGGGCTGCTCCAGGCAGGTCAGAGCAGTGCAGGGGGAGGAGAGGAGAAAG
GGAGGAAGCTGGGCTGTGTGGTCCCCATGAAGGCATTCAGAGTCCACCTGCAGACA
GCGAGAGCCCCAGGAAGGTTTGCACAGCTGTGCCCCAAGCACCTTGGCCTCCTCTCA
GCTCGCCGAGGAGGCACGCTAGAGCCGCCTTCCCGGTGGGAGCCCTCTGTCCCACA
GGGAGCGGGGAGCCAGCTTTGCTGGGGCCCTACCTGCATGCCCAGCCTTACCCCTCA
TTCTCACAGCACAGATGAGGTTGAGACCATGCAGTCAATGCATTGCTTAAGGTCTCT
TATTTACAAAAAAAAACCTTAAACATAGTCGCTGTCATTCAGACATTCAGAGAATGG
TTGGCCACAAACAATGACCAAGTATTGCTTGGCTTAACTTGAAGGCCTGCTGTCTCC
TTCTGGGGGTCAGGGACGCAGCTCCACCCTCACCACTAGCCCACCCTGCCCGTGGGC
ATAACCTTGACGAAGAGAGAATGATTGGCATCTGCTTTTCTCTTTTCTTTGCTAAT
AATTCTGTTCCTGGCTGCCGAGAGTGAAGTTTCACCATGTGGAGGTTTGGCTCCTAT
CACCTGGTGGTCTGATTCATACCCTAGCCTGAGGCTCCACTGGAAGATCTCGCAGCC
TCAGTGTATGGGAAACCCTTTCCCCAGGCTTGTCCCAGCACTGCCGCTCCCCACCCC
TGAGCCAGGACCCCAGAGGATGGCCATGCCCCGTGCCTGGCAGAGGTCTGGTGCCA
GCACTGGGAGCTGCTCCGCCCTTGCCTTGGGGCCGAGGGAGCCCTCGTCCACCCCTG
CACAGCAGCTGGGCACAGAGGAGCGCTCTTCCATCTTGACCAGGACTGCACCAAGA
AGCACCAGGTGTCTTCAGCCTCCAACCTCCGGGGCGACCTTCTCTTCCAGCCACAGT
CCCATGAGGGCCCCTAGCCAGGGACACTGGTCTGTAAATTGTAATCCTTTCTCCAGC
CCAGCTCTCCACTTGTTCCTTGTGTGAGCTGAGCAGGCAGTGCACCTCTGAGTGTCC
CTTTTGTAAGGCCCAGGGGTTGCACTGAGTCTGCAGAGGCCGCGACCTCCTAGAACG
CTGTGGGTGCAGGTGAGCCGGCGTGTCCTGGGGAGATGCTGCCAGCACACAGGGGC
CCTCCTGCTGCCAGCAGGTTGGGGTGGTTAAGTCTTATTAGTGTCTATTCTTAAAATT
AAGTGGGCTGGAGAAGAATGGAGCTCCACATGCCAGCACCGTATATGGAATACAAA
AGCTGGGGAAGCAGGGCCTGCCTTACAGGTGTGGCTGACTCTGAGCCCAGGCCTGC
```

TABLE 5-continued

Nucleotide Sequences of Biodosimetry Biomarker Genes

AGGGGTGGAGGGCAGTCCCTCAGAATCCCAGAGGCAGTCCCAGCCTCAGAACCCAG
GATAGGAAATGGGTGTGTTTAGTGGGGAAAGGGACGGGGTGCAGACGGCAGGGCC
AGTATGGGGCCCCCTCCCTCTCCTCTCCTCTCCTATGGTGAGCCCAGCGTGGGCACC
GGGCCGTCTCAGCCGTGTTCCCAGGGCTGGGAGGACAGCTCTGGCCCTTCTTAGGCC
TAGCCTCGTCCCAAGCTAAATGTAAGCCAGTTGGGCTGTGTTAAAGGAAGCAGTGTT
TTTGGTTCGATTCTGCCTCTGTAGCTCAAGGGGGGCAGCCCCCAGAGTCCTGTGCAT
TCTGCCAAGGCTCCATAGCTTTGCCAAATGCACGGAGCTCTGCCATTCCGGTGCAGT
GCAGGCCTTGCGAAGGGTTTATCTGCGTTCGTCTCGGTGGGCTTCTCCTGCATGGGA
GTTGTGTTCCTGTGCAAGGGGGAGCTTTGCTCCAGGACAGGATGACTGTCTTCCCTA
TTCTTAGGGACAAGTCCCAAGATGCCAGAAAGGCAGTCTCCCAAGGACCCACCATG
CAGAAGTGTCAATAAACCACAAGTTCTGAACTCTGTAAAAAAAAAAAAA

PPP2R1A (SEQ ID NO: 19; CR4503401).

ATGGCGGCGGCCGACGGCGACGACTCGCTGTACCCCATCGCGGTGCTCATAGACGA
ACTCCGCAATGAGGACGTTCAGCTTCGCCTCAACAGCATCAAGAAGCTGTCCACCAT
CGCCTTGGCCCTTGGGGTTGAAAGGACCCGAAGTGAGCTTCTGCCTTTCCTTACAGA
TACCATCTATGATGAAGATGAGGTCCTCCTGGCCCTGGCAGAACAGCTGGGAACCTT
CACTACCCTGGTGGGAGGCCCAGAGTACGTGCACTGCCTGCTGCCACCGCTGGAGTC
GCTGGCCACAGTGGAGGAGACAGTGGTGCGGGACAAGGCAGTGGAGTCCTTACGGG
CCATCTCACACGAGCACTCGCCCTCTGACCTGGAGGCGCACTTTGTGCCGCTAGTGA
AGCGGCTGGCGGGCGGCGACTGGTTCACCTCCCGCACCTCGGCCTGCGGCCTCTTCT
CCGTCTGCTACCCCCGAGTGTCCAGTGCTGTGAAGGCGGAACTTCGACAGTACTTCC
GGAACCTGTGCTCAGATGACACCCCCATGGTGCGGCGGGCCGCAGCCTCCAAGCTG
GGGGAGTTTGCCAAGGTGCTGGAGCTGGACAACGTCAAGAGTGAGATCATCCCCAT
GTTCTCCAACCTGGCCTCTGACGAGCAGGACTCGGTGCGGCTGCTGGCGGTGGAGG
CGTGCGTGAACATCGCCCAGCTTCTGCCCCAGGAGGATCTGGAGGCCCTGGTGATGC
CCACTCTGCGCCAGGCCGCTGAAGACAAGTCCTGGCGCGTCCGCTACATGGTGGCTG
ACAAGTTCACAGAGCTCCAGAAAGCAGTGGGGCCTGAGATCACCAAGACAGACCTG
GTCCCTGCCTTCCAGAACCTGATGAAAGACTGTGAGGCCGAGGTGAGGGCCGCAGC
CTCCCACAAGGTCAAAGAGTTCTGTGAAAAACCTCTCAGCTGACTGTCGGGAGAATGT
GATCATGTCCCAGATCTTGCCCTGCATCAAGGAGCTGGTGTCCGATGCCAACCAACA
TGTCAAGTCTGCCCTGGCCTCAGTCATCATGGGTCTCTCTCCCATCTTGGGCAAAGA
CAACACCATCGAGCACCTCTTGCCCCTCTTCCTGGCTCAGCTGAAGGATGAGTGCCC
TGAGGTACGGCTGAACATCATCTCTAACCTGGACTGTGTGAACGAGGTGATTGGCAT
CCGGCAGCTGTCCCAGTCCCTGCTCCCTGCCATTGTGGAGCTGGCTGAGGACGCCAA
GTGGCGGGTGCGGCTGGCCATCATTGAGTACATGCCCCTCCTGGCTGGACAGCTGGG
AGTGGAGTTCTTTGATGAGAAACTTAACTCCTTGTGCATGGCCTGGCTTGTGGATCA
TGTATATGCCATCCGCGAGGCAGCCACCAGCAACCTGAAGAAGCTAGTGGAAAAGT
TTGGGAAGGAGTGGGCCCATGCCACAATCATCCCCAAGGTCTTGGCCATGTCCGGA
GACCCCAACTACCTGCACCGCATGACTACGCTCTTCTGCATCAATGTGCTGTCTGAG
GTCTGTGGGCAGGACATCACCACCAAGCACATGCTACCCACGGTTCTGCGCATGGCT
GGGGACCCGGTTGCCAATGTCCGCTTCAATGTGGCCAAGTCTCTGCAGAAGATAGG
GCCCATCCCGGACAACAGCACCTTGCAGAGTGAAGTCAAGCCCATCCTAGAGAAGC
TGACCCAGGACCAGGATGTGGACGTCAAATACTTTGCCCAGGAGGCTCTGACTGTTC
TGTCTCTCGCC

CFLAR (SEQ ID NO: 20; NM_003879.5).

ATACTCAGTCACACAAGCCATAGCAGGAAACAGCGAGCTTGCAGCCTCACCGACGA
GTCTCAACTAAAAGGGACTCCCGGAGCTAGGGGTGGGACTCGGCCTCACACAGTG
AGTGCCGGCTATTGGACTTTTGTCCAGTGACAGCTGAGACAACAAGGACCACGGGA
GGAGGTGTAGGAGAGAAGCGCCGCGAACAGCGATCGCCCAGCACCAAGTCCGCTTC
CAGGCTTTCGGTTTCTTTGCCTCCATCTTGGGTGCGCCTTCCCGGCGTCTAGGGGAGC
GAAGGCTGAGGTGGCAGCGGCAGGAGAGTCCGGCCGCGACAGGACGAACTCCCCC
ACTGGAAAGGATTCTGAAAGAAATGAAGTCAGCCCTCAGAAATGAAGTTGACTGCC
TGCTGGCTTTCTGTTGACTGGCCCGGAGCTGTACTGCAAGACCCTTGTGAGCTTCCCT
AGTCTAAGAGTAGGATGTCTGCTGAAGTCATCCATCAGGTTGAAGAAGCACTTGATA
CAGATGAGAAGGAGATGCTGCTCTTTTTGTGCCGGGATGTTGCTATAGATGTGGTTC
CACCTAATGTCAGGGACCTTCTGGATATTTTACGGGAAAGAGGTAAGCTGTCTGTCG
GGGACTTGGCTGAACTGCTCTACAGAGTGAGGCGATTTGACCTGCTCAAACGTATCT
TGAAGATGGACAGAAAAGCTGTGGAGACCCACCTGCTCAGGAACCCTCACCTTGTTT
CGGACTATAGAGTGCTGATGGCAGAGATTGGTGAGGATTTGGATAAATCTGATGTGT
CCTCATTAATTTTCCTCATGAAGGATTACATGGGCCGAGGCAAGATAAGCAAGGAG
AAGAGTTTCTTGGACCTTGTGGTTGAGTTGGAGAAACTAAATCTGGTTGCCCCAGAT
CAACTGGATTTATTAGAAAAATGCCTAAAGAACATCCACAGAATAGACCTGAAGAC
AAAAATCCAGAAGTACAAGCAGTCTGTTCAAGGAGCAGGGACAAGTTACAGGAATG
TTCTCCAAGCAGCAATCCAAAAGAGTCTCAAGGATCCTTCAAATAACTTCAGGCTCC
ATAATGGGAGAAGTAAAGAACAAAGACTTAAGGAACAGCTTGGCGCTCAACAAGA
ACCAGTGAAGAAATCCATTCAGGAATCAGAAGCTTTTTTGCCTCAGAGCATACCTGA
AGAGAGATACAAGATGAAGAGCAAGCCCCTAGGAATCTGCCTGATAATCGATTGCA
TTGGCAATGAGACAGAGCTTCTTCGAGACACCTTCACTTCCCTGGGCTATGAAGTCC
AGAAATTCTTGCATCTCAGTATGCATGGTATATCCCAGATTCTTGGCCAATTTGCCTG
TATGCCCGAGCACCGAGACTACGACAGCTTTGTGTGTGTCCTGGTGAGCCGAGGAG
GCTCCCAGAGTGTGTATGGTGTGGATCAGACTCACTCAGGGCTCCCCCTGCATCACA
TCAGGAGGATGTTCATGGGAGATTCATGCCCTTATCTAGCAGGGAAGCCAAAGATG
TTTTTTATTCAGAACATGTGGTGTCAGAGGGCCAGCTGGAGGACAGCAGCCTCTTG
GAGGTGGATGGGCCAGCGATGAAGAATGTGGAATTCAAGGCTCAGAAGCGAGGGCT

TABLE 5-continued

Nucleotide Sequences of Biodosimetry Biomarker Genes

```
GTGCACAGTTCACCGAGAAGCTGACTTCTTCTGGAGCCTGTGTACTGCGGACATGTC
CCTGCTGGAGCAGTCTCACAGCTCACCATCCCTGTACCTGCAGTGCCTCTCCCAGAA
ACTGAGACAAGAAAGAAAACGCCCACTCCTGGATCTTCACATTGAACTCAATGGCT
ACATGTATGATTGGAACAGCAGAGTTTCTGCCAAGGAGAAATATTATGTCTGGCTGC
AGCACACTCTGAGAAAGAAACTTATCCTCTCCTACACATAAGAAACCAAAAGGCTG
GGCGTAGTGGCTCACACCTGTAATCCCAGCACTTTGGGAGGCCAAGGAGGGCAGAT
CACTTCAGGTCAGGAGTTCGAGACCAGCCTGGCCAACATGGTAAACGCTGTCCCTA
GTAAAAATACAAAAATTAGCTGGGTGTGGGTGTGGGTACCTGTATTCCCAGTTACTT
GGGAGGCTGAGGTGGGAGGATCTTTTGAACCCAGGAGTTCAGGGTCATAGCATGCT
GTGATTGTGCCTACGAATAGCCACTGCATACCAACCTGGGCAATATAGCAAGATCCC
ATCTCTTTAAAAAAAAAAAAAAAGGACAGGAACTATCTTACTCAATGTATTAGTCAT
GTTTCTCTAGAGGGACAGAACTAATAGGATACATGTATATAAAAAGGGGAGTTTATT
AAGGAGTATTGACTCACATGATCACAGGGTTAGGTCCCACAATAGGTCATCTGCAA
GCAAGGAAGCCAATTCAAGTCCCAAAGCTGAAGAACTTGGAGTCCAATGTTTGAGG
GCAGGAAGCATTCAGCATGAGAGAAAGATGGAGGCCAGAAGACTACACCAGTCTA
GTCTTTCCATGTTTTGCCTGCTTTTATTCTGGCAGTGCTGGCAGCTGATTAGATGGTG
CCCACCCAGATTGAGGATGGTCTGCCTTTCCCAGTCCACTGACTCAAATGTTAAATC
TCCTTTGGCAGCACCCTCACAGATGTACCCGGGAACACTTTGCATCCTTCTATTCAAT
CAAGTTGATACTCAGTATTAACCATCACAGTCCATTTGGGCAACTATACCAAATTAC
CATAGACCAGGTGACTTAAACAGCAGTTTATTTCTCACAGTTCCGGAGGCTGGGAAAT
CCAACATCTAAGTGGTAGCATATCTGGTGTCTGGTAAGGCATGCTTCCAGATCTTAC
CAGATGTCAGTCTTTTGATGTTCTCACATGGCAGAAAAGAGGATGCAAACTCTCAA
GTATATCTTTAAGGGCACAAATTCCATTCATGAGGGCTCTACCCTCATCACCTAATT
ACCTCCCAAAGGCCCCACCTTCTGATACTGTCACTTTGGGGATACTGTCTCCCCTTTG
AATTCTGGGGGAATACAAACATTCAGTTTGTAACAATAGCCTTATGATTTAGAGGT
TACTTGTTCATTCACCTAGACCTCAAATTGCATTTTACAGCTAGTCAAGTATATCTTT
CTCTGATTTGATAGTGTGACCTAAAAGGGGACCATTGTTTGAAATATCATTAGAGTT
GCTTATTATTATTATTATTATTATTATTATTATTATTATTGAGACAGAGT
TTCATTCTGCTGCCCAGGCTGGAGTGCAGTGGCATCATCTTGGCTCATTGCAACCTCT
GCCTTCTGGGTTCAAGCGATTCTCCTGCCTCAGCCTCCCGAGTAGCTGGGATTACAG
GCTCCTGCCACCACACCCGGCTAATTTTTGTATTTTTAGTGGAGACAGGGTTTCACC
ATGTTGGCCAGCGTGGTCTTGAACTCCTGACCTCAGGTGATTCACCAGCCTCGGCCT
CCCAAAGTGCTGGGATTACAGGTGTGAGCCACTGCACCTGGCCTATTATTATTTTA
AATTTTTTTTTTTAATTGATCATTCTTGGGTGTTTCTCACAGAGGGTGATTTGGCAG
GGTCACAGGACAATAGTGGAGGGAAGGTCAGCAGATAAACAAGTGAACAAAGGTC
TCTGGTTTTCCTAGGCAGAGGACCCTGCCGGCCTTCCGCAGTGTTTGTGTCCCTGGGTA
CTTGAGATTAGGGAGTGGTGATGACTCTTAAGGAGCATGCTGCCTTCAAGCATCTGT
TTAACAAAGCACATCTTGCACTGCCCTTAATCCATTTAACCCTGAGTGGACACAGCA
CATGTTTCAGAGAGCACAGGGTTGGGGGTAAGGTCATAGATCAACAGCATCCTAAG
GCAGAAGAATTTTTCTTAGTACAGAACAAAATGAAGTCTCCCATGTCTACTTCTTTCT
ACACAGACACAGCAACAATCTGATTTCTCTATCTTTTCCCCACCTTTCCCCCTTTTCT
ATTCCACAAAACCGCCATCGTCATCATGGCCTGTTCTCAATGAGCTGTTGGGTACAC
CTCCCAGACGGGGTGGCGGCTGGGCAGAGGGGCTCCTCACTTCCCAGATGGGGCGG
CCAGGCGGACGCGCCCCCCACCTCCCTCCCGGACGGGATAGCTGGCCGGCGCGGGG
CTGACCCCCACCTCCCTCCCGACGGGGCGGCTGGCCGGGCGGGGCTGACCCCC
ACGCCTCCCTCCCGGACGGGGCGGCTGCCAGGCGGAGGGGCTCCTCACTTCTCAGA
CGGGGTGGCTGCTGGGCGGAGACGCTCCTCACTTCCCAGACAGGGTGGCTGTCGGG
CGGAGGGGCTCCTCACTTCTCAGACGGGGCAGCTGCGGGCGGAGGGGCTCCTCACTT
TCTCAGACGGGGTGGCCGGGCAGAGAAGCTCCTCACATCCCAGACGGGGGGGCGGG
GCAGAGGCGCTCCCCACATCTCAGACGATGGCGGCCGGGCAGAGACGCTCCTCAC
TTCATCCCAGACGGGGTGGCGGCCGGGCAGAAGCTGTAATCTCGGCACCCTGGGGG
GCCAAGGCAGGCGGCTGGGAGGCGGAGGCCGTAGCCAGCTGAGATCACACCACTGC
ACTCCAGCCTGGGCAACATTGAGCACTGAGTGGACGAGACTCTGCCCGCAATCCCG
GCACCTCGGGAGGCCGAGGCTGGCAGATCACTCGCAGTCAGGAGCTGGAGACCAGC
CCGGCCAACACAGTGAAACCCTGTCTCCACCAAAAAAATACGAAAACCAGTCAGGC
GTGGCGGCGCCCGCAATGGCAGGCACGCGGCAGGCCGAGGCGGGAGAATCAGGCA
GGGAGGCTGCAGTGAGCCGAGATGGCAGCAGTACAGTCCAGCTTCGGCTCGGCATC
AGAGGGAGACCGTGGGGAGAGGGAGAAGAGAGGGAGGGGGAGAGGGCTATTTTTA
AAATTTTTTAAAATTGCTGAACAGGGGTACCTCTGGGCAGTGTGTCAGAATACCACT
TTTTAAATATTTTATGATTTATTTATTTTTCTATTTCTTGAGGTTTTAACTGATGTGTA
TCTGTATGTCTATTTGTGTATATTTTGTCATGATCATGTAACAGAGTCTGAAAAGTGT
CGAAGAGACAGTTTTCAGGAACAACAAGCAATTATTCCTACTTTCCAAGTTATTTTG
ATGCCATGGTGGCTCATACCTATAATCTGAGTACTTTGGGAGGCTGAGGTGGACTGA
TCACTTGAGCCCAGGAGTTTGAGACCAGCCTGGGCAACATAGCAAGACTCCATCTCT
ACAAAAAAAGACAAAATTTAGCTGAGCGTGGTGGCGTGTTCCTGTAGTCCCAGCTA
CTTGGGAGGCTGAAGTGAGTGGATCCCCTGAGCCCAGAGAGGTCAAGGTTGTGATG
AGCTGTGATCACACCACTGCACTTCAGCATGGGAGACAGAGTGAGACCCTGTTTCAG
AAAAAATAAATAAATAAAACCACCAGCACCACAAACAACAACAAAAAGTTATTTTG
TACTTGTTTTGAGCACAGGACTCCTGAGGGTATCTTTGCATTTAATATTACATAGGG
GTGCCAGTGGGAAGTAATGTGTATGCTTGGCCTCATGAGCTAAAACCCTGTGTTAAT
TATGACAGAAGGAAAGTGTGTGAGAGAGATCTTAACTACCTAGCAGCTCTAGCTGC
CATCTTGAACCATGAAGATACGGGCCACACGTAGGGGTAGCTGGGTAGTGAGCAGC
AAGAAGCCTTGTTGGATGAGGGCACGAAGGAGCAGAATCACTGGAATCACTGTGTC
AGCCCTAATTACCTACCTCTGGACTTTTATGTGAGGGGAAAAAAAATTGACAGTTTA
TATTTATCTCAACCTAGTTAACCCAAGTGATGCATTGTTATGAGATTAAATGTTTGG
AGGCCGGGTGCGGTGGCTCACGCCTATAATCCCAGCCCTTTGGGAGGCCAAGGCGG
GCGGATCACGAGGTCAGGAGATCAAGACCATCCTGGCTAACATGTAAAACCCCGTC
TCTACTAAAAATACAAAAAATTAGCCAGGCGTTGTGGCGGTCGCCTGTAGTCCCTGC
```

TABLE 5-continued

Nucleotide Sequences of Biodosimetry Biomarker Genes

```
TATTTGGGAGGCCGAGGCAAGAGAACGGCATGAACCTGGGAGGTGGAGCTTGCAGC
GAGCTGAGATCTTGCCACTGCACTCCAGCCTGGGCGACAGTGCGAGACTCTGTCTCA
AAAATAAATAAATAAATAAATAATAAATAAAATGTTTGGAATGTTGGCTTCATCCCT
GGGATGCAAGGCTGGTTCAACATACGCAAATCAAGAAACATAATTCATCACATAAA
CAGAACTAAAGACAAAAACCACATGATTATCTCAATAGATACAGAAAAGGCCTTCA
ATAAAATTCAACGTTGCTTCATGTTAAAAACTCTCAATAAACTAGGTATTGATGGAA
AATATCTCAAAATAATAACCATTTATGACAAACCCACAGCCATTATCATACTGAATG
GGCAAAAGCTGGAAGCATTCCCCTTGAAAACTGGCACAAGACAGGGATGCCGTCTC
ACCACTCCTATTTAACATAGTATTGGAAGTTCTGGCCAAGAAAATCAGGCAAGAGA
AACAAATAAGGGGTATTCAAATAGGAAAAGAGGAAGTAAAACTGTGTTTGCAGATG
ACATGATACTATATCTAGAAAACCCCATTATCTCCACCCAAAAGTTCCTTAAGCTGA
TAAGCAACTTCAGCAAAGTCTCAGGATACAAAATCAATGTGCAGAAATCACAAGCA
TTCTATACACCAACAATACACAAGCAGAGAGCCAAATCATGAATGAACTCCCATTC
ACAGTTGCTAGAAAGAGAATAAAATACCTAGGAATACAGCTAATAAGATGTGAAGG
ATCTCTTCAAGGAGAACTACAAACCACTGCTCAAGGAAATAAGAGAGGACACAAAT
GAAAAAACATTCCATTCTCGTGGATAGGAAGAATCAATATCATGAAAATGGCCATA
CTACCCAAAGTAATTTATAGGTTCATTGCTATTCCCATTAAACTACTATTGACATTCT
TCACAGAATTAGAAAAAACTACTTTAAAATTCAATGGAACCAAAAAGAGCCCG
TATAACCAAGACAACAATAAGCAAAAAGAACAAAGCTGGAAGCATCACACTACCC
AACTTCAAAGTATACTGCAAGGCTACAGTAGCCAAAATGGCATGGTACTGGTACAA
AAACAGACACATAGACCAATGGAACAGAATAGAGACCAGAGAAAGAAGACCACAC
ATCTACAGCCATCTGATCATCGACAAACCTGACAAAAACAAGCAATGGGGAAAAGA
TTCCCTATTTAATAAATGGTGCTGGGAAAACTGGCTAGCCATATGCAGAAAATTGAA
ACTGACCCCTTCCTTACACCTTATACAAAAATTAACTCAAGATTAAAGACTTAATGT
AAAACCTAAAACTATAAAAACCCTAGAAGAAAATCTATTTAATACCATTCAAGACA
TAGGCACAAGCAAAGGTTTCATGACAAAAACATCAAAAGCAATTGCAACAAAAGCA
AAAATTACAAATGGGATCTAATTAAACTAAAGAGCTCCTGCACAGCAAAAGAAACT
ATCATTAGAGTGAACAGGCAACCTACAGAATGGGAGAACATTTTTGCAATCTATCCA
TCTGACAAAGGTCTAATATCCAGAACCTACAAGGAACTTAAAACAAATTTACAAGG
AAAAAAACAACCCCATCAAAAGTGGACAAAGGACATGAACAGACACTTCTCAAA
AGAAGACATTTATGTGGCCAACAAACATATAAAAAAAAGCTCAACCTTACTGATCA
TTAGAGAAATGCAAAGGAGAACCACAATGAGATACCATCTCATGCCGGTCAGAATG
GTGATTATTAAAAAGTCAAAAAACAACAGATGCTGGCGAGGCTGTGGAGAAGTAGG
AACACTTTTACATTGTTGGTGGGAATGTAAATTAGTTCAACCGTTGTGGAAGTGTGT
GTGGCTATTCCTCAAAGATCTAGAACTAGAAATACTATTTGTCCCAGCAATCCCATT
ACTGGGTATATACCCAAAGGAATATAAACCATTTTATTATAAAGATACATGCACATT
TTTGTTCATTGCAGCACTCTTCACAATAGCAAAGACACAATAGCAAATGCCCATCAA
AGATAGACTGGATAAAGAAAATGTGGTACATATACACCATGGAATACTGTGCAGTG
CAGCCATTACAGCTTTTGGTGATACAGTGAATCAGATTTTTCATTAATTCTTTTAATT
GGTTATTACTGAACGTGAAAAAGTAATGTTTGTATTGAAATCTTGATCTGGCCATG
TTTCTATTTTAAATTCATAAAGAATTCTAACAAGAGGAATTCCAAGAATGTCATAAA
TGGATGTTTCTCCATGGATGAAGGAACTGTTTTATTCACTTGCTGATAATTCAGCCTA
ATCCAGTTTGACATCATATAGATAAGTAGTTGAATTATGGATTTAAAATACATATCA
TTTTCTAACTCCAAAGGTAATACTTATTTAAATGGTTTTGAAAATATAGAAAGGCAC
AATTTCTTTTTAAATCTGTTATTCTCCACCACCACTCAATCTGTCTATCATCTATCTCT
CCATTCATTCTTCCATTTGTTTATATCTGTTAATCTTTGTATGTGTTCATGTATAGCTT
TTACATGATTGGAATCATAATGCATATTCCATTTTGAAGTCTGCTTTTTTTTACACAA
AAATATGTTGTGAATATTTTCCTATATTATGAAATATCATTAGCTGAGCTTTTAGAAT
TGACTGCATGTTTTGGTACCATTTAGATATAGTTTAAGATACTTAGAAGTTATGTGGC
TTTGCCACTATGGATGAATCTTATTTACTCAATATTAATTACTTACAAATAACCTCAC
CTAAACACTACTCAGCCATAAAAAGGAATGAATTAATGACATTCACAGCAACCTGG
AGACTATTACTCTAAAGGAAGTAACTGAGGAATGGAAAACCAAACATTGTATGTTC
TCACTCATAAGTGGGAGATAAGCTATGAGGATGCAAAGGCATAAGAAGGATACAAT
GGACTTTGGGGACTTAGGGGAAAGGGTGGGAGGGGGGTGAAGGATAAAAGAATAC
AAATTGGGTTCAGTGTATACTGCTCAGGTGATGGGTGCACCAGAATCTCACAAGTAA
CCACTTAATTACTTACGCATGTAACCAGATACCACCTGTTCCCCAAACACCTATGGA
AATAATTTTGTTTTTTTTTTAAAAAAGGAATGAGATCATGTCCTTTGCAGGGACATG
GATGAAGCTGGAAGCCATTATCCTCAGCAAACTAACAGAGGAGCAGGAAACCAAAC
ACCACATGTTCTCACTTGTAAGCGGAAGCTGAACAATGAGAACACACGGACACAGG
GATGAGATCAACACACACTGGGGCCTGATGCAGGGGCCGTAGCGGGGAGAGCATCA
GGATAACTAGCTAATGCATGTGGGGCTTAATACCTAGGTGATAGGTTGATAGGTGCA
GCAAACCACCATGGACACGTTTACCTATGTAACAAACCCGCACATCCTGCACTTGT
ATCCAGAACTTAAAATATTTTAAAAATCTTTAGAGAATACAAAAAAAAAAAAAAAAG
ATTCTTCAATGCATACACAATAAAATTGCAGTTCAGTCAAACATTGGAAGTCTTTCT
CTGACTGTCTAGTTGGTATCTTCATTTTCAGCTTCTTCAAGATCCCACTCCAAACACT
GTTAGCTCAGCCAAATTGAACAGCTCATATCTCCTACCTCTGGATCTTTGGTTCTGGT
GATTGTATATTTCTGGACCATCTGGAACCCCAGCATATCACCCTACCCCACATCTCC
ACATCCCCAAAATATAACCATACTTCAAGGGCAGTTCAAATACCATCTCCTTCTATC
CTCCATGAAGTCAGTTATCTCTTCCATTGGAATTATCGCCCCCTCTCCTGAACAGTAC
TATTTCGTGTGAATCTCCTCCAAGCCTTCTTTTCATTTTATATCTCATGCTGTAATTCT
TGGAAAGTATGCTGTAGCTCAAGTGCAGAATTCTCATCAGTTTTATCTTTATATCTCT
CCTAAACACTTTACCTGATGAAGAGCCTGGCATACACATAAATATATATTGAATGAA
TCAGTGATGGATTGAAAAGAGAAATGATGGATCTCCTAAATTTTAACTTTTATAAAA
TATTTTGATACATTCATGACCTTACTTTAGCAAGCAATGAACGTGATGTAAACTATT
GTTGATATAGTTTTTATATTGGAAGTGTAAGTAGTTTGTGGCATGGGATTGTGACAT
ATCCTAGGTTTCCTCATCTTCTTTTTATTGAAATGTAATTCACAAGCCATAAAATTTG
CCCCTTTAAAGTAAATGATGCAGTGGATTTTAGTATATTTACAGAGTTGTGCAATCA
TCACCACTATCTAATTCCAGAACATTTCCATCTACCTAGAAACTCCATACCAGTGAG
```

TABLE 5-continued

Nucleotide Sequences of Biodosimetry Biomarker Genes

CTGCCACTCTAATCCTCCTCTTCCCCCAGCCTCTAGAAACAATAATCCATTTTCTGTC
TCTATGATTTGCCTGTTCTAGATATTTTATAAAAATAAACATGTGGCCTTTCGTGTCT
GACTTCCTTCACTTAAAAAAAAAAAAAAAAAA

DHRS13 (SEQ ID NO: 21; NM_144683.3).

CGCCTCCGCCTTCGGAGGCTGACGCGCCCGGGCGCCGTTCCAGGCCTGTGCAGGGC
GGATCGGCAGCCGCCTGGCGGCGATCCAGGGCGGTGCGGGGCCTGGGCGGGAGCCG
GGAGGCGCGGCCGGCATGGAGGCGCTGCTGCTGGGCGCGGGGTTGCTGCTGGGCGC
TTACGTGCTTGTCTACTACAACCTGGTGAAGGCCCCGCCGTGCGGCGGCATGGGCAA
CCTGCGGGGCCGCACGGCCGTGGTCACGGGCGCCAACAGCGGCATCGGAAAGATGA
CGGCGCTGGAGCTGGCGCGCCGGGGAGCGCGCGTGGTGCTGGCCTGCCGCAGCCAG
GAGCGCGGGGAGGCGGCTGCCTTCGACCTCCGCCAGGAGAGTGGGAACAATGAGGT
CATCTTCATGGCCTTGGACTTGGCCAGTCTGGCCTCGGTGCGGGCCTTTGCCACTGC
CTTTCTGAGCTCTGAGCCACGGTTGGACATCCTCATCCACAATGCCGGTATCAGTTC
CTGTGGCCGGACCCGTGAGGCGTTTAACCTGCTGCTTCGGGTGAACCATATCGGTCC
CTTTCTGCTGACACATCTGCTGCTGCCTTGCCTGAAGGCATGTGCCCCTAGCCGCGT
GGTGGTGGTAGCCTCAGCTGCCCACTGTCGGGGACGTCTTGACTTCAAACGCCTGGA
CCGCCCAGTGGTGGGCTGGCGGCAGGAGCTGCGGGCATATGCTGACACTAAGCTGG
CTAATGTACTGTTTGCCCGGGAGCTCGCCAACCAGCTTGAGGCCACTGGCGTCACCT
GCTATGCAGCCCACCCAGGGCCTGTGAACTCGGAGCTGTTCCTGCGCCATGTTCCTG
GATGGCTGCGCCCACTTTTGCGCCCATTGGCTTGGCTGGTGCTCCGGGCACCAAGAG
GGGGTGCCCAGACACCCCTGTATTGTGCTCTACAAGAGGGCATCGAGCCCCTCAGTG
GGAGATATTTTGCCAACTGCCATGTGGAAGAGGTGCCTCCAGCTGCCCGAGACGAC
CGGGCAGCCCATCGGCTATGGGAGGCCAGCAAGAGGCTGGCAGGGCTTGGGCCTGG
GGAGGATGCTGAACCCGATGAAGACCCCCAGTCTGAGGACTCAGAGGCCCCATCTT
CTCTAAGCACCCCCACCCTGAGGAGCCCACAGTTTCTCAACCTTACCCCAGCCCTC
AGAGCTCACCAGATTTGTCTAAGATGACGCACCGAATTCAGGCTAAAGTTGAGCCTG
AGATCCAGCTCTCCTAACCCTCAGGCCAGGATGCTTGCCATGGCACTTCATGGTCCT
TGAAAACCTCGGATGTGTGCGAGGCCATGCCCTGGACACTGACGGGTTTGTGATCTT
GACCTCCGTGGTTACTTTCTGGGGCCCCAAGCTGTGCCCTGGACATCTCTTTTCTGG
TTGAAGGAATAATGGGTGATTATTTCTTCCTGAGAGTGACAGTAACCCCAGATGGAG
AGATAGGGGTATGCTAGACACTGTGCTTCTCGGAAATTTGGATGTAGTATTTTCAGG
CCCCACCCTTATTGATTCTGATCAGCTCTGGAGCAGAGGCAGGGAGTTTGCAATGTG
ATGCACTGCCAACATTGAGAATTAGTGAACTGATCCCTTTGCAACCGTCTAGCTAGG
TAGTTAAATTACCCCCATGTTAATGAAGCGGAATTAGGCTCCCGAGCTAAGGGACTC
GCCTAGGGTCTCACAGTGAGTAGGAGGAGGGCCTGGGATCTGAACCCAAGGGTCTG
AGGCCAGGGCCGACTGCCGTAAGATGGGTGCTGAGAAGTGAGTCAGGGCAGGGCA
GCTGGTATCGAGGTGCCCCATGGGAGTAAGGGGACGCCTTCCGGGCGGATGCAGGG
CTGGGGTCATCTGTATCTGAAGCCCCTCGGAATAAAGCGCGTTGACCGCCGAAAAA
AAAAAAAAAAAAAAA

ACAA1 (SEQ ID NO: 22; NM_001607.3).

GGGTTCCCAGGCCGACTCTCCTTGTGGTTGGCTGAGGCTGGAGGTGGACGGGACTTT
TGGAGGGTCGCTCGCGTCTGTTCGCAGAGCTGTGGGCGGAGTTGAGGCCTTGGAGG
CTGAGATGTGGTTCTGCGCGTGTGCGGACGGCTGTCTGTTAACTCCGCGGTCAGTTC
CCGGACTGGTGGCTGGTCTGCAGGGTTGACCTGCGCAATGCAGAGGCTGCAGGTAG
TGCTGGGCCACCTGAGGGGTCCGGCCGATTCCGGCTGGATGCCGCAGGCCGCGCCTT
GCCTGAGCGGTGCCCCGCAGGCCTCGGCCGCGGACGTGGTGGTGGTGCACGGGCGG
CGCACGGCCATCTGCCGGGCGGGCCGCGGCGGCTTCAAGGACACCACCCCCGACGA
GCTTCTCTCGGCAGTCATGACCGCGGTTCTCAAGGACGTGAATCTGAGGCCGGAACA
GCTGGGGGACATCTGTGTCGGAAATGTGCTGCAGCCTGGGGCCGGGGCAATCATGG
CCCGAATCGCCCAGTTTCTGAGTGACATCCCGGAGACTGTGCCTTTGTCCACTGTCA
ATAGACAGTGTTCGTCGGGGCTACAGGCAGTGGCCAGCATAGCAGGTGGCATCAGA
AATGGGTCTTATGACATTGGCATGGCCTGTGGGGTGGAGTCCATGTCCTTGGCTGAC
AGAGGGAACCCTGGAAATATTACTTCGCGCTTGATGGAGAAGGAGAAGGCCAGAGA
TTGCCTGATTCCTATGGGGATAACCTCTGAGAATGTGGCTGAGCGGTTTGGCATTTC
ACGGGAGAAGCAGGATACCTTTGCCCTGGCTTCCCAGCAGAAGGCAGCAAGAGCCC
AGAGCAAGGGCTGTTTCCAAGCTGAGATTGTGCCTGTGACCACCACGGTCCATGATG
ACAAGGGCACCAAGAGGAGCATCACTGTGACCCAGGATGAGGGTATCCGCCCCAGC
ACCACCATGGAGGGCCTGGCCAAACTGAAGCCTGCCTTCAAGAAAGATGGTTCTAC
CACAGCTGGAAACTCTAGCCAGGTGAGTGATGGGCAGCTGCCATCCTGCTGGCCC
GGAGGTCCAAGGCAGAAGAGTTGGGCCTTCCCATCCTTGGGGTCCTGAGGTCTTATG
CAGTGGTTGGGGTCCCACCTGACATCATGGGCATTGGACCTGCCTATGCCATCCCAG
TAGCTTTGCAAAAAGCAGGGCTGACAGTGAGTGACGTGGACATCTTCGAGATCAAT
GAGGCCTTTGCAAGCCAGGCTGCCTACTGTGTGGAGAAGCTACGACTCCCCCCTGAG
AAGGTGAACCCCCTGGGGGGTGCAGTGGCCTTAGGGCACCCACTGGGCTGCACTGG
GGCACGACAGGTCATCACGCTGCTCAATGAGCTGAAGCGCCGTGGGAAGAGGGCAT
ACGGAGTGGTGTCCATGTGCATCGGGACTGGAATGGGAGCCGCTGCCGTCTTTGAAT
ACCCTGGGAACTGAGTGAGGTCCCAGGCTGGAGGCGCTACGCAGACAGTCCTGCTG
CTCTAGCAGCAAGGCAGTAACACCACAAAAGCAAAACCACATGGGAAAACTCAGC
ACTGGTGGTGGTGGCAGTGGACAGATCAAGGCACTTCAACTCATTTGGAAAATGTG
AACACTGATGACATGGTATAGGAGTGGGTGGGGTGTTGAGCCACCCATCAGACCCT
CTTTAGCTGTGCAAGATAAAAGCAGCCTGGGTCACCCAGGCCACAAGGCCATGGTT
AATTCTTAAGGCAAGGCAAATCCATGGATGAGAAGTGCAATGGGCATAGTAAAAGT
GCATGAATTTATCTTAAAAAAAAAAAAAAAAAAAAAAA

TABLE 5-continued

Nucleotide Sequences of Biodosimetry Biomarker Genes

INPP5J (SEQ ID NO: 23; NM_001284285.1).

```
CAGGTTGAAATGGCTGATGACATCACTGGTTCCCGGGAGCGGTAGAGCTGGAGCCG
GAGCCAAGGGAGTCCAGGCTGCCGGGGGCTGCAGACATGGAGGGCCAGAGCAGCA
GGGGCAGCAGGAGGCCAGGGACCCGGGCTGGCCTGGGTTCCCTGCCCATGCCCCAG
GGTGTTGCCCAAACTGGGGCACCCTCCAAGGTGGACTCAAGTTTTCAGCTCCCAGCA
AAGAAGAACGCAGCCCTAGGACCCTCGGAACCAAGGTTGGCTCTGGCACCTGTAGG
GCCACGGGCAGCTATGTCAGCTTCCTCGGAAGGACCGAGGCTGGCTCTGGCATCTCC
CCGACCAATCCTGGCTCCACTGTGTACCCCTGAAGGGCAGAAAACAGCTACTGCCC
ACCGCAGCTCCAGCCTGGCCCCAACATCTGTGGGCCAGCTGGTGATGTCTGCCTCAG
CTGGACCAAAGCCTCCCCCAGCGACCACAGGCTCAGTTCTGGCTCTGGACGTCCCTGG
GGCTGGTGATGCCTGCCTCAGCAGGGCCAAGATCTCCCCCAGTCACCCTGGGGCCCA
ATCTGGCCCCAACCTCCAGAGACCAGAAGCAGGAGCCACCTGCCTCCGTGGGACCC
AAGCCAACACTGGCAGCCTCTGGCCTGAGCCTGGCCCTGGCTTCTGAGGAGCAGCC
CCCAGAACTCCCCTCCACCCCTTCCCCGGTGCCCAGTCCAGTTCTGTCTCCAACTCAG
GAACAGGCCCTGGCTCCAGCATCCACGGCATCAGGCGCAGCCTCTGTGGGACAGAC
ATCAGCTAGAAAGAGGGATGCCCCAGCCCCTAGACCTCTCCCTGCTTCTGAGGGGC
ATCTCCAGCCTCCAGCTCAGACATCTGGTCCTACAGGCTCCCCACCCTGCATCCAAA
CCTCCCCAGACCCTCGGCTCTCCCCTCCTTCCGAGCCCGGCCTGAGGCCCTCCACA
GCAGCCCTGAGGATCCTGTTTTGCCACGGCCACCCCAGACCTTGCCCTTGGATGTGG
GCCAGGGTCCTTCAGAGCCTGGCACTCACTCCCCTGGACTTCTGTCCCCCACCTTCC
GGCCTGGGGCCCCCTCAGGCCAGACTGTGCCCCCACCTCTGCCCAAGCCACCCCGAT
CACCCAGCCGTTCCCCAAGCCACTCCCCGAATCGCTCTCCCTGTGTTCCCCCAGCCC
CTGACATGGCCCTCCCAAGGCTTGGCACACAGAGTACAGGGCCTGGCAGGTGCCTG
AGCCCCAACCTTCAGGCCCAAGAAGCCCCAGCCCCAGTCACCACCTCCTCTTCTACA
TCCACCCTGTCATCCTCCCCTTGGTCAGCTCAGCCTACCTGGAAGAGCGACCCCGGC
TTCCGGATCACTGTGGTCACATGGAACGTGGGCACTGCCATGCCCCCAGACGATGTC
ACATCCCTCCTCCACCTGGGCGGTGGTGACGACAGCGACGGCGCAGACATGGATCGC
CATAGGGTTGCAGGAAGTGAACTCCATGCTCAACAAGCGACTCAAGGACGCCCTCT
TCACGGACCAGTGGAGTGAGCTGTTCATGGATGCGCTAGGGCCCTTCAACTTCGTGC
TGGTGAGTTCGGTGAGGATGCAGGGTGTCATCCTGCTGCTGTTCGCCAAGTACTACC
ACCTGCCCTTCCTGCGAGACGTGCAGACCGACTGCACGCGCACTGGCCTGGGCGGCT
ACTGGGGTAACAAGGGTGGCGTGAGCGTGCGCCTGGCGGCCTTCGGGCACATGCTC
TGCTTCCTGAACTGCCACTTGCCTGCGCATATGGACAAGGCGGAGCAGCGCAAAGA
CAACTTCCAGACCATCCTCAGCCTCCAGCAGTTCCAAGGGCCGGGCGCACAGGGCA
TCCTGGATCATGACCTCGTGTTCTGGTTCGGGGACCTGAACTTCCGCATTGAGAGCT
ATGACCTGCACTTTGTCAAGTTTGCCATCGACAGTGACCAGCTCCATCAGCTCTGGG
AGAAGGACCAGCTCAACATGGCCAAGAACACCTGGCCCATTCTGAAGGGCTTTCAG
GAGGGGCCCCTCAACTTCGCTCCCACCTTCAAGTTTGATGTGGGTACCAACAAATAC
GATACCAGTGCCAAGAAACGGAAGCCAGCTTGGACAGACCGTATCCTATGGAAGGT
CAAGGCTCCAGGTGGGGGTCCCAGCCCCTCAGGACGGAAGAGCCACCGACTCCAGG
TGACGCAGCACAGCTACCGCAGCCACATGGAATACACAGTCAGCGACCACAAGCCT
GTGGCTGCCCAGTTCCTCCTGCAGTTTGCCTTCAGGGACGACATGCCACTGGTGCGG
CTGGAGGTGGCAGATGAGTGGGTGCGGCCCGAGCAGGCGGTGGTGAGGTACCGCAT
GGAAACAGTGTTCGCCCGCAGCTCCTGGGACTGGATCGGCTTATACCGGGTGGGTTT
CCGCCATTGCAAGGACTATGTGGCTTATGTCTGGGCCAAACATGAAGATGTGGATGG
GAATACCTACCAGGTAACATTCAGTGAGGAATCACTGCCCAAGGGCCATGGAGACT
TCATCCTGGGCTACTATAGTCACAACCACAGCATCCTCATCGGCATCACTGAACCCT
TCCAGATCTCGCTGCCTTCCTCGGAGTTGGCCAGCAGCAGCACAGACAGCTCAGGCA
CCAGCTCAGAGGGAGAGGATGACAGCACACTGGAGCTCCTTGCACCCAAGTCCCGC
AGCCCCAGTCCTGGCAAGTCCAAGCGACACCGCAGCCGCAGCCCGGGACTGGCCAG
GTTCCCTGGGCTTGCCCTACGGCCCTCATCCCGTGAACGCCGTGGTGCCAGCCGTAG
CCCCTCACCCCAGAGCCGCCGCCTGTCCCGAGTGGCTCCTGACAGGAGCAGTAATG
GCAGCAGCCGGGGCAGTAGTGAAGAGGGGCCCTCTGGGTTGCCTGGCCCCTGGGCC
TTCCCACCAGCTGTGCCTCGAAGCCTGGGCCTGTTGCCCGCCTTGCGCCTAGAGACT
GTAGACCCTGGTGGTGGTGGCTCCTGGGGACCTGATCGGGAGGCCCTGGCGCCCAA
CAGCCTGTCTCCTAGTCCCCAGGGCCATCGGGGGCTGGAGGAAGGGGGCCTGGGGC
CCTGAGGGTGGGGTAGGCAGATGGGCCAAGGTGACCACCATTCTGCCTCAATCTTTT
GCAAGCCCACCTGCCTCTCTCCTGCTGCTCCTCCAGCTGTATCTGCACCTGCCTCTCT
GTCCTGGCCAGGGGTGGACAACTGGGGTCCCCCAAAACTCAGTCCTGGCACCTCAA
CTGTGACAATCAGCAAAGCCCCACCCAGGCCCCCATCTGGGATGATGGGAGAGCTC
TGGCAGATGTCCCAATCCTGGAGGTCATCCATTAGGAATTAAATTCTCCAGCCTCAA
AAAAAAAAAAAAAA
```

OAZ1 (SEQ ID NO: 24; NM_004152.2).

```
TTTTGCAACGGCGAGCAGCGGCGGCGGCGCGGAGAGACGCAGCGGAGGTTTTCCT
GGTTTCGGACCCCAGCGGCCGGATGGTGAAATCCTCCCTGCAGCGGATCCTCAATAG
CCACTGCTTCGCCAGAGAGAAGGAAGGGGATAAACCCAGCGCCACCATCCACGCCA
GCCGCACCATGCCGCTCCTAAGCCTGCACAGCCGCGGCGGCAGCAGCAGTGAGAGT
TCCAGGGTCTCCCTCCACTGCTGTAGTAACCCGGGTCCGGGGCCTCGGTGGTGCTCC
TGATGCCCCTCACCCACCCCTGAAGATCCCAGGTGGGCGAGGGAATAGTCAGAGGG
ATCACAATCTTTCAGCTAACTTATTCTACTCCGATGATCGGCTGAATGTAACAGAGG
AACTAACGTCCAACGACAAGACGAGGATTCTCAACGTCCAGTCCAGGCTCACAGAC
GCCAAACGCATTAACTGGCGAACAGTGCTGAGTGGCGGCAGCCTCTACATCGAGAT
CCCGGGCGGCGCGCTGCCCGAGGGGAGCAAGGACAGCTTTGCAGTTCTCCTGGAGT
TCGCTGAGGAGCAGCTGCGAGCCGACCATGTCTTCATTTGCTTCCACAAGAACCGCG
AGGACAGAGCCGCCTTGCTCCGAACCTTCAGCTTTTTGGGCTTTGAGATTGTGAGAC
```

TABLE 5-continued

Nucleotide Sequences of Biodosimetry Biomarker Genes

CGGGGCATCCCCTTGTCCCCAAGAGACCCGACGCTTGCTTCATGGCCTACACGTTCG
AGAGAGAGTCTTCGGGAGAGGAGGAGGAGTAGGGCCGCCTCGGGGCTGGGCATCC
GGCCCCTGGGGCCACCCCTTGTCAGCCGGGTGGGTAGGAACCGTAGACTCGCTCATC
TCGCCTGGGTTTGTCCGCATGTTGTAATCGTGCAAATAAACGCTCACTCCGAATTAG
CGGTGTATTTCTTGAAGTTTAATATTGTGTTTGTGATACTGAAGTATTTGCTTTAATT
CTAAATAAAAATTTATATTTTACTTTTTTATTGCTGGTTTAAGATGATTCAGATTATC
CTTGTACTTTGAGGAGAAGTTTCTTATTTGGAGTCTTTTGGAAACAGTCTTAGTCTTT
TAACTTGGAAAGATGAGGTATTAATCCCCTCCATTGCTCTCCAAAAGCCAATAAAGT
GATTACACCCGA

PNOC (SEQ ID NO: 25; NM_006228).

GCCAGGAAGGCTTGCAGGTTCTGCTGTTTGGTTGCTGAAGGGGGTCAGTGTGTGTAT
GTGTCATGGAGGTGGGCAGGGAAGGGGAGGGCTGTGCGTGGGGGAGAGGATATAT
ATGCTGGTGTGGCTGAGAAAGCGGAACCGAGCCTCGCATCCATCGGAGGGAGCCGG
GGACTGACAGCTCTCAGCACCTGCTTCCTGCTCCTGCACCATGAAAGTCCTGCTTTG
TGACCTGCTGCTGCTCAGTCTCTTCTCCAGTGTGTTCAGCAGTTGTCAGAGGGACTGT
CTCACATGCCAGGAGAAGCTCCACCCAGCCCTGGACAGCTTCGACCTGGAGGTGTG
CATCCTCGAGTGTGAAGAGAAGGTCTTCCCCAGCCCCCTCTGGACTCCATGCACCAA
GGTCATGGCCAGGAGCTCTTGGCAGCTCAGCCCTGCCGCCCCAGAGCATGTGGCGG
CTGCTCTCTACCAGCCGAGAGCTTCGGAGATGCAGCATCTGCGGCGAATGCCCCGA
GTCCGGAGCTTGTTCCAGGAGCAGGAAGAGCCCGAGCCTGGCATGGAGGAGGCTGG
TGAGATGGAGCAGAAGCAGCTGCAGAAGAGATTTGGGGGCTTCACCGGGGCCCGGA
AGTCGGCCAGGAAGTTGGCCAATCAGAAGCGGTTCAGTGAGTTTATGAGGCAATAC
TTGGTCCTGAGCATGCAGTCCAGCCAGCGCCGGCGCACCCTGCACCAGAATGGTAA
TGTGTAGCCGGAAGGGGCGCTCCTCCCAGCTGTACCGGCACTGCAACCCATGAGC
GTCCAGGTGATCCCCCAAACAGCATGTGCTCAGCCCCAGACCTGCCGCCTGGGAATC
AGGATTCCTTCTTCCCCAAGGCACTGAGCGCCTGCAGATCCCGCAGGCTTCGTTTGC
CTCCAGAACCTTCCCGTCTGATTGTTCCTCCCCAGCCCCTGGCATGTTTCACCACAA
CCCTGTTGCTACATCAGAGTGTATTTTGTAATTCCTCTAGCTACCATTTCAATAGCC
CCATCTCTCCTGCTCACCCGCCTCTTGCCCCTTCTAGGGGCAGGTGAAAGGAATAGG
AAATTGAACCTGGGGTTTTGACTTGCCACTGCCATAACTTGTTTGTAAAAGAGCTGT
TCTTTTTGACTGATTGTTTAAACAACGATTTCTCCATTAAACTTCTACTGAGCAAAT
GGTTAATAAAAAAAAAAAAAAAAAA

PDE4B (SEQ ID NO: 26; NM_002600).

AGAGCGCTGCGGCCGCGGCGGTGCAGCAGAGGCGCCTCGGGCAGGAGGAGGGCGG
CTTCTGCGAGGGCAGCCTGAGGTATTAAAAAGTGTCAGCAAACTGCATTGAATAAC
AGACATCCTAAGAGGGGATATTTTCCACCTCTATAATGAAGAAAAGCAGGAGTGTG
ATGACGGTGATGGCTGATGATAATGTTAAAGATTATTTTGAATGTAGCTTGAGTAAA
TCCTACAGTTCTTCCAGTAACACACTTGGGATCGACCTCTGGAGAGGGAGAAGGTGT
TGCTCAGGAAACTTACAGTTACCACCACTGTCTCAAAGACAGAGTGAAAGGGCAAG
GACTCCTGAGGGAGATGGTATTTCCAGGCCGACCACACTGCCTTTGACAACGCTTCC
AAGCATTGCTATTACAACTGTAAGCCAGGAGTGCTTTGATGTGGAAAATGGCCCTTC
CCCAGGTCGGAGTCCACTGGATCCCCAGGCCAGCTCTTCCGCTGGGCTGGTACTTCA
CGCCACCTTTCCTGGGCACAGCCAGCGCAGAGAGTCATTTCTCTACAGATCAGACAG
CGACTATGACTTGTCACCAAAGGCGATGTCGAGAAACTCTTCTCTTCCAAGCGAGCA
ACACGGCGATGACTTGATTGTAACTCCTTTTGCCCAGGTCCTTGCCAGCTTGCGAAG
TGTGAGAAACAACTTCACTATACTGACAAACCTTCATGGTACATCTAACAAGAGGTC
CCCAGCTGCTAGTCAGCCTCCTGTCTCCAGAGTCAACCCACAAGAAGAATCTTATCA
AAAATTAGCAATGGAAACGCTGGAGGAATTAGACTGGTGTTTAGACCAGCTAGAGA
CCATACAGACCTACCGGTCTGTCAGTGAGATGGCTTCTAACAAGTTCAAAAGAATGC
TGAACCGGGAGCTGACACACCTCTCAGAGATGAGCCGATCAGGGAACCAGGTGTCT
GAATACATTTCAAATACTTTCTTAGACAAGCAGAATGATGTGGAGATCCCATCTCCT
ACCCAGAAAGACAGGGAGAAAAAGAAAAAGCAGCAGCTCATGACCCAGATAAGTG
GAGTGAAGAAATTAATGCATAGTTCAAGCCTAAACAATACAAGCATCTCACGCTTTG
GAGTCAACACTGAAAATGAAGATCACCTGGCCAAGGAGCTGGAAGACCTGAACAAA
TGGGGTCTTAACATCTTTAATGTGGCTGGATATTCTCACAATAGACCCCTAACATGC
ATCATGTATGCTATATTCCAGGAAAGAGACCTCCTAAAGACATTCAGAATCTCATCT
GACACATTTATAACCTACATGATGACTTTAGAAGACCATTACCATTCTGACGTGGCA
TATCACAACAGCCTGCACGCTGCTGATGTAGCCCAGTCGACCCATGTTCTCCTTTCT
ACACCAGCATTAGACGCTGTCTTCACAGATTTGGAGATCCTGGCTGCCATTTTTGCA
GCTGCCATCCATGACGTTGATCATCCTGGAGTCTCCAATCAGTTTCTCATCAACACA
AATTCAGAACTTGCTTTGATGTATAATGATGAATCTGTGTTGGAAAATCATCACCTT
GCTGTGGGTTTCAAACTGCTGCAAGAAGAACACTGTGACATCTTCATGAATCTCACC
AAGAAGCAGCGTCAGACACTCAGGAAGATGGTTATTGACATGGTGTTAGCAACTGA
TATGTCTAAACATATGAGCCTGCTGGCAGACCTGAAGACAATGGTAGAAACGAAGA
AAGTTACAAGTTCAGGCGTTCTTCTCCTAGACAACTATACCGATCGCATTCAGGTCC
TTCGCAACATGGTACACTGTGCAGACCTGAGCAACCCCACCAAGTCCTTGGAATTGT
ATCGGCAATGGACAGACCGCATCATGGAGGAATTTTTCCAGCAGGGAGACAAAGAG
CGGGAGAGGGGAATGGAAATTAGCCCAATGTGTGATAAACACACAGCTTCTGTGGA
AAAATCCCAGGTTGGTTTCATCGACTACATTGTCCATCCATTGTGGGAGACATGGGC
AGATTTGGTACAGCCTGATGCTCAGGACATTCTCGATACCTTAGAAGATAACAGGAA
CTGGTATCAGAGCATGATACCTCAAAGTCCCTCCACCACCACTGGACGAGCAGAACA
GGGACTGCCAGGGTCTGATGGAGAAGTTTCAGTTTGAACTGACTCTCGATGAGGAA
GATTCTGAAGGACCTGAGAAGGAGGGAGAGGGACACAGCTATTTCAGCAGCACAAA
GACGCTTTGTGTGATTGATCCAGAAAACAGAGATTCCCTGGGAGAGACTGACATAG

TABLE 5-continued

Nucleotide Sequences of Biodosimetry Biomarker Genes

```
ACATTGCAACAGAAGACAAGTCCCCCGTGGATACATAATCCCCCTCTCCCTGTGGAG
ATGAACATTCTATCCTTGATGAGCATGCCAGCTATGTGGTAGGGCCAGCCCACCATG
GGGGCCAAGACCTGCACAGGACAAGGGCCACCTGGCCTTTCAGTTACTTGAGTTTGG
AGTCAGAAAGCAAGACCAGGAAGCAAATAGCAGCTCAGGAAATCCCACGGTTGACT
TGCCTTGATGGCAAGCTTGGTGGAGAGGGCTGAAGCTGTTGCTGGGGGCCGATTCTG
ATCAAGACACATGGCTTGAAAATGGAAGACACAAAACTGAGAGATCATTCTGCACT
AAGTTTCGGGAACTTATCCCCGACAGTGACTGAACTCACTGACTAATAACTTCATTT
ATGAATCTTCTCACTTGTCCCTTTGTCTGCCAACCTGTGTGCCTTTTTTGTAAAACATT
TTCATGTCTTTAAAATGCCTGTTGAATACCTGGAGTTTAGTATCAACTTCTACACAGA
TAAGCTTTCAAAGTTGACAAACTTTTTTGACTCTTTCTGGAAAAGGGAAAGAAAATA
GTCTTCCTTCTTTCTTGGGCAATATCCTTCACTTTACTACAGTTACTTTTGCAAACAG
ACAGAAAGGATACACTTCTAACCACATTTTACTTCCTTCCCCTGTTGTCCAGTCCAAC
TCCACAGTCACTCTTAAAACTTCTCTCTGTTTGCCTGCCTCCAACAGTACTTTTAACT
TTTTGCTGTAAACAGAATAAAATTGAACAAATTAGGGGGTAGAAAGGAGCAGTGGT
GTCGTTCACCGTGAGAGTCTGCATAGAACTCAGCAGTGTGCCCTGCTGTGTCTTGGA
CCCTGCCCCCCACAGGAGTTGTACAGTCCCTGGCCCTGTTCCCTACCTCCTCTCTTCA
CCCCGTTAGGCTGTTTTCAATGTAATGCTGCCGTCCTTCTCTTGCACTGCCTTCTGCG
CTAACACCTCCATTCCTGTTTATAACCGTGTATTTATTACTTAATGTATATAATGTAA
TGTTTTGTAAGTTATTAATTTATATATCTAACATTGCCTGCCAATGGTGGTGTTAAAT
TTGTGTAGAAAACTCTGCCTAAGAGTTACGACTTTTTCTTGTAATGTTTTGTATTGTG
TATTATATAACCCAAACGTCACTTAGTAGAGACATATGGCCCCCTTGGCAGAGAGGA
CAGGGGTGGGCTTTTGTTCAAAGGGTCTGCCCTTTCCCTGCCTGAGTTGCTACTTCTG
CACAACCCCTTTATGAACCAGTTTTGGAAACAATATTCTCACATTAGATACTAAATG
GTTTATACTGAGCTTTTACTTTTGTATAGCTTGATAGGGGCAGGGGGCAATGGGATG
TAGTTTTTACCCAGGTTCTATCCAAATCTATGTGGGCATGAGTTGGGTTATAACTGG
ATCCTACTATCATTGTGGCTTTGGTTCAAAAGGAAACACTACATTTGCTCACAGATG
ATTCTTCTGAATGCTCCCGAACTACTGACTTTGAAGAGGTAGCCTCCTGCCTGCCATT
AAGCAGGAATGTCATGTTCCAGTTCATTACAAAAGAAAACAATAAAACAATGTGAA
TTTTTATAATAAAATGTGAACTGATGTAGCAAATTACGCAAATGTGAAGCCTCTTCT
GATAACACTTGTTAGGCCTCTTACTGATGTCAGTTTCAGTTTGTAAAATATGTTTCAT
GCTTTCAGTTCAGCATTGTGACTCAGTAATTACAGAAAATGGCACAAATGTGCATGA
CCAATGTATGTCTATGAACACTGCATTGTTTCAGGTGGACATTTTATCATTTTCAAAT
GTTTCTCACAATGTATGTTATAGTATTATTATTATATATTGTGTTCAAATGCATTCTA
AAGAGACTTTTATATGAGGTGAATAAAGAAAAGCATGATTAGATTAAAAAAA
```

SCARB1 (SEQ ID NO: 27; NM_005505.4).

```
GCTCAGGCCCCGCCCCTGCCGCCGGAATCCTGAAGCCCAAGGCTGCCCGGGGGCGG
TCCGGCGGCGCCGGCGATGGGGCATAAAACCACTGGCCACCTGCCGGGCTGCTCCT
GCGTGCGCTGCCGTCCCGGATCCACCGTGCCTCTGCGGCCTGCGTGCCCGGAGTCCC
CGCCTGTGTCGTCTCTGTCGCCGTCCCCGTCTCCTGCCAGGCGCGGAGCCCTGCGAG
CCGCGGGTGGGCCCCAGGCGCGCAGACATGGGCTGCTCCGCCAAAGCGCGCTGGGC
TGCCGGGGCGCTGGGCGTCGCGGGGCTACTGTGCGCTGTGCTGGGCGCTGTCATGAT
CGTGATGGTGCCGTCGCTCATCAAGCAGCAGGTCCTTAAGAACGTGCGCATCGACCC
CAGTAGCCTGTCCTTCAACATGTGGAAGGAGATCCCTATCCCCTTCTATCTCTCCGTC
TACTTCTTTGACGTCATGAACCCCAGCGAGATCCTGAAGGGCGAGAAGCCGCAGGT
GCGGGAGCGCGGGCCCTACGTGTACAGGGAGTTCAGGCACAAAAGCAACATCACCT
TCAACAACAACGACACCGTGTCCTTCCTCGAGTACCGCACCTTCCAGTTCCAGCCCT
CCAAGTCCCACGGCTCGGAGAGCGACTACATCGTCATGCCCAACATCCTGGTCTTGG
GTGCGGCGGTGATGATGGAGAATAAGCCCATGACCCTGAAGCTCATCATGACCTTG
GCATTCACCACCCTCGGCGAACGTGCCTTCATGAACCGCACTGTGGGTGAGATCATG
TGGGGCTACAAGGACCCCCTTGTGAATCTCATCAACAAGTACTTTCCAGGCATGTTC
CCCTTCAAGGACAAGTTCGGATTATTTGCTGAGCTCAACAACTCCGACTCTGGGCTC
TTCACGGTGTTCACGGGGGTCCAGAACATCAGCAGGATCCACCTCGTGGACAAGTG
GAACGGGCTGAGCAAGGTTGACTTCTGGCATTCCGATCAGTGCAACATGATCAATG
GAACTTCTGGGCAAATGTGGCCGCCCTTCATGACTCCTGAGTCCTCGCTGGAGTTCT
ACAGCCCGGAGGCCTGCCGATCCATGAAGCTAATGTACAAGGAGTCAGGGGTGTTT
GAAGGCATCCCCACCTATCGCTTCGTGGCTCCCAAAACCCTGTTTGCCAACGGGTCC
ATCTACCCACCCAACGAAGGCTTCTGCCCGTGCCTGGAGTCTGGAATTCAGAACGTC
AGCACCTGCAGGTTCAGTGCCCCCTTGTTTCTCTCCCATCCTCACTTCCTCAACGCTG
ACCCGGTTCTGGCAGAAGCGGTGACTGGCCTGCACCCTAACCAGGAGGCACACTCC
TTGTTCCTGGACATCCACCCGGTCACGGGAATCCCCATGAACTGCTCTGTGAAACTG
CAGCTGAGCCTCTACATGAAATCTGTCGCAGGCATTGGACAAACTGGGAAGATTGA
GCCTGTGGTCCTGCCGCTGCTCTGGTTTGCAGAGAGCGGGGCCATGGAGGGGGAGA
CTCTTCACACATTCTACACTCAGCTGGTGTTGATGCCCAAGGTGATGCACTATGCCC
AGTACGTCCTCCTGGCGCTGGGCTGCGTCCTGCTGCTGGTCCCTGTCATCTGCCAAA
TCCGGAGCCAAGAGAAATGCTATTTATTTTGGAGTAGTAGTAAAAGGGCTCAAAG
GATAAGGAGGCCATTCAGGCCTATTCTGAATCCCTGATGACATCAGCTCCCAAGGGC
TCTGTGCTGCAGGAAGCAAAACTGTAGGGTCCTGAGGACACCGTGAGCCAGCCAGG
CCTGGCCGCTGGGCCTGACCGGCCCCCAGCCCCTACACCCCGCTTCTCCCGGACTC
TCCCAGCGGACAGCCCCCAGCCCCACAGCCTGAGCCTCCCAGCTGCCATGTGCCTG
TTGCACACCTGCACACACGCCCTGGCACACATACACACATGCGTGCAGGCTTGTGCA
GACACTCAGGGATGGAGCTGCTGCTGAAGGGACTTGTAGGGGAGAGGCTCGTCAACA
AGCACTGTTCTGGAACCTTCTCTCCACGTGGCCCACAGGCCTGACCACAGGGGCTGT
GGGTCCTGCGTCCCCTTCCTCGGGTGAGCCTGGCCTGTCCCGTTCAGCCGTTGGGCC
CAGGCTTCCTCCCCTCCAAGGTGAAACACTGCAGTCCCGGTGTGGTGGCTCCCCATG
CAGGACGGGCCAGGCTGGGAGTGCCGCCTTCCTGTGCCAAATTCAGTGGGGACTCA
GTGCCCAGGCCCTGGCCACGAGCTTTGGCCTTGGTCTACCTGCCAGGCCAGGCAAAG
```

TABLE 5-continued

Nucleotide Sequences of Biodosimetry Biomarker Genes

CGCCTTTACACAGGCCTCGGAAAACAATGGAGTGAGCACAAGATGCCCTGTGCAGC
TGCCCGAGGGTCTCCGCCCACCCCGGCCGGACTTTGATCCCCCCGAAGTCTTCACAG
GCACTGCATCGGGTTGTCTGGCGCCCTTTTCCTCCAGCCTAAACTGACATCATCCTAT
GGACTGAGCCGGCCACTCTCTGGCCGAAGTGGCCGCAGGCTGTGCCCCCGAGCTGC
CCCCACCCCCTCACAGGGTCCCTCAGATTATAGGTGCCCAGGCTGAGGTGAAGAGG
CCTGGGGGCCCTGCCTTCCGGGCGCTCCTGGACCCTGGGGCAAACCTGTGACCCTTT
TCTACTGGAATAGAAATGAGTTTTATCATCTTTGAAAAATAATTCACTCTTGAAGTA
ATAAACGTTTAAAAAAATGGGAAAAAAAAAAAAAAAAAA

TMEM9B (SEQ ID NO: 28; NM_020644.2).

GTGCGCGAACGGCTCCGGCCCGCACGGGTCGCCAGAGGCGACTGTGTGACACTCGG
AGTTTGCTGGGGTCTCCGTGGGCGGGAGGACTTTCCAGCGCAATGGCGACTCCCTAA
GCCCCGCAGCTTCTGCGCCCGGGAAAGATATCCAAGAGATGCAAAGCTCTACTGGG
CCCAGGCTGCCACCCCAGAGGCCCCCTTCCGTCCCGGGGCCGGGGCTAGGCCAAGG
CGGGCACCAGGACTGCCCAGCCTCCCGGCCCTTCGCACTGGTAACCGGTTCCGGGGC
GGATGCTTTTTGCATCTGACCCGGCGCGCCCGGTGACGCCTTCGCGTCCAGACGGAA
GTGCGGGCGGAGGATCCCCAGCCGGGTCCCAAGCCTGTGCCTGAGCCTGAGCCTGA
GCCTGAGCCCGAGCCGGGAGCCGGTCGCGGGGGCTCCGGGCTGTGGGACCGCTGGG
CCCCCAGCGATGGCGACCCTGTGGGGAGGCCTTCTTCGGCTTGGCTCCTTGCTCAGC
CTGTCGTGCCTGGCGCTTTCCGTGCTGCTGCTGGCGCAGCTGTCAGACGCCGCCAAG
AATTTCGAGGATGTCAGATGTAAATGTATCTGCCCTCCCTATAAAGAAAATTCTGGG
CATATTTATAATAAGAACATATCTCAGAAAGATTGTGATTGCTCATGTTGTGGAG
CCCATGCCTGTGCGGGGGCCTGATGTAGAAGCATACTGTCTACGCTGTGAATGCAAA
TATGAAGAAAGAAGCTCTGTCACAATCAAGGTTACCATTATAATTTATCTCTCCATT
TTGGGCCTTCTACTTCTGTACATGGTATATCTTACTCTGGTTGAGCCCATACTGAAGA
GGCGCCTCTTTGGACATGCACAGTTGATACAGAGTGATGATGATATTGGGGATCACC
AGCCTTTTGCAAATGCACACGATGTGCTAGCCCGCTCCCGCAGTCGAGCCAACGTGC
TGAACAAGGTAGAATATGCACAGCAGCGCTGGAAGCTTCAAGTCCAAGAGCAGCGA
AAGTCTGTCTTTGACCGGCATGTTGTCCTCAGCTAATTGGGAATTGAATTCAAGGTG
ACTAGAAAGAAACAGGCAGACAACTGGAAAGAACTGACTGGGTTTTGCTGGGTTTC
ATTTTAATACCTTGTTGATTTCACCAACTGTTGCTGGAAGATTCAAAACTGGAAGCA
AAAACTTGCTTGATTTTTTTTCTTGTTAACGTAATAATAGAGACATTTTAAAAGCA
CACAGCTCAAAGTCAGCCAATAAGTCTTTTCCTATTTGTGACTTTTACTAATAAAAAT
AAATCTGCCTGTAAATTATCTTGAAGTCCTTTACCTGGAACAAGCACTCTCTTTTTCA
CCACATAGTTTTAACTTGACTTTCAAGATAATTTTCAGGGTTTTTGTTGTTGTTGTTTT
TTGTTTGTTTGTTTGGTGGGAGAGGGGAGGGATGCCTGGGAAGTGGTTAACAACTT
TTTTCAAGTCACTTTACTAAACAAACTTTTGTAAATAGACCTTACCTTCTATTTTCGA
GTTTCATTTATATTTTGCAGTGTAGCCAGCCTCATCAAAGAGCTGACTTACTCATTTG
ACTTTTTGCACTGACTGTATTATCTGGGTATCTGCTGTGTCTGCACTTCATGGTAAACG
GGATCTAAAATGCCTGGTGGCTTTTCACAAAAAGCAGATTTTCTTCATGTACTGTGA
TGTCTGATGCAATGCATCCTAGAACAAACTGGCCATTTGCTAGTTTACTCTAAAGAC
TAAACATAGTCTTGGTGTGTGGTCTTACTCATCTTCTAGTACCTTTAAGGACAAAT
CCTAAGGACTTGGACACTTGCAATAAAGAAATTTTATTTTAAACCCAAGCCTCCCTG
GATTGATAATATATACACATTTGTCAGCATTTCCGGTCGTGGTGAGAGGCAGCTGTT
TGAGCTCCAATGTGTGCAGCTTTGAACTAGGGCTGGGGTTGTGGGTGCCTCTTCTGA
AAGGTCTAACCATTATTGGATAACTGGCTTTTTTCTTCCTATGTCCTCTTTGGAATGT
AACAATAAAAATAATTTTTGAAACATCCATCAGTGTATCTATCTATGTCTCCTAGTTT
TTTCCTCCTCCCTCTTTTGCTGTATAATGAGATTGAAGATATAAAGACATTTTGTACC
CTGTAAAAAAAA

PPP6R3 (SEQ ID NO: 29; XM_005274081).

AACTCAAGGCCTGCTTGATACGTCCGCCATTTTGGGCGCTTCGCTGATGGTGTCGGT
GAGCGCGTTTCCCGCCTGAGCGCAACTAGCGGCGGGTCGTGGGCACCTCCAGGAGA
GCTTGTTTCATATCCATATCCCACTGTATTCCTGCTAATCTGCTAATGCAGTAAATTG
GAGGGAAAACTGTTACCAGGATAACCTGTAATGGGCAAGGAGCCACAAAGAAGAAA
ACATTTCTTTTAATTTTTAAACTTGGTTTGAAAGACCAGCATGTTTTGGAAATTTGAT
CTTCACTCATCATCCCACATAGACACACTTCTAGAAAGAGAAGATGTAACACTGAAG
GAGTTAATGGATGAGGAAGATGTTTTACAGGAATGTAAAGCTCAGAACCGCAAACT
TATAGAGTTTCTGTTAAAAGCAGAATGTCTCGAAGATTTAGTCTCATTCATTATAGA
AGAACCACCTCAAGACATGGATGAAAAGATCAGATACAAGTATCCAAATATATCTT
GTGAGTTGCTCACTTCTGATGTCTCCCAGATGAATGATAGACTGGGAGAAGATGAAT
CCTTGCTAATGAAATTATATAGCTTCCTCCTAAACGATTCCCCTTTGAATCCACTACT
TGCCAGTTTCTTCAGCAAGGTGCTAAGTATTCTTATCAGCAGAAAACCAGAACAGAT
TGTGGATTTCTTAAAGAAGAAGCATGATTTTGTAGACCCTTATTATAAAGCACATAGG
AACTTCTGCTATCATGGATTTGTTGCTCAGGCTCCTGACGTGTATCGAACCTCCACAG
CCCAGGCAAGATGTGCTGAATTGGTTAAATGAGGAGAAAATTATCCAGAGGCTTGT
GGAAATAGTTCATCCATCGCAAGAAGAAGATCGACATTCAAATGCATCACAATCAC
TTTGTGAAATTGTTCGCCTGAGCAGAGACCAGATGTTACAAATTCAGAACAGTACAG
AGCCCGACCCCCTGCTTGCCACTCTAGAAAAGCAAGAATTATAGAGCAGCTTCTAT
CAAATATTTTCCACAAGGAGAAAAATGAGTCAGCCATAGTCAGTGCAATCCAGATA
TTGCTGACTTTACTTGAGACACGACGACCAACATTTGAAGGCCATATAGAGATCTGC
CCACCAGGCATGAGCCATTCAGCTTGTTCAGTAAACAAGAGTGTTCTAGAAGCCATC
AGAGGAAGACTTGGATCTTTTTCATGAACTCCTGCTGGAGCCACCCAAGAAAAGTGT
GATGAAGACCACATGGGGTGTGCTGGATCCTCCTGTGGGGAATACCCGGTTGAATGT
CATTAGGTTGATATCCAGCCTGCTTCAAACCAATACCAGCAGTATAAATGGGGACCT
TATGGAGCTGAATAGCATTGGAGTCATATTGAACATGTTCTTCAAGTATACATGGAA

TABLE 5-continued

Nucleotide Sequences of Biodosimetry Biomarker Genes

```
TAACTTTTTGCATACACAAGTGGAAATTTGTATTGCACTGATTCTTGCAAGTCCTTTT
GAAAACACAGAAAATGCCACAATTACCGATCAAGACTCCACTGGTGATAATTTGTT
ATTAAAACATCTTTTCCAAAAATGTCAATTAATAGAACGAATACTTGAAGCCTGGGA
AATGAATGAGAAGAAACAGGCTGAGGGAGGAAGACGGCATGGTTACATGGGACAC
CTAACGAGGATAGCTAACTGTATCGTGCACAGCACTGACAAGGGCCCCAACAGTGC
ATTAGTGCAGCAGCTTATCAAAGATCTTCCCGACGAAGTCAGGGAACGATGGGAGA
CGTTCTGCACAAGCTCCTTAGGAGAAACTAACAAGAGGAACACGGTAGATCTAGTT
ACAACCTGCCATATTCATTCATCCAGTGATGATGAAATTGACTTTAAAGAAACGGGT
TTCTCACAGGATTCTTCTTTGCAGCAAGCCTTTTCTGATTATCAGATGCAACAAATGA
CGTCCAATTTTATTGACCAGTTTGGCTTCAACGATGAGAAGTTTGCAGATCAAGATG
ACATTGGCAATGTTTCTTTTGATCGAGTATCAGACATCAACTTTACTCTCAATACAAA
TGAAAGTGGAAATATTGCCTTGTTTGAAGCATGTTGTAAGGAAAGAATACAACAGTT
TGATGATGGTGGCTCTGATGAGGAAGATATATGGGAGGAAAAGCACATCGCATTCA
CACCAGAATCCCAAAGACGATCCAGCTCGGGGAGTACAGACAGTGAGGAAAGTAC
AGACTCTGAAGAAGAAGATGGAGCAAAGCAAGACTTGTTTGAACCCAGCAGTGCCA
ACACGGAGGATAAAATGGAGGTGGACCTGAGTGAACCACCCAACTGGTCAGCTAAC
TTTGATGTCCCAATGGAAACAACCCACGGTGCTCCATTGGATTCTGTGGGATCTGAT
GTCTGGAGCACAGAGGAGCCGATGCCAACTAAAGAGACGGGCTGGGCTTCTTTTC
AGAGTTCACGTCTTCCCTGAGCACAAAAGATTCTTTAAGGAGTAATTCTCCAGTGGA
AATGGAAACCAGCACTGAACCCATGGACCCTCTGACTCCCAGTGCGGCTGCCCTGG
CAGTGCAGCCAGAAGCGGCAGGCAGTGTGGCCATGGAAGCCAGCTCTGACGGAGA
GGAGGATGCAGAAAGTACAGACAAGGTAACTGAGACAGTGATGAATGGCGGCATG
AAGGAAACGCTCAGCCTCACTGTAGATGCCAAGACAGAGACTGCGGTCTTCAAAAG
TGAGGAAGGGAAACTGTCTACCTCTCAAGATGCTGCTTGTAAAGACGCAGAGGAGT
GTCCCGAGACTGCAGAGGCGAAGTGCGCGGCGCCCAGGCCTCCCAGCAGCAGTCCC
GAGCAGAGTGCCTCCGATGCCTGTCTGTTGCTCCTTAGGACTGGCCAACCAAGCGCA
CCAGGTGACACTTCAGTGAATGGCCCTGTATGACGGGTACGTCTGCTGCTGCTGAC
TGAGGACTGCAGACCGCCACCACTCAGGGGCTCTGGAGGGGTCAGCTGGAGCCCAC
CAAGCTGTCACTGCTGCACTCACTCTGCAAGGGATCAGGACCAGCAACCTTTATATT
CTAGATTCTAAGACATTGTACAGAGAAATTCAGAAGTGTAAAAATATTGCACATTGA
CAAATACCAAGAATTTTTGCGTATGTTTATATTGTATTGTTCTAAATAATGGGTAGCC
TGTGAAATAAGATCTTGCCACCCATGTAATAATAGTAGTAATACTATAGTTAAAATG
GCTGTAAGAATAGTTTTATAAAAGTGAATACACAGATCTATTGTATTTGAAACATAA
CTTTGACAATTATTAGTGTGACCAAAGTATTAGGCGGTTTTCATACATTTTTCACCTT
GTACAAAATTATGAATTCATTTTCCTCCAGGCCGACAAGGAGTTGTAGAATGAAAA
TGCCCTCTAAGTGTTATTTTGGTTGTTCTAACTTACAAAAGTGATTTTGAATAAGAAA
TATTTGGTGTTCTTTTTATAACCAGTTTTTGATTGGTAATTGTTTTCTGTATTGTTTAA
AACGGATCAAAAATGTAAGTCTATTGGTAGAGATTAAGTAAAGTATTTATTGCTACA
TCATAGTTGATAAATTGATGTTATCGTAAAGCCATATGTTCTGTTCAAGTCTTGTTTG
CTTGAAATGATTATTCCTACAAGTGAAACACTAGACTATTTGGAGTGTATATGGCTT
GTGTTTTGGGATTTTTTTTTTTTTTTTGGCTTTTGTTTTTGTTGTTTTTTGTTTCAT
TTGGTAGTTCATCTGCCTTTTAACCCATTCACCAAAATTTACCTTGTTAACAAGCATC
ACCAATGAACATTTCAGAGCAATCTGCATATTTAACAGACCTAAAATAAATCCTATT
AGGCAAGTCAGTTGAAAATGCTCGTGCTGCTAATGGAATTAGAGTGCGTTCATTTTA
CAGGCTAGTATTTTAAAAGTAGAAATCAAAATCTGGCACCGAAGCATGCTAATTGTT
TACTGTACCTTGTGAGGTTTTCACTCATAAATTTAAACCAGTGTATTTTTTTAGAACT
GGTTTGTGTATATATATAGTGATTATGGATACTAATTCAATGTAATTTATAATTTTCT
ATGTCAATACAAAAATACATCACAGCCTTCTCAAACAGCTCAAGCAATATATTGTAT
ATTGCCATATCGTCTGGTGAAAGGGTTAAATTACTTCACCTCTTGCACTTTTAGATGC
AAATCAGTTTTTCATTTCTGTAATAGAAAATTATTCACGTATTTTTACATCATTTGTTT
TTCCTGACCAGTATTTAAAACCAAAAGGATATTCTGAAAAATGGCCAACAATTTTTT
TAGAAGTAGCATCCCAAGCAGCGTGCCTAAACATTACATTGCATATGGAAATAAAA
GAATCAAACGTCTAATGCCTTATTATTTCTGATTTCCTTTTTCATTTTAAGTGGTGTG
GAGATTCCAGCACTCCCAGGACAGTGGAGTCAGCAGTAAGCCCTGGGACAGGTGGC
AAGGGTGGGTCCCTTGACCTTTGCACGCCTCCTCAGGAACCCCCTTTCCCGGGTGAG
CCCCTCTCTGAAGACTGTCCTTGGGCCTCCTCTGGAAGCAGCACCCCCAGAGGAC
AGGGCTCCTCCTGCTTGCCTCAGGGCTGCCTGACTTGAATGGCGTTGGACCTCGGGG
ATTACTGGTAGATAATATGCTCTGGTCTCGCCTGGTGGTGAGTTTTGCCAGCCATGG
CCAGGGTTTGGCTCCACTGGTGGCACACGTGGCCTCCGTGGTATGGACCTGGTGGCT
TCTCCATCCCACTGTGCCTCTGTGGTATGGACCTGGTGGCTTCTCCATCCTACCCAA
GGTAACAGTGTCTTGCTTCATCCCACTGACTGCTGGGAGAGAGCCTCTGGGACTTTT
CTTTGGGGCATCATTTTGTTTTGTCTTTCGTAGCAGGGAAAGGATATGACAATGGGG
AGGACAGTTCTTTTGGAGGTTGGAGGGGCCAAGCCAAGGACAGGAGCAAGTGTGCC
CTCATTTTGTTTCTACTTTTAATTTCTGTGTGTTGGCCATACTGAATTATGAGACTAA
CAGATGTCTACAATACAATACCTGTATTCAAAATAACAAAAATAAAGCCTGATTCTT
TGTTTCTAGAAA
```

We claim:

1. A radiation biodosimetry assay system, comprising a plurality of in vitro nucleic acid amplification reaction mixtures, each amplification reaction mixture comprising:
   (i) a probe of at least 10 nucleotides directed to SEQ ID NOs: 6, 8, 9, 10 or 14, or the complementary sequence thereof, labeled with a fluorescent dye and a quencher; and
   (ii) one or more primer pairs, each primer pair comprising primers of at least 10 nucleotides directed to SEQ ID NOs: 6, 8, 9, 10, or 14, or a complementary sequence thereof, wherein the system comprises primer pairs of at least 10 nucleotides and probes of at least 10 nucleotides directed to at least three of SEQ ID NOs: 6, 8, 9, 10, or 14, or the complementary sequences thereof.

2. The radiation biodosimetry assay system of claim 1, wherein the radiation biodosimetry assay system additionally comprises mRNA or cDNA from a subject exposed to ionizing radiation before the mRNA or cDNA was obtained.

3. The radiation biodosimetry assay system of claim 1, wherein the in vitro nucleic acid amplification reaction mixtures are provided in a multi-well plate.

4. The radiation biodosimetry assay system of claim 3, wherein at least two nucleic acid probes directed to at least two different nucleic acid targets are in the same wells of the multi-well plate.

5. The radiation biodosimetry assay system of claim 1, wherein the system comprises primer pairs directed to at least four of SEQ ID NOs: 6, 8, 9, 10, or 14, or complementary sequences thereof.

6. The radiation biodosimetry assay system of claim 1, wherein the system comprises primer pairs of at least 10 nucleotides and probes of at least 10 nucleotides directed to SEQ ID NOs: 6, 8, and 10, or the complementary sequences thereof.

7. The radiation biodosimetry assay system of claim 1, wherein the system comprises primer pairs of at least 10 nucleotides and probes of at least 10 nucleotides directed to SEQ ID NOs: 6, 8, and 14, the complementary sequences thereof.

8. The radiation biodosimetry assay system of claim 1, wherein the system comprises primer pairs of at least 10 nucleotides and probes of at least 10 nucleotides directed to SEQ ID NOs: 8, 9, and 10, or the complementary sequences thereof.

9. The radiation biodosimetry assay system of claim 1, wherein the system comprises primer pairs of at least 10 nucleotides and probes of at least 10 nucleotides directed to SEQ ID NOs: 8, 9, and 14, or the complementary sequences thereof.

10. The radiation biodosimetry assay system of claim 1, wherein the system comprises primer pairs of at least 10 nucleotides and probes of at least 10 nucleotides directed to SEQ ID NOs: 6, 9, and 10, or the complementary sequences thereof.

11. The radiation biodosimetry assay system of claim 1, wherein the system comprises primer pairs of at least 10 nucleotides and probes of at least 10 nucleotides directed to SEQ ID NOs: 6, 9, and 14, or the complementary sequences thereof.

12. The radiation biodosimetry assay system of claim 1, wherein the system comprises primer pairs of at least 10 nucleotides and probes of at least 10 nucleotides directed to SEQ ID NOs: 6, 8, and 9, or the complementary sequences thereof.

13. A radiation biomarker assay kit, comprising
   a nucleic acid probe set comprising a plurality of nucleic acid probes of at least 10 nucleotides each that are directed to at least three of SEQ ID NOs: 6, 8, 9, 10, or 14 or the complementary sequences thereof, the nucleic acid probe set further comprising a probe detectably labeled with a fluorescent dye and a quencher and configured for PCR amplification, a set of primer pairs comprising a plurality of primer pairs each comprising primers of at least 10 nucleotides that are directed to at least three of SEQ ID NOs: 6, 8, 9, 10, or 14 or the complementary sequences thereof, and
   instructions for calculating an estimate of absorbed radiation dose from a fluorescence value obtained by contacting in vitro an mRNA or cDNA sample from a human subject suspected of suffering from radiation exposure to the nucleic acid probe set and a thermostable polymerase under PCR conditions.

14. The radiation biomarker assay kit of claim 13, wherein the nucleic acid probe set comprises no more than 100 probes.

15. The radiation biomarker assay kit of claim 13, wherein the nucleic acid probe set comprises nucleic acid probes directed to each of SEQ ID NOs: 6, 8, 9, 10, and 14 or the complementary sequences thereof.

16. The radiation biomarker assay kit of claim 13, further comprising radiation exposure positive and negative control mRNA samples or cDNAs thereof.

17. The radiation biomarker assay kit of claim 13, further comprising a nucleic acid probe of at least 10 nucleotides directed to at least one of SEQ. ID NOs:14, 16, 17, 25, or 29, or the complementary sequences thereof.

18. The radiation biomarker assay kit of claim 17, wherein the probe set comprises no more than 100 probes.

19. The radiation biomarker assay kit of claim 17, wherein the nucleic acid probes are provided in a multi-well plate.

20. The radiation biomarker assay kit of claim 19, wherein at least two nucleic acid probes directed to at least two different nucleic acid targets are in the same wells of the multi-well plate.

21. The radiation biomarker assay kit of claim 17, further comprising radiation exposure positive and negative control mRNA samples or cDNAs thereof.

22. The radiation biomarker assay kit of claim 13, wherein the kit comprises nucleic acid probes directed to at least four of SEQ ID NOs: 6, 8, 9, 10, or 14, or complementary sequences thereof.

* * * * *

UNITED STATES PATENT AND TRADEMARK OFFICE
CERTIFICATE OF CORRECTION

| | | |
|---|---|---|
| PATENT NO. | : 10,435,747 B2 | Page 1 of 1 |
| APPLICATION NO. | : 14/823433 | |
| DATED | : October 8, 2019 | |
| INVENTOR(S) | : Joshua LaBaer et al. | |

It is certified that error appears in the above-identified patent and that said Letters Patent is hereby corrected as shown below:

In the Specification

Column 1, Line 14, under the heading
STATEMENT REGARDING FEDERALLY SPONSORED RESEARCH OR DEVELOPMENT:

"This invention was made with government support under HHS0100201000008-C awarded by Biomedical Advanced Research and Development Authority. The government has certain rights in the invention."

Should be:
--This invention was made with government support under HHSO100201000008C awarded by Biomedical Advanced Research and Development Authority. The government has certain rights in the invention.--.

Signed and Sealed this
Thirty-first Day of December, 2019

Andrei Iancu
*Director of the United States Patent and Trademark Office*